(12) United States Patent
Adam et al.

(10) Patent No.: US 7,303,892 B1
(45) Date of Patent: Dec. 4, 2007

(54) CRYSTALLIZATION OF AKT3

(75) Inventors: Eric Adam, Gex (FR); Oleg Brodsky, San Diego, CA (US); Mark W. Knuth, El Cajon, CA (US); Jacek Nowakowski, San Diego, CA (US); Nikola P. Pavletich, New York, NY (US); Devon A. Thompson, San Diego, CA (US); Robert A. Wijnands, Vista, CA (US)

(73) Assignee: Takeda San Diego, Inc., San Diego, CA (US)

( * ) Notice: Subject to any disclaimer, the term of this patent is extended or adjusted under 35 U.S.C. 154(b) by 374 days.

(21) Appl. No.: 10/601,311

(22) Filed: Jun. 20, 2003

Related U.S. Application Data

(60) Provisional application No. 60/400,207, filed on Jul. 31, 2002.

(51) Int. Cl.
 *C12Q 1/48* (2006.01)
 *C12N 9/12* (2006.01)
 *G06F 19/00* (2006.01)

(52) U.S. Cl. .......................... 435/15; 435/194; 702/27

(58) Field of Classification Search .................... None
 See application file for complete search history.

(56) References Cited

U.S. PATENT DOCUMENTS 6,881,555 B2 * 4/2005 Guo et al. ................ 435/69.1
2004/0137518 A1 7/2004 Lambert et al.

OTHER PUBLICATIONS

Wiencek et al. New strategies for protein crystal growth. Ann. Rev. Biomed. Eng. 1999, 1, 505-534.*
Gilliland et al. Crystallization of biological molecules for X-ray diffraction studies. Current Opinion in Structure Biology 1996, 6, 595-603.*
Ke et al. Crystallization of RNA and RNA-protein complexes. Methods 34, 2004, 408-414.*
Brunger, Axel T. et al., "Crystallography & NMR System: A New Software Suite for Macromolecular Structure Determination", Acta Cryst. (1998) D54, pp. 905-921.
Hegyi, Heidi et al., "The Relationship between Protein Structure and Function: a Comprehensive Survey with Application to the Yeast Genome", J. Mol. Biol. (1999) 288, 147-164.
Yang, Jing, et al., "Molecular Mechanism for the Regulation of Protein Kinase B/Akt by Hydrophobic Motif Phosphorylation", Molecular Cell, vol. 9, (2002), pp. 1227-1240.

* cited by examiner

*Primary Examiner*—Nashaat T. Nashed
(74) *Attorney, Agent, or Firm*—David J. Weitz

(57) ABSTRACT

Provided are crystals relating to AKT3 and its various uses.

14 Claims, 53 Drawing Sheets

FIGURE 1A

Amino acid sequence for full-length human wild type AKT3 [SEQ. ID No. 1]

(Residues 136-461 are underlined)

```
MSDVTIVKEG  WVQKRGEYIK  NWRPRYFLLK  TDGSFIGYKE  KPQDVDLPYP  LNNFSVAKCQ   60
LMKTERPKPN  TFIIRCLQWT  TVIERTFHVD  TPEEREEWTE  AIQAVADRLQ  RQEEERMNCS  120
PTSQIDNIGE  EEMDASTTHH  KRKTMNDFDY  LKLLGKGTFG  KVILVREKAS  GKYYAMKILK  180
KEVIIAKDEV  AHTLTESRVL  KNTRHPFLTS  LKYSFQTKDR  LCFVMEYVNG  GELFFHLSRE  240
RVFSEDRTRF  YGAEIVSALD  YLHSGKIVYR  DLKLENLMLD  KDGHIKITDF  GLCKEGITDA  300
ATMKTFCGTP  EYLAPEVLED  NDYGRAVDWW  GLGVVMYEMM  CGRLPFYNQD  HEKLFELILM  360
EDIKFPRTLS  SDAKSLLSGL  LIKDPNKRLG  GGPDDAKEIM  RHSFFSGVNW  QDVYDKKLVP  420
PFKPQVTSET  DTRYFDEEFT  AQTITITPPE  KYDEDGMDCM  DNERRPHFPQ  FSYSASGRE   479
```

Human cDNA sequence encoding residues 136-461 of AKT3 [SEQ. ID No. 2]

```
TCTACAACCC  ATCATAAAAG  AAAGACAATG  AATGATTTTG  ACTATTTGAA  ACTACTAGGT   60
AAAGGCACTT  TTGGGAAAGT  TATTTTGGTT  CGAGAGAAGG  CAAGTGGAAA  ATACTATGCT  120
ATGAAGATTC  TGAAGAAAGA  AGTCATTATT  GCAAAGGATG  AAGTGGCACA  CACTCTAACT  180
GAAAGCAGAG  TATTAAAGAA  CACTAGACAT  CCCTTTTTAA  CATCCTTGAA  ATATTCCTTC  240
CAGACAAAAG  ACCGTTTGTG  TTTTGTGATG  GAATATGTTA  ATGGGGGCGA  GCTGTTTTTC  300
CATTTGTCGA  GAGAGCGGGT  GTTCTCTGAG  GACCGCACAC  GTTTCTATGG  TGCAGAAATT  360
GTCTCTGCCT  TGGACTATCT  ACATTCCGGA  AAGATTGTGT  ACCGTGATCT  CAAGTTGGAG  420
AATCTAATGC  TGGACAAAGA  TGGCCACATA  AAAATTACAG  ATTTTGGACT  TTGCAAAGAA  480
GGGATCACAG  ATGCAGCCAC  CATGAAGACA  TTCTGTGGCA  CTCCAGAATA  TCTGGCACCA  540
GAGGTGTTAG  AAGATAATGA  CTATGGCCGA  GCAGTAGACT  GGTGGGGCCT  AGGGGTTGTC  600
ATGTATGAAA  TGATGTGTGG  GAGGTTACCT  TTCTACAACC  AGGACCATGA  GAAACTTTTT  660
GAATTAATAT  TAATGGAAGA  CATTAAATTT  CCTCGAACAC  TCTCTTCAGA  TGCAAAATCA  720
TTGCTTTCAG  GGCTCTTGAT  AAAGGATCCA  AATAAACGCC  TTGGTGGAGG  ACCAGATGAT  780
GCAAAAGAAA  TTATGAGACA  CAGTTTCTTC  TCTGGAGTAA  ACTGGCAAGA  TGTATATGAT  840
AAAAAGCTTG  TACCTCCTTT  TAAACCTCAA  GTAACATCTG  AGACAGATAC  TAGATATTTT  900
GATGAAGAAT  TTACAGCTCA  GACTATTACA  ATAACACCAC  CTGAAAAATA  TGATGAGGAT  960
GGTATGGACT  GCATGGAC                                                  978
```

FIGURE 1B

Amino acid sequence for residues 136-461 of AKT3 with a cleavable
N-terminal intein tag [SEQ. ID No. 3]
(N-terminal intein tag and cleavage site are underlined. The intein tag was
subsequently cleaved resulting in CRSL (residues 227-230 of SEQ. ID No. 3) fused
to the N-terminal of amino acids 136-461 of SEQ. ID No. 1)

```
MKIEEGKLTN PGVSAWQVNT AYTAGQLVTY NGKTYKCLQP HTSLAGWEPS NVPALWQLQN    60
NGNNGLELRE SGAISGDSLI SLASTGKRVS IKDLLDEKDF EIWAINEQTM KLESAKVSRV   120
FCTGKKLVYI LKTRLGRTIK ATANHRFLTI DGWKRLDELS LKEHIALPRK LESSSLQLSP   180
EIEKLSQSDI YWDSIVSITE TGVEEVFDLT VPGPHNFVAN DIIVHNCRSL STTHHKRKTM   240
NDFDYLKLLG KGTFGKVILV REKASGKYYA MKILKKEVII AKDEVAHTLT ESRVLKNTRH   300
PFLTSLKYSF QTKDRLCFVM EYVNGGELFF HLSRERVFSE DRTRFYGAEI VSALDYLHSG   360
KIVYRDLKLE NLMLDKDGHI KITDFGLCKE GITDAATMKT FCGTPEYLAP EVLEDNDYGR   420
AVDWWGLGVV MYEMMCGRLP FYNQDHEKLF ELILMEDIKF PRTLSSDAKS LLSGLLIKDP   480
NKRLGGGPDD AKEIMRHSFF SGVNWQDVYD KKLVPPFKPQ VTSETDTRYF DEEFTAQTIT   540
ITPPEKYDED GMDCMD                                                  556
```

Amino acid sequence for residues 227-556 of SEQ. ID No. 3
[SEQ. ID No. 4]

```
CRSLSTTHHK RKTMNDFDYL KLLGKGTFGK VILVREKASG KYYAMKILKK EVIIAKDEVA    60
HTLTESRVLK NTRHPFLTSL KYSFQTKDRL CFVMEYVNGG ELFFHLSRER VFSEDRTRFY   120
GAEIVSALDY LHSGKIVYRD LKLENLMLDK DGHIKITDFG LCKEGITDAA TMKTFCGTPE   180
YLAPEVLEDN DYGRAVDWWG LGVVMYEMMC GRLPFYNQDH EKLFELILME DIKFPRTLSS   240
DAKSLLSGLL IKDPNKRLGG GPDDAKEIMR HSFFSGVNWQ DVYDKKLVPP FKPQVTSETD   300
TRYFDEEFTA QTITITPPEK YDEDGMDCMD                                   360
```

FIGURE 3

LEGEND

Column headings from left to right are (A)'Atom Number', (B)'Atom Type', (C)'Amino Acid', (D)'Chain Identifier', (E)'Amino Acid Number', (F)'X Coordinate', (G)'Y Coordinate', (H)'Z Coordinate', (I)'Occupancy' (OCC) and (J)'B factor'.

| A | B | C | D | E | F | G | H | I | J |
|---|---|---|---|---|---|---|---|---|---|
| 1 | N | ALA | A | 143 | 27.613 | 21.426 | 18.330 | 1.00 | 56.59 |
| 2 | CA | ALA | A | 143 | 27.589 | 21.831 | 19.763 | 1.00 | 55.76 |
| 3 | CB | ALA | A | 143 | 26.926 | 23.219 | 19.916 | 1.00 | 55.31 |
| 4 | C | ALA | A | 143 | 26.846 | 20.766 | 20.571 | 1.00 | 55.57 |
| 5 | O | ALA | A | 143 | 26.228 | 19.865 | 19.993 | 1.00 | 55.81 |
| 6 | N | THR | A | 144 | 26.900 | 20.874 | 21.902 | 1.00 | 55.25 |
| 7 | CA | THR | A | 144 | 26.124 | 20.003 | 22.791 | 1.00 | 55.15 |
| 8 | CB | THR | A | 144 | 26.996 | 18.895 | 23.405 | 1.00 | 55.63 |
| 9 | OG1 | THR | A | 144 | 26.204 | 18.162 | 24.335 | 1.00 | 56.59 |
| 10 | CG2 | THR | A | 144 | 28.166 | 19.433 | 24.268 | 1.00 | 56.08 |
| 11 | C | THR | A | 144 | 25.325 | 20.689 | 23.927 | 1.00 | 54.84 |
| 12 | O | THR | A | 144 | 25.587 | 21.820 | 24.332 | 1.00 | 53.60 |
| 13 | N | MET | A | 145 | 24.339 | 19.937 | 24.405 | 1.00 | 54.67 |
| 14 | CA | MET | A | 145 | 23.434 | 20.306 | 25.483 | 1.00 | 55.13 |
| 15 | CB | MET | A | 145 | 22.710 | 19.049 | 25.977 | 1.00 | 55.68 |
| 16 | CG | MET | A | 145 | 21.377 | 19.327 | 26.609 | 1.00 | 59.01 |
| 17 | SD | MET | A | 145 | 20.093 | 19.612 | 25.367 | 1.00 | 65.68 |
| 18 | CE | MET | A | 145 | 19.623 | 17.862 | 25.083 | 1.00 | 65.56 |
| 19 | C | MET | A | 145 | 24.104 | 21.007 | 26.660 | 1.00 | 54.31 |
| 20 | O | MET | A | 145 | 23.574 | 21.998 | 27.190 | 1.00 | 53.51 |
| 21 | N | ASN | A | 146 | 25.268 | 20.499 | 27.062 | 1.00 | 53.64 |
| 22 | CA | ASN | A | 146 | 25.969 | 21.048 | 28.221 | 1.00 | 53.16 |
| 23 | CB | ASN | A | 146 | 26.828 | 19.955 | 28.906 | 1.00 | 53.72 |
| 24 | CG | ASN | A | 146 | 25.989 | 18.678 | 29.297 | 1.00 | 55.84 |
| 25 | OD1 | ASN | A | 146 | 25.215 | 18.670 | 30.287 | 1.00 | 57.11 |
| 26 | ND2 | ASN | A | 146 | 26.133 | 17.617 | 28.500 | 1.00 | 56.58 |
| 27 | C | ASN | A | 146 | 26.722 | 22.387 | 27.936 | 1.00 | 51.68 |
| 28 | O | ASN | A | 146 | 27.149 | 23.065 | 28.867 | 1.00 | 50.30 |
| 29 | N | ASP | A | 147 | 26.790 | 22.811 | 26.665 | 1.00 | 50.87 |
| 30 | CA | ASP | A | 147 | 27.302 | 24.163 | 26.293 | 1.00 | 49.95 |
| 31 | CB | ASP | A | 147 | 27.847 | 24.205 | 24.862 | 1.00 | 50.01 |
| 32 | CG | ASP | A | 147 | 28.785 | 23.047 | 24.567 | 1.00 | 52.58 |
| 33 | OD1 | ASP | A | 147 | 29.754 | 22.832 | 25.342 | 1.00 | 52.20 |
| 34 | OD2 | ASP | A | 147 | 28.589 | 22.282 | 23.603 | 1.00 | 53.64 |
| 35 | C | ASP | A | 147 | 26.286 | 25.296 | 26.439 | 1.00 | 48.64 |
| 36 | O | ASP | A | 147 | 26.592 | 26.457 | 26.142 | 1.00 | 48.17 |
| 37 | N | PHE | A | 148 | 25.088 | 24.970 | 26.893 | 1.00 | 47.24 |
| 38 | CA | PHE | A | 148 | 24.050 | 25.982 | 27.086 | 1.00 | 46.40 |
| 39 | CB | PHE | A | 148 | 22.926 | 25.761 | 26.097 | 1.00 | 45.87 |
| 40 | CG | PHE | A | 148 | 23.369 | 25.808 | 24.679 | 1.00 | 47.18 |
| 41 | CD1 | PHE | A | 148 | 23.472 | 27.037 | 24.004 | 1.00 | 46.78 |
| 42 | CE1 | PHE | A | 148 | 23.890 | 27.078 | 22.680 | 1.00 | 47.32 |

FIGURE 3 (Cont.)

| A | B | C | D | E | F | G | H | I | J |
|---|---|---|---|---|---|---|---|---|---|
| 43 | CZ | PHE | A | 148 | 24.216 | 25.881 | 22.027 | 1.00 | 47.99 |
| 44 | CE2 | PHE | A | 148 | 24.125 | 24.661 | 22.701 | 1.00 | 45.37 |
| 45 | CD2 | PHE | A | 148 | 23.700 | 24.635 | 24.012 | 1.00 | 45.84 |
| 46 | C | PHE | A | 148 | 23.491 | 25.981 | 28.497 | 1.00 | 45.09 |
| 47 | O | PHE | A | 148 | 23.275 | 24.910 | 29.094 | 1.00 | 46.15 |
| 48 | N | ASP | A | 149 | 23.310 | 27.199 | 29.028 | 1.00 | 43.15 |
| 49 | CA | ASP | A | 149 | 22.473 | 27.458 | 30.176 | 1.00 | 41.09 |
| 50 | CB | ASP | A | 149 | 22.824 | 28.801 | 30.823 | 1.00 | 41.57 |
| 51 | CG | ASP | A | 149 | 24.214 | 28.835 | 31.379 | 1.00 | 39.52 |
| 52 | OD1 | ASP | A | 149 | 24.916 | 29.847 | 31.249 | 1.00 | 40.39 |
| 53 | OD2 | ASP | A | 149 | 24.690 | 27.886 | 31.953 | 1.00 | 42.91 |
| 54 | C | ASP | A | 149 | 20.998 | 27.489 | 29.717 | 1.00 | 40.21 |
| 55 | O | ASP | A | 149 | 20.617 | 28.152 | 28.746 | 1.00 | 38.69 |
| 56 | N | TYR | A | 150 | 20.165 | 26.804 | 30.465 | 1.00 | 37.78 |
| 57 | CA | TYR | A | 150 | 18.763 | 26.691 | 30.142 | 1.00 | 35.91 |
| 58 | CB | BTYR | A | 150 | 18.337 | 25.259 | 30.386 | 0.35 | 34.84 |
| 59 | CB | ATYR | A | 150 | 18.232 | 25.291 | 30.525 | 0.65 | 36.17 |
| 60 | CG | BTYR | A | 150 | 19.063 | 24.445 | 29.355 | 0.35 | 31.35 |
| 61 | CG | ATYR | A | 150 | 16.729 | 25.210 | 30.733 | 0.65 | 38.71 |
| 62 | CD1 | BTYR | A | 150 | 20.350 | 23.946 | 29.590 | 0.35 | 28.93 |
| 63 | CD1 | ATYR | A | 150 | 15.852 | 25.489 | 29.700 | 0.65 | 42.75 |
| 64 | CE1 | BTYR | A | 150 | 21.010 | 23.250 | 28.614 | 0.35 | 26.50 |
| 65 | CE1 | ATYR | A | 150 | 14.456 | 25.426 | 29.895 | 0.65 | 42.81 |
| 66 | CZ | BTYR | A | 150 | 20.395 | 23.097 | 27.376 | 0.35 | 24.84 |
| 67 | CZ | ATYR | A | 150 | 13.937 | 25.079 | 31.097 | 0.65 | 39.84 |
| 68 | OH | BTYR | A | 150 | 20.972 | 22.435 | 26.367 | 0.35 | 20.72 |
| 69 | OH | ATYR | A | 150 | 12.571 | 25.024 | 31.226 | 0.65 | 41.57 |
| 70 | CE2 | BTYR | A | 150 | 19.156 | 23.601 | 27.134 | 0.35 | 25.67 |
| 71 | CE2 | ATYR | A | 150 | 14.771 | 24.791 | 32.127 | 0.65 | 40.86 |
| 72 | CD2 | BTYR | A | 150 | 18.516 | 24.282 | 28.097 | 0.35 | 26.83 |
| 73 | CD2 | ATYR | A | 150 | 16.177 | 24.859 | 31.951 | 0.65 | 39.81 |
| 74 | C | TYR | A | 150 | 18.149 | 27.732 | 30.992 | 1.00 | 34.31 |
| 75 | O | TYR | A | 150 | 18.236 | 27.658 | 32.179 | 1.00 | 33.94 |
| 76 | N | LEU | A | 151 | 17.620 | 28.777 | 30.379 | 1.00 | 31.69 |
| 77 | CA | LEU | A | 151 | 17.156 | 29.933 | 31.154 | 1.00 | 30.71 |
| 78 | CB | LEU | A | 151 | 17.565 | 31.231 | 30.499 | 1.00 | 28.81 |
| 79 | CG | LEU | A | 151 | 19.071 | 31.447 | 30.392 | 1.00 | 30.65 |
| 80 | CD1 | LEU | A | 151 | 19.334 | 32.781 | 29.736 | 1.00 | 34.12 |
| 81 | CD2 | LEU | A | 151 | 19.845 | 31.407 | 31.719 | 1.00 | 31.52 |
| 82 | C | LEU | A | 151 | 15.666 | 29.969 | 31.431 | 1.00 | 29.81 |
| 83 | O | LEU | A | 151 | 15.263 | 30.309 | 32.536 | 1.00 | 31.55 |
| 84 | N | LYS | A | 152 | 14.866 | 29.711 | 30.419 | 1.00 | 30.25 |
| 85 | CA | LYS | A | 152 | 13.413 | 29.763 | 30.539 | 1.00 | 30.97 |
| 86 | CB | LYS | A | 152 | 12.923 | 31.221 | 30.475 | 1.00 | 30.72 |
| 87 | CG | LYS | A | 152 | 11.548 | 31.390 | 31.102 | 1.00 | 32.43 |
| 88 | CD | LYS | A | 152 | 11.090 | 32.801 | 31.230 | 1.00 | 33.30 |
| 89 | CE | LYS | A | 152 | 9.613 | 32.826 | 31.718 | 1.00 | 33.00 |
| 90 | NZ | LYS | A | 152 | 9.416 | 34.171 | 32.254 | 1.00 | 37.78 |
| 91 | C | LYS | A | 152 | 12.674 | 28.938 | 29.489 | 1.00 | 30.89 |
| 92 | O | LYS | A | 152 | 13.064 | 28.931 | 28.341 | 1.00 | 28.77 |
| 93 | N | LEU | A | 153 | 11.562 | 28.308 | 29.890 | 1.00 | 32.36 |

FIGURE 3 (Cont.)

| A | B | C | D | E | F | G | H | I | J |
|---|---|---|---|---|---|---|---|---|---|
| 94 | CA | LEU | A | 153 | 10.641 | 27.649 | 28.964 | 1.00 | 33.66 |
| 95 | CB | LEU | A | 153 | 9.631 | 26.795 | 29.735 | 1.00 | 33.94 |
| 96 | CG | LEU | A | 153 | 8.589 | 25.998 | 28.942 | 1.00 | 36.00 |
| 97 | CD1 | LEU | A | 153 | 9.257 | 24.919 | 28.146 | 1.00 | 35.57 |
| 98 | CD2 | LEU | A | 153 | 7.518 | 25.412 | 29.876 | 1.00 | 35.12 |
| 99 | C | LEU | A | 153 | 9.875 | 28.715 | 28.215 | 1.00 | 35.28 |
| 100 | O | LEU | A | 153 | 9.204 | 29.522 | 28.837 | 1.00 | 34.35 |
| 101 | N | LEU | A | 154 | 9.982 | 28.732 | 26.885 | 1.00 | 37.27 |
| 102 | CA | LEU | A | 154 | 9.263 | 29.713 | 26.055 | 1.00 | 39.00 |
| 103 | CB | LEU | A | 154 | 10.121 | 30.137 | 24.870 | 1.00 | 38.72 |
| 104 | CG | LEU | A | 154 | 11.424 | 30.783 | 25.302 | 1.00 | 38.94 |
| 105 | CD1 | LEU | A | 154 | 12.271 | 31.167 | 24.075 | 1.00 | 37.98 |
| 106 | CD2 | LEU | A | 154 | 11.110 | 31.983 | 26.230 | 1.00 | 39.60 |
| 107 | C | LEU | A | 154 | 7.923 | 29.192 | 25.548 | 1.00 | 41.36 |
| 108 | O | LEU | A | 154 | 6.985 | 29.953 | 25.380 | 1.00 | 40.97 |
| 109 | N | GLY | A | 155 | 7.850 | 27.889 | 25.298 | 1.00 | 44.10 |
| 110 | CA | GLY | A | 155 | 6.630 | 27.273 | 24.804 | 1.00 | 45.84 |
| 111 | C | GLY | A | 155 | 6.770 | 25.780 | 24.674 | 1.00 | 47.67 |
| 112 | O | GLY | A | 155 | 7.853 | 25.265 | 24.395 | 1.00 | 48.36 |
| 113 | N | LYS | A | 156 | 5.680 | 25.081 | 24.940 | 1.00 | 51.03 |
| 114 | CA | LYS | A | 156 | 5.620 | 23.644 | 24.792 | 1.00 | 53.17 |
| 115 | CB | LYS | A | 156 | 5.309 | 22.925 | 26.110 | 1.00 | 53.97 |
| 116 | CG | LYS | A | 156 | 6.086 | 21.583 | 26.267 | 1.00 | 55.78 |
| 117 | CD | LYS | A | 156 | 5.735 | 20.775 | 27.548 | 1.00 | 58.04 |
| 118 | CE | LYS | A | 156 | 6.784 | 19.673 | 27.837 | 1.00 | 58.71 |
| 119 | NZ | LYS | A | 156 | 6.325 | 18.606 | 28.820 | 1.00 | 59.67 |
| 120 | C | LYS | A | 156 | 4.562 | 23.354 | 23.751 | 1.00 | 55.06 |
| 121 | O | LYS | A | 156 | 3.556 | 24.079 | 23.600 | 1.00 | 54.87 |
| 122 | N | GLY | A | 157 | 4.794 | 22.271 | 23.031 | 1.00 | 56.52 |
| 123 | CA | GLY | A | 157 | 4.143 | 22.098 | 21.754 | 1.00 | 57.69 |
| 124 | C | GLY | A | 157 | 3.215 | 20.917 | 21.712 | 1.00 | 57.99 |
| 125 | O | GLY | A | 157 | 2.004 | 21.086 | 21.811 | 1.00 | 58.76 |
| 126 | N | THR | A | 158 | 3.810 | 19.731 | 21.613 | 1.00 | 58.39 |
| 127 | CA | THR | A | 158 | 3.211 | 18.542 | 20.970 | 1.00 | 58.32 |
| 128 | CB | THR | A | 158 | 2.113 | 18.860 | 19.864 | 1.00 | 58.73 |
| 129 | OG1 | THR | A | 158 | 1.752 | 20.254 | 19.848 | 1.00 | 58.25 |
| 130 | CG2 | THR | A | 158 | 0.785 | 18.121 | 20.151 | 1.00 | 59.37 |
| 131 | C | THR | A | 158 | 4.408 | 17.907 | 20.293 | 1.00 | 57.81 |
| 132 | O | THR | A | 158 | 4.752 | 16.763 | 20.582 | 1.00 | 56.92 |
| 133 | N | PHE | A | 159 | 5.072 | 18.697 | 19.436 | 1.00 | 57.35 |
| 134 | CA | PHE | A | 159 | 6.325 | 18.253 | 18.788 | 1.00 | 57.63 |
| 135 | CB | PHE | A | 159 | 6.688 | 19.084 | 17.523 | 1.00 | 58.38 |
| 136 | CG | PHE | A | 159 | 5.493 | 19.638 | 16.736 | 1.00 | 62.37 |
| 137 | CD1 | PHE | A | 159 | 4.965 | 18.933 | 15.644 | 1.00 | 65.08 |
| 138 | CE1 | PHE | A | 159 | 3.879 | 19.453 | 14.908 | 1.00 | 66.54 |
| 139 | CZ | PHE | A | 159 | 3.328 | 20.709 | 15.258 | 1.00 | 66.96 |
| 140 | CE2 | PHE | A | 159 | 3.855 | 21.423 | 16.341 | 1.00 | 66.31 |
| 141 | CD2 | PHE | A | 159 | 4.936 | 20.897 | 17.063 | 1.00 | 65.11 |
| 142 | C | PHE | A | 159 | 7.528 | 18.249 | 19.782 | 1.00 | 55.53 |
| 143 | O | PHE | A | 159 | 8.542 | 17.545 | 19.586 | 1.00 | 55.50 |
| 144 | N | GLY | A | 160 | 7.398 | 19.018 | 20.851 | 1.00 | 52.95 |

FIGURE 3 (Cont.)

| A | B | C | D | E | F | G | H | I | J |
|---|---|---|---|---|---|---|---|---|---|
| 145 | CA  | GLY | A | 160 |  8.490 | 19.238 | 21.781 | 1.00 | 51.32 |
| 146 | C   | GLY | A | 160 |  8.356 | 20.626 | 22.377 | 1.00 | 49.57 |
| 147 | O   | GLY | A | 160 |  7.247 | 21.107 | 22.603 | 1.00 | 49.01 |
| 148 | N   | LYS | A | 161 |  9.475 | 21.303 | 22.603 | 1.00 | 48.15 |
| 149 | CA  | LYS | A | 161 |  9.434 | 22.609 | 23.304 | 1.00 | 46.94 |
| 150 | CB  | LYS | A | 161 |  9.606 | 22.383 | 24.816 | 1.00 | 46.24 |
| 151 | CG  | LYS | A | 161 | 10.793 | 21.523 | 25.217 | 1.00 | 45.93 |
| 152 | CD  | LYS | A | 161 | 10.724 | 21.221 | 26.734 | 1.00 | 47.94 |
| 153 | CE  | LYS | A | 161 | 11.710 | 20.116 | 27.181 | 1.00 | 51.18 |
| 154 | NZ  | LYS | A | 161 | 11.119 | 19.106 | 28.149 | 1.00 | 50.37 |
| 155 | C   | LYS | A | 161 | 10.488 | 23.591 | 22.842 | 1.00 | 45.35 |
| 156 | O   | LYS | A | 161 | 11.448 | 23.210 | 22.173 | 1.00 | 45.56 |
| 157 | N   | VAL | A | 162 | 10.313 | 24.858 | 23.190 | 1.00 | 43.55 |
| 158 | CA  | VAL | A | 162 | 11.339 | 25.849 | 22.860 | 1.00 | 42.26 |
| 159 | CB  | VAL | A | 162 | 10.906 | 26.863 | 21.734 | 1.00 | 41.69 |
| 160 | CG1 | VAL | A | 162 |  9.547 | 27.467 | 21.960 | 1.00 | 44.44 |
| 161 | CG2 | VAL | A | 162 | 11.921 | 27.971 | 21.568 | 1.00 | 40.67 |
| 162 | C   | VAL | A | 162 | 11.795 | 26.506 | 24.154 | 1.00 | 40.82 |
| 163 | O   | VAL | A | 162 | 10.990 | 26.842 | 25.004 | 1.00 | 40.66 |
| 164 | N   | ILE | A | 163 | 13.097 | 26.645 | 24.312 | 1.00 | 38.88 |
| 165 | CA  | ILE | A | 163 | 13.627 | 27.213 | 25.528 | 1.00 | 38.44 |
| 166 | CB  | ILE | A | 163 | 14.231 | 26.108 | 26.417 | 1.00 | 38.78 |
| 167 | CG1 | ILE | A | 163 | 15.383 | 25.454 | 25.692 | 1.00 | 40.67 |
| 168 | CD1 | ILE | A | 163 | 15.773 | 24.127 | 26.261 | 1.00 | 44.54 |
| 169 | CG2 | ILE | A | 163 | 13.135 | 25.049 | 26.766 | 1.00 | 39.83 |
| 170 | C   | ILE | A | 163 | 14.661 | 28.289 | 25.225 | 1.00 | 37.18 |
| 171 | O   | ILE | A | 163 | 15.497 | 28.153 | 24.348 | 1.00 | 35.16 |
| 172 | N   | LEU | A | 164 | 14.579 | 29.362 | 25.985 | 1.00 | 35.00 |
| 173 | CA  | LEU | A | 164 | 15.561 | 30.402 | 25.949 | 1.00 | 33.82 |
| 174 | CB  | LEU | A | 164 | 15.066 | 31.585 | 26.762 | 1.00 | 32.52 |
| 175 | CG  | LEU | A | 164 | 15.659 | 33.004 | 26.602 | 1.00 | 33.49 |
| 176 | CD1 | LEU | A | 164 | 15.821 | 33.714 | 27.918 | 1.00 | 29.71 |
| 177 | CD2 | LEU | A | 164 | 16.881 | 33.148 | 25.737 | 1.00 | 32.24 |
| 178 | C   | LEU | A | 164 | 16.825 | 29.814 | 26.578 | 1.00 | 34.07 |
| 179 | O   | LEU | A | 164 | 16.753 | 29.258 | 27.668 | 1.00 | 33.06 |
| 180 | N   | VAL | A | 165 | 17.966 | 29.985 | 25.907 | 1.00 | 33.82 |
| 181 | CA  | VAL | A | 165 | 19.257 | 29.483 | 26.372 | 1.00 | 34.27 |
| 182 | CB  | VAL | A | 165 | 19.694 | 28.156 | 25.677 | 1.00 | 33.38 |
| 183 | CG1 | VAL | A | 165 | 18.703 | 27.063 | 25.942 | 1.00 | 34.86 |
| 184 | CG2 | VAL | A | 165 | 19.920 | 28.315 | 24.196 | 1.00 | 36.18 |
| 185 | C   | VAL | A | 165 | 20.342 | 30.560 | 26.230 | 1.00 | 34.75 |
| 186 | O   | VAL | A | 165 | 20.197 | 31.503 | 25.462 | 1.00 | 34.31 |
| 187 | N   | ARG | A | 166 | 21.401 | 30.444 | 27.012 | 1.00 | 36.09 |
| 188 | CA  | ARG | A | 166 | 22.615 | 31.242 | 26.797 | 1.00 | 38.19 |
| 189 | CB  | ARG | A | 166 | 23.038 | 31.978 | 28.063 | 1.00 | 38.27 |
| 190 | CG  | ARG | A | 166 | 24.324 | 32.858 | 27.880 | 1.00 | 40.41 |
| 191 | CD  | ARG | A | 166 | 24.686 | 33.741 | 29.046 | 1.00 | 39.91 |
| 192 | NE  | ARG | A | 166 | 24.291 | 33.060 | 30.239 | 1.00 | 43.64 |
| 193 | CZ  | ARG | A | 166 | 23.413 | 33.464 | 31.163 | 1.00 | 38.88 |
| 194 | NH1 | ARG | A | 166 | 23.214 | 32.615 | 32.145 | 1.00 | 36.64 |
| 195 | NH2 | ARG | A | 166 | 22.777 | 34.652 | 31.145 | 1.00 | 34.34 |

FIGURE 3 (Cont.)

| A | B | C | D | E | F | G | H | I | J |
|---|---|---|---|---|---|---|---|---|---|
| 196 | C | ARG | A | 166 | 23.696 | 30.244 | 26.396 | 1.00 | 39.07 |
| 197 | O | ARG | A | 166 | 23.805 | 29.207 | 27.038 | 1.00 | 38.53 |
| 198 | N | GLU | A | 167 | 24.495 | 30.529 | 25.356 | 1.00 | 40.88 |
| 199 | CA | GLU | A | 167 | 25.672 | 29.665 | 25.079 | 1.00 | 42.34 |
| 200 | CB | GLU | A | 167 | 26.203 | 29.766 | 23.641 | 1.00 | 42.73 |
| 201 | CG | GLU | A | 167 | 27.470 | 28.902 | 23.449 | 1.00 | 44.80 |
| 202 | CD | GLU | A | 167 | 27.907 | 28.648 | 21.992 | 1.00 | 48.94 |
| 203 | OE1 | GLU | A | 167 | 28.871 | 27.844 | 21.825 | 1.00 | 51.18 |
| 204 | OE2 | GLU | A | 167 | 27.329 | 29.229 | 21.037 | 1.00 | 48.74 |
| 205 | C | GLU | A | 167 | 26.763 | 30.078 | 26.042 | 1.00 | 42.80 |
| 206 | O | GLU | A | 167 | 27.172 | 31.224 | 26.025 | 1.00 | 42.15 |
| 207 | N | LYS | A | 168 | 27.215 | 29.157 | 26.886 | 1.00 | 44.62 |
| 208 | CA | LYS | A | 168 | 28.091 | 29.525 | 28.024 | 1.00 | 46.38 |
| 209 | CB | LYS | A | 168 | 28.487 | 28.353 | 28.949 | 1.00 | 46.84 |
| 210 | CG | LYS | A | 168 | 27.769 | 26.990 | 28.761 | 1.00 | 47.22 |
| 211 | CD | LYS | A | 168 | 27.001 | 26.491 | 29.972 | 1.00 | 46.74 |
| 212 | CE | LYS | A | 168 | 27.798 | 25.545 | 30.825 | 1.00 | 46.78 |
| 213 | NZ | LYS | A | 168 | 27.178 | 24.199 | 30.993 | 1.00 | 43.80 |
| 214 | C | LYS | A | 168 | 29.330 | 30.205 | 27.480 | 1.00 | 47.80 |
| 215 | O | LYS | A | 168 | 29.651 | 31.309 | 27.919 | 1.00 | 49.04 |
| 216 | N | ALA | A | 169 | 29.971 | 29.570 | 26.483 | 1.00 | 48.63 |
| 217 | CA | ALA | A | 169 | 31.140 | 30.119 | 25.767 | 1.00 | 48.75 |
| 218 | CB | ALA | A | 169 | 31.478 | 29.247 | 24.520 | 1.00 | 48.79 |
| 219 | C | ALA | A | 169 | 31.003 | 31.585 | 25.342 | 1.00 | 48.70 |
| 220 | O | ALA | A | 169 | 31.774 | 32.430 | 25.800 | 1.00 | 48.77 |
| 221 | N | SER | A | 170 | 30.034 | 31.864 | 24.458 | 1.00 | 48.26 |
| 222 | CA | SER | A | 170 | 29.851 | 33.194 | 23.883 | 1.00 | 47.54 |
| 223 | CB | SER | A | 170 | 29.121 | 33.107 | 22.531 | 1.00 | 48.26 |
| 224 | OG | SER | A | 170 | 27.773 | 32.708 | 22.680 | 1.00 | 48.57 |
| 225 | C | SER | A | 170 | 29.083 | 34.159 | 24.741 | 1.00 | 46.45 |
| 226 | O | SER | A | 170 | 29.211 | 35.362 | 24.562 | 1.00 | 46.29 |
| 227 | N | GLY | A | 171 | 28.261 | 33.655 | 25.655 | 1.00 | 45.01 |
| 228 | CA | GLY | A | 171 | 27.365 | 34.519 | 26.401 | 1.00 | 43.87 |
| 229 | C | GLY | A | 171 | 26.175 | 35.030 | 25.584 | 1.00 | 43.19 |
| 230 | O | GLY | A | 171 | 25.426 | 35.876 | 26.052 | 1.00 | 42.57 |
| 231 | N | LYS | A | 172 | 25.986 | 34.499 | 24.377 | 1.00 | 42.18 |
| 232 | CA | LYS | A | 172 | 24.907 | 34.933 | 23.509 | 1.00 | 41.48 |
| 233 | CB | LYS | A | 172 | 25.345 | 34.893 | 22.031 | 1.00 | 42.58 |
| 234 | CG | LYS | A | 172 | 26.511 | 35.836 | 21.754 | 1.00 | 45.22 |
| 235 | CD | LYS | A | 172 | 26.650 | 36.220 | 20.276 | 1.00 | 50.37 |
| 236 | CE | LYS | A | 172 | 27.937 | 37.061 | 20.039 | 1.00 | 52.45 |
| 237 | NZ | LYS | A | 172 | 28.086 | 37.540 | 18.619 | 1.00 | 54.65 |
| 238 | C | LYS | A | 172 | 23.642 | 34.096 | 23.730 | 1.00 | 39.50 |
| 239 | O | LYS | A | 172 | 23.704 | 32.908 | 24.019 | 1.00 | 38.89 |
| 240 | N | TYR | A | 173 | 22.502 | 34.749 | 23.548 | 1.00 | 37.64 |
| 241 | CA | TYR | A | 173 | 21.180 | 34.167 | 23.781 | 1.00 | 36.10 |
| 242 | CB | TYR | A | 173 | 20.270 | 35.280 | 24.391 | 1.00 | 35.74 |
| 243 | CG | TYR | A | 173 | 20.865 | 35.820 | 25.675 | 1.00 | 35.74 |
| 244 | CD1 | TYR | A | 173 | 21.511 | 37.055 | 25.724 | 1.00 | 36.50 |
| 245 | CE1 | TYR | A | 173 | 22.099 | 37.519 | 26.940 | 1.00 | 39.86 |
| 246 | CZ | TYR | A | 173 | 22.040 | 36.728 | 28.097 | 1.00 | 38.71 |

FIGURE 3 (Cont.)

| A | B | C | D | E | F | G | H | I | J |
|---|---|---|---|---|---|---|---|---|---|
| 247 | OH | TYR | A | 173 | 22.621 | 37.150 | 29.311 | 1.00 | 41.50 |
| 248 | CE2 | TYR | A | 173 | 21.409 | 35.490 | 28.031 | 1.00 | 36.11 |
| 249 | CD2 | TYR | A | 173 | 20.844 | 35.050 | 26.830 | 1.00 | 35.49 |
| 250 | C | TYR | A | 173 | 20.592 | 33.551 | 22.506 | 1.00 | 35.32 |
| 251 | O | TYR | A | 173 | 20.683 | 34.135 | 21.446 | 1.00 | 35.85 |
| 252 | N | TYR | A | 174 | 19.977 | 32.379 | 22.638 | 1.00 | 35.39 |
| 253 | CA | TYR | A | 174 | 19.303 | 31.649 | 21.572 | 1.00 | 35.07 |
| 254 | CB | TYR | A | 174 | 20.227 | 30.532 | 21.036 | 1.00 | 35.56 |
| 255 | CG | TYR | A | 174 | 21.491 | 31.096 | 20.394 | 1.00 | 37.31 |
| 256 | CD1 | TYR | A | 174 | 22.692 | 31.036 | 21.044 | 1.00 | 39.79 |
| 257 | CE1 | TYR | A | 174 | 23.857 | 31.574 | 20.473 | 1.00 | 41.73 |
| 258 | CZ | TYR | A | 174 | 23.809 | 32.196 | 19.249 | 1.00 | 41.92 |
| 259 | OH | TYR | A | 174 | 24.962 | 32.717 | 18.751 | 1.00 | 43.79 |
| 260 | CE2 | TYR | A | 174 | 22.604 | 32.302 | 18.560 | 1.00 | 42.49 |
| 261 | CD2 | TYR | A | 174 | 21.446 | 31.761 | 19.143 | 1.00 | 39.57 |
| 262 | C | TYR | A | 174 | 17.991 | 31.038 | 22.033 | 1.00 | 35.65 |
| 263 | O | TYR | A | 174 | 17.768 | 30.808 | 23.233 | 1.00 | 35.44 |
| 264 | N | ALA | A | 175 | 17.106 | 30.783 | 21.082 | 1.00 | 35.44 |
| 265 | CA | ALA | A | 175 | 16.005 | 29.857 | 21.289 | 1.00 | 36.69 |
| 266 | CB | ALA | A | 175 | 14.738 | 30.317 | 20.547 | 1.00 | 36.11 |
| 267 | C | ALA | A | 175 | 16.441 | 28.504 | 20.764 | 1.00 | 38.39 |
| 268 | O | ALA | A | 175 | 16.913 | 28.414 | 19.639 | 1.00 | 37.49 |
| 269 | N | MET | A | 176 | 16.343 | 27.474 | 21.600 | 1.00 | 39.77 |
| 270 | CA | MET | A | 176 | 16.609 | 26.113 | 21.182 | 1.00 | 40.54 |
| 271 | CB | MET | A | 176 | 17.536 | 25.397 | 22.144 | 1.00 | 40.53 |
| 272 | CG | MET | A | 176 | 17.822 | 23.935 | 21.781 | 1.00 | 38.48 |
| 273 | SD | MET | A | 176 | 18.579 | 23.012 | 23.202 | 1.00 | 36.64 |
| 274 | CE | MET | A | 176 | 20.220 | 23.657 | 23.136 | 1.00 | 35.82 |
| 275 | C | MET | A | 176 | 15.300 | 25.409 | 21.110 | 1.00 | 41.96 |
| 276 | O | MET | A | 176 | 14.620 | 25.276 | 22.108 | 1.00 | 42.83 |
| 277 | N | LYS | A | 177 | 14.913 | 25.033 | 19.899 | 1.00 | 44.12 |
| 278 | CA | LYS | A | 177 | 13.760 | 24.175 | 19.681 | 1.00 | 46.59 |
| 279 | CB | LYS | A | 177 | 13.347 | 24.291 | 18.224 | 1.00 | 46.25 |
| 280 | CG | LYS | A | 177 | 11.959 | 23.816 | 17.858 | 1.00 | 48.93 |
| 281 | CD | LYS | A | 177 | 11.851 | 23.488 | 16.324 | 1.00 | 49.90 |
| 282 | CE | LYS | A | 177 | 11.441 | 24.694 | 15.480 | 1.00 | 51.14 |
| 283 | NZ | LYS | A | 177 | 11.345 | 24.383 | 13.995 | 1.00 | 52.61 |
| 284 | C | LYS | A | 177 | 14.260 | 22.780 | 20.013 | 1.00 | 48.27 |
| 285 | O | LYS | A | 177 | 15.285 | 22.391 | 19.503 | 1.00 | 48.35 |
| 286 | N | ILE | A | 178 | 13.598 | 22.071 | 20.927 | 1.00 | 51.11 |
| 287 | CA | ILE | A | 178 | 13.958 | 20.679 | 21.269 | 1.00 | 53.00 |
| 288 | CB | ILE | A | 178 | 14.283 | 20.500 | 22.794 | 1.00 | 53.29 |
| 289 | CG1 | ILE | A | 178 | 15.430 | 21.413 | 23.242 | 1.00 | 54.01 |
| 290 | CD1 | ILE | A | 178 | 15.781 | 21.226 | 24.764 | 1.00 | 54.35 |
| 291 | CG2 | ILE | A | 178 | 14.693 | 19.048 | 23.138 | 1.00 | 53.69 |
| 292 | C | ILE | A | 178 | 12.782 | 19.784 | 20.849 | 1.00 | 54.73 |
| 293 | O | ILE | A | 178 | 11.673 | 19.879 | 21.384 | 1.00 | 54.11 |
| 294 | N | LEU | A | 179 | 13.064 | 18.923 | 19.874 | 1.00 | 57.27 |
| 295 | CA | LEU | A | 179 | 12.073 | 18.122 | 19.166 | 1.00 | 59.19 |
| 296 | CB | LEU | A | 179 | 12.199 | 18.380 | 17.654 | 1.00 | 59.37 |
| 297 | CG | LEU | A | 179 | 11.209 | 19.356 | 16.997 | 1.00 | 59.68 |

FIGURE 3 (Cont.)

| A | B | C | D | E | F | G | H | I | J |
|---|---|---|---|---|---|---|---|---|---|
| 298 | CD1 | LEU | A | 179 | 10.729 | 20.458 | 17.939 | 1.00 | 59.23 |
| 299 | CD2 | LEU | A | 179 | 11.844 | 19.951 | 15.758 | 1.00 | 60.68 |
| 300 | C | LEU | A | 179 | 12.267 | 16.631 | 19.484 | 1.00 | 60.77 |
| 301 | O | LEU | A | 179 | 13.355 | 16.075 | 19.292 | 1.00 | 61.13 |
| 302 | N | LYS | A | 180 | 11.217 | 16.002 | 20.008 | 1.00 | 62.56 |
| 303 | CA | LYS | A | 180 | 11.259 | 14.585 | 20.331 | 1.00 | 63.85 |
| 304 | CB | LYS | A | 180 | 10.162 | 14.203 | 21.343 | 1.00 | 64.15 |
| 305 | CG | LYS | A | 180 | 10.677 | 13.678 | 22.725 | 1.00 | 65.44 |
| 306 | CD | LYS | A | 180 | 11.140 | 12.164 | 22.815 | 1.00 | 66.17 |
| 307 | CE | LYS | A | 180 | 10.376 | 11.126 | 21.918 | 1.00 | 66.21 |
| 308 | NZ | LYS | A | 180 | 9.175 | 10.554 | 22.568 | 1.00 | 64.58 |
| 309 | C | LYS | A | 180 | 11.086 | 13.840 | 19.020 | 1.00 | 64.76 |
| 310 | O | LYS | A | 180 | 10.089 | 14.034 | 18.311 | 1.00 | 64.21 |
| 311 | N | LYS | A | 181 | 12.094 | 13.034 | 18.692 | 1.00 | 66.59 |
| 312 | CA | LYS | A | 181 | 12.081 | 12.150 | 17.523 | 1.00 | 68.04 |
| 313 | CB | LYS | A | 181 | 13.166 | 11.062 | 17.655 | 1.00 | 67.86 |
| 314 | CG | LYS | A | 181 | 14.485 | 11.438 | 16.989 | 1.00 | 67.53 |
| 315 | CD | LYS | A | 181 | 15.719 | 10.892 | 17.701 | 1.00 | 67.59 |
| 316 | CE | LYS | A | 181 | 16.888 | 11.887 | 17.674 | 1.00 | 67.74 |
| 317 | NZ | LYS | A | 181 | 18.219 | 11.238 | 17.534 | 1.00 | 67.39 |
| 318 | C | LYS | A | 181 | 10.707 | 11.507 | 17.297 | 1.00 | 69.59 |
| 319 | O | LYS | A | 181 | 10.056 | 11.799 | 16.294 | 1.00 | 69.63 |
| 320 | N | GLU | A | 182 | 10.250 | 10.694 | 18.257 | 1.00 | 71.20 |
| 321 | CA | GLU | A | 182 | 9.074 | 9.838 | 18.047 | 1.00 | 72.54 |
| 322 | CB | GLU | A | 182 | 8.720 | 9.040 | 19.318 | 1.00 | 72.68 |
| 323 | CG | GLU | A | 182 | 8.049 | 7.692 | 19.040 | 1.00 | 73.73 |
| 324 | CD | GLU | A | 182 | 8.740 | 6.889 | 17.931 | 1.00 | 75.31 |
| 325 | OE1 | GLU | A | 182 | 8.285 | 6.952 | 16.759 | 1.00 | 76.11 |
| 326 | OE2 | GLU | A | 182 | 9.748 | 6.203 | 18.218 | 1.00 | 75.34 |
| 327 | C | GLU | A | 182 | 7.820 | 10.551 | 17.512 | 1.00 | 73.31 |
| 328 | O | GLU | A | 182 | 7.022 | 9.934 | 16.803 | 1.00 | 73.95 |
| 329 | N | VAL | A | 183 | 7.658 | 11.832 | 17.834 | 1.00 | 74.01 |
| 330 | CA | VAL | A | 183 | 6.435 | 12.577 | 17.502 | 1.00 | 74.67 |
| 331 | CB | VAL | A | 183 | 6.255 | 13.836 | 18.409 | 1.00 | 74.56 |
| 332 | CG1 | VAL | A | 183 | 4.857 | 14.446 | 18.205 | 1.00 | 74.30 |
| 333 | CG2 | VAL | A | 183 | 6.521 | 13.506 | 19.886 | 1.00 | 74.42 |
| 334 | C | VAL | A | 183 | 6.360 | 13.052 | 16.044 | 1.00 | 75.33 |
| 335 | O | VAL | A | 183 | 5.277 | 13.056 | 15.441 | 1.00 | 75.50 |
| 336 | N | ILE | A | 184 | 7.485 | 13.508 | 15.497 | 1.00 | 76.13 |
| 337 | CA | ILE | A | 184 | 7.488 | 14.007 | 14.117 | 1.00 | 76.89 |
| 338 | CB | ILE | A | 184 | 8.622 | 15.088 | 13.825 | 1.00 | 77.15 |
| 339 | CG1 | ILE | A | 184 | 10.027 | 14.571 | 14.170 | 1.00 | 77.30 |
| 340 | CD1 | ILE | A | 184 | 10.993 | 14.660 | 13.011 | 1.00 | 76.92 |
| 341 | CG2 | ILE | A | 184 | 8.320 | 16.437 | 14.537 | 1.00 | 76.77 |
| 342 | C | ILE | A | 184 | 7.532 | 12.825 | 13.144 | 1.00 | 77.10 |
| 343 | O | ILE | A | 184 | 6.975 | 12.911 | 12.053 | 1.00 | 76.66 |
| 344 | N | ILE | A | 185 | 8.156 | 11.717 | 13.555 | 1.00 | 77.67 |
| 345 | CA | ILE | A | 185 | 8.038 | 10.457 | 12.789 | 1.00 | 78.20 |
| 346 | CB | ILE | A | 185 | 9.117 | 9.325 | 13.211 | 1.00 | 78.33 |
| 347 | CG1 | ILE | A | 185 | 8.543 | 7.892 | 13.187 | 1.00 | 79.36 |
| 348 | CD1 | ILE | A | 185 | 9.599 | 6.789 | 12.845 | 1.00 | 79.87 |

FIGURE 3 (Cont.)

| A | B | C | D | E | F | G | H | I | J |
|---|---|---|---|---|---|---|---|---|---|
| 349 | CG2 | ILE | A | 185 | 9.764 | 9.583 | 14.553 | 1.00 | 78.39 |
| 350 | C | ILE | A | 185 | 6.572 | 9.976 | 12.789 | 1.00 | 78.15 |
| 351 | O | ILE | A | 185 | 6.050 | 9.566 | 11.753 | 1.00 | 78.23 |
| 352 | N | ALA | A | 186 | 5.898 | 10.079 | 13.929 | 1.00 | 78.27 |
| 353 | CA | ALA | A | 186 | 4.504 | 9.650 | 14.031 | 1.00 | 78.24 |
| 354 | CB | ALA | A | 186 | 4.059 | 9.644 | 15.487 | 1.00 | 78.34 |
| 355 | C | ALA | A | 186 | 3.546 | 10.496 | 13.177 | 1.00 | 78.08 |
| 356 | O | ALA | A | 186 | 2.515 | 10.001 | 12.748 | 1.00 | 78.13 |
| 357 | N | LYS | A | 187 | 3.879 | 11.757 | 12.917 | 1.00 | 77.90 |
| 358 | CA | LYS | A | 187 | 3.005 | 12.618 | 12.115 | 1.00 | 77.82 |
| 359 | CB | LYS | A | 187 | 2.531 | 13.815 | 12.953 | 1.00 | 77.94 |
| 360 | CG | LYS | A | 187 | 1.007 | 13.992 | 13.053 | 1.00 | 77.78 |
| 361 | CD | LYS | A | 187 | 0.658 | 15.348 | 13.705 | 1.00 | 77.17 |
| 362 | CE | LYS | A | 187 | -0.823 | 15.467 | 14.044 | 1.00 | 77.05 |
| 363 | NZ | LYS | A | 187 | -1.206 | 14.686 | 15.250 | 1.00 | 75.25 |
| 364 | C | LYS | A | 187 | 3.690 | 13.068 | 10.809 | 1.00 | 77.72 |
| 365 | O | LYS | A | 187 | 3.229 | 14.001 | 10.148 | 1.00 | 77.73 |
| 366 | N | ASP | A | 188 | 4.775 | 12.376 | 10.442 | 1.00 | 77.59 |
| 367 | CA | ASP | A | 188 | 5.486 | 12.554 | 9.153 | 1.00 | 77.44 |
| 368 | CB | ASP | A | 188 | 4.659 | 11.977 | 7.998 | 1.00 | 77.52 |
| 369 | CG | ASP | A | 188 | 4.536 | 10.474 | 8.075 | 1.00 | 78.00 |
| 370 | OD1 | ASP | A | 188 | 4.797 | 9.887 | 9.150 | 1.00 | 77.81 |
| 371 | OD2 | ASP | A | 188 | 4.181 | 9.792 | 7.101 | 1.00 | 79.29 |
| 372 | C | ASP | A | 188 | 5.949 | 13.969 | 8.795 | 1.00 | 76.77 |
| 373 | O | ASP | A | 188 | 5.928 | 14.357 | 7.617 | 1.00 | 76.75 |
| 374 | N | GLU | A | 189 | 6.362 | 14.720 | 9.819 | 1.00 | 76.07 |
| 375 | CA | GLU | A | 189 | 7.123 | 15.963 | 9.652 | 1.00 | 75.11 |
| 376 | CB | GLU | A | 189 | 6.733 | 16.983 | 10.735 | 1.00 | 75.09 |
| 377 | CG | GLU | A | 189 | 5.287 | 17.457 | 10.646 | 1.00 | 74.73 |
| 378 | CD | GLU | A | 189 | 5.067 | 18.520 | 9.580 | 1.00 | 74.41 |
| 379 | OE1 | GLU | A | 189 | 4.307 | 19.464 | 9.844 | 1.00 | 74.11 |
| 380 | OE2 | GLU | A | 189 | 5.638 | 18.422 | 8.476 | 1.00 | 74.51 |
| 381 | C | GLU | A | 189 | 8.639 | 15.696 | 9.690 | 1.00 | 74.36 |
| 382 | O | GLU | A | 189 | 9.427 | 16.614 | 9.917 | 1.00 | 74.31 |
| 383 | N | VAL | A | 190 | 9.044 | 14.441 | 9.464 | 1.00 | 73.18 |
| 384 | CA | VAL | A | 190 | 10.461 | 14.082 | 9.357 | 1.00 | 72.17 |
| 385 | CB | VAL | A | 190 | 10.662 | 12.533 | 9.101 | 1.00 | 72.54 |
| 386 | CG1 | VAL | A | 190 | 12.093 | 12.198 | 8.679 | 1.00 | 72.42 |
| 387 | CG2 | VAL | A | 190 | 10.304 | 11.723 | 10.350 | 1.00 | 72.85 |
| 388 | C | VAL | A | 190 | 11.101 | 14.917 | 8.246 | 1.00 | 70.72 |
| 389 | O | VAL | A | 190 | 12.083 | 15.625 | 8.484 | 1.00 | 70.50 |
| 390 | N | ALA | A | 191 | 10.513 | 14.860 | 7.053 | 1.00 | 68.83 |
| 391 | CA | ALA | A | 191 | 11.080 | 15.532 | 5.886 | 1.00 | 67.41 |
| 392 | CB | ALA | A | 191 | 10.458 | 14.997 | 4.585 | 1.00 | 67.17 |
| 393 | C | ALA | A | 191 | 10.959 | 17.057 | 5.958 | 1.00 | 65.81 |
| 394 | O | ALA | A | 191 | 11.873 | 17.747 | 5.550 | 1.00 | 65.26 |
| 395 | N | HIS | A | 192 | 9.845 | 17.578 | 6.467 | 1.00 | 64.55 |
| 396 | CA | HIS | A | 192 | 9.654 | 19.028 | 6.554 | 1.00 | 63.34 |
| 397 | CB | HIS | A | 192 | 8.249 | 19.376 | 7.068 | 1.00 | 63.93 |
| 398 | CG | HIS | A | 192 | 8.105 | 20.795 | 7.552 | 1.00 | 65.94 |
| 399 | ND1 | HIS | A | 192 | 7.236 | 21.153 | 8.562 | 1.00 | 68.28 |

FIGURE 3 (Cont.)

| A | B | C | D | E | F | G | H | I | J |
|---|---|---|---|---|---|---|---|---|---|
| 400 | CE1 | HIS | A | 192 | 7.330 | 22.455 | 8.785 | 1.00 | 69.38 |
| 401 | NE2 | HIS | A | 192 | 8.227 | 22.959 | 7.953 | 1.00 | 68.87 |
| 402 | CD2 | HIS | A | 192 | 8.721 | 21.944 | 7.164 | 1.00 | 68.14 |
| 403 | C | HIS | A | 192 | 10.716 | 19.643 | 7.460 | 1.00 | 61.94 |
| 404 | O | HIS | A | 192 | 11.408 | 20.592 | 7.096 | 1.00 | 60.76 |
| 405 | N | THR | A | 193 | 10.849 | 19.067 | 8.637 | 1.00 | 60.53 |
| 406 | CA | THR | A | 193 | 11.742 | 19.575 | 9.653 | 1.00 | 59.78 |
| 407 | CB | THR | A | 193 | 11.621 | 18.702 | 10.884 | 1.00 | 59.81 |
| 408 | OG1 | THR | A | 193 | 10.267 | 18.745 | 11.366 | 1.00 | 60.92 |
| 409 | CG2 | THR | A | 193 | 12.496 | 19.239 | 12.026 | 1.00 | 59.77 |
| 410 | C | THR | A | 193 | 13.202 | 19.641 | 9.226 | 1.00 | 59.30 |
| 411 | O | THR | A | 193 | 13.886 | 20.618 | 9.522 | 1.00 | 58.63 |
| 412 | N | LEU | A | 194 | 13.696 | 18.602 | 8.563 | 1.00 | 58.75 |
| 413 | CA | LEU | A | 194 | 15.093 | 18.596 | 8.120 | 1.00 | 59.00 |
| 414 | CB | LEU | A | 194 | 15.600 | 17.172 | 7.928 | 1.00 | 59.15 |
| 415 | CG | LEU | A | 194 | 15.518 | 16.349 | 9.217 | 1.00 | 59.79 |
| 416 | CD1 | LEU | A | 194 | 15.358 | 14.875 | 8.861 | 1.00 | 60.51 |
| 417 | CD2 | LEU | A | 194 | 16.717 | 16.591 | 10.188 | 1.00 | 59.77 |
| 418 | C | LEU | A | 194 | 15.291 | 19.415 | 6.847 | 1.00 | 58.88 |
| 419 | O | LEU | A | 194 | 16.382 | 19.924 | 6.598 | 1.00 | 57.88 |
| 420 | N | THR | A | 195 | 14.222 | 19.541 | 6.060 | 1.00 | 59.22 |
| 421 | CA | THR | A | 195 | 14.217 | 20.370 | 4.856 | 1.00 | 59.93 |
| 422 | CB | THR | A | 195 | 12.855 | 20.256 | 4.104 | 1.00 | 60.17 |
| 423 | OG1 | THR | A | 195 | 12.498 | 18.873 | 3.931 | 1.00 | 61.53 |
| 424 | CG2 | THR | A | 195 | 12.970 | 20.779 | 2.676 | 1.00 | 59.84 |
| 425 | C | THR | A | 195 | 14.457 | 21.808 | 5.246 | 1.00 | 60.14 |
| 426 | O | THR | A | 195 | 15.406 | 22.465 | 4.776 | 1.00 | 60.39 |
| 427 | N | GLU | A | 196 | 13.592 | 22.285 | 6.130 | 1.00 | 60.33 |
| 428 | CA | GLU | A | 196 | 13.692 | 23.620 | 6.652 | 1.00 | 60.65 |
| 429 | CB | GLU | A | 196 | 12.570 | 23.867 | 7.628 | 1.00 | 60.98 |
| 430 | CG | GLU | A | 196 | 12.711 | 25.183 | 8.353 | 1.00 | 63.20 |
| 431 | CD | GLU | A | 196 | 11.680 | 25.281 | 9.417 | 1.00 | 65.82 |
| 432 | OE1 | GLU | A | 196 | 11.986 | 24.893 | 10.573 | 1.00 | 67.42 |
| 433 | OE2 | GLU | A | 196 | 10.561 | 25.692 | 9.053 | 1.00 | 69.13 |
| 434 | C | GLU | A | 196 | 14.996 | 23.798 | 7.383 | 1.00 | 60.14 |
| 435 | O | GLU | A | 196 | 15.625 | 24.829 | 7.269 | 1.00 | 60.55 |
| 436 | N | SER | A | 197 | 15.392 | 22.804 | 8.163 | 1.00 | 59.68 |
| 437 | CA | SER | A | 197 | 16.584 | 22.947 | 8.986 | 1.00 | 59.12 |
| 438 | CB | SER | A | 197 | 17.018 | 21.635 | 9.628 | 1.00 | 58.78 |
| 439 | OG | SER | A | 197 | 18.420 | 21.619 | 9.771 | 1.00 | 56.82 |
| 440 | C | SER | A | 197 | 17.696 | 23.470 | 8.107 | 1.00 | 59.11 |
| 441 | O | SER | A | 197 | 18.276 | 24.515 | 8.417 | 1.00 | 58.22 |
| 442 | N | ARG | A | 198 | 17.957 | 22.737 | 7.016 | 1.00 | 59.14 |
| 443 | CA | ARG | A | 198 | 19.016 | 23.062 | 6.048 | 1.00 | 59.54 |
| 444 | CB | ARG | A | 198 | 19.044 | 22.027 | 4.925 | 1.00 | 60.25 |
| 445 | CG | ARG | A | 198 | 20.103 | 20.904 | 5.055 | 1.00 | 62.43 |
| 446 | CD | ARG | A | 198 | 20.421 | 20.242 | 3.700 | 1.00 | 65.15 |
| 447 | NE | ARG | A | 198 | 19.256 | 20.373 | 2.823 | 1.00 | 66.57 |
| 448 | CZ | ARG | A | 198 | 18.167 | 19.592 | 2.868 | 1.00 | 68.16 |
| 449 | NH1 | ARG | A | 198 | 17.155 | 19.836 | 2.035 | 1.00 | 67.13 |
| 450 | NH2 | ARG | A | 198 | 18.091 | 18.556 | 3.719 | 1.00 | 68.57 |

FIGURE 3 (Cont.)

| A | B | C | D | E | F | G | H | I | J |
|---|---|---|---|---|---|---|---|---|---|
| 451 | C | ARG | A | 198 | 18.829 | 24.444 | 5.399 | 1.00 | 59.23 |
| 452 | O | ARG | A | 198 | 19.808 | 25.150 | 5.137 | 1.00 | 59.17 |
| 453 | N | VAL | A | 199 | 17.578 | 24.812 | 5.126 | 1.00 | 58.30 |
| 454 | CA | VAL | A | 199 | 17.271 | 26.139 | 4.609 | 1.00 | 58.30 |
| 455 | CB | VAL | A | 199 | 15.766 | 26.290 | 4.279 | 1.00 | 58.46 |
| 456 | CG1 | VAL | A | 199 | 15.371 | 27.780 | 4.073 | 1.00 | 58.34 |
| 457 | CG2 | VAL | A | 199 | 15.417 | 25.424 | 3.062 | 1.00 | 58.98 |
| 458 | C | VAL | A | 199 | 17.754 | 27.212 | 5.591 | 1.00 | 57.78 |
| 459 | O | VAL | A | 199 | 18.767 | 27.865 | 5.318 | 1.00 | 57.82 |
| 460 | N | LEU | A | 200 | 17.079 | 27.366 | 6.737 | 1.00 | 57.19 |
| 461 | CA | LEU | A | 200 | 17.485 | 28.371 | 7.754 | 1.00 | 56.65 |
| 462 | CB | LEU | A | 200 | 16.576 | 28.449 | 9.016 | 1.00 | 56.62 |
| 463 | CG | LEU | A | 200 | 15.285 | 27.659 | 9.302 | 1.00 | 58.97 |
| 464 | CD1 | LEU | A | 200 | 15.549 | 26.566 | 10.354 | 1.00 | 61.19 |
| 465 | CD2 | LEU | A | 200 | 14.104 | 28.529 | 9.761 | 1.00 | 59.55 |
| 466 | C | LEU | A | 200 | 18.948 | 28.275 | 8.185 | 1.00 | 55.30 |
| 467 | O | LEU | A | 200 | 19.492 | 29.267 | 8.657 | 1.00 | 55.24 |
| 468 | N | LYS | A | 201 | 19.571 | 27.107 | 7.997 | 1.00 | 54.50 |
| 469 | CA | LYS | A | 201 | 20.992 | 26.890 | 8.309 | 1.00 | 53.87 |
| 470 | CB | LYS | A | 201 | 21.251 | 25.397 | 8.523 | 1.00 | 54.43 |
| 471 | CG | LYS | A | 201 | 22.414 | 25.061 | 9.489 | 1.00 | 56.12 |
| 472 | CD | LYS | A | 201 | 22.322 | 23.567 | 9.965 | 1.00 | 57.15 |
| 473 | CE | LYS | A | 201 | 23.546 | 23.105 | 10.760 | 1.00 | 58.68 |
| 474 | NZ | LYS | A | 201 | 24.241 | 24.219 | 11.499 | 1.00 | 58.76 |
| 475 | C | LYS | A | 201 | 21.956 | 27.384 | 7.223 | 1.00 | 52.69 |
| 476 | O | LYS | A | 201 | 23.093 | 27.755 | 7.510 | 1.00 | 53.28 |
| 477 | N | ASN | A | 202 | 21.516 | 27.340 | 5.970 | 1.00 | 51.30 |
| 478 | CA | ASN | A | 202 | 22.311 | 27.801 | 4.840 | 1.00 | 49.63 |
| 479 | CB | ASN | A | 202 | 22.190 | 26.803 | 3.696 | 1.00 | 50.03 |
| 480 | CG | ASN | A | 202 | 23.438 | 25.950 | 3.533 | 1.00 | 52.44 |
| 481 | OD1 | ASN | A | 202 | 23.968 | 25.805 | 2.418 | 1.00 | 55.49 |
| 482 | ND2 | ASN | A | 202 | 23.935 | 25.412 | 4.646 | 1.00 | 49.75 |
| 483 | C | ASN | A | 202 | 21.882 | 29.173 | 4.345 | 1.00 | 47.67 |
| 484 | O | ASN | A | 202 | 22.321 | 29.606 | 3.297 | 1.00 | 48.70 |
| 485 | N | THR | A | 203 | 21.013 | 29.862 | 5.066 | 1.00 | 44.75 |
| 486 | CA | THR | A | 203 | 20.580 | 31.186 | 4.600 | 1.00 | 42.80 |
| 487 | CB | THR | A | 203 | 19.109 | 31.188 | 4.233 | 1.00 | 41.99 |
| 488 | OG1 | THR | A | 203 | 18.340 | 30.680 | 5.321 | 1.00 | 43.37 |
| 489 | CG2 | THR | A | 203 | 18.809 | 30.263 | 3.095 | 1.00 | 43.53 |
| 490 | C | THR | A | 203 | 20.838 | 32.265 | 5.640 | 1.00 | 40.68 |
| 491 | O | THR | A | 203 | 20.788 | 32.003 | 6.871 | 1.00 | 40.98 |
| 492 | N | ARG | A | 204 | 21.096 | 33.472 | 5.146 | 1.00 | 38.05 |
| 493 | CA | ARG | A | 204 | 21.226 | 34.649 | 6.007 | 1.00 | 37.25 |
| 494 | CB | ARG | A | 204 | 22.676 | 34.841 | 6.415 | 1.00 | 38.34 |
| 495 | CG | ARG | A | 204 | 23.004 | 33.925 | 7.691 | 1.00 | 46.44 |
| 496 | CD | ARG | A | 204 | 23.708 | 34.650 | 8.875 | 1.00 | 54.17 |
| 497 | NE | ARG | A | 204 | 24.838 | 35.449 | 8.356 | 1.00 | 60.02 |
| 498 | CZ | ARG | A | 204 | 25.971 | 34.933 | 7.850 | 1.00 | 64.03 |
| 499 | NH1 | ARG | A | 204 | 26.919 | 35.745 | 7.395 | 1.00 | 66.29 |
| 500 | NH2 | ARG | A | 204 | 26.170 | 33.614 | 7.793 | 1.00 | 65.13 |
| 501 | C | ARG | A | 204 | 20.585 | 35.910 | 5.442 | 1.00 | 33.37 |

FIGURE 3 (Cont.)

| A | B | C | D | E | F | G | H | I | J |
|---|---|---|---|---|---|---|---|---|---|
| 502 | O | ARG | A | 204 | 20.981 | 36.405 | 4.411 | 1.00 | 32.59 |
| 503 | N | HIS | A | 205 | 19.555 | 36.365 | 6.146 | 1.00 | 30.69 |
| 504 | CA | HIS | A | 205 | 18.638 | 37.451 | 5.751 | 1.00 | 27.95 |
| 505 | CB | HIS | A | 205 | 17.305 | 36.980 | 5.122 | 1.00 | 26.74 |
| 506 | CG | HIS | A | 205 | 16.701 | 38.038 | 4.278 | 1.00 | 26.02 |
| 507 | ND1 | HIS | A | 205 | 16.338 | 39.251 | 4.739 | 1.00 | 20.10 |
| 508 | CE1 | HIS | A | 205 | 16.127 | 40.091 | 3.756 | 1.00 | 27.65 |
| 509 | NE2 | HIS | A | 205 | 16.182 | 39.398 | 2.666 | 1.00 | 23.45 |
| 510 | CD2 | HIS | A | 205 | 16.381 | 38.078 | 2.992 | 1.00 | 28.82 |
| 511 | C | HIS | A | 205 | 18.173 | 38.115 | 7.022 | 1.00 | 27.20 |
| 512 | O | HIS | A | 205 | 17.758 | 37.438 | 7.966 | 1.00 | 24.49 |
| 513 | N | PRO | A | 206 | 18.121 | 39.428 | 7.012 | 1.00 | 26.74 |
| 514 | CA | PRO | A | 206 | 17.755 | 40.167 | 8.206 | 1.00 | 26.45 |
| 515 | CB | PRO | A | 206 | 17.735 | 41.604 | 7.722 | 1.00 | 27.72 |
| 516 | CG | PRO | A | 206 | 18.514 | 41.626 | 6.583 | 1.00 | 28.61 |
| 517 | CD | PRO | A | 206 | 18.434 | 40.324 | 5.898 | 1.00 | 27.01 |
| 518 | C | PRO | A | 206 | 16.363 | 39.779 | 8.663 | 1.00 | 25.70 |
| 519 | O | PRO | A | 206 | 16.108 | 39.944 | 9.846 | 1.00 | 24.35 |
| 520 | N | PHE | A | 207 | 15.508 | 39.295 | 7.752 | 1.00 | 23.25 |
| 521 | CA | PHE | A | 207 | 14.172 | 38.976 | 8.128 | 1.00 | 25.09 |
| 522 | CB | PHE | A | 207 | 13.153 | 39.763 | 7.308 | 1.00 | 23.87 |
| 523 | CG | PHE | A | 207 | 13.465 | 41.220 | 7.265 | 1.00 | 23.27 |
| 524 | CD1 | PHE | A | 207 | 13.647 | 41.907 | 8.403 | 1.00 | 20.44 |
| 525 | CE1 | PHE | A | 207 | 13.953 | 43.240 | 8.344 | 1.00 | 25.33 |
| 526 | CZ | PHE | A | 207 | 14.161 | 43.833 | 7.154 | 1.00 | 22.29 |
| 527 | CE2 | PHE | A | 207 | 14.042 | 43.150 | 6.040 | 1.00 | 21.60 |
| 528 | CD2 | PHE | A | 207 | 13.660 | 41.862 | 6.082 | 1.00 | 21.44 |
| 529 | C | PHE | A | 207 | 13.879 | 37.523 | 8.237 | 1.00 | 26.37 |
| 530 | O | PHE | A | 207 | 12.741 | 37.136 | 8.503 | 1.00 | 28.02 |
| 531 | N | LEU | A | 208 | 14.918 | 36.723 | 8.141 | 1.00 | 28.91 |
| 532 | CA | LEU | A | 208 | 14.801 | 35.310 | 8.335 | 1.00 | 30.45 |
| 533 | CB | LEU | A | 208 | 15.417 | 34.533 | 7.180 | 1.00 | 31.45 |
| 534 | CG | LEU | A | 208 | 14.513 | 34.237 | 5.993 | 1.00 | 34.82 |
| 535 | CD1 | LEU | A | 208 | 15.423 | 33.735 | 4.856 | 1.00 | 35.96 |
| 536 | CD2 | LEU | A | 208 | 13.500 | 33.164 | 6.418 | 1.00 | 38.73 |
| 537 | C | LEU | A | 208 | 15.514 | 34.970 | 9.634 | 1.00 | 30.78 |
| 538 | O | LEU | A | 208 | 16.648 | 35.390 | 9.877 | 1.00 | 29.94 |
| 539 | N | THR | A | 209 | 14.810 | 34.239 | 10.466 | 1.00 | 31.30 |
| 540 | CA | THR | A | 209 | 15.386 | 33.645 | 11.673 | 1.00 | 34.81 |
| 541 | CB | THR | A | 209 | 14.273 | 32.949 | 12.421 | 1.00 | 34.40 |
| 542 | OG1 | THR | A | 209 | 13.406 | 33.969 | 12.920 | 1.00 | 39.53 |
| 543 | CG2 | THR | A | 209 | 14.797 | 32.302 | 13.659 | 1.00 | 38.71 |
| 544 | C | THR | A | 209 | 16.509 | 32.688 | 11.384 | 1.00 | 35.22 |
| 545 | O | THR | A | 209 | 16.313 | 31.703 | 10.727 | 1.00 | 37.10 |
| 546 | N | SER | A | 210 | 17.701 | 33.011 | 11.814 | 1.00 | 37.87 |
| 547 | CA | SER | A | 210 | 18.861 | 32.159 | 11.564 | 1.00 | 40.12 |
| 548 | CB | SER | A | 210 | 20.132 | 32.974 | 11.764 | 1.00 | 40.91 |
| 549 | OG | SER | A | 210 | 21.238 | 32.083 | 11.966 | 1.00 | 44.58 |
| 550 | C | SER | A | 210 | 18.941 | 30.955 | 12.507 | 1.00 | 41.03 |
| 551 | O | SER | A | 210 | 18.949 | 31.122 | 13.725 | 1.00 | 41.43 |
| 552 | N | LEU | A | 211 | 19.032 | 29.767 | 11.940 | 1.00 | 42.25 |

FIGURE 3 (Cont.)

| A | B | C | D | E | F | G | H | I | J |
|---|---|---|---|---|---|---|---|---|---|
| 553 | CA | LEU | A | 211 | 19.451 | 28.559 | 12.649 | 1.00 | 43.74 |
| 554 | CB | LEU | A | 211 | 19.009 | 27.341 | 11.866 | 1.00 | 44.39 |
| 555 | CG | LEU | A | 211 | 19.104 | 25.999 | 12.584 | 1.00 | 47.26 |
| 556 | CD1 | LEU | A | 211 | 18.017 | 25.070 | 12.037 | 1.00 | 48.59 |
| 557 | CD2 | LEU | A | 211 | 20.436 | 25.407 | 12.335 | 1.00 | 49.77 |
| 558 | C | LEU | A | 211 | 20.961 | 28.509 | 12.775 | 1.00 | 44.63 |
| 559 | O | LEU | A | 211 | 21.654 | 28.390 | 11.768 | 1.00 | 44.28 |
| 560 | N | LYS | A | 212 | 21.460 | 28.617 | 14.003 | 1.00 | 45.30 |
| 561 | CA | LYS | A | 212 | 22.894 | 28.644 | 14.293 | 1.00 | 46.62 |
| 562 | CB | LYS | A | 212 | 23.152 | 29.515 | 15.529 | 1.00 | 47.37 |
| 563 | CG | LYS | A | 212 | 24.607 | 29.935 | 15.815 | 1.00 | 50.28 |
| 564 | CD | LYS | A | 212 | 25.444 | 30.302 | 14.578 | 1.00 | 53.94 |
| 565 | CE | LYS | A | 212 | 25.106 | 31.692 | 14.012 | 1.00 | 57.34 |
| 566 | NZ | LYS | A | 212 | 23.636 | 32.041 | 14.065 | 1.00 | 58.81 |
| 567 | C | LYS | A | 212 | 23.531 | 27.258 | 14.480 | 1.00 | 46.79 |
| 568 | O | LYS | A | 212 | 24.632 | 27.011 | 13.956 | 1.00 | 46.55 |
| 569 | N | TYR | A | 213 | 22.887 | 26.365 | 15.238 | 1.00 | 47.23 |
| 570 | CA | TYR | A | 213 | 23.402 | 24.977 | 15.361 | 1.00 | 48.03 |
| 571 | CB | TYR | A | 213 | 24.162 | 24.720 | 16.654 | 1.00 | 47.89 |
| 572 | CG | TYR | A | 213 | 25.125 | 25.756 | 17.079 | 1.00 | 48.90 |
| 573 | CD1 | TYR | A | 213 | 26.329 | 25.916 | 16.414 | 1.00 | 52.56 |
| 574 | CE1 | TYR | A | 213 | 27.243 | 26.868 | 16.818 | 1.00 | 54.08 |
| 575 | CZ | TYR | A | 213 | 26.949 | 27.670 | 17.904 | 1.00 | 53.47 |
| 576 | OH | TYR | A | 213 | 27.860 | 28.616 | 18.314 | 1.00 | 57.01 |
| 577 | CE2 | TYR | A | 213 | 25.760 | 27.520 | 18.578 | 1.00 | 51.26 |
| 578 | CD2 | TYR | A | 213 | 24.867 | 26.554 | 18.172 | 1.00 | 49.26 |
| 579 | C | TYR | A | 213 | 22.286 | 23.980 | 15.372 | 1.00 | 48.30 |
| 580 | O | TYR | A | 213 | 21.134 | 24.294 | 15.722 | 1.00 | 47.58 |
| 581 | N | SER | A | 214 | 22.640 | 22.764 | 15.009 | 1.00 | 48.56 |
| 582 | CA | SER | A | 214 | 21.778 | 21.628 | 15.237 | 1.00 | 50.22 |
| 583 | CB | SER | A | 214 | 21.076 | 21.197 | 13.967 | 1.00 | 50.27 |
| 584 | OG | SER | A | 214 | 22.037 | 20.811 | 13.008 | 1.00 | 50.34 |
| 585 | C | SER | A | 214 | 22.612 | 20.474 | 15.800 | 1.00 | 51.57 |
| 586 | O | SER | A | 214 | 23.832 | 20.371 | 15.579 | 1.00 | 51.04 |
| 587 | N | PHE | A | 215 | 21.939 | 19.640 | 16.570 | 1.00 | 53.13 |
| 588 | CA | PHE | A | 215 | 22.547 | 18.467 | 17.179 | 1.00 | 54.67 |
| 589 | CB | PHE | A | 215 | 23.616 | 18.804 | 18.257 | 1.00 | 54.82 |
| 590 | CG | PHE | A | 215 | 23.114 | 19.649 | 19.408 | 1.00 | 55.41 |
| 591 | CD1 | PHE | A | 215 | 22.513 | 19.057 | 20.517 | 1.00 | 55.27 |
| 592 | CE1 | PHE | A | 215 | 22.075 | 19.837 | 21.580 | 1.00 | 55.27 |
| 593 | CZ | PHE | A | 215 | 22.249 | 21.212 | 21.546 | 1.00 | 54.04 |
| 594 | CE2 | PHE | A | 215 | 22.871 | 21.797 | 20.464 | 1.00 | 54.08 |
| 595 | CD2 | PHE | A | 215 | 23.305 | 21.029 | 19.413 | 1.00 | 53.23 |
| 596 | C | PHE | A | 215 | 21.434 | 17.627 | 17.740 | 1.00 | 55.60 |
| 597 | O | PHE | A | 215 | 20.272 | 18.016 | 17.730 | 1.00 | 55.25 |
| 598 | N | GLN | A | 216 | 21.788 | 16.439 | 18.182 | 1.00 | 57.28 |
| 599 | CA | GLN | A | 216 | 20.787 | 15.507 | 18.663 | 1.00 | 58.66 |
| 600 | CB | GLN | A | 216 | 20.376 | 14.561 | 17.534 | 1.00 | 58.90 |
| 601 | CG | GLN | A | 216 | 21.510 | 14.235 | 16.562 | 1.00 | 58.23 |
| 602 | CD | GLN | A | 216 | 21.161 | 13.117 | 15.614 | 1.00 | 58.73 |
| 603 | OE1 | GLN | A | 216 | 20.857 | 11.996 | 16.048 | 1.00 | 60.23 |

FIGURE 3 (Cont.)

| A | B | C | D | E | F | G | H | I | J |
|---|---|---|---|---|---|---|---|---|---|
| 604 | NE2 | GLN | A | 216 | 21.201 | 13.406 | 14.319 | 1.00 | 57.86 |
| 605 | C | GLN | A | 216 | 21.345 | 14.739 | 19.855 | 1.00 | 60.00 |
| 606 | O | GLN | A | 216 | 22.569 | 14.625 | 20.005 | 1.00 | 59.68 |
| 607 | N | THR | A | 217 | 20.435 | 14.308 | 20.732 | 1.00 | 61.80 |
| 608 | CA | THR | A | 217 | 20.679 | 13.233 | 21.687 | 1.00 | 63.47 |
| 609 | CB | THR | A | 217 | 20.107 | 13.588 | 23.101 | 1.00 | 63.97 |
| 610 | OG1 | THR | A | 217 | 18.687 | 13.831 | 23.048 | 1.00 | 64.68 |
| 611 | CG2 | THR | A | 217 | 20.720 | 14.920 | 23.635 | 1.00 | 64.41 |
| 612 | C | THR | A | 217 | 20.025 | 11.980 | 21.077 | 1.00 | 64.19 |
| 613 | O | THR | A | 217 | 19.496 | 12.053 | 19.965 | 1.00 | 64.41 |
| 614 | N | LYS | A | 218 | 20.068 | 10.840 | 21.762 | 1.00 | 64.94 |
| 615 | CA | LYS | A | 218 | 19.474 | 9.626 | 21.183 | 1.00 | 65.75 |
| 616 | CB | LYS | A | 218 | 19.843 | 8.355 | 21.974 | 1.00 | 66.06 |
| 617 | CG | LYS | A | 218 | 21.167 | 7.680 | 21.512 | 1.00 | 67.24 |
| 618 | CD | LYS | A | 218 | 21.022 | 6.833 | 20.217 | 1.00 | 68.75 |
| 619 | CE | LYS | A | 218 | 22.388 | 6.565 | 19.546 | 1.00 | 69.61 |
| 620 | NZ | LYS | A | 218 | 22.331 | 5.701 | 18.291 | 1.00 | 70.98 |
| 621 | C | LYS | A | 218 | 17.947 | 9.757 | 21.012 | 1.00 | 65.76 |
| 622 | O | LYS | A | 218 | 17.380 | 9.161 | 20.092 | 1.00 | 65.95 |
| 623 | N | ASP | A | 219 | 17.297 | 10.559 | 21.861 | 1.00 | 65.43 |
| 624 | CA | ASP | A | 219 | 15.833 | 10.683 | 21.837 | 1.00 | 65.23 |
| 625 | CB | ASP | A | 219 | 15.234 | 10.337 | 23.223 | 1.00 | 65.71 |
| 626 | CG | ASP | A | 219 | 15.099 | 8.810 | 23.457 | 1.00 | 67.31 |
| 627 | OD1 | ASP | A | 219 | 15.293 | 8.027 | 22.485 | 1.00 | 68.83 |
| 628 | OD2 | ASP | A | 219 | 14.808 | 8.304 | 24.580 | 1.00 | 67.69 |
| 629 | C | ASP | A | 219 | 15.280 | 12.032 | 21.329 | 1.00 | 64.15 |
| 630 | O | ASP | A | 219 | 14.076 | 12.116 | 21.100 | 1.00 | 64.62 |
| 631 | N | ARG | A | 220 | 16.133 | 13.048 | 21.118 | 1.00 | 62.48 |
| 632 | CA | ARG | A | 220 | 15.684 | 14.400 | 20.705 | 1.00 | 61.27 |
| 633 | CB | ARG | A | 220 | 15.540 | 15.301 | 21.943 | 1.00 | 61.68 |
| 634 | CG | ARG | A | 220 | 14.266 | 15.031 | 22.813 | 1.00 | 64.11 |
| 635 | CD | ARG | A | 220 | 14.529 | 14.630 | 24.284 | 1.00 | 67.95 |
| 636 | NE | ARG | A | 220 | 15.367 | 15.607 | 24.999 | 1.00 | 70.51 |
| 637 | CZ | ARG | A | 220 | 15.845 | 15.458 | 26.237 | 1.00 | 71.81 |
| 638 | NH1 | ARG | A | 220 | 15.587 | 14.357 | 26.948 | 1.00 | 71.25 |
| 639 | NH2 | ARG | A | 220 | 16.595 | 16.430 | 26.762 | 1.00 | 72.94 |
| 640 | C | ARG | A | 220 | 16.614 | 15.072 | 19.663 | 1.00 | 59.27 |
| 641 | O | ARG | A | 220 | 17.810 | 14.762 | 19.602 | 1.00 | 58.52 |
| 642 | N | LEU | A | 221 | 16.043 | 15.944 | 18.819 | 1.00 | 56.93 |
| 643 | CA | LEU | A | 221 | 16.817 | 16.881 | 17.968 | 1.00 | 55.42 |
| 644 | CB | LEU | A | 221 | 16.563 | 16.679 | 16.460 | 1.00 | 55.83 |
| 645 | CG | LEU | A | 221 | 15.244 | 16.169 | 15.875 | 1.00 | 57.46 |
| 646 | CD1 | LEU | A | 221 | 15.098 | 16.649 | 14.438 | 1.00 | 59.01 |
| 647 | CD2 | LEU | A | 221 | 15.177 | 14.661 | 15.909 | 1.00 | 57.56 |
| 648 | C | LEU | A | 221 | 16.638 | 18.386 | 18.314 | 1.00 | 53.50 |
| 649 | O | LEU | A | 221 | 15.529 | 18.902 | 18.501 | 1.00 | 52.01 |
| 650 | N | CYS | A | 222 | 17.776 | 19.074 | 18.330 | 1.00 | 51.12 |
| 651 | CA | CYS | A | 222 | 17.895 | 20.377 | 18.924 | 1.00 | 49.13 |
| 652 | CB | CYS | A | 222 | 18.952 | 20.372 | 20.030 | 1.00 | 49.43 |
| 653 | SG | CYS | A | 222 | 18.608 | 19.254 | 21.413 | 1.00 | 50.32 |
| 654 | C | CYS | A | 222 | 18.318 | 21.333 | 17.852 | 1.00 | 47.20 |

FIGURE 3 (Cont.)

| A | B | C | D | E | F | G | H | I | J |
|---|---|---|---|---|---|---|---|---|---|
| 655 | O | CYS | A | 222 | 19.293 | 21.075 | 17.149 | 1.00 | 44.42 |
| 656 | N | PHE | A | 223 | 17.576 | 22.442 | 17.767 | 1.00 | 45.39 |
| 657 | CA | PHE | A | 223 | 17.815 | 23.515 | 16.805 | 1.00 | 44.50 |
| 658 | CB | PHE | A | 223 | 16.636 | 23.619 | 15.858 | 1.00 | 45.03 |
| 659 | CG | PHE | A | 223 | 16.432 | 22.383 | 15.064 | 1.00 | 47.88 |
| 660 | CD1 | PHE | A | 223 | 17.359 | 22.020 | 14.097 | 1.00 | 50.66 |
| 661 | CE1 | PHE | A | 223 | 17.205 | 20.847 | 13.359 | 1.00 | 53.05 |
| 662 | CZ | PHE | A | 223 | 16.138 | 20.013 | 13.616 | 1.00 | 53.63 |
| 663 | CE2 | PHE | A | 223 | 15.222 | 20.351 | 14.604 | 1.00 | 53.95 |
| 664 | CD2 | PHE | A | 223 | 15.375 | 21.538 | 15.326 | 1.00 | 51.51 |
| 665 | C | PHE | A | 223 | 18.006 | 24.804 | 17.558 | 1.00 | 43.36 |
| 666 | O | PHE | A | 223 | 17.093 | 25.272 | 18.262 | 1.00 | 42.55 |
| 667 | N | VAL | A | 224 | 19.214 | 25.340 | 17.466 | 1.00 | 41.80 |
| 668 | CA | VAL | A | 224 | 19.565 | 26.553 | 18.170 | 1.00 | 41.33 |
| 669 | CB | VAL | A | 224 | 20.995 | 26.502 | 18.721 | 1.00 | 40.84 |
| 670 | CG1 | VAL | A | 224 | 21.333 | 27.760 | 19.455 | 1.00 | 41.30 |
| 671 | CG2 | VAL | A | 224 | 21.157 | 25.298 | 19.676 | 1.00 | 43.05 |
| 672 | C | VAL | A | 224 | 19.382 | 27.685 | 17.168 | 1.00 | 41.39 |
| 673 | O | VAL | A | 224 | 20.214 | 27.867 | 16.244 | 1.00 | 39.55 |
| 674 | N | MET | A | 225 | 18.262 | 28.390 | 17.337 | 1.00 | 40.30 |
| 675 | CA | MET | A | 225 | 17.870 | 29.560 | 16.526 | 1.00 | 41.41 |
| 676 | CB | MET | A | 225 | 16.400 | 29.442 | 16.148 | 1.00 | 42.44 |
| 677 | CG | MET | A | 225 | 16.072 | 28.126 | 15.433 | 1.00 | 46.65 |
| 678 | SD | MET | A | 225 | 14.314 | 27.888 | 15.525 | 1.00 | 55.08 |
| 679 | CE | MET | A | 225 | 14.105 | 26.503 | 14.408 | 1.00 | 54.47 |
| 680 | C | MET | A | 225 | 18.029 | 30.901 | 17.267 | 1.00 | 39.37 |
| 681 | O | MET | A | 225 | 18.072 | 30.947 | 18.485 | 1.00 | 37.06 |
| 682 | N | GLU | A | 226 | 18.175 | 31.959 | 16.478 | 1.00 | 37.79 |
| 683 | CA | GLU | A | 226 | 18.120 | 33.350 | 16.901 | 1.00 | 37.01 |
| 684 | CB | GLU | A | 226 | 17.781 | 34.210 | 15.684 | 1.00 | 38.55 |
| 685 | CG | GLU | A | 226 | 18.739 | 35.329 | 15.379 | 1.00 | 40.61 |
| 686 | CD | GLU | A | 226 | 18.174 | 36.171 | 14.268 | 1.00 | 40.82 |
| 687 | OE1 | GLU | A | 226 | 17.800 | 35.618 | 13.196 | 1.00 | 36.47 |
| 688 | OE2 | GLU | A | 226 | 18.086 | 37.378 | 14.504 | 1.00 | 45.67 |
| 689 | C | GLU | A | 226 | 16.951 | 33.498 | 17.865 | 1.00 | 35.04 |
| 690 | O | GLU | A | 226 | 15.886 | 32.983 | 17.591 | 1.00 | 33.62 |
| 691 | N | TYR | A | 227 | 17.162 | 34.170 | 18.989 | 1.00 | 33.67 |
| 692 | CA | TYR | A | 227 | 16.082 | 34.440 | 19.946 | 1.00 | 32.81 |
| 693 | CB | TYR | A | 227 | 16.623 | 34.653 | 21.366 | 1.00 | 32.04 |
| 694 | CG | TYR | A | 227 | 15.597 | 35.036 | 22.370 | 1.00 | 30.69 |
| 695 | CD1 | TYR | A | 227 | 15.756 | 36.150 | 23.185 | 1.00 | 30.75 |
| 696 | CE1 | TYR | A | 227 | 14.801 | 36.487 | 24.134 | 1.00 | 32.02 |
| 697 | CZ | TYR | A | 227 | 13.690 | 35.691 | 24.263 | 1.00 | 33.74 |
| 698 | OH | TYR | A | 227 | 12.691 | 35.978 | 25.169 | 1.00 | 32.70 |
| 699 | CE2 | TYR | A | 227 | 13.539 | 34.595 | 23.471 | 1.00 | 34.29 |
| 700 | CD2 | TYR | A | 227 | 14.497 | 34.248 | 22.567 | 1.00 | 32.81 |
| 701 | C | TYR | A | 227 | 15.372 | 35.686 | 19.464 | 1.00 | 32.46 |
| 702 | O | TYR | A | 227 | 15.970 | 36.723 | 19.321 | 1.00 | 31.78 |
| 703 | N | VAL | A | 228 | 14.087 | 35.590 | 19.186 | 1.00 | 33.17 |
| 704 | CA | VAL | A | 228 | 13.374 | 36.811 | 18.809 | 1.00 | 32.87 |
| 705 | CB | VAL | A | 228 | 12.986 | 36.919 | 17.266 | 1.00 | 33.29 |

FIGURE 3 (Cont.)

| A | B | C | D | E | F | G | H | I | J |
|---|---|---|---|---|---|---|---|---|---|
| 706 | CG1 | VAL | A | 228 | 13.669 | 35.838 | 16.426 | 1.00 | 35.88 |
| 707 | CG2 | VAL | A | 228 | 11.506 | 36.940 | 16.989 | 1.00 | 35.76 |
| 708 | C | VAL | A | 228 | 12.275 | 37.007 | 19.797 | 1.00 | 31.21 |
| 709 | O | VAL | A | 228 | 11.526 | 36.109 | 20.087 | 1.00 | 30.95 |
| 710 | N | ASN | A | 229 | 12.197 | 38.260 | 20.206 | 1.00 | 31.18 |
| 711 | CA | ASN | A | 229 | 11.619 | 38.778 | 21.437 | 1.00 | 31.49 |
| 712 | CB | ASN | A | 229 | 12.659 | 39.841 | 22.000 | 1.00 | 31.60 |
| 713 | CG | ASN | A | 229 | 12.758 | 39.673 | 23.320 | 1.00 | 34.15 |
| 714 | OD1 | ASN | A | 229 | 13.287 | 40.440 | 24.138 | 1.00 | 34.25 |
| 715 | ND2 | ASN | A | 229 | 12.166 | 38.561 | 23.650 | 1.00 | 39.75 |
| 716 | C | ASN | A | 229 | 10.319 | 39.588 | 21.402 | 1.00 | 29.79 |
| 717 | O | ASN | A | 229 | 9.742 | 39.931 | 22.463 | 1.00 | 28.73 |
| 718 | N | GLY | A | 230 | 9.947 | 39.999 | 20.215 | 1.00 | 27.85 |
| 719 | CA | GLY | A | 230 | 8.957 | 41.048 | 20.012 | 1.00 | 27.97 |
| 720 | C | GLY | A | 230 | 7.540 | 40.516 | 19.883 | 1.00 | 28.22 |
| 721 | O | GLY | A | 230 | 6.627 | 41.273 | 19.642 | 1.00 | 28.49 |
| 722 | N | GLY | A | 231 | 7.358 | 39.211 | 20.077 | 1.00 | 28.46 |
| 723 | CA | GLY | A | 231 | 6.059 | 38.579 | 19.989 | 1.00 | 28.31 |
| 724 | C | GLY | A | 231 | 5.626 | 38.138 | 18.588 | 1.00 | 29.49 |
| 725 | O | GLY | A | 231 | 6.081 | 38.657 | 17.554 | 1.00 | 28.94 |
| 726 | N | GLU | A | 232 | 4.697 | 37.190 | 18.585 | 1.00 | 30.77 |
| 727 | CA | GLU | A | 232 | 4.030 | 36.677 | 17.409 | 1.00 | 32.46 |
| 728 | CB | GLU | A | 232 | 3.170 | 35.478 | 17.843 | 1.00 | 33.46 |
| 729 | CG | GLU | A | 232 | 3.979 | 34.259 | 18.210 | 1.00 | 39.48 |
| 730 | CD | GLU | A | 232 | 3.364 | 32.968 | 17.706 | 1.00 | 47.07 |
| 731 | OE1 | GLU | A | 232 | 2.967 | 32.923 | 16.521 | 1.00 | 52.17 |
| 732 | OE2 | GLU | A | 232 | 3.280 | 31.997 | 18.500 | 1.00 | 51.49 |
| 733 | C | GLU | A | 232 | 3.102 | 37.718 | 16.765 | 1.00 | 32.02 |
| 734 | O | GLU | A | 232 | 2.328 | 38.363 | 17.479 | 1.00 | 31.77 |
| 735 | N | LEU | A | 233 | 3.150 | 37.860 | 15.442 | 1.00 | 30.95 |
| 736 | CA | LEU | A | 233 | 2.201 | 38.746 | 14.757 | 1.00 | 31.67 |
| 737 | CB | LEU | A | 233 | 2.511 | 38.963 | 13.277 | 1.00 | 30.88 |
| 738 | CG | LEU | A | 233 | 3.348 | 40.221 | 12.994 | 1.00 | 31.40 |
| 739 | CD1 | LEU | A | 233 | 3.339 | 40.482 | 11.507 | 1.00 | 32.54 |
| 740 | CD2 | LEU | A | 233 | 2.915 | 41.510 | 13.752 | 1.00 | 28.72 |
| 741 | C | LEU | A | 233 | 0.787 | 38.296 | 14.891 | 1.00 | 32.09 |
| 742 | O | LEU | A | 233 | -0.094 | 39.138 | 14.949 | 1.00 | 32.59 |
| 743 | N | PHE | A | 234 | 0.565 | 36.994 | 14.962 | 1.00 | 32.97 |
| 744 | CA | PHE | A | 234 | -0.754 | 36.442 | 15.266 | 1.00 | 34.67 |
| 745 | CB | PHE | A | 234 | -0.687 | 34.905 | 15.316 | 1.00 | 35.89 |
| 746 | CG | PHE | A | 234 | -2.037 | 34.239 | 15.506 | 1.00 | 38.80 |
| 747 | CD1 | PHE | A | 234 | -2.609 | 34.157 | 16.763 | 1.00 | 43.32 |
| 748 | CE1 | PHE | A | 234 | -3.857 | 33.555 | 16.933 | 1.00 | 46.08 |
| 749 | CZ | PHE | A | 234 | -4.534 | 33.038 | 15.838 | 1.00 | 44.87 |
| 750 | CE2 | PHE | A | 234 | -3.969 | 33.117 | 14.585 | 1.00 | 43.73 |
| 751 | CD2 | PHE | A | 234 | -2.727 | 33.712 | 14.430 | 1.00 | 42.80 |
| 752 | C | PHE | A | 234 | -1.298 | 37.060 | 16.563 | 1.00 | 35.22 |
| 753 | O | PHE | A | 234 | -2.391 | 37.571 | 16.608 | 1.00 | 35.26 |
| 754 | N | PHE | A | 235 | -0.499 | 37.091 | 17.615 | 1.00 | 37.17 |
| 755 | CA | PHE | A | 235 | -0.988 | 37.713 | 18.826 | 1.00 | 37.36 |
| 756 | CB | PHE | A | 235 | -0.230 | 37.214 | 20.064 | 1.00 | 38.98 |

FIGURE 3 (Cont.)

| A | B | C | D | E | F | G | H | I | J |
|---|---|---|---|---|---|---|---|---|---|
| 757 | CG | PHE | A | 235 | -0.517 | 35.745 | 20.365 | 1.00 | 44.21 |
| 758 | CD1 | PHE | A | 235 | -1.849 | 35.288 | 20.462 | 1.00 | 50.14 |
| 759 | CE1 | PHE | A | 235 | -2.140 | 33.916 | 20.711 | 1.00 | 51.53 |
| 760 | CZ | PHE | A | 235 | -1.091 | 33.003 | 20.834 | 1.00 | 52.21 |
| 761 | CE2 | PHE | A | 235 | 0.249 | 33.454 | 20.696 | 1.00 | 52.42 |
| 762 | CD2 | PHE | A | 235 | 0.520 | 34.812 | 20.476 | 1.00 | 48.68 |
| 763 | C | PHE | A | 235 | -1.130 | 39.208 | 18.714 | 1.00 | 35.98 |
| 764 | O | PHE | A | 235 | -2.167 | 39.745 | 19.110 | 1.00 | 35.57 |
| 765 | N | HIS | A | 236 | -0.177 | 39.901 | 18.098 | 1.00 | 33.54 |
| 766 | CA | HIS | A | 236 | -0.399 | 41.307 | 17.850 | 1.00 | 32.94 |
| 767 | CB | HIS | A | 236 | 0.821 | 41.949 | 17.205 | 1.00 | 31.69 |
| 768 | CG | HIS | A | 236 | 2.005 | 41.984 | 18.098 | 1.00 | 32.03 |
| 769 | ND1 | HIS | A | 236 | 3.122 | 41.209 | 17.886 | 1.00 | 36.25 |
| 770 | CE1 | HIS | A | 236 | 4.020 | 41.469 | 18.814 | 1.00 | 34.68 |
| 771 | NE2 | HIS | A | 236 | 3.521 | 42.377 | 19.631 | 1.00 | 37.30 |
| 772 | CD2 | HIS | A | 236 | 2.262 | 42.718 | 19.199 | 1.00 | 31.95 |
| 773 | C | HIS | A | 236 | -1.662 | 41.659 | 17.037 | 1.00 | 33.20 |
| 774 | O | HIS | A | 236 | -2.310 | 42.653 | 17.319 | 1.00 | 32.96 |
| 775 | N | LEU | A | 237 | -1.966 | 40.895 | 15.999 | 1.00 | 33.76 |
| 776 | CA | LEU | A | 237 | -3.151 | 41.148 | 15.193 | 1.00 | 35.25 |
| 777 | CB | LEU | A | 237 | -3.059 | 40.392 | 13.866 | 1.00 | 34.72 |
| 778 | CG | LEU | A | 237 | -4.114 | 40.588 | 12.792 | 1.00 | 35.21 |
| 779 | CD1 | LEU | A | 237 | -4.107 | 42.012 | 12.307 | 1.00 | 34.74 |
| 780 | CD2 | LEU | A | 237 | -3.849 | 39.653 | 11.660 | 1.00 | 35.26 |
| 781 | C | LEU | A | 237 | -4.451 | 40.778 | 15.976 | 1.00 | 37.03 |
| 782 | O | LEU | A | 237 | -5.455 | 41.472 | 15.875 | 1.00 | 35.08 |
| 783 | N | SER | A | 238 | -4.418 | 39.686 | 16.743 | 1.00 | 39.15 |
| 784 | CA | SER | A | 238 | -5.562 | 39.315 | 17.600 | 1.00 | 40.93 |
| 785 | CB | SER | A | 238 | -5.186 | 38.189 | 18.549 | 1.00 | 41.23 |
| 786 | OG | SER | A | 238 | -4.834 | 37.060 | 17.790 | 1.00 | 44.46 |
| 787 | C | SER | A | 238 | -6.010 | 40.484 | 18.438 | 1.00 | 41.92 |
| 788 | O | SER | A | 238 | -7.182 | 40.886 | 18.365 | 1.00 | 42.51 |
| 789 | N | ARG | A | 239 | -5.061 | 41.079 | 19.165 | 1.00 | 42.33 |
| 790 | CA | ARG | A | 239 | -5.345 | 42.205 | 20.061 | 1.00 | 42.82 |
| 791 | CB | ARG | A | 239 | -4.169 | 42.466 | 20.997 | 1.00 | 43.79 |
| 792 | CG | ARG | A | 239 | -3.698 | 41.211 | 21.797 | 1.00 | 46.59 |
| 793 | CD | ARG | A | 239 | -2.426 | 41.428 | 22.647 | 1.00 | 51.59 |
| 794 | NE | ARG | A | 239 | -1.679 | 42.602 | 22.172 | 1.00 | 55.88 |
| 795 | CZ | ARG | A | 239 | -0.390 | 42.621 | 21.784 | 1.00 | 56.40 |
| 796 | NH1 | ARG | A | 239 | 0.114 | 43.767 | 21.325 | 1.00 | 53.22 |
| 797 | NH2 | ARG | A | 239 | 0.389 | 41.523 | 21.867 | 1.00 | 59.60 |
| 798 | C | ARG | A | 239 | -5.730 | 43.488 | 19.339 | 1.00 | 42.41 |
| 799 | O | ARG | A | 239 | -6.567 | 44.243 | 19.832 | 1.00 | 43.11 |
| 800 | N | GLU | A | 240 | -5.150 | 43.743 | 18.171 | 1.00 | 40.74 |
| 801 | CA | GLU | A | 240 | -5.375 | 44.994 | 17.469 | 1.00 | 39.44 |
| 802 | CB | GLU | A | 240 | -4.143 | 45.389 | 16.671 | 1.00 | 40.40 |
| 803 | CG | GLU | A | 240 | -2.938 | 45.666 | 17.541 | 1.00 | 44.80 |
| 804 | CD | GLU | A | 240 | -2.625 | 47.145 | 17.687 | 1.00 | 50.66 |
| 805 | OE1 | GLU | A | 240 | -1.438 | 47.427 | 18.000 | 1.00 | 53.92 |
| 806 | OE2 | GLU | A | 240 | -3.545 | 48.015 | 17.517 | 1.00 | 52.84 |
| 807 | C | GLU | A | 240 | -6.523 | 44.896 | 16.502 | 1.00 | 37.57 |

FIGURE 3 (Cont.)

| A | B | C | D | E | F | G | H | I | J |
|---|---|---|---|---|---|---|---|---|---|
| 808 | O | GLU | A | 240 | -7.019 | 45.925 | 16.048 | 1.00 | 37.06 |
| 809 | N | ARG | A | 241 | -6.901 | 43.656 | 16.181 | 1.00 | 35.42 |
| 810 | CA | ARG | A | 241 | -7.916 | 43.283 | 15.190 | 1.00 | 34.60 |
| 811 | CB | ARG | A | 241 | -9.282 | 43.944 | 15.501 | 1.00 | 35.77 |
| 812 | CG | ARG | A | 241 | -9.538 | 44.023 | 17.032 | 1.00 | 40.66 |
| 813 | CD | ARG | A | 241 | -10.911 | 43.557 | 17.486 | 1.00 | 49.26 |
| 814 | NE | ARG | A | 241 | -11.999 | 44.155 | 16.700 | 1.00 | 54.30 |
| 815 | CZ | ARG | A | 241 | -13.274 | 43.768 | 16.751 | 1.00 | 58.21 |
| 816 | NH1 | ARG | A | 241 | -14.177 | 44.384 | 15.984 | 1.00 | 60.74 |
| 817 | NH2 | ARG | A | 241 | -13.657 | 42.775 | 17.557 | 1.00 | 58.62 |
| 818 | C | ARG | A | 241 | -7.464 | 43.501 | 13.755 | 1.00 | 32.45 |
| 819 | O | ARG | A | 241 | -7.639 | 42.634 | 12.940 | 1.00 | 32.84 |
| 820 | N | VAL | A | 242 | -6.824 | 44.625 | 13.454 | 1.00 | 30.95 |
| 821 | CA | VAL | A | 242 | -6.507 | 45.014 | 12.099 | 1.00 | 30.79 |
| 822 | CB | VAL | A | 242 | -7.730 | 45.678 | 11.411 | 1.00 | 31.41 |
| 823 | CG1 | VAL | A | 242 | -8.181 | 46.917 | 12.142 | 1.00 | 32.42 |
| 824 | CG2 | VAL | A | 242 | -7.483 | 46.010 | 10.040 | 1.00 | 33.11 |
| 825 | C | VAL | A | 242 | -5.297 | 45.925 | 12.204 | 1.00 | 30.06 |
| 826 | O | VAL | A | 242 | -5.158 | 46.640 | 13.180 | 1.00 | 29.32 |
| 827 | N | PHE | A | 243 | -4.352 | 45.805 | 11.263 | 1.00 | 27.62 |
| 828 | CA | PHE | A | 243 | -3.250 | 46.752 | 11.213 | 1.00 | 26.16 |
| 829 | CB | PHE | A | 243 | -1.942 | 46.080 | 10.855 | 1.00 | 24.79 |
| 830 | CG | PHE | A | 243 | -1.429 | 45.064 | 11.864 | 1.00 | 26.39 |
| 831 | CD1 | PHE | A | 243 | -0.595 | 44.065 | 11.439 | 1.00 | 23.32 |
| 832 | CE1 | PHE | A | 243 | -0.082 | 43.174 | 12.276 | 1.00 | 23.98 |
| 833 | CZ | PHE | A | 243 | -0.325 | 43.278 | 13.596 | 1.00 | 23.20 |
| 834 | CE2 | PHE | A | 243 | -1.148 | 44.236 | 14.040 | 1.00 | 22.24 |
| 835 | CD2 | PHE | A | 243 | -1.661 | 45.159 | 13.215 | 1.00 | 24.14 |
| 836 | C | PHE | A | 243 | -3.620 | 47.771 | 10.146 | 1.00 | 25.43 |
| 837 | O | PHE | A | 243 | -4.417 | 47.470 | 9.211 | 1.00 | 25.04 |
| 838 | N | SER | A | 244 | -3.097 | 49.001 | 10.287 | 1.00 | 25.12 |
| 839 | CA | SER | A | 244 | -3.259 | 50.016 | 9.254 | 1.00 | 22.85 |
| 840 | CB | SER | A | 244 | -2.590 | 51.333 | 9.653 | 1.00 | 22.93 |
| 841 | OG | SER | A | 244 | -1.188 | 51.178 | 9.638 | 1.00 | 23.17 |
| 842 | C | SER | A | 244 | -2.551 | 49.505 | 7.967 | 1.00 | 22.52 |
| 843 | O | SER | A | 244 | -1.648 | 48.645 | 8.021 | 1.00 | 21.62 |
| 844 | N | GLU | A | 245 | -2.946 | 50.071 | 6.845 | 1.00 | 21.72 |
| 845 | CA | GLU | A | 245 | -2.316 | 49.768 | 5.576 | 1.00 | 22.32 |
| 846 | CB | GLU | A | 245 | -2.893 | 50.546 | 4.430 | 1.00 | 21.61 |
| 847 | CG | GLU | A | 245 | -4.368 | 50.222 | 4.218 | 1.00 | 23.45 |
| 848 | CD | GLU | A | 245 | -4.831 | 50.628 | 2.846 | 1.00 | 23.93 |
| 849 | OE1 | GLU | A | 245 | -6.025 | 50.832 | 2.694 | 1.00 | 28.22 |
| 850 | OE2 | GLU | A | 245 | -3.991 | 50.824 | 1.919 | 1.00 | 28.46 |
| 851 | C | GLU | A | 245 | -0.806 | 50.023 | 5.647 | 1.00 | 22.17 |
| 852 | O | GLU | A | 245 | -0.046 | 49.207 | 5.100 | 1.00 | 19.46 |
| 853 | N | ASP | A | 246 | -0.399 | 51.079 | 6.333 | 1.00 | 20.83 |
| 854 | CA | ASP | A | 246 | 1.033 | 51.418 | 6.351 | 1.00 | 23.13 |
| 855 | CB | ASP | A | 246 | 1.333 | 52.866 | 6.714 | 1.00 | 23.29 |
| 856 | CG | ASP | A | 246 | 2.779 | 53.230 | 6.342 | 1.00 | 26.73 |
| 857 | OD1 | ASP | A | 246 | 3.146 | 53.104 | 5.135 | 1.00 | 27.69 |
| 858 | OD2 | ASP | A | 246 | 3.625 | 53.616 | 7.180 | 1.00 | 31.09 |

FIGURE 3 (Cont.)

| A | B | C | D | E | F | G | H | I | J |
|---|---|---|---|---|---|---|---|---|---|
| 859 | C | ASP | A | 246 | 1.874 | 50.463 | 7.197 | 1.00 | 22.65 |
| 860 | O | ASP | A | 246 | 2.984 | 50.064 | 6.826 | 1.00 | 21.09 |
| 861 | N | ARG | A | 247 | 1.301 | 50.032 | 8.294 | 1.00 | 22.78 |
| 862 | CA | ARG | A | 247 | 1.939 | 49.013 | 9.094 | 1.00 | 22.68 |
| 863 | CB | ARG | A | 247 | 1.178 | 48.864 | 10.416 | 1.00 | 22.58 |
| 864 | CG | ARG | A | 247 | 1.647 | 47.785 | 11.286 | 1.00 | 25.96 |
| 865 | CD | ARG | A | 247 | 1.302 | 48.014 | 12.735 | 1.00 | 32.03 |
| 866 | NE | ARG | A | 247 | 1.813 | 46.920 | 13.546 | 1.00 | 29.53 |
| 867 | CZ | ARG | A | 247 | 1.346 | 46.612 | 14.755 | 1.00 | 31.25 |
| 868 | NH1 | ARG | A | 247 | 0.403 | 47.352 | 15.322 | 1.00 | 29.54 |
| 869 | NH2 | ARG | A | 247 | 1.868 | 45.597 | 15.433 | 1.00 | 30.76 |
| 870 | C | ARG | A | 247 | 2.015 | 47.696 | 8.347 | 1.00 | 22.31 |
| 871 | O | ARG | A | 247 | 3.048 | 47.012 | 8.416 | 1.00 | 18.57 |
| 872 | N | THR | A | 248 | 0.938 | 47.349 | 7.627 | 1.00 | 21.73 |
| 873 | CA | THR | A | 248 | 0.954 | 46.144 | 6.807 | 1.00 | 22.28 |
| 874 | CB | THR | A | 248 | -0.385 | 45.849 | 6.196 | 1.00 | 23.04 |
| 875 | OG1 | THR | A | 248 | -1.371 | 45.698 | 7.224 | 1.00 | 21.20 |
| 876 | CG2 | THR | A | 248 | -0.363 | 44.532 | 5.484 | 1.00 | 23.28 |
| 877 | C | THR | A | 248 | 2.000 | 46.235 | 5.701 | 1.00 | 21.54 |
| 878 | O | THR | A | 248 | 2.757 | 45.284 | 5.441 | 1.00 | 19.91 |
| 879 | N | ARG | A | 249 | 2.011 | 47.374 | 5.048 | 1.00 | 21.79 |
| 880 | CA | ARG | A | 249 | 3.042 | 47.717 | 4.079 | 1.00 | 22.13 |
| 881 | CB | ARG | A | 249 | 2.926 | 49.148 | 3.650 | 1.00 | 22.36 |
| 882 | CG | ARG | A | 249 | 4.086 | 49.642 | 2.725 | 1.00 | 22.21 |
| 883 | CD | ARG | A | 249 | 3.929 | 51.028 | 2.297 | 1.00 | 24.82 |
| 884 | NE | ARG | A | 249 | 2.723 | 51.190 | 1.471 | 1.00 | 26.63 |
| 885 | CZ | ARG | A | 249 | 1.635 | 51.848 | 1.799 | 1.00 | 22.82 |
| 886 | NH1 | ARG | A | 249 | 1.498 | 52.466 | 2.966 | 1.00 | 22.73 |
| 887 | NH2 | ARG | A | 249 | 0.681 | 51.916 | 0.908 | 1.00 | 24.89 |
| 888 | C | ARG | A | 249 | 4.456 | 47.516 | 4.602 | 1.00 | 21.40 |
| 889 | O | ARG | A | 249 | 5.321 | 47.028 | 3.900 | 1.00 | 20.28 |
| 890 | N | PHE | A | 250 | 4.672 | 47.898 | 5.831 | 1.00 | 21.38 |
| 891 | CA | PHE | A | 250 | 5.977 | 47.753 | 6.444 | 1.00 | 21.64 |
| 892 | CB | PHE | A | 250 | 6.033 | 48.508 | 7.783 | 1.00 | 22.55 |
| 893 | CG | PHE | A | 250 | 7.215 | 48.127 | 8.639 | 1.00 | 21.61 |
| 894 | CD1 | PHE | A | 250 | 8.396 | 48.853 | 8.559 | 1.00 | 25.73 |
| 895 | CE1 | PHE | A | 250 | 9.546 | 48.481 | 9.327 | 1.00 | 26.87 |
| 896 | CZ | PHE | A | 250 | 9.483 | 47.417 | 10.162 | 1.00 | 25.82 |
| 897 | CE2 | PHE | A | 250 | 8.231 | 46.662 | 10.279 | 1.00 | 26.31 |
| 898 | CD2 | PHE | A | 250 | 7.152 | 47.020 | 9.481 | 1.00 | 25.82 |
| 899 | C | PHE | A | 250 | 6.305 | 46.271 | 6.646 | 1.00 | 20.13 |
| 900 | O | PHE | A | 250 | 7.384 | 45.814 | 6.283 | 1.00 | 18.97 |
| 901 | N | TYR | A | 251 | 5.362 | 45.471 | 7.172 | 1.00 | 21.72 |
| 902 | CA | TYR | A | 251 | 5.657 | 44.047 | 7.344 | 1.00 | 21.46 |
| 903 | CB | TYR | A | 251 | 4.631 | 43.343 | 8.222 | 1.00 | 23.43 |
| 904 | CG | TYR | A | 251 | 4.535 | 43.895 | 9.618 | 1.00 | 23.56 |
| 905 | CD1 | TYR | A | 251 | 3.287 | 44.113 | 10.215 | 1.00 | 25.34 |
| 906 | CE1 | TYR | A | 251 | 3.206 | 44.620 | 11.536 | 1.00 | 24.06 |
| 907 | CZ | TYR | A | 251 | 4.368 | 44.925 | 12.196 | 1.00 | 25.14 |
| 908 | OH | TYR | A | 251 | 4.321 | 45.412 | 13.463 | 1.00 | 26.23 |
| 909 | CE2 | TYR | A | 251 | 5.610 | 44.705 | 11.598 | 1.00 | 24.32 |

FIGURE 3 (Cont.)

| A | B | C | D | E | F | G | H | I | J |
|---|---|---|---|---|---|---|---|---|---|
| 910 | CD2 | TYR | A | 251 | 5.675 | 44.203 | 10.348 | 1.00 | 24.40 |
| 911 | C | TYR | A | 251 | 5.766 | 43.389 | 6.018 | 1.00 | 19.73 |
| 912 | O | TYR | A | 251 | 6.639 | 42.546 | 5.781 | 1.00 | 20.27 |
| 913 | N | GLY | A | 252 | 4.864 | 43.725 | 5.131 | 1.00 | 19.43 |
| 914 | CA | GLY | A | 252 | 4.901 | 43.185 | 3.775 | 1.00 | 19.08 |
| 915 | C | GLY | A | 252 | 6.195 | 43.404 | 3.013 | 1.00 | 18.06 |
| 916 | O | GLY | A | 252 | 6.705 | 42.498 | 2.292 | 1.00 | 19.99 |
| 917 | N | ALA | A | 253 | 6.742 | 44.591 | 3.126 | 1.00 | 17.75 |
| 918 | CA | ALA | A | 253 | 7.993 | 44.889 | 2.439 | 1.00 | 16.77 |
| 919 | CB | ALA | A | 253 | 8.356 | 46.288 | 2.634 | 1.00 | 18.73 |
| 920 | C | ALA | A | 253 | 9.100 | 44.018 | 2.981 | 1.00 | 17.45 |
| 921 | O | ALA | A | 253 | 9.889 | 43.492 | 2.217 | 1.00 | 17.68 |
| 922 | N | GLU | A | 254 | 9.198 | 43.891 | 4.313 | 1.00 | 18.65 |
| 923 | CA | GLU | A | 254 | 10.226 | 43.063 | 4.918 | 1.00 | 19.23 |
| 924 | CB | GLU | A | 254 | 10.252 | 43.268 | 6.427 | 1.00 | 19.92 |
| 925 | CG | GLU | A | 254 | 10.505 | 44.668 | 6.798 | 1.00 | 18.63 |
| 926 | CD | GLU | A | 254 | 10.963 | 44.835 | 8.216 | 1.00 | 23.18 |
| 927 | OE1 | GLU | A | 254 | 10.469 | 44.076 | 9.069 | 1.00 | 20.45 |
| 928 | OE2 | GLU | A | 254 | 11.763 | 45.780 | 8.480 | 1.00 | 22.90 |
| 929 | C | GLU | A | 254 | 10.099 | 41.598 | 4.507 | 1.00 | 20.78 |
| 930 | O | GLU | A | 254 | 11.071 | 41.001 | 4.101 | 1.00 | 23.34 |
| 931 | N | ILE | A | 255 | 8.888 | 41.063 | 4.466 | 1.00 | 21.92 |
| 932 | CA | ILE | A | 255 | 8.634 | 39.725 | 3.975 | 1.00 | 20.76 |
| 933 | CB | ILE | A | 255 | 7.139 | 39.354 | 4.172 | 1.00 | 21.33 |
| 934 | CG1 | ILE | A | 255 | 6.745 | 39.360 | 5.662 | 1.00 | 22.43 |
| 935 | CD1 | ILE | A | 255 | 5.270 | 39.208 | 5.881 | 1.00 | 21.96 |
| 936 | CG2 | ILE | A | 255 | 6.812 | 37.998 | 3.520 | 1.00 | 23.09 |
| 937 | C | ILE | A | 255 | 9.007 | 39.618 | 2.495 | 1.00 | 21.60 |
| 938 | O | ILE | A | 255 | 9.621 | 38.628 | 2.074 | 1.00 | 21.03 |
| 939 | N | VAL | A | 256 | 8.592 | 40.585 | 1.692 | 1.00 | 21.12 |
| 940 | CA | VAL | A | 256 | 8.963 | 40.595 | 0.258 | 1.00 | 20.94 |
| 941 | CB | VAL | A | 256 | 8.417 | 41.817 | -0.437 | 1.00 | 21.78 |
| 942 | CG1 | VAL | A | 256 | 9.103 | 42.052 | -1.784 | 1.00 | 23.92 |
| 943 | CG2 | VAL | A | 256 | 6.884 | 41.686 | -0.652 | 1.00 | 20.75 |
| 944 | C | VAL | A | 256 | 10.485 | 40.520 | 0.098 | 1.00 | 21.95 |
| 945 | O | VAL | A | 256 | 10.995 | 39.768 | -0.714 | 1.00 | 20.00 |
| 946 | N | SER | A | 257 | 11.205 | 41.281 | 0.918 | 1.00 | 22.44 |
| 947 | CA | SER | A | 257 | 12.651 | 41.287 | 0.884 | 1.00 | 21.70 |
| 948 | CB | SER | A | 257 | 13.194 | 42.228 | 1.892 | 1.00 | 21.86 |
| 949 | OG | SER | A | 257 | 14.579 | 42.349 | 1.738 | 1.00 | 22.08 |
| 950 | C | SER | A | 257 | 13.231 | 39.907 | 1.134 | 1.00 | 21.79 |
| 951 | O | SER | A | 257 | 14.102 | 39.469 | 0.345 | 1.00 | 20.59 |
| 952 | N | ALA | A | 258 | 12.754 | 39.239 | 2.189 | 1.00 | 22.18 |
| 953 | CA | ALA | A | 258 | 13.166 | 37.864 | 2.481 | 1.00 | 23.73 |
| 954 | CB | ALA | A | 258 | 12.583 | 37.334 | 3.789 | 1.00 | 22.49 |
| 955 | C | ALA | A | 258 | 12.831 | 36.920 | 1.341 | 1.00 | 24.04 |
| 956 | O | ALA | A | 258 | 13.660 | 36.089 | 0.967 | 1.00 | 24.46 |
| 957 | N | LEU | A | 259 | 11.640 | 37.025 | 0.783 | 1.00 | 24.97 |
| 958 | CA | LEU | A | 259 | 11.250 | 36.068 | -0.253 | 1.00 | 25.73 |
| 959 | CB | LEU | A | 259 | 9.755 | 36.084 | -0.510 | 1.00 | 26.21 |
| 960 | CG | LEU | A | 259 | 8.848 | 35.670 | 0.635 | 1.00 | 25.77 |

FIGURE 3 (Cont.)

| A | B | C | D | E | F | G | H | I | J |
|---|---|---|---|---|---|---|---|---|---|
| 961 | CD1 | LEU | A | 259 | 7.473 | 36.038 | 0.291 | 1.00 | 25.09 |
| 962 | CD2 | LEU | A | 259 | 8.920 | 34.251 | 0.840 | 1.00 | 28.71 |
| 963 | C | LEU | A | 259 | 12.025 | 36.306 | -1.547 | 1.00 | 25.63 |
| 964 | O | LEU | A | 259 | 12.378 | 35.371 | -2.225 | 1.00 | 24.57 |
| 965 | N | ASP | A | 260 | 12.327 | 37.559 | -1.858 | 1.00 | 26.41 |
| 966 | CA | ASP | A | 260 | 13.150 | 37.856 | -3.007 | 1.00 | 27.18 |
| 967 | CB | ASP | A | 260 | 13.366 | 39.354 | -3.083 | 1.00 | 27.69 |
| 968 | CG | ASP | A | 260 | 14.244 | 39.775 | -4.245 | 1.00 | 27.39 |
| 969 | OD1 | ASP | A | 260 | 14.959 | 40.747 | -4.093 | 1.00 | 26.79 |
| 970 | OD2 | ASP | A | 260 | 14.297 | 39.199 | -5.344 | 1.00 | 30.71 |
| 971 | C | ASP | A | 260 | 14.497 | 37.115 | -2.835 | 1.00 | 27.61 |
| 972 | O | ASP | A | 260 | 14.915 | 36.435 | -3.729 | 1.00 | 27.56 |
| 973 | N | TYR | A | 261 | 15.152 | 37.270 | -1.679 | 1.00 | 27.09 |
| 974 | CA | TYR | A | 261 | 16.397 | 36.602 | -1.363 | 1.00 | 27.34 |
| 975 | CB | TYR | A | 261 | 16.805 | 36.985 | 0.063 | 1.00 | 27.51 |
| 976 | CG | TYR | A | 261 | 17.902 | 36.083 | 0.642 | 1.00 | 28.63 |
| 977 | CD1 | TYR | A | 261 | 17.587 | 35.096 | 1.573 | 1.00 | 29.48 |
| 978 | CE1 | TYR | A | 261 | 18.560 | 34.295 | 2.131 | 1.00 | 30.22 |
| 979 | CZ | TYR | A | 261 | 19.861 | 34.390 | 1.687 | 1.00 | 31.30 |
| 980 | OH | TYR | A | 261 | 20.790 | 33.541 | 2.261 | 1.00 | 35.01 |
| 981 | CE2 | TYR | A | 261 | 20.211 | 35.301 | 0.705 | 1.00 | 26.41 |
| 982 | CD2 | TYR | A | 261 | 19.223 | 36.168 | 0.202 | 1.00 | 26.63 |
| 983 | C | TYR | A | 261 | 16.336 | 35.058 | -1.494 | 1.00 | 28.06 |
| 984 | O | TYR | A | 261 | 17.188 | 34.415 | -2.115 | 1.00 | 29.23 |
| 985 | N | LEU | A | 262 | 15.325 | 34.474 | -0.883 | 1.00 | 28.62 |
| 986 | CA | LEU | A | 262 | 15.096 | 33.048 | -0.941 | 1.00 | 27.41 |
| 987 | CB | LEU | A | 262 | 13.920 | 32.636 | -0.066 | 1.00 | 26.54 |
| 988 | CG | LEU | A | 262 | 14.224 | 32.603 | 1.432 | 1.00 | 27.60 |
| 989 | CD1 | LEU | A | 262 | 12.924 | 32.302 | 2.162 | 1.00 | 28.93 |
| 990 | CD2 | LEU | A | 262 | 15.345 | 31.596 | 1.877 | 1.00 | 28.18 |
| 991 | C | LEU | A | 262 | 14.921 | 32.561 | -2.374 | 1.00 | 26.95 |
| 992 | O | LEU | A | 262 | 15.618 | 31.627 | -2.792 | 1.00 | 26.42 |
| 993 | N | HIS | A | 263 | 14.048 | 33.201 | -3.131 | 1.00 | 27.06 |
| 994 | CA | HIS | A | 263 | 13.862 | 32.859 | -4.561 | 1.00 | 26.94 |
| 995 | CB | HIS | A | 263 | 12.728 | 33.638 | -5.201 | 1.00 | 25.67 |
| 996 | CG | HIS | A | 263 | 11.419 | 33.377 | -4.557 | 1.00 | 22.17 |
| 997 | ND1 | HIS | A | 263 | 10.338 | 34.191 | -4.704 | 1.00 | 18.69 |
| 998 | CE1 | HIS | A | 263 | 9.330 | 33.726 | -3.991 | 1.00 | 19.70 |
| 999 | NE2 | HIS | A | 263 | 9.707 | 32.604 | -3.437 | 1.00 | 23.80 |
| 1000 | CD2 | HIS | A | 263 | 11.022 | 32.372 | -3.767 | 1.00 | 20.64 |
| 1001 | C | HIS | A | 263 | 15.080 | 33.011 | -5.439 | 1.00 | 28.42 |
| 1002 | O | HIS | A | 263 | 15.273 | 32.219 | -6.317 | 1.00 | 29.97 |
| 1003 | N | SER | A | 264 | 15.842 | 34.079 | -5.237 | 1.00 | 29.39 |
| 1004 | CA | SER | A | 264 | 17.086 | 34.269 | -5.908 | 1.00 | 30.32 |
| 1005 | CB | SER | A | 264 | 17.737 | 35.546 | -5.430 | 1.00 | 30.28 |
| 1006 | OG | SER | A | 264 | 18.367 | 35.287 | -4.139 | 1.00 | 35.06 |
| 1007 | C | SER | A | 264 | 18.030 | 33.087 | -5.642 | 1.00 | 30.94 |
| 1008 | O | SER | A | 264 | 18.832 | 32.808 | -6.478 | 1.00 | 30.95 |
| 1009 | N | GLY | A | 265 | 17.935 | 32.444 | -4.473 | 1.00 | 31.74 |
| 1010 | CA | GLY | A | 265 | 18.637 | 31.215 | -4.186 | 1.00 | 32.11 |
| 1011 | C | GLY | A | 265 | 17.884 | 29.949 | -4.541 | 1.00 | 32.76 |

FIGURE 3 (Cont.)

| A | B | C | D | E | F | G | H | I | J |
|---|---|---|---|---|---|---|---|---|---|
| 1012 | O | GLY | A | 265 | 18.229 | 28.852 | -4.072 | 1.00 | 33.14 |
| 1013 | N | LYS | A | 266 | 16.852 | 30.075 | -5.361 | 1.00 | 33.66 |
| 1014 | CA | LYS | A | 266 | 16.087 | 28.913 | -5.830 | 1.00 | 34.59 |
| 1015 | CB | LYS | A | 266 | 16.989 | 27.969 | -6.671 | 1.00 | 35.67 |
| 1016 | CG | LYS | A | 266 | 17.583 | 28.673 | -7.931 | 1.00 | 38.24 |
| 1017 | CD | LYS | A | 266 | 19.134 | 28.487 | -8.038 | 1.00 | 44.00 |
| 1018 | CE | LYS | A | 266 | 20.012 | 29.495 | -7.186 | 1.00 | 43.89 |
| 1019 | NZ | LYS | A | 266 | 21.464 | 29.049 | -7.107 | 1.00 | 41.88 |
| 1020 | C | LYS | A | 266 | 15.403 | 28.156 | -4.707 | 1.00 | 34.02 |
| 1021 | O | LYS | A | 266 | 15.176 | 26.947 | -4.834 | 1.00 | 35.42 |
| 1022 | N | ILE | A | 267 | 15.043 | 28.877 | -3.635 | 1.00 | 32.73 |
| 1023 | CA | ILE | A | 267 | 14.295 | 28.328 | -2.511 | 1.00 | 32.17 |
| 1024 | CB | ILE | A | 267 | 14.969 | 28.645 | -1.173 | 1.00 | 32.82 |
| 1025 | CG1 | ILE | A | 267 | 16.307 | 27.900 | -1.067 | 1.00 | 34.90 |
| 1026 | CD1 | ILE | A | 267 | 17.181 | 28.458 | 0.020 | 1.00 | 39.76 |
| 1027 | CG2 | ILE | A | 267 | 14.059 | 28.225 | 0.030 | 1.00 | 33.79 |
| 1028 | C | ILE | A | 267 | 12.871 | 28.875 | -2.533 | 1.00 | 31.89 |
| 1029 | O | ILE | A | 267 | 12.633 | 30.076 | -2.806 | 1.00 | 31.10 |
| 1030 | N | VAL | A | 268 | 11.928 | 27.966 | -2.318 | 1.00 | 30.53 |
| 1031 | CA | VAL | A | 268 | 10.560 | 28.309 | -2.120 | 1.00 | 30.99 |
| 1032 | CB | VAL | A | 268 | 9.584 | 27.366 | -2.903 | 1.00 | 30.76 |
| 1033 | CG1 | VAL | A | 268 | 8.178 | 27.884 | -2.722 | 1.00 | 30.49 |
| 1034 | CG2 | VAL | A | 268 | 9.890 | 27.354 | -4.346 | 1.00 | 33.10 |
| 1035 | C | VAL | A | 268 | 10.281 | 28.117 | -0.638 | 1.00 | 30.34 |
| 1036 | O | VAL | A | 268 | 10.523 | 27.040 | -0.118 | 1.00 | 28.16 |
| 1037 | N | TYR | A | 269 | 9.713 | 29.131 | 0.028 | 1.00 | 30.42 |
| 1038 | CA | TYR | A | 269 | 9.455 | 29.020 | 1.450 | 1.00 | 30.59 |
| 1039 | CB | TYR | A | 269 | 9.344 | 30.413 | 2.093 | 1.00 | 31.42 |
| 1040 | CG | TYR | A | 269 | 9.331 | 30.372 | 3.563 | 1.00 | 31.50 |
| 1041 | CD1 | TYR | A | 269 | 8.220 | 30.710 | 4.259 | 1.00 | 33.60 |
| 1042 | CE1 | TYR | A | 269 | 8.192 | 30.642 | 5.606 | 1.00 | 35.63 |
| 1043 | CZ | TYR | A | 269 | 9.285 | 30.207 | 6.283 | 1.00 | 38.00 |
| 1044 | OH | TYR | A | 269 | 9.234 | 30.093 | 7.665 | 1.00 | 45.14 |
| 1045 | CE2 | TYR | A | 269 | 10.421 | 29.847 | 5.620 | 1.00 | 37.55 |
| 1046 | CD2 | TYR | A | 269 | 10.439 | 29.916 | 4.268 | 1.00 | 37.11 |
| 1047 | C | TYR | A | 269 | 8.261 | 28.112 | 1.828 | 1.00 | 31.52 |
| 1048 | O | TYR | A | 269 | 8.356 | 27.318 | 2.807 | 1.00 | 30.25 |
| 1049 | N | ARG | A | 270 | 7.151 | 28.227 | 1.093 | 1.00 | 31.50 |
| 1050 | CA | ARG | A | 270 | 5.946 | 27.376 | 1.246 | 1.00 | 32.42 |
| 1051 | CB | ARG | A | 270 | 6.238 | 25.864 | 1.084 | 1.00 | 34.10 |
| 1052 | CG | ARG | A | 270 | 7.040 | 25.386 | -0.128 | 1.00 | 37.73 |
| 1053 | CD | ARG | A | 270 | 7.973 | 24.179 | 0.120 | 1.00 | 45.29 |
| 1054 | NE | ARG | A | 270 | 9.218 | 24.576 | 0.860 | 1.00 | 53.01 |
| 1055 | CZ | ARG | A | 270 | 10.478 | 24.119 | 0.639 | 1.00 | 52.63 |
| 1056 | NH1 | ARG | A | 270 | 10.733 | 23.214 | -0.308 | 1.00 | 51.30 |
| 1057 | NH2 | ARG | A | 270 | 11.486 | 24.595 | 1.380 | 1.00 | 52.51 |
| 1058 | C | ARG | A | 270 | 5.214 | 27.573 | 2.585 | 1.00 | 32.66 |
| 1059 | O | ARG | A | 270 | 4.015 | 27.362 | 2.651 | 1.00 | 32.51 |
| 1060 | N | ASP | A | 271 | 5.914 | 28.003 | 3.632 | 1.00 | 32.77 |
| 1061 | CA | ASP | A | 271 | 5.396 | 27.930 | 5.001 | 1.00 | 33.99 |
| 1062 | CB | ASP | A | 271 | 6.488 | 27.354 | 5.931 | 1.00 | 34.49 |

FIGURE 3 (Cont.)

| A | B | C | D | E | F | G | H | I | J |
|---|---|---|---|---|---|---|---|---|---|
| 1063 | CG | ASP | A | 271 | 6.717 | 25.860 | 5.733 | 1.00 | 35.71 |
| 1064 | OD1 | ASP | A | 271 | 6.066 | 25.246 | 4.877 | 1.00 | 38.14 |
| 1065 | OD2 | ASP | A | 271 | 7.548 | 25.208 | 6.401 | 1.00 | 41.97 |
| 1066 | C | ASP | A | 271 | 5.006 | 29.306 | 5.509 | 1.00 | 34.63 |
| 1067 | O | ASP | A | 271 | 4.922 | 29.506 | 6.745 | 1.00 | 35.15 |
| 1068 | N | LEU | A | 272 | 4.803 | 30.266 | 4.582 | 1.00 | 34.31 |
| 1069 | CA | LEU | A | 272 | 4.461 | 31.623 | 4.961 | 1.00 | 34.56 |
| 1070 | CB | LEU | A | 272 | 4.593 | 32.628 | 3.812 | 1.00 | 35.18 |
| 1071 | CG | LEU | A | 272 | 5.000 | 34.089 | 4.093 | 1.00 | 34.95 |
| 1072 | CD1 | LEU | A | 272 | 4.306 | 35.045 | 3.129 | 1.00 | 35.50 |
| 1073 | CD2 | LEU | A | 272 | 4.856 | 34.512 | 5.516 | 1.00 | 33.99 |
| 1074 | C | LEU | A | 272 | 3.047 | 31.658 | 5.470 | 1.00 | 33.89 |
| 1075 | O | LEU | A | 272 | 2.099 | 31.328 | 4.767 | 1.00 | 34.24 |
| 1076 | N | LYS | A | 273 | 2.920 | 32.111 | 6.697 | 1.00 | 33.64 |
| 1077 | CA | LYS | A | 273 | 1.612 | 32.280 | 7.323 | 1.00 | 32.43 |
| 1078 | CB | LYS | A | 273 | 0.965 | 30.945 | 7.701 | 1.00 | 32.54 |
| 1079 | CG | LYS | A | 273 | 1.647 | 30.146 | 8.822 | 1.00 | 33.11 |
| 1080 | CD | LYS | A | 273 | 1.081 | 28.655 | 8.924 | 1.00 | 35.90 |
| 1081 | CE | LYS | A | 273 | 2.089 | 27.561 | 8.430 | 1.00 | 35.49 |
| 1082 | NZ | LYS | A | 273 | 1.486 | 26.153 | 8.578 | 1.00 | 41.33 |
| 1083 | C | LYS | A | 273 | 1.843 | 33.125 | 8.520 | 1.00 | 30.78 |
| 1084 | O | LYS | A | 273 | 2.982 | 33.262 | 8.927 | 1.00 | 30.02 |
| 1085 | N | LEU | A | 274 | 0.756 | 33.677 | 9.078 | 1.00 | 29.80 |
| 1086 | CA | LEU | A | 274 | 0.821 | 34.673 | 10.133 | 1.00 | 30.63 |
| 1087 | CB | LEU | A | 274 | -0.591 | 35.143 | 10.426 | 1.00 | 31.41 |
| 1088 | CG | LEU | A | 274 | -0.792 | 36.267 | 11.416 | 1.00 | 34.36 |
| 1089 | CD1 | LEU | A | 274 | -0.233 | 37.579 | 10.822 | 1.00 | 34.62 |
| 1090 | CD2 | LEU | A | 274 | -2.296 | 36.357 | 11.691 | 1.00 | 35.88 |
| 1091 | C | LEU | A | 274 | 1.502 | 34.159 | 11.390 | 1.00 | 30.57 |
| 1092 | O | LEU | A | 274 | 2.316 | 34.822 | 11.987 | 1.00 | 29.18 |
| 1093 | N | GLU | A | 275 | 1.193 | 32.919 | 11.719 | 1.00 | 31.86 |
| 1094 | CA | GLU | A | 275 | 1.826 | 32.157 | 12.803 | 1.00 | 33.17 |
| 1095 | CB | GLU | A | 275 | 1.119 | 30.794 | 12.872 | 1.00 | 34.59 |
| 1096 | CG | GLU | A | 275 | -0.389 | 30.984 | 13.169 | 1.00 | 38.41 |
| 1097 | CD | GLU | A | 275 | -1.310 | 30.775 | 11.956 | 1.00 | 46.05 |
| 1098 | OE1 | GLU | A | 275 | -1.151 | 31.414 | 10.853 | 1.00 | 44.97 |
| 1099 | OE2 | GLU | A | 275 | -2.241 | 29.961 | 12.125 | 1.00 | 51.01 |
| 1100 | C | GLU | A | 275 | 3.368 | 31.973 | 12.666 | 1.00 | 32.00 |
| 1101 | O | GLU | A | 275 | 4.044 | 31.744 | 13.667 | 1.00 | 31.96 |
| 1102 | N | ASN | A | 276 | 3.906 | 32.103 | 11.451 | 1.00 | 29.62 |
| 1103 | CA | ASN | A | 276 | 5.346 | 32.006 | 11.216 | 1.00 | 29.68 |
| 1104 | CB | ASN | A | 276 | 5.634 | 31.194 | 9.928 | 1.00 | 29.45 |
| 1105 | CG | ASN | A | 276 | 5.527 | 29.635 | 10.154 | 1.00 | 32.16 |
| 1106 | OD1 | ASN | A | 276 | 5.415 | 29.174 | 11.271 | 1.00 | 32.76 |
| 1107 | ND2 | ASN | A | 276 | 5.591 | 28.870 | 9.086 | 1.00 | 31.97 |
| 1108 | C | ASN | A | 276 | 6.058 | 33.358 | 11.133 | 1.00 | 29.11 |
| 1109 | O | ASN | A | 276 | 7.130 | 33.445 | 10.579 | 1.00 | 29.92 |
| 1110 | N | LEU | A | 277 | 5.422 | 34.399 | 11.654 | 1.00 | 28.83 |
| 1111 | CA | LEU | A | 277 | 5.893 | 35.762 | 11.593 | 1.00 | 27.79 |
| 1112 | CB | LEU | A | 277 | 4.933 | 36.656 | 10.798 | 1.00 | 26.69 |
| 1113 | CG | LEU | A | 277 | 4.757 | 36.361 | 9.287 | 1.00 | 26.91 |

FIGURE 3 (Cont.)

| A | B | C | D | E | F | G | H | I | J |
|---|---|---|---|---|---|---|---|---|---|
| 1114 | CD1 | LEU | A | 277 | 3.726 | 37.285 | 8.709 | 1.00 | 25.76 |
| 1115 | CD2 | LEU | A | 277 | 6.028 | 36.404 | 8.554 | 1.00 | 25.32 |
| 1116 | C | LEU | A | 277 | 5.991 | 36.235 | 13.026 | 1.00 | 27.70 |
| 1117 | O | LEU | A | 277 | 5.038 | 36.165 | 13.771 | 1.00 | 30.28 |
| 1118 | N | MET | A | 278 | 7.136 | 36.712 | 13.414 | 1.00 | 28.30 |
| 1119 | CA | MET | A | 278 | 7.333 | 37.254 | 14.740 | 1.00 | 29.84 |
| 1120 | CB | MET | A | 278 | 8.336 | 36.407 | 15.499 | 1.00 | 29.99 |
| 1121 | CG | MET | A | 278 | 7.765 | 35.024 | 15.823 | 1.00 | 37.12 |
| 1122 | SD | MET | A | 278 | 8.596 | 34.264 | 17.262 | 1.00 | 45.50 |
| 1123 | CE | MET | A | 278 | 7.661 | 35.024 | 18.482 | 1.00 | 47.33 |
| 1124 | C | MET | A | 278 | 7.922 | 38.606 | 14.591 | 1.00 | 28.58 |
| 1125 | O | MET | A | 278 | 8.304 | 38.957 | 13.508 | 1.00 | 27.99 |
| 1126 | N | LEU | A | 279 | 8.028 | 39.354 | 15.687 | 1.00 | 27.04 |
| 1127 | CA | LEU | A | 279 | 8.750 | 40.605 | 15.625 | 1.00 | 27.02 |
| 1128 | CB | LEU | A | 279 | 7.906 | 41.712 | 16.165 | 1.00 | 26.13 |
| 1129 | CG | LEU | A | 279 | 6.571 | 42.004 | 15.472 | 1.00 | 29.67 |
| 1130 | CD1 | LEU | A | 279 | 6.018 | 43.232 | 16.052 | 1.00 | 27.80 |
| 1131 | CD2 | LEU | A | 279 | 6.762 | 42.158 | 13.995 | 1.00 | 28.96 |
| 1132 | C | LEU | A | 279 | 9.966 | 40.451 | 16.484 | 1.00 | 25.67 |
| 1133 | O | LEU | A | 279 | 9.897 | 39.803 | 17.478 | 1.00 | 24.03 |
| 1134 | N | ASP | A | 280 | 11.048 | 41.104 | 16.118 | 1.00 | 26.47 |
| 1135 | CA | ASP | A | 280 | 12.207 | 41.181 | 16.961 | 1.00 | 27.07 |
| 1136 | CB | ASP | A | 280 | 13.486 | 41.241 | 16.130 | 1.00 | 25.81 |
| 1137 | CG | ASP | A | 280 | 13.674 | 42.548 | 15.367 | 1.00 | 25.82 |
| 1138 | OD1 | ASP | A | 280 | 12.943 | 43.574 | 15.602 | 1.00 | 25.20 |
| 1139 | OD2 | ASP | A | 280 | 14.557 | 42.649 | 14.497 | 1.00 | 22.34 |
| 1140 | C | ASP | A | 280 | 12.027 | 42.356 | 17.917 | 1.00 | 29.22 |
| 1141 | O | ASP | A | 280 | 11.043 | 43.113 | 17.848 | 1.00 | 29.35 |
| 1142 | N | LYS | A | 281 | 12.986 | 42.518 | 18.800 | 1.00 | 31.63 |
| 1143 | CA | LYS | A | 281 | 12.867 | 43.499 | 19.870 | 1.00 | 33.75 |
| 1144 | CB | LYS | A | 281 | 14.118 | 43.458 | 20.770 | 1.00 | 34.90 |
| 1145 | CG | LYS | A | 281 | 15.254 | 44.403 | 20.463 | 1.00 | 37.97 |
| 1146 | CD | LYS | A | 281 | 16.421 | 43.754 | 19.753 | 1.00 | 46.47 |
| 1147 | CE | LYS | A | 281 | 17.448 | 43.257 | 20.724 | 1.00 | 49.32 |
| 1148 | NZ | LYS | A | 281 | 16.881 | 42.069 | 21.453 | 1.00 | 53.87 |
| 1149 | C | LYS | A | 281 | 12.604 | 44.916 | 19.307 | 1.00 | 33.40 |
| 1150 | O | LYS | A | 281 | 11.990 | 45.745 | 19.982 | 1.00 | 32.50 |
| 1151 | N | ASP | A | 282 | 13.063 | 45.163 | 18.072 | 1.00 | 32.45 |
| 1152 | CA | ASP | A | 282 | 12.923 | 46.477 | 17.429 | 1.00 | 32.13 |
| 1153 | CB | ASP | A | 282 | 14.159 | 46.758 | 16.553 | 1.00 | 32.63 |
| 1154 | CG | ASP | A | 282 | 15.417 | 46.862 | 17.373 | 1.00 | 31.55 |
| 1155 | OD1 | ASP | A | 282 | 15.429 | 47.661 | 18.313 | 1.00 | 35.08 |
| 1156 | OD2 | ASP | A | 282 | 16.380 | 46.132 | 17.258 | 1.00 | 35.53 |
| 1157 | C | ASP | A | 282 | 11.620 | 46.664 | 16.632 | 1.00 | 31.63 |
| 1158 | O | ASP | A | 282 | 11.355 | 47.762 | 16.160 | 1.00 | 31.26 |
| 1159 | N | GLY | A | 283 | 10.798 | 45.606 | 16.497 | 1.00 | 30.18 |
| 1160 | CA | GLY | A | 283 | 9.597 | 45.672 | 15.665 | 1.00 | 29.39 |
| 1161 | C | GLY | A | 283 | 9.753 | 45.309 | 14.192 | 1.00 | 28.80 |
| 1162 | O | GLY | A | 283 | 8.757 | 45.492 | 13.423 | 1.00 | 28.55 |
| 1163 | N | HIS | A | 284 | 10.951 | 44.842 | 13.789 | 1.00 | 26.87 |
| 1164 | CA | HIS | A | 284 | 11.188 | 44.252 | 12.447 | 1.00 | 26.95 |

FIGURE 3 (Cont.)

| A | B | C | D | E | F | G | H | I | J |
|---|---|---|---|---|---|---|---|---|---|
| 1165 | CB | HIS | A | 284 | 12.692 | 44.283 | 12.002 | 1.00 | 27.01 |
| 1166 | CG | HIS | A | 284 | 13.201 | 45.654 | 11.762 | 1.00 | 25.98 |
| 1167 | ND1 | HIS | A | 284 | 12.601 | 46.489 | 10.864 | 1.00 | 23.47 |
| 1168 | CE1 | HIS | A | 284 | 13.181 | 47.684 | 10.930 | 1.00 | 30.83 |
| 1169 | NE2 | HIS | A | 284 | 14.182 | 47.622 | 11.790 | 1.00 | 26.45 |
| 1170 | CD2 | HIS | A | 284 | 14.219 | 46.362 | 12.323 | 1.00 | 27.01 |
| 1171 | C | HIS | A | 284 | 10.695 | 42.791 | 12.424 | 1.00 | 27.75 |
| 1172 | O | HIS | A | 284 | 10.632 | 42.108 | 13.454 | 1.00 | 28.66 |
| 1173 | N | ILE | A | 285 | 10.387 | 42.310 | 11.235 | 1.00 | 27.80 |
| 1174 | CA | ILE | A | 285 | 9.837 | 40.993 | 11.056 | 1.00 | 28.29 |
| 1175 | CB | ILE | A | 285 | 8.990 | 40.901 | 9.739 | 1.00 | 29.57 |
| 1176 | CG1 | ILE | A | 285 | 7.591 | 40.385 | 10.080 | 1.00 | 32.65 |
| 1177 | CD1 | ILE | A | 285 | 6.589 | 40.973 | 9.384 | 1.00 | 34.40 |
| 1178 | CG2 | ILE | A | 285 | 9.535 | 39.930 | 8.777 | 1.00 | 31.57 |
| 1179 | C | ILE | A | 285 | 10.934 | 39.962 | 11.123 | 1.00 | 28.06 |
| 1180 | O | ILE | A | 285 | 12.060 | 40.201 | 10.794 | 1.00 | 26.08 |
| 1181 | N | LYS | A | 286 | 10.554 | 38.793 | 11.583 | 1.00 | 28.68 |
| 1182 | CA | LYS | A | 286 | 11.423 | 37.673 | 11.551 | 1.00 | 29.29 |
| 1183 | CB | LYS | A | 286 | 12.144 | 37.535 | 12.865 | 1.00 | 29.53 |
| 1184 | CG | LYS | A | 286 | 13.581 | 37.204 | 12.654 | 1.00 | 31.76 |
| 1185 | CD | LYS | A | 286 | 14.508 | 38.382 | 12.814 | 1.00 | 34.00 |
| 1186 | CE | LYS | A | 286 | 15.821 | 37.936 | 12.240 | 1.00 | 36.66 |
| 1187 | NZ | LYS | A | 286 | 16.953 | 38.853 | 12.397 | 1.00 | 38.45 |
| 1188 | C | LYS | A | 286 | 10.514 | 36.523 | 11.195 | 1.00 | 30.07 |
| 1189 | O | LYS | A | 286 | 9.569 | 36.196 | 11.925 | 1.00 | 31.14 |
| 1190 | N | ILE | A | 287 | 10.761 | 35.956 | 10.015 | 1.00 | 30.63 |
| 1191 | CA | ILE | A | 287 | 10.072 | 34.763 | 9.602 | 1.00 | 33.01 |
| 1192 | CB | ILE | A | 287 | 10.189 | 34.574 | 8.116 | 1.00 | 32.75 |
| 1193 | CG1 | ILE | A | 287 | 9.706 | 35.812 | 7.402 | 1.00 | 28.88 |
| 1194 | CD1 | ILE | A | 287 | 9.996 | 35.828 | 6.006 | 1.00 | 30.66 |
| 1195 | CG2 | ILE | A | 287 | 9.431 | 33.334 | 7.738 | 1.00 | 34.40 |
| 1196 | C | ILE | A | 287 | 10.703 | 33.543 | 10.312 | 1.00 | 34.96 |
| 1197 | O | ILE | A | 287 | 11.909 | 33.289 | 10.193 | 1.00 | 34.06 |
| 1198 | N | THR | A | 288 | 9.874 | 32.797 | 11.005 | 1.00 | 37.62 |
| 1199 | CA | THR | A | 288 | 10.336 | 31.714 | 11.819 | 1.00 | 41.84 |
| 1200 | CB | THR | A | 288 | 10.663 | 32.209 | 13.222 | 1.00 | 42.16 |
| 1201 | OG1 | THR | A | 288 | 10.783 | 31.082 | 14.117 | 1.00 | 49.33 |
| 1202 | CG2 | THR | A | 288 | 9.562 | 32.974 | 13.810 | 1.00 | 40.34 |
| 1203 | C | THR | A | 288 | 9.353 | 30.566 | 11.924 | 1.00 | 44.96 |
| 1204 | O | THR | A | 288 | 8.156 | 30.671 | 11.627 | 1.00 | 46.08 |
| 1205 | N | ASP | A | 289 | 9.907 | 29.441 | 12.339 | 1.00 | 48.34 |
| 1206 | CA | ASP | A | 289 | 9.159 | 28.236 | 12.561 | 1.00 | 50.20 |
| 1207 | CB | ASP | A | 289 | 9.588 | 27.209 | 11.526 | 1.00 | 50.63 |
| 1208 | CG | ASP | A | 289 | 8.886 | 25.898 | 11.702 | 1.00 | 52.58 |
| 1209 | OD1 | ASP | A | 289 | 7.733 | 25.931 | 12.178 | 1.00 | 56.25 |
| 1210 | OD2 | ASP | A | 289 | 9.391 | 24.800 | 11.399 | 1.00 | 55.66 |
| 1211 | C | ASP | A | 289 | 9.531 | 27.801 | 13.982 | 1.00 | 51.29 |
| 1212 | O | ASP | A | 289 | 10.534 | 27.088 | 14.184 | 1.00 | 51.86 |

FIGURE 3 (Cont.)

| A | B | C | D | E | F | G | H | I | J |
|---|---|---|---|---|---|---|---|---|---|
| 1218 | N | ALA | A | 310 | -3.839 | 25.261 | 6.463 | 1.00 | 48.88 |
| 1219 | CA | ALA | A | 310 | -4.416 | 24.894 | 5.157 | 1.00 | 47.76 |
| 1220 | CB | ALA | A | 310 | -5.095 | 23.596 | 5.246 | 1.00 | 48.51 |
| 1221 | C | ALA | A | 310 | -5.388 | 25.937 | 4.548 | 1.00 | 47.69 |
| 1222 | O | ALA | A | 310 | -5.769 | 25.851 | 3.354 | 1.00 | 46.74 |
| 1223 | N | ALA | A | 311 | -5.788 | 26.915 | 5.360 | 1.00 | 46.47 |
| 1224 | CA | ALA | A | 311 | -6.417 | 28.134 | 4.838 | 1.00 | 45.80 |
| 1225 | CB | ALA | A | 311 | -7.020 | 28.974 | 6.000 | 1.00 | 45.55 |
| 1226 | C | ALA | A | 311 | -5.401 | 28.965 | 4.000 | 1.00 | 44.30 |
| 1227 | O | ALA | A | 311 | -5.769 | 29.959 | 3.352 | 1.00 | 44.24 |
| 1228 | N | TYR | A | 312 | -4.142 | 28.516 | 3.997 | 1.00 | 42.33 |
| 1229 | CA | TYR | A | 312 | -3.083 | 29.159 | 3.270 | 1.00 | 41.51 |
| 1230 | CB | TYR | A | 312 | -1.824 | 29.190 | 4.113 | 1.00 | 41.43 |
| 1231 | CG | TYR | A | 312 | -1.886 | 30.248 | 5.176 | 1.00 | 41.63 |
| 1232 | CD1 | TYR | A | 312 | -2.406 | 29.952 | 6.434 | 1.00 | 40.11 |
| 1233 | CE1 | TYR | A | 312 | -2.475 | 30.907 | 7.420 | 1.00 | 44.04 |
| 1234 | CZ | TYR | A | 312 | -2.015 | 32.197 | 7.153 | 1.00 | 42.14 |
| 1235 | OH | TYR | A | 312 | -2.072 | 33.136 | 8.132 | 1.00 | 43.35 |
| 1236 | CE2 | TYR | A | 312 | -1.507 | 32.523 | 5.903 | 1.00 | 42.78 |
| 1237 | CD2 | TYR | A | 312 | -1.437 | 31.545 | 4.920 | 1.00 | 41.84 |
| 1238 | C | TYR | A | 312 | -2.752 | 28.483 | 1.978 | 1.00 | 41.09 |
| 1239 | O | TYR | A | 312 | -1.899 | 28.988 | 1.240 | 1.00 | 41.27 |
| 1240 | N | LEU | A | 313 | -3.396 | 27.367 | 1.666 | 1.00 | 39.84 |
| 1241 | CA | LEU | A | 313 | -2.930 | 26.598 | 0.508 | 1.00 | 39.72 |
| 1242 | CB | LEU | A | 313 | -3.424 | 25.146 | 0.562 | 1.00 | 40.24 |
| 1243 | CG | LEU | A | 313 | -2.845 | 24.377 | 1.760 | 1.00 | 42.25 |
| 1244 | CD1 | LEU | A | 313 | -3.576 | 23.073 | 1.945 | 1.00 | 45.88 |
| 1245 | CD2 | LEU | A | 313 | -1.357 | 24.137 | 1.572 | 1.00 | 45.90 |
| 1246 | C | LEU | A | 313 | -3.310 | 27.308 | -0.786 | 1.00 | 37.48 |
| 1247 | O | LEU | A | 313 | -4.399 | 27.798 | -0.930 | 1.00 | 36.25 |
| 1248 | N | ALA | A | 314 | -2.349 | 27.426 | -1.687 | 1.00 | 37.11 |
| 1249 | CA | ALA | A | 314 | -2.560 | 28.107 | -2.942 | 1.00 | 37.08 |
| 1250 | CB | ALA | A | 314 | -1.252 | 28.480 | -3.529 | 1.00 | 36.54 |
| 1251 | C | ALA | A | 314 | -3.318 | 27.202 | -3.911 | 1.00 | 37.20 |
| 1252 | O | ALA | A | 314 | -3.135 | 25.992 | -3.902 | 1.00 | 36.19 |
| 1253 | N | PRO | A | 315 | -4.090 | 27.789 | -4.807 | 1.00 | 37.50 |
| 1254 | CA | PRO | A | 315 | -4.874 | 26.997 | -5.757 | 1.00 | 37.89 |
| 1255 | CB | PRO | A | 315 | -5.396 | 28.029 | -6.744 | 1.00 | 37.58 |
| 1256 | CG | PRO | A | 315 | -5.304 | 29.326 | -6.046 | 1.00 | 37.46 |
| 1257 | CD | PRO | A | 315 | -4.263 | 29.231 | -5.001 | 1.00 | 37.56 |
| 1258 | C | PRO | A | 315 | -3.996 | 25.945 | -6.460 | 1.00 | 38.76 |
| 1259 | O | PRO | A | 315 | -4.394 | 24.802 | -6.460 | 1.00 | 39.54 |
| 1260 | N | GLU | A | 316 | -2.841 | 26.316 | -7.003 | 1.00 | 39.05 |
| 1261 | CA | GLU | A | 316 | -2.002 | 25.390 | -7.742 | 1.00 | 39.37 |
| 1262 | CB | GLU | A | 316 | -0.816 | 26.092 | -8.404 | 1.00 | 38.88 |
| 1263 | CG | GLU | A | 316 | 0.221 | 26.651 | -7.436 | 1.00 | 36.82 |
| 1264 | CD | GLU | A | 316 | -0.092 | 28.077 | -7.025 | 1.00 | 32.38 |
| 1265 | OE1 | GLU | A | 316 | 0.833 | 28.855 | -6.706 | 1.00 | 34.71 |
| 1266 | OE2 | GLU | A | 316 | -1.256 | 28.430 | -7.065 | 1.00 | 23.79 |

FIGURE 3 (Cont.)

| A | B | C | D | E | F | G | H | I | J |
|---|---|---|---|---|---|---|---|---|---|
| 1267 | C | GLU | A | 316 | -1.479 | 24.185 | -6.947 | 1.00 | 41.11 |
| 1268 | O | GLU | A | 316 | -1.129 | 23.160 | -7.569 | 1.00 | 41.25 |
| 1269 | N | VAL | A | 317 | -1.383 | 24.275 | -5.625 | 1.00 | 42.32 |
| 1270 | CA | VAL | A | 317 | -1.018 | 23.072 | -4.875 | 1.00 | 44.64 |
| 1271 | CB | VAL | A | 317 | -0.208 | 23.289 | -3.527 | 1.00 | 44.83 |
| 1272 | CG1 | VAL | A | 317 | 0.406 | 24.697 | -3.414 | 1.00 | 43.75 |
| 1273 | CG2 | VAL | A | 317 | -1.000 | 22.863 | -2.280 | 1.00 | 46.07 |
| 1274 | C | VAL | A | 317 | -2.260 | 22.167 | -4.717 | 1.00 | 46.14 |
| 1275 | O | VAL | A | 317 | -2.145 | 20.954 | -4.814 | 1.00 | 45.21 |
| 1276 | N | LEU | A | 318 | -3.433 | 22.767 | -4.532 | 1.00 | 48.12 |
| 1277 | CA | LEU | A | 318 | -4.684 | 22.000 | -4.579 | 1.00 | 50.41 |
| 1278 | CB | LEU | A | 318 | -5.911 | 22.913 | -4.331 | 1.00 | 50.46 |
| 1279 | CG | LEU | A | 318 | -5.896 | 23.647 | -2.969 | 1.00 | 50.31 |
| 1280 | CD1 | LEU | A | 318 | -7.248 | 24.305 | -2.604 | 1.00 | 48.93 |
| 1281 | CD2 | LEU | A | 318 | -5.412 | 22.747 | -1.841 | 1.00 | 49.77 |
| 1282 | C | LEU | A | 318 | -4.784 | 21.177 | -5.893 | 1.00 | 51.59 |
| 1283 | O | LEU | A | 318 | -4.792 | 19.941 | -5.850 | 1.00 | 51.32 |
| 1284 | N | GLU | A | 319 | -4.765 | 21.864 | -7.039 | 1.00 | 53.07 |
| 1285 | CA | GLU | A | 319 | -4.741 | 21.218 | -8.365 | 1.00 | 54.48 |
| 1286 | CB | GLU | A | 319 | -4.856 | 22.267 | -9.470 | 1.00 | 54.86 |
| 1287 | CG | GLU | A | 319 | -6.108 | 23.131 | -9.409 | 1.00 | 57.53 |
| 1288 | CD | GLU | A | 319 | -6.163 | 24.185 | -10.499 | 1.00 | 61.78 |
| 1289 | OE1 | GLU | A | 319 | -5.072 | 24.656 | -10.929 | 1.00 | 65.20 |
| 1290 | OE2 | GLU | A | 319 | -7.299 | 24.557 | -10.908 | 1.00 | 63.11 |
| 1291 | C | GLU | A | 319 | -3.479 | 20.376 | -8.632 | 1.00 | 55.11 |
| 1292 | O | GLU | A | 319 | -3.387 | 19.697 | -9.652 | 1.00 | 54.54 |
| 1293 | N | ASP | A | 320 | -2.505 | 20.471 | -7.726 | 1.00 | 56.22 |
| 1294 | CA | ASP | A | 320 | -1.234 | 19.760 | -7.804 | 1.00 | 57.07 |
| 1295 | CB | ASP | A | 320 | -1.455 | 18.235 | -7.861 | 1.00 | 57.58 |
| 1296 | CG | ASP | A | 320 | -0.179 | 17.449 | -7.645 | 1.00 | 58.44 |
| 1297 | OD1 | ASP | A | 320 | 0.742 | 18.004 | -6.991 | 1.00 | 60.58 |
| 1298 | OD2 | ASP | A | 320 | -0.005 | 16.284 | -8.100 | 1.00 | 60.04 |
| 1299 | C | ASP | A | 320 | -0.388 | 20.257 | -8.977 | 1.00 | 57.41 |
| 1300 | O | ASP | A | 320 | -0.716 | 20.024 | -10.135 | 1.00 | 58.00 |
| 1313 | N | GLY | A | 324 | 5.603 | 26.512 | -7.760 | 1.00 | 34.10 |
| 1314 | CA | GLY | A | 324 | 6.899 | 27.057 | -7.457 | 1.00 | 31.14 |
| 1315 | C | GLY | A | 324 | 6.866 | 28.292 | -6.556 | 1.00 | 29.43 |
| 1316 | O | GLY | A | 324 | 6.074 | 28.428 | -5.609 | 1.00 | 27.34 |

FIGURE 3 (Cont.)

| A | B | C | D | E | F | G | H | I | J |
|---|---|---|---|---|---|---|---|---|---|
| 1317 | N | ARG | A | 325 | 7.748 | 29.222 | -6.888 | 1.00 | 27.50 |
| 1318 | CA | ARG | A | 325 | 7.972 | 30.369 | -6.066 | 1.00 | 27.57 |
| 1319 | CB | ARG | A | 325 | 9.165 | 31.105 | -6.616 | 1.00 | 27.61 |
| 1320 | CG | ARG | A | 325 | 8.930 | 31.703 | -7.906 | 1.00 | 28.72 |
| 1321 | CD | ARG | A | 325 | 10.160 | 32.213 | -8.615 | 1.00 | 32.95 |
| 1322 | NE | ARG | A | 325 | 9.872 | 32.232 | -10.050 | 1.00 | 33.69 |
| 1323 | CZ | ARG | A | 325 | 9.072 | 33.078 | -10.672 | 1.00 | 32.54 |
| 1324 | NH1 | ARG | A | 325 | 8.886 | 32.929 | -11.989 | 1.00 | 34.44 |
| 1325 | NH2 | ARG | A | 325 | 8.496 | 34.090 | -10.032 | 1.00 | 32.26 |
| 1326 | C | ARG | A | 325 | 6.680 | 31.250 | -5.961 | 1.00 | 27.17 |
| 1327 | O | ARG | A | 325 | 6.449 | 31.899 | -4.962 | 1.00 | 26.97 |
| 1328 | N | ALA | A | 326 | 5.790 | 31.135 | -6.931 | 1.00 | 25.46 |
| 1329 | CA | ALA | A | 326 | 4.560 | 31.876 | -6.917 | 1.00 | 27.38 |
| 1330 | CB | ALA | A | 326 | 3.781 | 31.667 | -8.242 | 1.00 | 27.48 |
| 1331 | C | ALA | A | 326 | 3.678 | 31.558 | -5.728 | 1.00 | 26.95 |
| 1332 | O | ALA | A | 326 | 2.882 | 32.416 | -5.345 | 1.00 | 27.55 |
| 1333 | N | VAL | A | 327 | 3.768 | 30.357 | -5.154 | 1.00 | 26.30 |
| 1334 | CA | VAL | A | 327 | 2.950 | 30.053 | -3.968 | 1.00 | 26.28 |
| 1335 | CB | VAL | A | 327 | 3.015 | 28.556 | -3.430 | 1.00 | 27.10 |
| 1336 | CG1 | VAL | A | 327 | 2.760 | 27.592 | -4.477 | 1.00 | 29.10 |
| 1337 | CG2 | VAL | A | 327 | 4.321 | 28.239 | -2.763 | 1.00 | 30.22 |
| 1338 | C | VAL | A | 327 | 3.316 | 30.958 | -2.793 | 1.00 | 25.11 |
| 1339 | O | VAL | A | 327 | 2.507 | 31.151 | -1.926 | 1.00 | 23.28 |
| 1340 | N | ASP | A | 328 | 4.537 | 31.510 | -2.763 | 1.00 | 24.80 |
| 1341 | CA | ASP | A | 328 | 4.920 | 32.384 | -1.669 | 1.00 | 24.22 |
| 1342 | CB | ASP | A | 328 | 6.414 | 32.609 | -1.594 | 1.00 | 23.46 |
| 1343 | CG | ASP | A | 328 | 7.162 | 31.390 | -1.131 | 1.00 | 25.77 |
| 1344 | OD1 | ASP | A | 328 | 8.386 | 31.261 | -1.486 | 1.00 | 21.78 |
| 1345 | OD2 | ASP | A | 328 | 6.597 | 30.551 | -0.405 | 1.00 | 19.33 |
| 1346 | C | ASP | A | 328 | 4.233 | 33.736 | -1.809 | 1.00 | 24.05 |
| 1347 | O | ASP | A | 328 | 4.031 | 34.381 | -0.839 | 1.00 | 23.44 |
| 1348 | N | TRP | A | 329 | 3.937 | 34.154 | -3.017 | 1.00 | 22.55 |
| 1349 | CA | TRP | A | 329 | 3.192 | 35.361 | -3.231 | 1.00 | 23.10 |
| 1350 | CB | TRP | A | 329 | 3.335 | 35.802 | -4.706 | 1.00 | 23.96 |
| 1351 | CG | TRP | A | 329 | 4.779 | 35.975 | -5.043 | 1.00 | 24.02 |
| 1352 | CD1 | TRP | A | 329 | 5.428 | 35.444 | -6.117 | 1.00 | 25.23 |
| 1353 | NE1 | TRP | A | 329 | 6.758 | 35.795 | -6.091 | 1.00 | 20.77 |
| 1354 | CE2 | TRP | A | 329 | 6.995 | 36.573 | -5.005 | 1.00 | 22.40 |
| 1355 | CD2 | TRP | A | 329 | 5.766 | 36.704 | -4.305 | 1.00 | 23.81 |
| 1356 | CE3 | TRP | A | 329 | 5.753 | 37.453 | -3.105 | 1.00 | 25.65 |
| 1357 | CZ3 | TRP | A | 329 | 6.926 | 38.038 | -2.671 | 1.00 | 25.47 |
| 1358 | CH2 | TRP | A | 329 | 8.134 | 37.876 | -3.376 | 1.00 | 22.24 |
| 1359 | CZ2 | TRP | A | 329 | 8.181 | 37.137 | -4.555 | 1.00 | 26.13 |
| 1360 | C | TRP | A | 329 | 1.757 | 35.186 | -2.850 | 1.00 | 22.79 |
| 1361 | O | TRP | A | 329 | 1.166 | 36.072 | -2.233 | 1.00 | 23.14 |
| 1362 | N | TRP | A | 330 | 1.186 | 34.026 | -3.148 | 1.00 | 23.88 |
| 1363 | CA | TRP | A | 330 | -0.126 | 33.723 | -2.609 | 1.00 | 23.28 |
| 1364 | CB | TRP | A | 330 | -0.574 | 32.311 | -3.061 | 1.00 | 24.71 |
| 1365 | CG | TRP | A | 330 | -1.820 | 31.892 | -2.453 | 1.00 | 23.64 |
| 1366 | CD1 | TRP | A | 330 | -1.978 | 31.346 | -1.234 | 1.00 | 24.48 |
| 1367 | NE1 | TRP | A | 330 | -3.311 | 31.116 | -0.995 | 1.00 | 25.02 |

FIGURE 3 (Cont.)

| A | B | C | D | E | F | G | H | I | J |
|---|---|---|---|---|---|---|---|---|---|
| 1368 | CE2 | TRP | A | 330 | -4.025 | 31.550 | -2.081 | 1.00 | 25.12 |
| 1369 | CD2 | TRP | A | 330 | -3.104 | 32.056 | -3.006 | 1.00 | 23.08 |
| 1370 | CE3 | TRP | A | 330 | -3.578 | 32.583 | -4.208 | 1.00 | 22.67 |
| 1371 | CZ3 | TRP | A | 330 | -4.924 | 32.548 | -4.461 | 1.00 | 24.37 |
| 1372 | CH2 | TRP | A | 330 | -5.822 | 32.079 | -3.499 | 1.00 | 26.35 |
| 1373 | CZ2 | TRP | A | 330 | -5.392 | 31.570 | -2.304 | 1.00 | 23.96 |
| 1374 | C | TRP | A | 330 | -0.101 | 33.851 | -1.094 | 1.00 | 22.00 |
| 1375 | O | TRP | A | 330 | -0.919 | 34.555 | -0.487 | 1.00 | 22.73 |
| 1376 | N | GLY | A | 331 | 0.859 | 33.209 | -0.475 | 1.00 | 20.39 |
| 1377 | CA | GLY | A | 331 | 1.008 | 33.300 | 0.965 | 1.00 | 20.55 |
| 1378 | C | GLY | A | 331 | 1.145 | 34.720 | 1.457 | 1.00 | 21.75 |
| 1379 | O | GLY | A | 331 | 0.587 | 35.115 | 2.497 | 1.00 | 19.73 |
| 1380 | N | LEU | A | 332 | 1.873 | 35.557 | 0.700 | 1.00 | 22.84 |
| 1381 | CA | LEU | A | 332 | 1.961 | 36.961 | 1.110 | 1.00 | 22.28 |
| 1382 | CB | LEU | A | 332 | 2.944 | 37.709 | 0.246 | 1.00 | 21.27 |
| 1383 | CG | LEU | A | 332 | 3.139 | 39.172 | 0.577 | 1.00 | 18.71 |
| 1384 | CD1 | LEU | A | 332 | 3.820 | 39.384 | 1.877 | 1.00 | 20.46 |
| 1385 | CD2 | LEU | A | 332 | 3.933 | 39.814 | -0.506 | 1.00 | 21.41 |
| 1386 | C | LEU | A | 332 | 0.582 | 37.648 | 1.027 | 1.00 | 22.30 |
| 1387 | O | LEU | A | 332 | 0.243 | 38.522 | 1.858 | 1.00 | 22.37 |
| 1388 | N | GLY | A | 333 | -0.171 | 37.339 | -0.008 | 1.00 | 22.00 |
| 1389 | CA | GLY | A | 333 | -1.540 | 37.853 | -0.142 | 1.00 | 22.63 |
| 1390 | C | GLY | A | 333 | -2.397 | 37.495 | 1.034 | 1.00 | 22.97 |
| 1391 | O | GLY | A | 333 | -3.055 | 38.362 | 1.594 | 1.00 | 25.37 |
| 1392 | N | VAL | A | 334 | -2.374 | 36.241 | 1.452 | 1.00 | 22.24 |
| 1393 | CA | VAL | A | 334 | -3.198 | 35.770 | 2.569 | 1.00 | 22.96 |
| 1394 | CB | VAL | A | 334 | -3.078 | 34.214 | 2.780 | 1.00 | 22.80 |
| 1395 | CG1 | VAL | A | 334 | -3.894 | 33.753 | 3.950 | 1.00 | 24.31 |
| 1396 | CG2 | VAL | A | 334 | -3.531 | 33.480 | 1.532 | 1.00 | 23.21 |
| 1397 | C | VAL | A | 334 | -2.845 | 36.557 | 3.810 | 1.00 | 23.75 |
| 1398 | O | VAL | A | 334 | -3.697 | 37.208 | 4.393 | 1.00 | 22.73 |
| 1399 | N | VAL | A | 335 | -1.563 | 36.584 | 4.124 | 1.00 | 23.34 |
| 1400 | CA | VAL | A | 335 | -1.022 | 37.339 | 5.261 | 1.00 | 24.30 |
| 1401 | CB | VAL | A | 335 | 0.491 | 37.103 | 5.295 | 1.00 | 24.14 |
| 1402 | CG1 | VAL | A | 335 | 1.158 | 37.998 | 6.199 | 1.00 | 28.41 |
| 1403 | CG2 | VAL | A | 335 | 0.770 | 35.592 | 5.663 | 1.00 | 28.79 |
| 1404 | C | VAL | A | 335 | -1.364 | 38.867 | 5.279 | 1.00 | 23.24 |
| 1405 | O | VAL | A | 335 | -1.819 | 39.406 | 6.303 | 1.00 | 20.67 |
| 1406 | N | MET | A | 336 | -1.140 | 39.540 | 4.153 | 1.00 | 22.60 |
| 1407 | CA | MET | A | 336 | -1.316 | 40.929 | 4.077 | 1.00 | 22.94 |
| 1408 | CB | MET | A | 336 | -0.588 | 41.544 | 2.891 | 1.00 | 22.31 |
| 1409 | CG | MET | A | 336 | 0.905 | 41.607 | 3.027 | 1.00 | 23.13 |
| 1410 | SD | MET | A | 336 | 1.654 | 42.409 | 1.587 | 1.00 | 22.32 |
| 1411 | CE | MET | A | 336 | 1.197 | 44.017 | 1.980 | 1.00 | 19.44 |
| 1412 | C | MET | A | 336 | -2.819 | 41.208 | 4.072 | 1.00 | 23.48 |
| 1413 | O | MET | A | 336 | -3.266 | 42.194 | 4.658 | 1.00 | 23.66 |
| 1414 | N | TYR | A | 337 | -3.611 | 40.297 | 3.512 | 1.00 | 24.56 |
| 1415 | CA | TYR | A | 337 | -5.074 | 40.391 | 3.586 | 1.00 | 23.91 |
| 1416 | CB | TYR | A | 337 | -5.784 | 39.292 | 2.775 | 1.00 | 25.20 |
| 1417 | CG | TYR | A | 337 | -7.318 | 39.443 | 2.688 | 1.00 | 24.69 |
| 1418 | CD1 | TYR | A | 337 | -8.117 | 39.063 | 3.751 | 1.00 | 26.76 |

FIGURE 3 (Cont.)

| A | B | C | D | E | F | G | H | I | J |
|---|---|---|---|---|---|---|---|---|---|
| 1419 | CE1 | TYR | A | 337 | -9.494 | 39.221 | 3.710 | 1.00 | 26.34 |
| 1420 | CZ | TYR | A | 337 | -10.078 | 39.736 | 2.596 | 1.00 | 24.96 |
| 1421 | OH | TYR | A | 337 | -11.410 | 39.827 | 2.601 | 1.00 | 29.80 |
| 1422 | CE2 | TYR | A | 337 | -9.323 | 40.107 | 1.491 | 1.00 | 24.81 |
| 1423 | CD2 | TYR | A | 337 | -7.943 | 39.935 | 1.541 | 1.00 | 25.85 |
| 1424 | C | TYR | A | 337 | -5.508 | 40.338 | 5.042 | 1.00 | 25.61 |
| 1425 | O | TYR | A | 337 | -6.308 | 41.186 | 5.495 | 1.00 | 24.24 |
| 1426 | N | GLU | A | 338 | -5.019 | 39.342 | 5.790 | 1.00 | 25.95 |
| 1427 | CA | GLU | A | 338 | -5.406 | 39.214 | 7.190 | 1.00 | 25.99 |
| 1428 | CB | GLU | A | 338 | -4.705 | 38.034 | 7.823 | 1.00 | 27.58 |
| 1429 | CG | GLU | A | 338 | -5.323 | 36.701 | 7.613 | 1.00 | 30.62 |
| 1430 | CD | GLU | A | 338 | -4.532 | 35.692 | 8.422 | 1.00 | 33.37 |
| 1431 | OE1 | GLU | A | 338 | -3.446 | 35.266 | 7.928 | 1.00 | 31.77 |
| 1432 | OE2 | GLU | A | 338 | -4.982 | 35.432 | 9.550 | 1.00 | 33.89 |
| 1433 | C | GLU | A | 338 | -4.990 | 40.424 | 8.007 | 1.00 | 26.17 |
| 1434 | O | GLU | A | 338 | -5.680 | 40.819 | 8.933 | 1.00 | 26.29 |
| 1435 | N | MET | A | 339 | -3.818 | 40.965 | 7.704 | 1.00 | 24.35 |
| 1436 | CA | MET | A | 339 | -3.334 | 42.121 | 8.403 | 1.00 | 24.65 |
| 1437 | CB | MET | A | 339 | -1.916 | 42.438 | 7.956 | 1.00 | 23.26 |
| 1438 | CG | MET | A | 339 | -0.902 | 41.399 | 8.525 | 1.00 | 24.80 |
| 1439 | SD | MET | A | 339 | 0.685 | 41.928 | 8.138 | 1.00 | 25.21 |
| 1440 | CE | MET | A | 339 | 1.620 | 40.615 | 8.637 | 1.00 | 29.40 |
| 1441 | C | MET | A | 339 | -4.241 | 43.333 | 8.188 | 1.00 | 25.08 |
| 1442 | O | MET | A | 339 | -4.526 | 44.036 | 9.128 | 1.00 | 23.75 |
| 1443 | N | MET | A | 340 | -4.646 | 43.574 | 6.944 | 1.00 | 25.38 |
| 1444 | CA | MET | A | 340 | -5.375 | 44.795 | 6.579 | 1.00 | 26.68 |
| 1445 | CB | MET | A | 340 | -5.178 | 45.147 | 5.116 | 1.00 | 26.67 |
| 1446 | CG | MET | A | 340 | -3.989 | 46.011 | 4.917 | 1.00 | 29.24 |
| 1447 | SD | MET | A | 340 | -3.789 | 46.585 | 3.271 | 1.00 | 30.93 |
| 1448 | CE | MET | A | 340 | -2.757 | 45.387 | 2.505 | 1.00 | 30.32 |
| 1449 | C | MET | A | 340 | -6.836 | 44.648 | 6.803 | 1.00 | 27.77 |
| 1450 | O | MET | A | 340 | -7.481 | 45.636 | 7.123 | 1.00 | 28.64 |
| 1451 | N | CYS | A | 341 | -7.366 | 43.433 | 6.623 | 1.00 | 26.76 |
| 1452 | CA | CYS | A | 341 | -8.802 | 43.191 | 6.722 | 1.00 | 28.33 |
| 1453 | CB | CYS | A | 341 | -9.302 | 42.312 | 5.572 | 1.00 | 27.75 |
| 1454 | SG | CYS | A | 341 | -8.791 | 42.981 | 4.004 | 1.00 | 26.61 |
| 1455 | C | CYS | A | 341 | -9.229 | 42.578 | 8.059 | 1.00 | 29.48 |
| 1456 | O | CYS | A | 341 | -10.386 | 42.643 | 8.393 | 1.00 | 30.18 |
| 1457 | N | GLY | A | 342 | -8.298 | 42.015 | 8.822 | 1.00 | 29.85 |
| 1458 | CA | GLY | A | 342 | -8.640 | 41.447 | 10.122 | 1.00 | 31.16 |
| 1459 | C | GLY | A | 342 | -9.238 | 40.045 | 10.094 | 1.00 | 31.82 |
| 1460 | O | GLY | A | 342 | -9.714 | 39.576 | 11.113 | 1.00 | 33.23 |
| 1461 | N | ARG | A | 343 | -9.177 | 39.370 | 8.947 | 1.00 | 32.19 |
| 1462 | CA | ARG | A | 343 | -9.589 | 37.991 | 8.829 | 1.00 | 32.42 |
| 1463 | CB | ARG | A | 343 | -11.113 | 37.902 | 8.841 | 1.00 | 33.30 |
| 1464 | CG | BARG | A | 343 | -11.796 | 38.764 | 7.781 | 0.35 | 31.89 |
| 1465 | CG | AARG | A | 343 | -11.918 | 38.746 | 7.832 | 0.65 | 34.12 |
| 1466 | CD | BARG | A | 343 | -13.148 | 38.254 | 7.319 | 0.35 | 31.96 |
| 1467 | CD | AARG | A | 343 | -13.175 | 39.441 | 8.473 | 0.65 | 38.32 |
| 1468 | NE | BARG | A | 343 | -13.367 | 38.530 | 5.900 | 0.35 | 32.06 |
| 1469 | NE | AARG | A | 343 | -14.435 | 39.175 | 7.764 | 0.65 | 41.31 |

FIGURE 3 (Cont.)

| A | B | C | D | E | F | G | H | I | J |
|---|---|---|---|---|---|---|---|---|---|
| 1470 | CZ | BARG | A | 343 | -13.352 | 37.613 | 4.931 | 0.35 | 30.74 |
| 1471 | CZ | AARG | A | 343 | -15.581 | 39.827 | 7.990 | 0.65 | 43.68 |
| 1472 | NH1 | BARG | A | 343 | -13.162 | 36.324 | 5.198 | 0.35 | 30.79 |
| 1473 | NH1 | AARG | A | 343 | -15.654 | 40.777 | 8.918 | 0.65 | 43.55 |
| 1474 | NH2 | BARG | A | 343 | -13.558 | 37.986 | 3.683 | 0.35 | 29.28 |
| 1475 | NH2 | AARG | A | 343 | -16.668 | 39.522 | 7.282 | 0.65 | 45.91 |
| 1476 | C | ARG | A | 343 | -9.017 | 37.387 | 7.544 | 1.00 | 32.29 |
| 1477 | O | ARG | A | 343 | -8.493 | 38.119 | 6.692 | 1.00 | 30.58 |
| 1478 | N | LEU | A | 344 | -9.125 | 36.059 | 7.426 | 1.00 | 31.72 |
| 1479 | CA | LEU | A | 344 | -8.673 | 35.306 | 6.248 | 1.00 | 31.52 |
| 1480 | CB | LEU | A | 344 | -8.756 | 33.824 | 6.512 | 1.00 | 32.22 |
| 1481 | CG | LEU | A | 344 | -7.720 | 33.229 | 7.468 | 1.00 | 34.87 |
| 1482 | CD1 | LEU | A | 344 | -8.081 | 31.746 | 7.818 | 1.00 | 34.89 |
| 1483 | CD2 | LEU | A | 344 | -6.327 | 33.325 | 6.910 | 1.00 | 35.79 |
| 1484 | C | LEU | A | 344 | -9.435 | 35.663 | 4.972 | 1.00 | 30.86 |
| 1485 | O | LEU | A | 344 | -10.575 | 36.033 | 5.022 | 1.00 | 32.28 |
| 1486 | N | PRO | A | 345 | -8.807 | 35.617 | 3.818 | 1.00 | 30.36 |
| 1487 | CA | PRO | A | 345 | -9.527 | 35.895 | 2.573 | 1.00 | 30.74 |
| 1488 | CB | PRO | A | 345 | -8.419 | 35.893 | 1.523 | 1.00 | 30.06 |
| 1489 | CG | PRO | A | 345 | -7.310 | 35.200 | 2.094 | 1.00 | 29.24 |
| 1490 | CD | PRO | A | 345 | -7.383 | 35.352 | 3.575 | 1.00 | 30.15 |
| 1491 | C | PRO | A | 345 | -10.562 | 34.809 | 2.242 | 1.00 | 32.98 |
| 1492 | O | PRO | A | 345 | -11.610 | 35.115 | 1.660 | 1.00 | 32.85 |
| 1493 | N | PHE | A | 346 | -10.230 | 33.583 | 2.620 | 1.00 | 35.46 |
| 1494 | CA | PHE | A | 346 | -11.077 | 32.390 | 2.438 | 1.00 | 38.20 |
| 1495 | CB | PHE | A | 346 | -10.497 | 31.485 | 1.354 | 1.00 | 37.35 |
| 1496 | CG | PHE | A | 346 | -10.101 | 32.208 | 0.107 | 1.00 | 37.66 |
| 1497 | CD1 | PHE | A | 346 | -11.061 | 32.593 | -0.803 | 1.00 | 36.30 |
| 1498 | CE1 | PHE | A | 346 | -10.715 | 33.264 | -1.946 | 1.00 | 38.99 |
| 1499 | CZ | PHE | A | 346 | -9.367 | 33.517 | -2.219 | 1.00 | 39.01 |
| 1500 | CE2 | PHE | A | 346 | -8.395 | 33.118 | -1.319 | 1.00 | 38.76 |
| 1501 | CD2 | PHE | A | 346 | -8.768 | 32.461 | -0.166 | 1.00 | 38.36 |
| 1502 | C | PHE | A | 346 | -11.143 | 31.581 | 3.733 | 1.00 | 40.04 |
| 1503 | O | PHE | A | 346 | -10.099 | 31.219 | 4.306 | 1.00 | 40.31 |
| 1504 | N | TYR | A | 347 | -12.356 | 31.276 | 4.178 | 1.00 | 43.19 |
| 1505 | CA | TYR | A | 347 | -12.530 | 30.459 | 5.373 | 1.00 | 46.44 |
| 1506 | CB | TYR | A | 347 | -12.390 | 31.304 | 6.641 | 1.00 | 46.95 |
| 1507 | CG | TYR | A | 347 | -12.550 | 30.513 | 7.933 | 1.00 | 51.35 |
| 1508 | CD1 | TYR | A | 347 | -11.435 | 30.003 | 8.609 | 1.00 | 54.27 |
| 1509 | CE1 | TYR | A | 347 | -11.584 | 29.281 | 9.805 | 1.00 | 56.96 |
| 1510 | CZ | TYR | A | 347 | -12.868 | 29.049 | 10.321 | 1.00 | 58.71 |
| 1511 | OH | TYR | A | 347 | -13.031 | 28.340 | 11.495 | 1.00 | 58.93 |
| 1512 | CE2 | TYR | A | 347 | -13.992 | 29.536 | 9.657 | 1.00 | 56.50 |
| 1513 | CD2 | TYR | A | 347 | -13.828 | 30.262 | 8.476 | 1.00 | 54.99 |
| 1514 | C | TYR | A | 347 | -13.868 | 29.725 | 5.390 | 1.00 | 47.74 |
| 1515 | O | TYR | A | 347 | -14.894 | 30.251 | 4.937 | 1.00 | 47.69 |
| 1516 | N | ASN | A | 348 | -13.802 | 28.511 | 5.937 | 1.00 | 49.82 |
| 1517 | CA | ASN | A | 348 | -14.943 | 27.609 | 6.219 | 1.00 | 51.57 |
| 1518 | CB | ASN | A | 348 | -15.481 | 26.958 | 4.940 | 1.00 | 51.43 |
| 1519 | CG | ASN | A | 348 | -16.901 | 26.404 | 5.095 | 1.00 | 51.76 |
| 1520 | OD1 | ASN | A | 348 | -17.821 | 26.851 | 4.413 | 1.00 | 53.81 |

FIGURE 3 (Cont.)

| A | B | C | D | E | F | G | H | I | J |
|---|---|---|---|---|---|---|---|---|---|
| 1521 | ND2 | ASN | A | 348 | -17.070 | 25.412 | 5.950 | 1.00 | 48.30 |
| 1522 | C | ASN | A | 348 | -14.377 | 26.523 | 7.122 | 1.00 | 53.12 |
| 1523 | O | ASN | A | 348 | -13.306 | 25.986 | 6.828 | 1.00 | 53.73 |
| 1524 | N | GLN | A | 349 | -15.049 | 26.184 | 8.218 | 1.00 | 55.05 |
| 1525 | CA | GLN | A | 349 | -14.524 | 25.095 | 9.073 | 1.00 | 56.50 |
| 1526 | CB | GLN | A | 349 | -15.216 | 25.037 | 10.444 | 1.00 | 56.99 |
| 1527 | CG | GLN | A | 349 | -16.774 | 24.949 | 10.443 | 1.00 | 58.42 |
| 1528 | CD | GLN | A | 349 | -17.381 | 25.273 | 11.810 | 1.00 | 60.33 |
| 1529 | OE1 | GLN | A | 349 | -18.475 | 24.806 | 12.137 | 1.00 | 61.94 |
| 1530 | NE2 | GLN | A | 349 | -16.672 | 26.075 | 12.603 | 1.00 | 60.33 |
| 1531 | C | GLN | A | 349 | -14.534 | 23.720 | 8.361 | 1.00 | 56.96 |
| 1532 | O | GLN | A | 349 | -13.763 | 22.833 | 8.716 | 1.00 | 57.76 |
| 1533 | N | ASP | A | 350 | -15.392 | 23.557 | 7.358 | 1.00 | 57.16 |
| 1534 | CA | ASP | A | 350 | -15.355 | 22.380 | 6.485 | 1.00 | 57.67 |
| 1535 | CB | ASP | A | 350 | -16.676 | 22.234 | 5.678 | 1.00 | 57.53 |
| 1536 | CG | ASP | A | 350 | -16.690 | 21.001 | 4.757 | 1.00 | 58.82 |
| 1537 | OD1 | ASP | A | 350 | -17.783 | 20.647 | 4.232 | 1.00 | 60.24 |
| 1538 | OD2 | ASP | A | 350 | -15.674 | 20.319 | 4.498 | 1.00 | 59.08 |
| 1539 | C | ASP | A | 350 | -14.151 | 22.512 | 5.548 | 1.00 | 57.26 |
| 1540 | O | ASP | A | 350 | -14.223 | 23.231 | 4.553 | 1.00 | 57.25 |
| 1541 | N | HIS | A | 351 | -13.082 | 21.769 | 5.846 | 1.00 | 57.04 |
| 1542 | CA | HIS | A | 351 | -11.830 | 21.844 | 5.083 | 1.00 | 57.18 |
| 1543 | CB | HIS | A | 351 | -10.602 | 21.131 | 5.793 | 1.00 | 57.57 |
| 1544 | CG | HIS | A | 351 | -10.937 | 19.916 | 6.640 | 1.00 | 60.46 |
| 1545 | ND1 | HIS | A | 351 | -11.577 | 19.993 | 7.864 | 1.00 | 62.18 |
| 1546 | CE1 | HIS | A | 351 | -11.714 | 18.781 | 8.375 | 1.00 | 61.83 |
| 1547 | NE2 | HIS | A | 351 | -11.159 | 17.915 | 7.544 | 1.00 | 62.57 |
| 1548 | CD2 | HIS | A | 351 | -10.661 | 18.599 | 6.455 | 1.00 | 62.43 |
| 1549 | C | HIS | A | 351 | -11.956 | 21.566 | 3.543 | 1.00 | 56.47 |
| 1550 | O | HIS | A | 351 | -11.018 | 21.848 | 2.797 | 1.00 | 57.57 |
| 1551 | N | GLU | A | 352 | -13.120 | 21.099 | 3.070 | 1.00 | 55.23 |
| 1552 | CA | GLU | A | 352 | -13.424 | 20.839 | 1.631 | 1.00 | 54.01 |
| 1553 | CB | GLU | A | 352 | -14.314 | 19.540 | 1.488 | 1.00 | 54.46 |
| 1554 | CG | GLU | A | 352 | -14.939 | 19.234 | 0.094 | 1.00 | 53.70 |
| 1555 | CD | GLU | A | 352 | -16.051 | 18.145 | 0.106 | 1.00 | 54.70 |
| 1556 | OE1 | GLU | A | 352 | -16.220 | 17.450 | 1.134 | 1.00 | 51.20 |
| 1557 | OE2 | GLU | A | 352 | -16.779 | 17.980 | -0.912 | 1.00 | 52.08 |
| 1558 | C | GLU | A | 352 | -14.145 | 22.006 | 0.918 | 1.00 | 52.81 |
| 1559 | O | GLU | A | 352 | -13.940 | 22.259 | -0.283 | 1.00 | 52.24 |
| 1560 | N | LYS | A | 353 | -15.059 | 22.646 | 1.634 | 1.00 | 51.63 |
| 1561 | CA | LYS | A | 353 | -15.653 | 23.894 | 1.176 | 1.00 | 51.24 |
| 1562 | CB | LYS | A | 353 | -16.889 | 24.254 | 2.001 | 1.00 | 51.57 |
| 1563 | CG | LYS | A | 353 | -18.079 | 24.726 | 1.149 | 1.00 | 54.06 |
| 1564 | CD | LYS | A | 353 | -17.726 | 25.935 | 0.258 | 1.00 | 56.42 |
| 1565 | CE | LYS | A | 353 | -18.898 | 26.363 | -0.642 | 1.00 | 58.10 |
| 1566 | NZ | LYS | A | 353 | -18.392 | 27.159 | -1.796 | 1.00 | 59.27 |
| 1567 | C | LYS | A | 353 | -14.603 | 25.037 | 1.263 | 1.00 | 49.82 |
| 1568 | O | LYS | A | 353 | -14.643 | 25.971 | 0.494 | 1.00 | 49.33 |
| 1569 | N | LEU | A | 354 | -13.658 | 24.942 | 2.189 | 1.00 | 48.47 |
| 1570 | CA | LEU | A | 354 | -12.571 | 25.929 | 2.266 | 1.00 | 47.90 |
| 1571 | CB | LEU | A | 354 | -11.676 | 25.582 | 3.453 | 1.00 | 47.81 |

FIGURE 3 (Cont.)

| A | B | C | D | E | F | G | H | I | J |
|---|---|---|---|---|---|---|---|---|---|
| 1572 | CG | LEU | A | 354 | -10.588 | 26.524 | 3.993 | 1.00 | 48.61 |
| 1573 | CD1 | LEU | A | 354 | -9.281 | 25.733 | 4.128 | 1.00 | 47.67 |
| 1574 | CD2 | LEU | A | 354 | -10.401 | 27.842 | 3.170 | 1.00 | 48.29 |
| 1575 | C | LEU | A | 354 | -11.788 | 25.901 | 0.940 | 1.00 | 47.07 |
| 1576 | O | LEU | A | 354 | -11.523 | 26.945 | 0.337 | 1.00 | 45.95 |
| 1577 | N | PHE | A | 355 | -11.458 | 24.677 | 0.502 | 1.00 | 46.25 |
| 1578 | CA | PHE | A | 355 | -10.731 | 24.411 | -0.752 | 1.00 | 45.83 |
| 1579 | CB | PHE | A | 355 | -10.441 | 22.889 | -0.878 | 1.00 | 45.99 |
| 1580 | CG | PHE | A | 355 | -9.337 | 22.350 | 0.060 | 1.00 | 46.34 |
| 1581 | CD1 | PHE | A | 355 | -8.981 | 20.998 | 0.001 | 1.00 | 46.58 |
| 1582 | CE1 | PHE | A | 355 | -7.983 | 20.464 | 0.827 | 1.00 | 46.76 |
| 1583 | CZ | PHE | A | 355 | -7.310 | 21.279 | 1.731 | 1.00 | 46.27 |
| 1584 | CE2 | PHE | A | 355 | -7.656 | 22.646 | 1.807 | 1.00 | 49.79 |
| 1585 | CD2 | PHE | A | 355 | -8.658 | 23.170 | 0.974 | 1.00 | 48.18 |
| 1586 | C | PHE | A | 355 | -11.505 | 24.929 | -1.981 | 1.00 | 45.11 |
| 1587 | O | PHE | A | 355 | -10.941 | 25.475 | -2.929 | 1.00 | 45.61 |
| 1588 | N | GLU | A | 356 | -12.813 | 24.760 | -1.931 | 1.00 | 44.31 |
| 1589 | CA | GLU | A | 356 | -13.728 | 25.279 | -2.928 | 1.00 | 43.85 |
| 1590 | CB | GLU | A | 356 | -15.142 | 24.825 | -2.536 | 1.00 | 44.25 |
| 1591 | CG | GLU | A | 356 | -15.931 | 24.245 | -3.685 | 1.00 | 47.46 |
| 1592 | CD | GLU | A | 356 | -16.045 | 25.231 | -4.812 | 1.00 | 52.15 |
| 1593 | OE1 | GLU | A | 356 | -15.818 | 24.831 | -6.003 | 1.00 | 58.19 |
| 1594 | OE2 | GLU | A | 356 | -16.357 | 26.412 | -4.493 | 1.00 | 54.62 |
| 1595 | C | GLU | A | 356 | -13.666 | 26.813 | -3.074 | 1.00 | 41.76 |
| 1596 | O | GLU | A | 356 | -13.572 | 27.364 | -4.172 | 1.00 | 41.42 |
| 1597 | N | LEU | A | 357 | -13.736 | 27.491 | -1.942 | 1.00 | 40.21 |
| 1598 | CA | LEU | A | 357 | -13.562 | 28.931 | -1.871 | 1.00 | 39.14 |
| 1599 | CB | LEU | A | 357 | -13.674 | 29.390 | -0.409 | 1.00 | 39.64 |
| 1600 | CG | LEU | A | 357 | -15.078 | 29.129 | 0.158 | 1.00 | 40.65 |
| 1601 | CD1 | LEU | A | 357 | -15.085 | 29.180 | 1.652 | 1.00 | 41.24 |
| 1602 | CD2 | LEU | A | 357 | -16.096 | 30.146 | -0.403 | 1.00 | 42.36 |
| 1603 | C | LEU | A | 357 | -12.231 | 29.345 | -2.478 | 1.00 | 37.30 |
| 1604 | O | LEU | A | 357 | -12.184 | 30.186 | -3.380 | 1.00 | 36.31 |
| 1605 | N | ILE | A | 358 | -11.154 | 28.703 | -2.039 | 1.00 | 36.05 |
| 1606 | CA | ILE | A | 358 | -9.802 | 29.019 | -2.538 | 1.00 | 34.95 |
| 1607 | CB | ILE | A | 358 | -8.748 | 28.184 | -1.821 | 1.00 | 34.12 |
| 1608 | CG1 | ILE | A | 358 | -8.586 | 28.727 | -0.396 | 1.00 | 32.56 |
| 1609 | CD1 | ILE | A | 358 | -7.721 | 27.866 | 0.552 | 1.00 | 30.07 |
| 1610 | CG2 | ILE | A | 358 | -7.408 | 28.163 | -2.597 | 1.00 | 34.33 |
| 1611 | C | ILE | A | 358 | -9.661 | 28.886 | -4.030 | 1.00 | 36.03 |
| 1612 | O | ILE | A | 358 | -8.982 | 29.682 | -4.639 | 1.00 | 34.12 |
| 1613 | N | LEU | A | 359 | -10.340 | 27.895 | -4.609 | 1.00 | 39.61 |
| 1614 | CA | LEU | A | 359 | -10.230 | 27.561 | -6.039 | 1.00 | 42.39 |
| 1615 | CB | LEU | A | 359 | -10.584 | 26.078 | -6.267 | 1.00 | 42.51 |
| 1616 | CG | LEU | A | 359 | -9.559 | 24.926 | -6.393 | 1.00 | 42.89 |
| 1617 | CD1 | LEU | A | 359 | -8.125 | 25.343 | -6.504 | 1.00 | 40.95 |
| 1618 | CD2 | LEU | A | 359 | -9.744 | 23.885 | -5.279 | 1.00 | 43.25 |
| 1619 | C | LEU | A | 359 | -11.167 | 28.388 | -6.922 | 1.00 | 44.42 |
| 1620 | O | LEU | A | 359 | -10.829 | 28.731 | -8.062 | 1.00 | 45.88 |
| 1621 | N | MET | A | 360 | -12.325 | 28.739 | -6.385 | 1.00 | 46.72 |
| 1622 | CA | MET | A | 360 | -13.412 | 29.267 | -7.195 | 1.00 | 48.17 |

FIGURE 3 (Cont.)

| A | B | C | D | E | F | G | H | I | J |
|---|---|---|---|---|---|---|---|---|---|
| 1623 | CB | MET | A | 360 | -14.632 | 28.326 | -7.096 | 1.00 | 49.41 |
| 1624 | CG | MET | A | 360 | -14.680 | 27.176 | -8.163 | 1.00 | 51.69 |
| 1625 | SD | MET | A | 360 | -16.351 | 26.962 | -8.928 | 1.00 | 58.43 |
| 1626 | CE | MET | A | 360 | -16.575 | 28.648 | -9.824 | 1.00 | 58.74 |
| 1627 | C | MET | A | 360 | -13.832 | 30.694 | -6.858 | 1.00 | 48.64 |
| 1628 | O | MET | A | 360 | -14.245 | 31.419 | -7.752 | 1.00 | 49.12 |
| 1629 | N | GLU | A | 361 | -13.736 | 31.118 | -5.601 | 1.00 | 48.75 |
| 1630 | CA | GLU | A | 361 | -14.347 | 32.388 | -5.213 | 1.00 | 48.79 |
| 1631 | CB | GLU | A | 361 | -14.940 | 32.303 | -3.815 | 1.00 | 49.83 |
| 1632 | CG | GLU | A | 361 | -16.214 | 31.452 | -3.762 | 1.00 | 51.95 |
| 1633 | CD | GLU | A | 361 | -17.436 | 32.131 | -4.350 | 1.00 | 54.93 |
| 1634 | OE1 | GLU | A | 361 | -17.693 | 32.002 | -5.580 | 1.00 | 57.03 |
| 1635 | OE2 | GLU | A | 361 | -18.164 | 32.775 | -3.564 | 1.00 | 59.24 |
| 1636 | C | GLU | A | 361 | -13.453 | 33.611 | -5.299 | 1.00 | 47.92 |
| 1637 | O | GLU | A | 361 | -12.281 | 33.567 | -4.963 | 1.00 | 47.00 |
| 1638 | N | ASP | A | 362 | -14.039 | 34.711 | -5.758 | 1.00 | 47.18 |
| 1639 | CA | ASP | A | 362 | -13.372 | 35.996 | -5.698 | 1.00 | 47.80 |
| 1640 | CB | ASP | A | 362 | -14.005 | 37.025 | -6.638 | 1.00 | 48.22 |
| 1641 | CG | ASP | A | 362 | -14.097 | 36.515 | -8.087 | 1.00 | 52.62 |
| 1642 | OD1 | ASP | A | 362 | -13.118 | 35.858 | -8.589 | 1.00 | 56.11 |
| 1643 | OD2 | ASP | A | 362 | -15.131 | 36.716 | -8.787 | 1.00 | 55.51 |
| 1644 | C | ASP | A | 362 | -13.339 | 36.496 | -4.255 | 1.00 | 45.91 |
| 1645 | O | ASP | A | 362 | -14.067 | 36.021 | -3.392 | 1.00 | 45.58 |
| 1646 | N | ILE | A | 363 | -12.451 | 37.446 | -4.032 | 1.00 | 44.24 |
| 1647 | CA | ILE | A | 363 | -12.148 | 37.960 | -2.721 | 1.00 | 43.22 |
| 1648 | CB | ILE | A | 363 | -10.593 | 38.204 | -2.679 | 1.00 | 43.27 |
| 1649 | CG1 | ILE | A | 363 | -10.030 | 37.593 | -1.436 | 1.00 | 44.24 |
| 1650 | CD1 | ILE | A | 363 | -9.764 | 36.230 | -1.697 | 1.00 | 44.91 |
| 1651 | CG2 | ILE | A | 363 | -10.168 | 39.612 | -2.773 | 1.00 | 43.09 |
| 1652 | C | ILE | A | 363 | -12.947 | 39.238 | -2.448 | 1.00 | 42.21 |
| 1653 | O | ILE | A | 363 | -13.185 | 39.999 | -3.360 | 1.00 | 41.03 |
| 1654 | N | LYS | A | 364 | -13.288 | 39.482 | -1.186 | 1.00 | 41.18 |
| 1655 | CA | LYS | A | 364 | -14.006 | 40.670 | -0.783 | 1.00 | 40.95 |
| 1656 | CB | LYS | A | 364 | -15.184 | 40.277 | 0.113 | 1.00 | 42.05 |
| 1657 | CG | LYS | A | 364 | -16.183 | 39.328 | -0.554 | 1.00 | 45.36 |
| 1658 | CD | LYS | A | 364 | -17.033 | 40.063 | -1.583 | 1.00 | 48.93 |
| 1659 | CE | LYS | A | 364 | -16.894 | 39.503 | -3.020 | 1.00 | 52.44 |
| 1660 | NZ | LYS | A | 364 | -17.249 | 40.555 | -4.069 | 1.00 | 53.14 |
| 1661 | C | LYS | A | 364 | -13.085 | 41.588 | 0.002 | 1.00 | 39.51 |
| 1662 | O | LYS | A | 364 | -12.164 | 41.113 | 0.682 | 1.00 | 39.63 |
| 1663 | N | PHE | A | 365 | -13.365 | 42.888 | -0.051 | 1.00 | 37.00 |
| 1664 | CA | PHE | A | 365 | -12.588 | 43.868 | 0.680 | 1.00 | 35.91 |
| 1665 | CB | PHE | A | 365 | -11.854 | 44.809 | -0.272 | 1.00 | 34.55 |
| 1666 | CG | PHE | A | 365 | -10.890 | 44.124 | -1.131 | 1.00 | 30.42 |
| 1667 | CD1 | PHE | A | 365 | -9.877 | 43.383 | -0.576 | 1.00 | 27.71 |
| 1668 | CE1 | PHE | A | 365 | -8.967 | 42.682 | -1.391 | 1.00 | 29.34 |
| 1669 | CZ | PHE | A | 365 | -9.110 | 42.742 | -2.764 | 1.00 | 29.57 |
| 1670 | CE2 | PHE | A | 365 | -10.158 | 43.478 | -3.319 | 1.00 | 29.35 |
| 1671 | CD2 | PHE | A | 365 | -11.056 | 44.123 | -2.517 | 1.00 | 30.70 |
| 1672 | C | PHE | A | 365 | -13.351 | 44.752 | 1.603 | 1.00 | 36.02 |
| 1673 | O | PHE | A | 365 | -14.424 | 45.198 | 1.310 | 1.00 | 36.91 |

FIGURE 3 (Cont.)

| A | B | C | D | E | F | G | H | I | J |
|---|---|---|---|---|---|---|---|---|---|
| 1674 | N | PRO | A | 366 | -12.710 | 45.130 | 2.673 | 1.00 | 36.16 |
| 1675 | CA | PRO | A | 366 | -13.226 | 46.250 | 3.428 | 1.00 | 37.46 |
| 1676 | CB | PRO | A | 366 | -12.126 | 46.549 | 4.460 | 1.00 | 36.81 |
| 1677 | CG | PRO | A | 366 | -11.486 | 45.218 | 4.644 | 1.00 | 36.81 |
| 1678 | CD | PRO | A | 366 | -11.465 | 44.602 | 3.232 | 1.00 | 36.07 |
| 1679 | C | PRO | A | 366 | -13.475 | 47.450 | 2.500 | 1.00 | 38.55 |
| 1680 | O | PRO | A | 366 | -12.977 | 47.640 | 1.366 | 1.00 | 39.00 |
| 1681 | N | ARG | A | 367 | -14.241 | 48.308 | 3.116 | 1.00 | 39.26 |
| 1682 | CA | ARG | A | 367 | -15.023 | 49.326 | 2.505 | 1.00 | 40.33 |
| 1683 | CB | ARG | A | 367 | -16.019 | 49.782 | 3.606 | 1.00 | 41.38 |
| 1684 | CG | ARG | A | 367 | -15.509 | 49.548 | 5.114 | 1.00 | 45.68 |
| 1685 | CD | ARG | A | 367 | -15.283 | 48.047 | 5.655 | 1.00 | 50.12 |
| 1686 | NE | ARG | A | 367 | -16.462 | 47.215 | 5.922 | 1.00 | 53.34 |
| 1687 | CZ | ARG | A | 367 | -17.154 | 46.483 | 5.026 | 1.00 | 57.31 |
| 1688 | NH1 | ARG | A | 367 | -18.200 | 45.776 | 5.450 | 1.00 | 59.86 |
| 1689 | NH2 | ARG | A | 367 | -16.863 | 46.469 | 3.724 | 1.00 | 56.70 |
| 1690 | C | ARG | A | 367 | -14.055 | 50.435 | 2.065 | 1.00 | 37.75 |
| 1691 | O | ARG | A | 367 | -13.906 | 50.704 | 0.879 | 1.00 | 40.28 |
| 1692 | N | THR | A | 368 | -13.305 | 50.967 | 3.014 | 1.00 | 35.18 |
| 1693 | CA | THR | A | 368 | -12.385 | 52.061 | 2.738 | 1.00 | 33.03 |
| 1694 | CB | THR | A | 368 | -12.404 | 53.047 | 3.891 | 1.00 | 33.16 |
| 1695 | OG1 | THR | A | 368 | -11.896 | 52.366 | 5.026 | 1.00 | 36.38 |
| 1696 | CG2 | THR | A | 368 | -13.834 | 53.474 | 4.261 | 1.00 | 29.83 |
| 1697 | C | THR | A | 368 | -10.957 | 51.613 | 2.489 | 1.00 | 30.70 |
| 1698 | O | THR | A | 368 | -10.015 | 52.441 | 2.579 | 1.00 | 30.15 |
| 1699 | N | LEU | A | 369 | -10.765 | 50.333 | 2.155 | 1.00 | 28.12 |
| 1700 | CA | LEU | A | 369 | -9.416 | 49.868 | 1.812 | 1.00 | 27.00 |
| 1701 | CB | LEU | A | 369 | -9.397 | 48.377 | 1.524 | 1.00 | 26.90 |
| 1702 | CG | LEU | A | 369 | -8.042 | 47.752 | 1.745 | 1.00 | 30.37 |
| 1703 | CD1 | LEU | A | 369 | -7.693 | 47.822 | 3.210 | 1.00 | 29.49 |
| 1704 | CD2 | LEU | A | 369 | -7.933 | 46.309 | 1.153 | 1.00 | 30.63 |
| 1705 | C | LEU | A | 369 | -8.947 | 50.616 | 0.574 | 1.00 | 25.48 |
| 1706 | O | LEU | A | 369 | -9.711 | 50.832 | -0.361 | 1.00 | 24.10 |
| 1707 | N | SER | A | 370 | -7.687 | 51.017 | 0.545 | 1.00 | 24.38 |
| 1708 | CA | SER | A | 370 | -7.208 | 51.804 | -0.583 | 1.00 | 22.17 |
| 1709 | CB | SER | A | 370 | -5.799 | 52.371 | -0.325 | 1.00 | 22.58 |
| 1710 | OG | SER | A | 370 | -4.822 | 51.380 | -0.381 | 1.00 | 20.99 |
| 1711 | C | SER | A | 370 | -7.258 | 51.030 | -1.872 | 1.00 | 22.21 |
| 1712 | O | SER | A | 370 | -7.169 | 49.793 | -1.916 | 1.00 | 20.67 |
| 1713 | N | SER | A | 371 | -7.411 | 51.777 | -2.959 | 1.00 | 22.30 |
| 1714 | CA | SER | A | 371 | -7.315 | 51.188 | -4.282 | 1.00 | 22.80 |
| 1715 | CB | SER | A | 371 | -7.461 | 52.278 | -5.347 | 1.00 | 22.40 |
| 1716 | OG | SER | A | 371 | -7.342 | 51.692 | -6.600 | 1.00 | 25.38 |
| 1717 | C | SER | A | 371 | -6.047 | 50.388 | -4.517 | 1.00 | 22.20 |
| 1718 | O | SER | A | 371 | -6.068 | 49.347 | -5.129 | 1.00 | 21.30 |
| 1719 | N | ASP | A | 372 | -4.915 | 50.938 | -4.121 | 1.00 | 23.02 |
| 1720 | CA | ASP | A | 372 | -3.644 | 50.245 | -4.293 | 1.00 | 23.39 |
| 1721 | CB | ASP | A | 372 | -2.476 | 51.120 | -3.816 | 1.00 | 22.52 |
| 1722 | CG | ASP | A | 372 | -2.114 | 52.198 | -4.806 | 1.00 | 24.79 |
| 1723 | OD1 | ASP | A | 372 | -1.344 | 53.107 | -4.459 | 1.00 | 22.99 |
| 1724 | OD2 | ASP | A | 372 | -2.582 | 52.236 | -5.963 | 1.00 | 28.01 |

FIGURE 3 (Cont.)

| A | B | C | D | E | F | G | H | I | J |
|---|---|---|---|---|---|---|---|---|---|
| 1725 | C | ASP | A | 372 | -3.587 | 48.950 | -3.491 | 1.00 | 22.58 |
| 1726 | O | ASP | A | 372 | -2.969 | 48.022 | -3.901 | 1.00 | 21.66 |
| 1727 | N | ALA | A | 373 | -4.129 | 48.955 | -2.283 | 1.00 | 21.68 |
| 1728 | CA | ALA | A | 373 | -4.153 | 47.779 | -1.456 | 1.00 | 22.27 |
| 1729 | CB | ALA | A | 373 | -4.609 | 48.147 | -0.021 | 1.00 | 22.26 |
| 1730 | C | ALA | A | 373 | -5.037 | 46.686 | -2.067 | 1.00 | 23.08 |
| 1731 | O | ALA | A | 373 | -4.670 | 45.524 | -2.069 | 1.00 | 22.70 |
| 1732 | N | LYS | A | 374 | -6.175 | 47.060 | -2.634 | 1.00 | 22.62 |
| 1733 | CA | LYS | A | 374 | -7.073 | 46.075 | -3.196 | 1.00 | 23.42 |
| 1734 | CB | LYS | A | 374 | -8.424 | 46.684 | -3.607 | 1.00 | 23.83 |
| 1735 | CG | LYS | A | 374 | -9.309 | 47.132 | -2.479 | 1.00 | 25.80 |
| 1736 | CD | LYS | A | 374 | -10.572 | 47.821 | -3.049 | 1.00 | 27.80 |
| 1737 | CE | LYS | A | 374 | -11.473 | 48.281 | -1.905 | 1.00 | 31.69 |
| 1738 | NZ | LYS | A | 374 | -12.476 | 49.294 | -2.384 | 1.00 | 30.22 |
| 1739 | C | LYS | A | 374 | -6.427 | 45.501 | -4.466 | 1.00 | 23.08 |
| 1740 | O | LYS | A | 374 | -6.561 | 44.340 | -4.733 | 1.00 | 22.25 |
| 1741 | N | SER | A | 375 | -5.771 | 46.355 | -5.258 | 1.00 | 22.20 |
| 1742 | CA | SER | A | 375 | -4.981 | 45.913 | -6.397 | 1.00 | 21.43 |
| 1743 | CB | SER | A | 375 | -4.334 | 47.136 | -7.024 | 1.00 | 21.77 |
| 1744 | OG | SER | A | 375 | -3.615 | 46.753 | -8.161 | 1.00 | 22.52 |
| 1745 | C | SER | A | 375 | -3.876 | 44.922 | -5.969 | 1.00 | 22.71 |
| 1746 | O | SER | A | 375 | -3.722 | 43.816 | -6.526 | 1.00 | 21.85 |
| 1747 | N | LEU | A | 376 | -3.068 | 45.324 | -4.984 | 1.00 | 21.22 |
| 1748 | CA | LEU | A | 376 | -2.029 | 44.431 | -4.482 | 1.00 | 20.80 |
| 1749 | CB | LEU | A | 376 | -1.322 | 45.044 | -3.248 | 1.00 | 20.99 |
| 1750 | CG | LEU | A | 376 | -0.202 | 44.166 | -2.705 | 1.00 | 20.69 |
| 1751 | CD1 | LEU | A | 376 | 0.955 | 44.266 | -3.629 | 1.00 | 23.78 |
| 1752 | CD2 | LEU | A | 376 | 0.119 | 44.618 | -1.351 | 1.00 | 24.66 |
| 1753 | C | LEU | A | 376 | -2.598 | 43.065 | -4.064 | 1.00 | 21.97 |
| 1754 | O | LEU | A | 376 | -2.126 | 42.081 | -4.462 | 1.00 | 19.49 |
| 1755 | N | LEU | A | 377 | -3.587 | 43.043 | -3.184 | 1.00 | 22.81 |
| 1756 | CA | LEU | A | 377 | -4.137 | 41.800 | -2.658 | 1.00 | 23.06 |
| 1757 | CB | LEU | A | 377 | -5.091 | 42.090 | -1.521 | 1.00 | 22.89 |
| 1758 | CG | LEU | A | 377 | -4.452 | 42.763 | -0.306 | 1.00 | 19.08 |
| 1759 | CD1 | LEU | A | 377 | -5.535 | 43.114 | 0.670 | 1.00 | 20.77 |
| 1760 | CD2 | LEU | A | 377 | -3.453 | 41.839 | 0.367 | 1.00 | 19.05 |
| 1761 | C | LEU | A | 377 | -4.824 | 40.953 | -3.726 | 1.00 | 24.65 |
| 1762 | O | LEU | A | 377 | -4.638 | 39.772 | -3.795 | 1.00 | 25.34 |
| 1763 | N | SER | A | 378 | -5.536 | 41.596 | -4.612 | 1.00 | 25.56 |
| 1764 | CA | SER | A | 378 | -6.118 | 40.961 | -5.767 | 1.00 | 25.91 |
| 1765 | CB | SER | A | 378 | -6.922 | 42.000 | -6.590 | 1.00 | 26.65 |
| 1766 | OG | SER | A | 378 | -8.064 | 42.409 | -5.862 | 1.00 | 28.99 |
| 1767 | C | SER | A | 378 | -5.068 | 40.334 | -6.653 | 1.00 | 23.59 |
| 1768 | O | SER | A | 378 | -5.193 | 39.192 | -7.031 | 1.00 | 23.67 |
| 1769 | N | GLY | A | 379 | -3.978 | 41.029 | -6.872 | 1.00 | 23.65 |
| 1770 | CA | GLY | A | 379 | -2.888 | 40.517 | -7.709 | 1.00 | 22.69 |
| 1771 | C | GLY | A | 379 | -2.162 | 39.329 | -7.129 | 1.00 | 22.67 |
| 1772 | O | GLY | A | 379 | -1.849 | 38.377 | -7.800 | 1.00 | 23.04 |
| 1773 | N | LEU | A | 380 | -1.859 | 39.423 | -5.855 | 1.00 | 21.45 |
| 1774 | CA | LEU | A | 380 | -1.238 | 38.387 | -5.100 | 1.00 | 20.56 |
| 1775 | CB | LEU | A | 380 | -1.021 | 38.957 | -3.702 | 1.00 | 21.00 |

FIGURE 3 (Cont.)

| A | B | C | D | E | F | G | H | I | J |
|---|---|---|---|---|---|---|---|---|---|
| 1776 | CG | LEU | A | 380 | 0.373 | 39.457 | -3.262 | 1.00 | 22.83 |
| 1777 | CD1 | LEU | A | 380 | 1.413 | 39.633 | -4.259 | 1.00 | 21.55 |
| 1778 | CD2 | LEU | A | 380 | 0.280 | 40.515 | -2.295 | 1.00 | 17.21 |
| 1779 | C | LEU | A | 380 | -2.185 | 37.160 | -4.972 | 1.00 | 21.14 |
| 1780 | O | LEU | A | 380 | -1.729 | 36.022 | -4.795 | 1.00 | 17.68 |
| 1781 | N | LEU | A | 381 | -3.492 | 37.410 | -4.958 | 1.00 | 20.72 |
| 1782 | CA | LEU | A | 381 | -4.446 | 36.310 | -4.774 | 1.00 | 22.48 |
| 1783 | CB | LEU | A | 381 | -5.447 | 36.588 | -3.620 | 1.00 | 21.24 |
| 1784 | CG | LEU | A | 381 | -4.844 | 36.788 | -2.225 | 1.00 | 20.38 |
| 1785 | CD1 | LEU | A | 381 | -5.907 | 37.276 | -1.254 | 1.00 | 17.61 |
| 1786 | CD2 | LEU | A | 381 | -4.206 | 35.547 | -1.667 | 1.00 | 23.69 |
| 1787 | C | LEU | A | 381 | -5.112 | 35.890 | -6.094 | 1.00 | 23.69 |
| 1788 | O | LEU | A | 381 | -6.142 | 35.176 | -6.089 | 1.00 | 23.96 |
| 1789 | N | ILE | A | 382 | -4.512 | 36.279 | -7.227 | 1.00 | 25.79 |
| 1790 | CA | ILE | A | 382 | -4.885 | 35.696 | -8.520 | 1.00 | 25.97 |
| 1791 | CB | ILE | A | 382 | -4.092 | 36.333 | -9.643 | 1.00 | 26.32 |
| 1792 | CG1 | ILE | A | 382 | -4.722 | 37.649 | -10.014 | 1.00 | 27.81 |
| 1793 | CD1 | ILE | A | 382 | -3.884 | 38.550 | -10.779 | 1.00 | 30.39 |
| 1794 | CG2 | ILE | A | 382 | -4.096 | 35.388 | -10.922 | 1.00 | 26.07 |
| 1795 | C | ILE | A | 382 | -4.690 | 34.181 | -8.516 | 1.00 | 26.92 |
| 1796 | O | ILE | A | 382 | -3.664 | 33.663 | -8.157 | 1.00 | 28.50 |
| 1797 | N | LYS | A | 383 | -5.669 | 33.429 | -8.958 | 1.00 | 29.20 |
| 1798 | CA | LYS | A | 383 | -5.655 | 31.984 | -8.753 | 1.00 | 29.11 |
| 1799 | CB | LYS | A | 383 | -7.078 | 31.460 | -8.992 | 1.00 | 32.04 |
| 1800 | CG | LYS | A | 383 | -8.143 | 32.326 | -8.264 | 1.00 | 33.86 |
| 1801 | CD | LYS | A | 383 | -8.969 | 31.477 | -7.402 | 1.00 | 35.60 |
| 1802 | CE | LYS | A | 383 | -10.044 | 32.291 | -6.720 | 1.00 | 36.10 |
| 1803 | NZ | LYS | A | 383 | -9.881 | 32.207 | -5.244 | 1.00 | 34.32 |
| 1804 | C | LYS | A | 383 | -4.620 | 31.233 | -9.598 | 1.00 | 28.49 |
| 1805 | O | LYS | A | 383 | -3.989 | 30.266 | -9.173 | 1.00 | 27.51 |
| 1806 | N | ASP | A | 384 | -4.440 | 31.712 | -10.796 | 1.00 | 29.41 |
| 1807 | CA | ASP | A | 384 | -3.462 | 31.200 | -11.728 | 1.00 | 29.33 |
| 1808 | CB | ASP | A | 384 | -3.894 | 31.680 | -13.133 | 1.00 | 29.51 |
| 1809 | CG | ASP | A | 384 | -3.019 | 31.140 | -14.233 | 1.00 | 30.60 |
| 1810 | OD1 | ASP | A | 384 | -2.006 | 30.474 | -13.925 | 1.00 | 34.66 |
| 1811 | OD2 | ASP | A | 384 | -3.248 | 31.358 | -15.425 | 1.00 | 35.44 |
| 1812 | C | ASP | A | 384 | -2.075 | 31.758 | -11.323 | 1.00 | 29.29 |
| 1813 | O | ASP | A | 384 | -1.883 | 32.929 | -11.455 | 1.00 | 29.71 |
| 1814 | N | PRO | A | 385 | -1.120 | 30.924 | -10.884 | 1.00 | 29.04 |
| 1815 | CA | PRO | A | 385 | 0.234 | 31.375 | -10.534 | 1.00 | 29.78 |
| 1816 | CB | PRO | A | 385 | 0.945 | 30.084 | -10.145 | 1.00 | 30.14 |
| 1817 | CG | PRO | A | 385 | 0.155 | 28.967 | -10.913 | 1.00 | 29.06 |
| 1818 | CD | PRO | A | 385 | -1.256 | 29.467 | -10.735 | 1.00 | 29.42 |
| 1819 | C | PRO | A | 385 | 1.026 | 32.058 | -11.631 | 1.00 | 30.30 |
| 1820 | O | PRO | A | 385 | 1.841 | 32.936 | -11.306 | 1.00 | 30.73 |
| 1821 | N | ASN | A | 386 | 0.762 | 31.703 | -12.881 | 1.00 | 31.15 |
| 1822 | CA | ASN | A | 386 | 1.349 | 32.371 | -14.065 | 1.00 | 31.67 |
| 1823 | CB | ASN | A | 386 | 0.988 | 31.637 | -15.343 | 1.00 | 31.33 |
| 1824 | CG | ASN | A | 386 | 1.570 | 30.219 | -15.402 | 1.00 | 34.84 |
| 1825 | OD1 | ASN | A | 386 | 0.879 | 29.306 | -15.819 | 1.00 | 44.08 |
| 1826 | ND2 | ASN | A | 386 | 2.836 | 30.048 | -15.016 | 1.00 | 32.10 |

FIGURE 3 (Cont.)

| A | B | C | D | E | F | G | H | I | J |
|---|---|---|---|---|---|---|---|---|---|
| 1827 | C | ASN | A | 386 | 0.890 | 33.814 | -14.239 | 1.00 | 30.94 |
| 1828 | O | ASN | A | 386 | 1.598 | 34.600 | -14.809 | 1.00 | 30.43 |
| 1829 | N | LYS | A | 387 | -0.301 | 34.139 | -13.760 | 1.00 | 30.69 |
| 1830 | CA | LYS | A | 387 | -0.803 | 35.512 | -13.863 | 1.00 | 29.83 |
| 1831 | CB | LYS | A | 387 | -2.222 | 35.495 | -14.430 | 1.00 | 30.94 |
| 1832 | CG | LYS | A | 387 | -2.274 | 34.773 | -15.820 | 1.00 | 32.59 |
| 1833 | CD | LYS | A | 387 | -3.631 | 34.909 | -16.513 | 1.00 | 39.54 |
| 1834 | CE | LYS | A | 387 | -3.577 | 34.278 | -17.971 | 1.00 | 40.66 |
| 1835 | NZ | LYS | A | 387 | -4.900 | 34.292 | -18.593 | 1.00 | 43.91 |
| 1836 | C | LYS | A | 387 | -0.740 | 36.293 | -12.542 | 1.00 | 28.98 |
| 1837 | O | LYS | A | 387 | -1.099 | 37.469 | -12.497 | 1.00 | 29.61 |
| 1838 | N | ARG | A | 388 | -0.308 | 35.637 | -11.483 | 1.00 | 27.31 |
| 1839 | CA | ARG | A | 388 | -0.260 | 36.251 | -10.153 | 1.00 | 27.19 |
| 1840 | CB | ARG | A | 388 | 0.076 | 35.220 | -9.132 | 1.00 | 28.06 |
| 1841 | CG | ARG | A | 388 | -0.311 | 35.508 | -7.736 | 1.00 | 30.64 |
| 1842 | CD | ARG | A | 388 | -1.231 | 34.409 | -7.246 | 1.00 | 35.37 |
| 1843 | NE | ARG | A | 388 | -0.379 | 33.393 | -6.794 | 1.00 | 34.52 |
| 1844 | CZ | ARG | A | 388 | -0.552 | 32.095 | -6.897 | 1.00 | 28.75 |
| 1845 | NH1 | ARG | A | 388 | 0.403 | 31.412 | -6.387 | 1.00 | 22.65 |
| 1846 | NH2 | ARG | A | 388 | -1.622 | 31.474 | -7.392 | 1.00 | 29.50 |
| 1847 | C | ARG | A | 388 | 0.846 | 37.235 | -10.140 | 1.00 | 25.87 |
| 1848 | O | ARG | A | 388 | 1.885 | 37.049 | -10.756 | 1.00 | 24.16 |
| 1849 | N | LEU | A | 389 | 0.614 | 38.306 | -9.422 | 1.00 | 25.00 |
| 1850 | CA | LEU | A | 389 | 1.650 | 39.264 | -9.142 | 1.00 | 23.41 |
| 1851 | CB | LEU | A | 389 | 0.992 | 40.329 | -8.282 | 1.00 | 23.54 |
| 1852 | CG | LEU | A | 389 | 1.429 | 41.786 | -8.294 | 1.00 | 27.87 |
| 1853 | CD1 | LEU | A | 389 | 1.814 | 42.232 | -6.911 | 1.00 | 29.84 |
| 1854 | CD2 | LEU | A | 389 | 2.352 | 42.341 | -9.406 | 1.00 | 26.92 |
| 1855 | C | LEU | A | 389 | 2.820 | 38.550 | -8.443 | 1.00 | 22.99 |
| 1856 | O | LEU | A | 389 | 2.618 | 37.806 | -7.491 | 1.00 | 23.84 |
| 1857 | N | GLY | A | 390 | 4.028 | 38.757 | -8.937 | 1.00 | 22.57 |
| 1858 | CA | GLY | A | 390 | 5.171 | 38.022 | -8.479 | 1.00 | 24.76 |
| 1859 | C | GLY | A | 390 | 5.462 | 36.755 | -9.272 | 1.00 | 25.49 |
| 1860 | O | GLY | A | 390 | 6.560 | 36.252 | -9.223 | 1.00 | 25.05 |
| 1861 | N | GLY | A | 391 | 4.494 | 36.324 | -10.062 | 1.00 | 25.79 |
| 1862 | CA | GLY | A | 391 | 4.552 | 35.071 | -10.780 | 1.00 | 26.23 |
| 1863 | C | GLY | A | 391 | 5.373 | 35.073 | -12.060 | 1.00 | 26.20 |
| 1864 | O | GLY | A | 391 | 5.618 | 34.017 | -12.612 | 1.00 | 26.40 |
| 1865 | N | GLY | A | 392 | 5.776 | 36.244 | -12.522 | 1.00 | 25.86 |
| 1866 | CA | GLY | A | 392 | 6.556 | 36.382 | -13.731 | 1.00 | 25.32 |
| 1867 | C | GLY | A | 392 | 8.042 | 36.281 | -13.504 | 1.00 | 25.44 |
| 1868 | O | GLY | A | 392 | 8.539 | 36.045 | -12.384 | 1.00 | 25.02 |
| 1869 | N | PRO | A | 393 | 8.789 | 36.387 | -14.590 | 1.00 | 25.41 |
| 1870 | CA | PRO | A | 393 | 10.225 | 36.097 | -14.513 | 1.00 | 26.39 |
| 1871 | CB | PRO | A | 393 | 10.703 | 36.201 | -15.960 | 1.00 | 27.00 |
| 1872 | CG | PRO | A | 393 | 9.638 | 37.096 | -16.640 | 1.00 | 26.70 |
| 1873 | CD | PRO | A | 393 | 8.339 | 36.791 | -15.932 | 1.00 | 25.06 |
| 1874 | C | PRO | A | 393 | 10.935 | 37.094 | -13.590 | 1.00 | 26.47 |
| 1875 | O | PRO | A | 393 | 12.004 | 36.778 | -13.165 | 1.00 | 26.90 |
| 1876 | N | ASP | A | 394 | 10.332 | 38.222 | -13.225 | 1.00 | 25.87 |
| 1877 | CA | ASP | A | 394 | 10.992 | 39.181 | -12.318 | 1.00 | 24.47 |

FIGURE 3 (Cont.)

| A | B | C | D | E | F | G | H | I | J |
|---|---|---|---|---|---|---|---|---|---|
| 1878 | CB | ASP | A | 394 | 10.736 | 40.648 | -12.729 | 1.00 | 24.62 |
| 1879 | CG | ASP | A | 394 | 11.988 | 41.468 | -12.742 | 1.00 | 24.07 |
| 1880 | OD1 | ASP | A | 394 | 11.928 | 42.718 | -12.927 | 1.00 | 26.04 |
| 1881 | OD2 | ASP | A | 394 | 13.090 | 40.940 | -12.630 | 1.00 | 24.86 |
| 1882 | C | ASP | A | 394 | 10.631 | 38.969 | -10.858 | 1.00 | 23.80 |
| 1883 | O | ASP | A | 394 | 11.187 | 39.628 | -9.965 | 1.00 | 22.60 |
| 1884 | N | ASP | A | 395 | 9.734 | 38.026 | -10.616 | 1.00 | 21.96 |
| 1885 | CA | ASP | A | 395 | 9.475 | 37.543 | -9.271 | 1.00 | 22.30 |
| 1886 | CB | ASP | A | 395 | 10.671 | 36.700 | -8.791 | 1.00 | 22.70 |
| 1887 | CG | ASP | A | 395 | 10.380 | 35.954 | -7.519 | 1.00 | 22.50 |
| 1888 | OD1 | ASP | A | 395 | 9.392 | 35.204 | -7.506 | 1.00 | 26.26 |
| 1889 | OD2 | ASP | A | 395 | 11.051 | 36.034 | -6.489 | 1.00 | 25.40 |
| 1890 | C | ASP | A | 395 | 9.102 | 38.729 | -8.340 | 1.00 | 22.76 |
| 1891 | O | ASP | A | 395 | 8.213 | 39.544 | -8.654 | 1.00 | 22.84 |
| 1892 | N | ALA | A | 396 | 9.826 | 38.876 | -7.252 | 1.00 | 22.47 |
| 1893 | CA | ALA | A | 396 | 9.578 | 39.898 | -6.261 | 1.00 | 22.79 |
| 1894 | CB | ALA | A | 396 | 10.571 | 39.801 | -5.197 | 1.00 | 23.11 |
| 1895 | C | ALA | A | 396 | 9.587 | 41.304 | -6.798 | 1.00 | 22.58 |
| 1896 | O | ALA | A | 396 | 8.958 | 42.146 | -6.220 | 1.00 | 20.87 |
| 1897 | N | LYS | A | 397 | 10.295 | 41.564 | -7.885 | 1.00 | 23.02 |
| 1898 | CA | LYS | A | 397 | 10.462 | 42.922 | -8.338 | 1.00 | 24.03 |
| 1899 | CB | LYS | A | 397 | 11.461 | 43.014 | -9.479 | 1.00 | 25.88 |
| 1900 | CG | LYS | A | 397 | 12.896 | 43.233 | -9.111 | 1.00 | 30.61 |
| 1901 | CD | LYS | A | 397 | 13.417 | 42.140 | -8.245 | 1.00 | 35.25 |
| 1902 | CE | LYS | A | 397 | 14.934 | 42.394 | -8.034 | 1.00 | 40.34 |
| 1903 | NZ | LYS | A | 397 | 15.504 | 42.087 | -6.656 | 1.00 | 45.17 |
| 1904 | C | LYS | A | 397 | 9.119 | 43.459 | -8.806 | 1.00 | 23.48 |
| 1905 | O | LYS | A | 397 | 8.864 | 44.669 | -8.695 | 1.00 | 22.60 |
| 1906 | N | GLU | A | 398 | 8.260 | 42.552 | -9.281 | 1.00 | 21.91 |
| 1907 | CA | GLU | A | 398 | 6.907 | 42.881 | -9.647 | 1.00 | 23.99 |
| 1908 | CB | GLU | A | 398 | 6.098 | 41.645 | -10.048 | 1.00 | 23.58 |
| 1909 | CG | GLU | A | 398 | 6.289 | 41.228 | -11.456 | 1.00 | 27.46 |
| 1910 | CD | GLU | A | 398 | 5.391 | 40.033 | -11.846 | 1.00 | 30.18 |
| 1911 | OE1 | GLU | A | 398 | 5.935 | 39.043 | -12.369 | 1.00 | 33.71 |
| 1912 | OE2 | GLU | A | 398 | 4.172 | 40.102 | -11.601 | 1.00 | 28.91 |
| 1913 | C | GLU | A | 398 | 6.178 | 43.455 | -8.488 | 1.00 | 23.30 |
| 1914 | O | GLU | A | 398 | 5.492 | 44.460 | -8.620 | 1.00 | 24.99 |
| 1915 | N | ILE | A | 399 | 6.307 | 42.793 | -7.341 | 1.00 | 22.84 |
| 1916 | CA | ILE | A | 399 | 5.702 | 43.310 | -6.125 | 1.00 | 23.19 |
| 1917 | CB | ILE | A | 399 | 5.646 | 42.231 | -5.004 | 1.00 | 22.86 |
| 1918 | CG1 | ILE | A | 399 | 4.583 | 41.225 | -5.427 | 1.00 | 23.49 |
| 1919 | CD1 | ILE | A | 399 | 4.976 | 39.905 | -5.538 | 1.00 | 25.82 |
| 1920 | CG2 | ILE | A | 399 | 5.245 | 42.836 | -3.687 | 1.00 | 22.11 |
| 1921 | C | ILE | A | 399 | 6.356 | 44.605 | -5.715 | 1.00 | 22.04 |
| 1922 | O | ILE | A | 399 | 5.634 | 45.548 | -5.363 | 1.00 | 23.81 |
| 1923 | N | MET | A | 400 | 7.659 | 44.726 | -5.852 | 1.00 | 20.53 |
| 1924 | CA | MET | A | 400 | 8.325 | 45.897 | -5.353 | 1.00 | 21.03 |
| 1925 | CB | MET | A | 400 | 9.867 | 45.746 | -5.384 | 1.00 | 21.58 |
| 1926 | CG | MET | A | 400 | 10.401 | 44.690 | -4.472 | 1.00 | 23.46 |
| 1927 | SD | MET | A | 400 | 12.106 | 44.216 | -4.838 | 1.00 | 29.54 |
| 1928 | CE | MET | A | 400 | 12.604 | 43.298 | -3.286 | 1.00 | 31.81 |

FIGURE 3 (Cont.)

| A | B | C | D | E | F | G | H | I | J |
|---|---|---|---|---|---|---|---|---|---|
| 1929 | C | MET | A | 400 | 7.994 | 47.121 | -6.145 | 1.00 | 21.59 |
| 1930 | O | MET | A | 400 | 8.085 | 48.263 | -5.616 | 1.00 | 22.30 |
| 1931 | N | ARG | A | 401 | 7.651 | 46.931 | -7.405 | 1.00 | 20.30 |
| 1932 | CA | ARG | A | 401 | 7.253 | 48.046 | -8.231 | 1.00 | 21.83 |
| 1933 | CB | ARG | A | 401 | 7.596 | 47.746 | -9.693 | 1.00 | 23.06 |
| 1934 | CG | ARG | A | 401 | 9.103 | 47.676 | -10.044 | 1.00 | 22.65 |
| 1935 | CD | ARG | A | 401 | 9.294 | 47.663 | -11.547 | 1.00 | 22.94 |
| 1936 | NE | ARG | A | 401 | 8.754 | 46.442 | -12.137 | 1.00 | 23.02 |
| 1937 | CZ | ARG | A | 401 | 9.395 | 45.325 | -12.402 | 1.00 | 19.80 |
| 1938 | NH1 | ARG | A | 401 | 10.674 | 45.161 | -12.136 | 1.00 | 24.84 |
| 1939 | NH2 | ARG | A | 401 | 8.724 | 44.335 | -12.913 | 1.00 | 26.97 |
| 1940 | C | ARG | A | 401 | 5.749 | 48.314 | -8.185 | 1.00 | 22.19 |
| 1941 | O | ARG | A | 401 | 5.276 | 49.156 | -8.919 | 1.00 | 21.78 |
| 1942 | N | HIS | A | 402 | 4.979 | 47.512 | -7.448 | 1.00 | 21.47 |
| 1943 | CA | HIS | A | 402 | 3.562 | 47.719 | -7.343 | 1.00 | 20.51 |
| 1944 | CB | HIS | A | 402 | 2.852 | 46.531 | -6.652 | 1.00 | 20.79 |
| 1945 | CG | HIS | A | 402 | 1.353 | 46.605 | -6.678 | 1.00 | 19.59 |
| 1946 | ND1 | HIS | A | 402 | 0.640 | 47.421 | -5.835 | 1.00 | 19.56 |
| 1947 | CE1 | HIS | A | 402 | -0.651 | 47.326 | -6.114 | 1.00 | 21.36 |
| 1948 | NE2 | HIS | A | 402 | -0.797 | 46.449 | -7.095 | 1.00 | 23.41 |
| 1949 | CD2 | HIS | A | 402 | 0.444 | 46.009 | -7.485 | 1.00 | 18.75 |
| 1950 | C | HIS | A | 402 | 3.282 | 49.054 | -6.628 | 1.00 | 21.62 |
| 1951 | O | HIS | A | 402 | 3.979 | 49.504 | -5.729 | 1.00 | 18.86 |
| 1952 | N | SER | A | 403 | 2.215 | 49.697 | -7.082 | 1.00 | 22.89 |
| 1953 | CA | SER | A | 403 | 1.838 | 51.003 | -6.605 | 1.00 | 22.72 |
| 1954 | CB | SER | A | 403 | 0.509 | 51.392 | -7.290 | 1.00 | 24.02 |
| 1955 | OG | SER | A | 403 | 0.265 | 52.733 | -6.951 | 1.00 | 28.87 |
| 1956 | C | SER | A | 403 | 1.656 | 51.060 | -5.102 | 1.00 | 22.42 |
| 1957 | O | SER | A | 403 | 1.924 | 52.074 | -4.479 | 1.00 | 23.13 |
| 1958 | N | PHE | A | 404 | 1.221 | 49.952 | -4.501 | 1.00 | 21.81 |
| 1959 | CA | PHE | A | 404 | 1.080 | 49.884 | -3.071 | 1.00 | 22.26 |
| 1960 | CB | PHE | A | 404 | 0.536 | 48.530 | -2.637 | 1.00 | 22.38 |
| 1961 | CG | PHE | A | 404 | 0.273 | 48.440 | -1.166 | 1.00 | 22.06 |
| 1962 | CD1 | PHE | A | 404 | 1.167 | 47.814 | -0.331 | 1.00 | 21.86 |
| 1963 | CE1 | PHE | A | 404 | 0.936 | 47.748 | 1.028 | 1.00 | 21.39 |
| 1964 | CZ | PHE | A | 404 | -0.211 | 48.283 | 1.574 | 1.00 | 19.95 |
| 1965 | CE2 | PHE | A | 404 | -1.087 | 48.966 | 0.751 | 1.00 | 20.66 |
| 1966 | CD2 | PHE | A | 404 | -0.859 | 49.029 | -0.603 | 1.00 | 21.93 |
| 1967 | C | PHE | A | 404 | 2.428 | 50.161 | -2.357 | 1.00 | 21.35 |
| 1968 | O | PHE | A | 404 | 2.433 | 50.698 | -1.243 | 1.00 | 21.12 |
| 1969 | N | PHE | A | 405 | 3.539 | 49.790 | -2.996 | 1.00 | 19.75 |
| 1970 | CA | PHE | A | 405 | 4.860 | 49.971 | -2.392 | 1.00 | 19.62 |
| 1971 | CB | PHE | A | 405 | 5.675 | 48.706 | -2.536 | 1.00 | 18.03 |
| 1972 | CG | PHE | A | 405 | 5.206 | 47.582 | -1.682 | 1.00 | 18.03 |
| 1973 | CD1 | PHE | A | 405 | 5.267 | 47.681 | -0.300 | 1.00 | 19.80 |
| 1974 | CE1 | PHE | A | 405 | 4.837 | 46.666 | 0.512 | 1.00 | 18.66 |
| 1975 | CZ | PHE | A | 405 | 4.341 | 45.519 | -0.031 | 1.00 | 15.34 |
| 1976 | CE2 | PHE | A | 405 | 4.234 | 45.417 | -1.397 | 1.00 | 17.61 |
| 1977 | CD2 | PHE | A | 405 | 4.653 | 46.441 | -2.230 | 1.00 | 16.41 |
| 1978 | C | PHE | A | 405 | 5.609 | 51.183 | -2.966 | 1.00 | 20.75 |
| 1979 | O | PHE | A | 405 | 6.817 | 51.283 | -2.823 | 1.00 | 23.52 |

FIGURE 3 (Cont.)

| A | B | C | D | E | F | G | H | I | J |
|---|---|---|---|---|---|---|---|---|---|
| 1980 | N | SER | A | 406 | 4.915 | 52.100 | -3.627 | 1.00 | 22.64 |
| 1981 | CA | SER | A | 406 | 5.594 | 53.163 | -4.402 | 1.00 | 23.48 |
| 1982 | CB | SER | A | 406 | 4.570 | 53.889 | -5.324 | 1.00 | 23.96 |
| 1983 | OG | SER | A | 406 | 3.695 | 54.675 | -4.509 | 1.00 | 23.82 |
| 1984 | C | SER | A | 406 | 6.397 | 54.178 | -3.556 | 1.00 | 21.75 |
| 1985 | O | SER | A | 406 | 7.174 | 54.934 | -4.068 | 1.00 | 23.27 |
| 1986 | N | GLY | A | 407 | 6.205 | 54.243 | -2.261 | 1.00 | 21.80 |
| 1987 | CA | GLY | A | 407 | 7.026 | 55.107 | -1.439 | 1.00 | 21.90 |
| 1988 | C | GLY | A | 407 | 8.216 | 54.357 | -0.812 | 1.00 | 21.96 |
| 1989 | O | GLY | A | 407 | 8.852 | 54.896 | 0.033 | 1.00 | 23.84 |
| 1990 | N | VAL | A | 408 | 8.521 | 53.148 | -1.237 | 1.00 | 21.10 |
| 1991 | CA | VAL | A | 408 | 9.391 | 52.276 | -0.472 | 1.00 | 21.32 |
| 1992 | CB | VAL | A | 408 | 8.799 | 50.858 | -0.315 | 1.00 | 22.06 |
| 1993 | CG1 | VAL | A | 408 | 9.803 | 49.902 | 0.229 | 1.00 | 22.65 |
| 1994 | CG2 | VAL | A | 408 | 7.567 | 50.852 | 0.616 | 1.00 | 21.48 |
| 1995 | C | VAL | A | 408 | 10.707 | 52.175 | -1.193 | 1.00 | 21.03 |
| 1996 | O | VAL | A | 408 | 10.775 | 51.882 | -2.393 | 1.00 | 20.85 |
| 1997 | N | ASN | A | 409 | 11.749 | 52.461 | -0.450 | 1.00 | 21.24 |
| 1998 | CA | ASN | A | 409 | 13.118 | 52.248 | -0.900 | 1.00 | 20.19 |
| 1999 | CB | ASN | A | 409 | 14.085 | 53.406 | -0.457 | 1.00 | 19.61 |
| 2000 | CG | ASN | A | 409 | 15.473 | 53.129 | -0.896 | 1.00 | 19.94 |
| 2001 | OD1 | ASN | A | 409 | 16.031 | 52.087 | -0.494 | 1.00 | 17.58 |
| 2002 | ND2 | ASN | A | 409 | 16.050 | 54.003 | -1.769 | 1.00 | 17.83 |
| 2003 | C | ASN | A | 409 | 13.580 | 50.891 | -0.486 | 1.00 | 18.85 |
| 2004 | O | ASN | A | 409 | 13.685 | 50.589 | 0.685 | 1.00 | 17.89 |
| 2005 | N | TRP | A | 410 | 13.833 | 50.017 | -1.471 | 1.00 | 20.00 |
| 2006 | CA | TRP | A | 410 | 13.980 | 48.585 | -1.212 | 1.00 | 21.26 |
| 2007 | CB | TRP | A | 410 | 13.666 | 47.765 | -2.505 | 1.00 | 21.93 |
| 2008 | CG | TRP | A | 410 | 12.206 | 47.803 | -2.723 | 1.00 | 20.75 |
| 2009 | CD1 | TRP | A | 410 | 11.511 | 48.682 | -3.496 | 1.00 | 23.23 |
| 2010 | NE1 | TRP | A | 410 | 10.161 | 48.496 | -3.331 | 1.00 | 22.45 |
| 2011 | CE2 | TRP | A | 410 | 9.946 | 47.494 | -2.439 | 1.00 | 19.65 |
| 2012 | CD2 | TRP | A | 410 | 11.227 | 47.038 | -2.015 | 1.00 | 18.81 |
| 2013 | CE3 | TRP | A | 410 | 11.294 | 46.037 | -1.052 | 1.00 | 17.41 |
| 2014 | CZ3 | TRP | A | 410 | 10.097 | 45.445 | -0.614 | 1.00 | 20.70 |
| 2015 | CH2 | TRP | A | 410 | 8.838 | 45.938 | -1.052 | 1.00 | 21.14 |
| 2016 | CZ2 | TRP | A | 410 | 8.760 | 46.950 | -1.981 | 1.00 | 20.79 |
| 2017 | C | TRP | A | 410 | 15.307 | 48.161 | -0.588 | 1.00 | 20.95 |
| 2018 | O | TRP | A | 410 | 15.327 | 47.230 | 0.166 | 1.00 | 19.59 |
| 2019 | N | GLN | A | 411 | 16.406 | 48.846 | -0.899 | 1.00 | 22.22 |
| 2020 | CA | GLN | A | 411 | 17.674 | 48.714 | -0.147 | 1.00 | 22.23 |
| 2021 | CB | GLN | A | 411 | 18.802 | 49.597 | -0.782 | 1.00 | 23.65 |
| 2022 | CG | GLN | A | 411 | 20.169 | 49.429 | -0.074 | 1.00 | 25.69 |
| 2023 | CD | GLN | A | 411 | 20.643 | 47.957 | -0.120 | 1.00 | 30.36 |
| 2024 | OE1 | GLN | A | 411 | 20.610 | 47.402 | -1.152 | 1.00 | 28.17 |
| 2025 | NE2 | GLN | A | 411 | 20.909 | 47.327 | 1.038 | 1.00 | 34.46 |
| 2026 | C | GLN | A | 411 | 17.493 | 49.093 | 1.303 | 1.00 | 22.40 |
| 2027 | O | GLN | A | 411 | 18.027 | 48.421 | 2.201 | 1.00 | 20.94 |
| 2028 | N | ASP | A | 412 | 16.733 | 50.170 | 1.557 | 1.00 | 21.51 |
| 2029 | CA | ASP | A | 412 | 16.431 | 50.572 | 2.926 | 1.00 | 21.10 |
| 2030 | CB | ASP | A | 412 | 15.631 | 51.829 | 2.928 | 1.00 | 22.05 |

FIGURE 3 (Cont.)

| A | B | C | D | E | F | G | H | I | J |
|---|---|---|---|---|---|---|---|---|---|
| 2031 | CG | ASP | A | 412 | 16.469 | 53.044 | 2.783 | 1.00 | 19.94 |
| 2032 | OD1 | ASP | A | 412 | 17.737 | 52.991 | 2.812 | 1.00 | 24.36 |
| 2033 | OD2 | ASP | A | 412 | 15.897 | 54.107 | 2.721 | 1.00 | 20.95 |
| 2034 | C | ASP | A | 412 | 15.650 | 49.544 | 3.690 | 1.00 | 21.78 |
| 2035 | O | ASP | A | 412 | 15.854 | 49.373 | 4.901 | 1.00 | 20.06 |
| 2036 | N | VAL | A | 413 | 14.779 | 48.818 | 2.975 | 1.00 | 21.64 |
| 2037 | CA | VAL | A | 413 | 14.027 | 47.748 | 3.602 | 1.00 | 21.09 |
| 2038 | CB | VAL | A | 413 | 13.016 | 47.113 | 2.628 | 1.00 | 19.13 |
| 2039 | CG1 | VAL | A | 413 | 12.553 | 45.776 | 3.193 | 1.00 | 20.70 |
| 2040 | CG2 | VAL | A | 413 | 11.863 | 48.056 | 2.390 | 1.00 | 20.59 |
| 2041 | C | VAL | A | 413 | 15.023 | 46.689 | 4.120 | 1.00 | 20.22 |
| 2042 | O | VAL | A | 413 | 15.051 | 46.352 | 5.297 | 1.00 | 19.97 |
| 2043 | N | TYR | A | 414 | 15.843 | 46.205 | 3.207 | 1.00 | 20.15 |
| 2044 | CA | TYR | A | 414 | 16.903 | 45.243 | 3.491 | 1.00 | 21.63 |
| 2045 | CB | TYR | A | 414 | 17.748 | 44.983 | 2.226 | 1.00 | 22.22 |
| 2046 | CG | TYR | A | 414 | 18.777 | 43.884 | 2.479 | 1.00 | 24.78 |
| 2047 | CD1 | TYR | A | 414 | 18.409 | 42.524 | 2.406 | 1.00 | 24.53 |
| 2048 | CE1 | TYR | A | 414 | 19.328 | 41.526 | 2.668 | 1.00 | 27.65 |
| 2049 | CZ | TYR | A | 414 | 20.619 | 41.858 | 3.038 | 1.00 | 28.09 |
| 2050 | OH | TYR | A | 414 | 21.498 | 40.847 | 3.350 | 1.00 | 32.73 |
| 2051 | CE2 | TYR | A | 414 | 21.001 | 43.195 | 3.159 | 1.00 | 27.24 |
| 2052 | CD2 | TYR | A | 414 | 20.064 | 44.188 | 2.899 | 1.00 | 27.58 |
| 2053 | C | TYR | A | 414 | 17.810 | 45.710 | 4.660 | 1.00 | 22.73 |
| 2054 | O | TYR | A | 414 | 18.086 | 44.949 | 5.588 | 1.00 | 22.31 |
| 2055 | N | ASP | A | 415 | 18.177 | 46.996 | 4.660 | 1.00 | 22.94 |
| 2056 | CA | ASP | A | 415 | 19.134 | 47.551 | 5.639 | 1.00 | 23.16 |
| 2057 | CB | ASP | A | 415 | 19.807 | 48.758 | 5.050 | 1.00 | 23.08 |
| 2058 | CG | ASP | A | 415 | 20.720 | 48.395 | 3.895 | 1.00 | 25.89 |
| 2059 | OD1 | ASP | A | 415 | 20.929 | 49.233 | 2.983 | 1.00 | 29.00 |
| 2060 | OD2 | ASP | A | 415 | 21.241 | 47.286 | 3.780 | 1.00 | 26.31 |
| 2061 | C | ASP | A | 415 | 18.485 | 47.896 | 6.938 | 1.00 | 23.66 |
| 2062 | O | ASP | A | 415 | 19.094 | 48.467 | 7.813 | 1.00 | 24.22 |
| 2063 | N | LYS | A | 416 | 17.206 | 47.570 | 7.043 | 1.00 | 25.07 |
| 2064 | CA | LYS | A | 416 | 16.420 | 47.765 | 8.217 | 1.00 | 25.99 |
| 2065 | CB | LYS | A | 416 | 16.989 | 46.950 | 9.397 | 1.00 | 26.96 |
| 2066 | CG | LYS | A | 416 | 16.948 | 45.483 | 9.186 | 1.00 | 29.79 |
| 2067 | CD | LYS | A | 416 | 16.738 | 44.711 | 10.568 | 1.00 | 35.94 |
| 2068 | CE | LYS | A | 416 | 17.992 | 44.188 | 11.167 | 1.00 | 39.00 |
| 2069 | NZ | LYS | A | 416 | 17.970 | 44.186 | 12.743 | 1.00 | 40.95 |
| 2070 | C | LYS | A | 416 | 16.338 | 49.241 | 8.590 | 1.00 | 26.66 |
| 2071 | O | LYS | A | 416 | 16.466 | 49.613 | 9.750 | 1.00 | 24.87 |
| 2072 | N | LYS | A | 417 | 16.073 | 50.064 | 7.588 | 1.00 | 27.31 |
| 2073 | CA | LYS | A | 417 | 16.082 | 51.486 | 7.754 | 1.00 | 28.26 |
| 2074 | CB | LYS | A | 417 | 17.017 | 52.097 | 6.670 | 1.00 | 29.63 |
| 2075 | CG | LYS | A | 417 | 18.539 | 52.114 | 7.037 | 1.00 | 28.45 |
| 2076 | CD | LYS | A | 417 | 19.367 | 52.793 | 5.951 | 1.00 | 30.01 |
| 2077 | CE | LYS | A | 417 | 20.891 | 52.512 | 6.060 | 1.00 | 33.67 |
| 2078 | NZ | LYS | A | 417 | 21.686 | 53.031 | 4.835 | 1.00 | 33.46 |
| 2079 | C | LYS | A | 417 | 14.677 | 52.091 | 7.690 | 1.00 | 28.78 |
| 2080 | O | LYS | A | 417 | 14.517 | 53.251 | 7.978 | 1.00 | 30.72 |
| 2081 | N | LEU | A | 418 | 13.650 | 51.329 | 7.323 | 1.00 | 29.45 |

FIGURE 3 (Cont.)

| A | B | C | D | E | F | G | H | I | J |
|---|---|---|---|---|---|---|---|---|---|
| 2082 | CA | LEU | A | 418 | 12.285 | 51.761 | 7.594 | 1.00 | 29.40 |
| 2083 | CB | LEU | A | 418 | 11.274 | 50.835 | 6.914 | 1.00 | 30.94 |
| 2084 | CG | LEU | A | 418 | 10.880 | 51.211 | 5.458 | 1.00 | 32.69 |
| 2085 | CD1 | LEU | A | 418 | 12.001 | 51.683 | 4.712 | 1.00 | 34.76 |
| 2086 | CD2 | LEU | A | 418 | 10.268 | 50.051 | 4.737 | 1.00 | 34.40 |
| 2087 | C | LEU | A | 418 | 12.047 | 51.822 | 9.098 | 1.00 | 29.69 |
| 2088 | O | LEU | A | 418 | 12.482 | 50.935 | 9.871 | 1.00 | 26.46 |
| 2089 | N | VAL | A | 419 | 11.333 | 52.851 | 9.545 | 1.00 | 29.40 |
| 2090 | CA | VAL | A | 419 | 11.012 | 52.882 | 10.961 | 1.00 | 30.43 |
| 2091 | CB | VAL | A | 419 | 10.930 | 54.349 | 11.618 | 1.00 | 32.72 |
| 2092 | CG1 | VAL | A | 419 | 11.277 | 55.480 | 10.663 | 1.00 | 33.99 |
| 2093 | CG2 | VAL | A | 419 | 9.648 | 54.589 | 12.404 | 1.00 | 34.20 |
| 2094 | C | VAL | A | 419 | 9.808 | 51.956 | 11.272 | 1.00 | 28.60 |
| 2095 | O | VAL | A | 419 | 8.743 | 52.072 | 10.673 | 1.00 | 25.54 |
| 2096 | N | PRO | A | 420 | 10.006 | 51.010 | 12.193 | 1.00 | 27.23 |
| 2097 | CA | PRO | A | 420 | 8.912 | 50.088 | 12.520 | 1.00 | 27.53 |
| 2098 | CB | PRO | A | 420 | 9.538 | 49.127 | 13.497 | 1.00 | 27.62 |
| 2099 | CG | PRO | A | 420 | 11.075 | 49.318 | 13.322 | 1.00 | 27.85 |
| 2100 | CD | PRO | A | 420 | 11.213 | 50.773 | 13.015 | 1.00 | 26.27 |
| 2101 | C | PRO | A | 420 | 7.708 | 50.862 | 13.123 | 1.00 | 27.87 |
| 2102 | O | PRO | A | 420 | 7.943 | 51.732 | 13.925 | 1.00 | 27.33 |
| 2103 | N | PRO | A | 421 | 6.479 | 50.606 | 12.668 | 1.00 | 28.50 |
| 2104 | CA | PRO | A | 421 | 5.314 | 51.391 | 13.093 | 1.00 | 30.22 |
| 2105 | CB | PRO | A | 421 | 4.249 | 51.069 | 12.013 | 1.00 | 29.67 |
| 2106 | CG | PRO | A | 421 | 4.562 | 49.708 | 11.676 | 1.00 | 31.16 |
| 2107 | CD | PRO | A | 421 | 6.086 | 49.577 | 11.702 | 1.00 | 29.18 |
| 2108 | C | PRO | A | 421 | 4.904 | 50.908 | 14.472 | 1.00 | 30.35 |
| 2109 | O | PRO | A | 421 | 4.150 | 51.578 | 15.109 | 1.00 | 31.07 |
| 2110 | N | PHE | A | 422 | 5.462 | 49.814 | 14.960 | 1.00 | 29.87 |
| 2111 | CA | PHE | A | 422 | 5.173 | 49.415 | 16.329 | 1.00 | 29.83 |
| 2112 | CB | PHE | A | 422 | 4.052 | 48.383 | 16.317 | 1.00 | 30.01 |
| 2113 | CG | PHE | A | 422 | 3.969 | 47.548 | 17.585 | 1.00 | 31.16 |
| 2114 | CD1 | PHE | A | 422 | 4.598 | 46.308 | 17.654 | 1.00 | 32.25 |
| 2115 | CE1 | PHE | A | 422 | 4.520 | 45.550 | 18.795 | 1.00 | 37.66 |
| 2116 | CZ | PHE | A | 422 | 3.828 | 46.026 | 19.903 | 1.00 | 36.57 |
| 2117 | CE2 | PHE | A | 422 | 3.187 | 47.253 | 19.848 | 1.00 | 37.96 |
| 2118 | CD2 | PHE | A | 422 | 3.255 | 48.011 | 18.680 | 1.00 | 34.72 |
| 2119 | C | PHE | A | 422 | 6.412 | 48.841 | 16.987 | 1.00 | 30.29 |
| 2120 | O | PHE | A | 422 | 7.038 | 47.935 | 16.449 | 1.00 | 28.19 |
| 2121 | N | LYS | A | 423 | 6.740 | 49.352 | 18.158 | 1.00 | 31.32 |
| 2122 | CA | LYS | A | 423 | 7.936 | 48.924 | 18.850 | 1.00 | 33.43 |
| 2123 | CB | LYS | A | 423 | 8.721 | 50.117 | 19.424 | 1.00 | 34.50 |
| 2124 | CG | LYS | A | 423 | 9.831 | 49.720 | 20.456 | 1.00 | 35.22 |
| 2125 | CD | LYS | A | 423 | 10.746 | 48.590 | 19.971 | 1.00 | 36.64 |
| 2126 | CE | LYS | A | 423 | 11.998 | 48.516 | 20.826 | 1.00 | 36.51 |
| 2127 | NZ | LYS | A | 423 | 11.718 | 47.780 | 22.051 | 1.00 | 38.24 |
| 2128 | C | LYS | A | 423 | 7.485 | 48.017 | 19.973 | 1.00 | 34.81 |
| 2129 | O | LYS | A | 423 | 6.814 | 48.507 | 20.895 | 1.00 | 33.83 |
| 2130 | N | PRO | A | 424 | 7.853 | 46.717 | 19.921 | 1.00 | 35.00 |
| 2131 | CA | PRO | A | 424 | 7.546 | 45.798 | 21.010 | 1.00 | 35.97 |
| 2132 | CB | PRO | A | 424 | 8.339 | 44.547 | 20.630 | 1.00 | 35.53 |

FIGURE 3 (Cont.)

| A | B | C | D | E | F | G | H | I | J |
|---|---|---|---|---|---|---|---|---|---|
| 2133 | CG | PRO | A | 424 | 8.330 | 44.548 | 19.180 | 1.00 | 34.10 |
| 2134 | CD | PRO | A | 424 | 8.579 | 46.010 | 18.850 | 1.00 | 35.64 |
| 2135 | C | PRO | A | 424 | 8.026 | 46.395 | 22.338 | 1.00 | 37.94 |
| 2136 | O | PRO | A | 424 | 9.167 | 46.910 | 22.430 | 1.00 | 37.46 |
| 2137 | N | GLN | A | 425 | 7.157 | 46.351 | 23.343 | 1.00 | 40.33 |
| 2138 | CA | GLN | A | 425 | 7.487 | 46.923 | 24.661 | 1.00 | 42.24 |
| 2139 | CB | GLN | A | 425 | 6.214 | 47.384 | 25.385 | 1.00 | 43.16 |
| 2140 | CG | GLN | A | 425 | 5.936 | 48.936 | 25.321 | 1.00 | 46.35 |
| 2141 | CD | GLN | A | 425 | 6.620 | 49.592 | 24.144 | 1.00 | 48.96 |
| 2142 | OE1 | GLN | A | 425 | 6.304 | 49.259 | 23.040 | 1.00 | 53.98 |
| 2143 | NE2 | GLN | A | 425 | 7.597 | 50.469 | 24.386 | 1.00 | 52.45 |
| 2144 | C | GLN | A | 425 | 8.263 | 45.878 | 25.495 | 1.00 | 42.95 |
| 2145 | O | GLN | A | 425 | 7.705 | 45.293 | 26.430 | 1.00 | 42.55 |
| 2146 | N | VAL | A | 426 | 9.536 | 45.669 | 25.138 | 1.00 | 43.39 |
| 2147 | CA | VAL | A | 426 | 10.438 | 44.766 | 25.872 | 1.00 | 43.92 |
| 2148 | CB | VAL | A | 426 | 11.038 | 43.658 | 24.970 | 1.00 | 43.70 |
| 2149 | CG1 | VAL | A | 426 | 9.985 | 42.684 | 24.569 | 1.00 | 43.77 |
| 2150 | CG2 | VAL | A | 426 | 11.727 | 44.219 | 23.754 | 1.00 | 43.47 |
| 2151 | C | VAL | A | 426 | 11.553 | 45.546 | 26.588 | 1.00 | 44.64 |
| 2152 | O | VAL | A | 426 | 12.107 | 46.500 | 26.041 | 1.00 | 45.88 |
| 2153 | N | THR | A | 427 | 11.820 | 45.160 | 27.836 | 1.00 | 44.79 |
| 2154 | CA | THR | A | 427 | 12.910 | 45.687 | 28.672 | 1.00 | 44.72 |
| 2155 | CB | THR | A | 427 | 13.044 | 44.765 | 29.945 | 1.00 | 45.67 |
| 2156 | OG1 | THR | A | 427 | 11.771 | 44.572 | 30.570 | 1.00 | 45.88 |
| 2157 | CG2 | THR | A | 427 | 13.978 | 45.368 | 31.031 | 1.00 | 47.03 |
| 2158 | C | THR | A | 427 | 14.251 | 45.580 | 27.988 | 1.00 | 43.87 |
| 2159 | O | THR | A | 427 | 15.124 | 46.390 | 28.206 | 1.00 | 43.43 |
| 2160 | N | SER | A | 428 | 14.432 | 44.490 | 27.240 | 1.00 | 43.22 |
| 2161 | CA | SER | A | 428 | 15.750 | 44.048 | 26.807 | 1.00 | 43.00 |
| 2162 | CB | SER | A | 428 | 16.549 | 43.537 | 28.008 | 1.00 | 43.29 |
| 2163 | OG | SER | A | 428 | 16.176 | 42.212 | 28.361 | 1.00 | 42.86 |
| 2164 | C | SER | A | 428 | 15.678 | 42.908 | 25.804 | 1.00 | 42.85 |
| 2165 | O | SER | A | 428 | 14.587 | 42.444 | 25.442 | 1.00 | 42.37 |
| 2166 | N | GLU | A | 429 | 16.855 | 42.433 | 25.405 | 1.00 | 42.00 |
| 2167 | CA | GLU | A | 429 | 16.958 | 41.395 | 24.373 | 1.00 | 41.86 |
| 2168 | CB | GLU | A | 429 | 18.392 | 41.282 | 23.831 | 1.00 | 42.00 |
| 2169 | CG | GLU | A | 429 | 19.464 | 41.213 | 24.911 | 1.00 | 44.58 |
| 2170 | CD | GLU | A | 429 | 20.813 | 40.763 | 24.395 | 1.00 | 46.71 |
| 2171 | OE1 | GLU | A | 429 | 21.786 | 40.801 | 25.166 | 1.00 | 50.93 |
| 2172 | OE2 | GLU | A | 429 | 20.918 | 40.354 | 23.236 | 1.00 | 49.36 |
| 2173 | C | GLU | A | 429 | 16.494 | 40.022 | 24.868 | 1.00 | 39.92 |
| 2174 | O | GLU | A | 429 | 16.091 | 39.186 | 24.043 | 1.00 | 38.13 |
| 2175 | N | THR | A | 430 | 16.538 | 39.803 | 26.193 | 1.00 | 37.87 |
| 2176 | CA | THR | A | 430 | 16.103 | 38.532 | 26.773 | 1.00 | 37.09 |
| 2177 | CB | THR | A | 430 | 17.030 | 38.020 | 27.926 | 1.00 | 37.40 |
| 2178 | OG1 | THR | A | 430 | 17.222 | 39.039 | 28.898 | 1.00 | 37.24 |
| 2179 | CG2 | THR | A | 430 | 18.446 | 37.697 | 27.412 | 1.00 | 36.76 |
| 2180 | C | THR | A | 430 | 14.684 | 38.520 | 27.267 | 1.00 | 36.35 |
| 2181 | O | THR | A | 430 | 14.144 | 37.430 | 27.501 | 1.00 | 37.32 |
| 2182 | N | ASP | A | 431 | 14.099 | 39.701 | 27.481 | 1.00 | 35.32 |
| 2183 | CA | ASP | A | 431 | 12.751 | 39.825 | 28.010 | 1.00 | 34.00 |

FIGURE 3 (Cont.)

| A | B | C | D | E | F | G | H | I | J |
|---|---|---|---|---|---|---|---|---|---|
| 2184 | CB | ASP | A | 431 | 12.249 | 41.234 | 27.786 | 1.00 | 34.47 |
| 2185 | CG | ASP | A | 431 | 10.979 | 41.503 | 28.525 | 1.00 | 36.77 |
| 2186 | OD1 | ASP | A | 431 | 10.662 | 42.670 | 28.723 | 1.00 | 38.12 |
| 2187 | OD2 | ASP | A | 431 | 10.216 | 40.612 | 28.943 | 1.00 | 42.23 |
| 2188 | C | ASP | A | 431 | 11.788 | 38.854 | 27.338 | 1.00 | 33.21 |
| 2189 | O | ASP | A | 431 | 11.702 | 38.800 | 26.109 | 1.00 | 32.19 |
| 2190 | N | THR | A | 432 | 11.081 | 38.071 | 28.130 | 1.00 | 31.83 |
| 2191 | CA | THR | A | 432 | 10.233 | 37.035 | 27.604 | 1.00 | 31.40 |
| 2192 | CB | THR | A | 432 | 10.485 | 35.711 | 28.367 | 1.00 | 31.74 |
| 2193 | OG1 | THR | A | 432 | 10.261 | 35.890 | 29.776 | 1.00 | 31.99 |
| 2194 | CG2 | THR | A | 432 | 11.939 | 35.263 | 28.248 | 1.00 | 28.05 |
| 2195 | C | THR | A | 432 | 8.754 | 37.401 | 27.659 | 1.00 | 32.43 |
| 2196 | O | THR | A | 432 | 7.924 | 36.553 | 27.418 | 1.00 | 32.58 |
| 2197 | N | ARG | A | 433 | 8.423 | 38.668 | 27.935 | 1.00 | 33.65 |
| 2198 | CA | ARG | A | 433 | 7.042 | 39.050 | 28.233 | 1.00 | 35.22 |
| 2199 | CB | ARG | A | 433 | 6.911 | 40.578 | 28.468 | 1.00 | 35.84 |
| 2200 | CG | ARG | A | 433 | 6.976 | 41.406 | 27.245 | 1.00 | 41.16 |
| 2201 | CD | ARG | A | 433 | 7.511 | 42.814 | 27.473 | 1.00 | 46.88 |
| 2202 | NE | ARG | A | 433 | 6.739 | 43.559 | 28.468 | 1.00 | 51.54 |
| 2203 | CZ | ARG | A | 433 | 7.202 | 44.040 | 29.623 | 1.00 | 52.25 |
| 2204 | NH1 | ARG | A | 433 | 8.462 | 43.887 | 29.985 | 1.00 | 51.87 |
| 2205 | NH2 | ARG | A | 433 | 6.371 | 44.696 | 30.429 | 1.00 | 55.75 |
| 2206 | C | ARG | A | 433 | 6.018 | 38.567 | 27.195 | 1.00 | 35.19 |
| 2207 | O | ARG | A | 433 | 4.938 | 38.125 | 27.575 | 1.00 | 35.41 |
| 2208 | N | TYR | A | 434 | 6.360 | 38.606 | 25.900 | 1.00 | 35.19 |
| 2209 | CA | TYR | A | 434 | 5.389 | 38.215 | 24.863 | 1.00 | 34.44 |
| 2210 | CB | TYR | A | 434 | 5.766 | 38.779 | 23.482 | 1.00 | 33.67 |
| 2211 | CG | TYR | A | 434 | 5.509 | 40.295 | 23.420 | 1.00 | 30.77 |
| 2212 | CD1 | TYR | A | 434 | 6.540 | 41.182 | 23.425 | 1.00 | 30.05 |
| 2213 | CE1 | TYR | A | 434 | 6.334 | 42.533 | 23.400 | 1.00 | 31.95 |
| 2214 | CZ | TYR | A | 434 | 5.038 | 43.016 | 23.357 | 1.00 | 32.36 |
| 2215 | OH | TYR | A | 434 | 4.836 | 44.365 | 23.290 | 1.00 | 36.03 |
| 2216 | CE2 | TYR | A | 434 | 3.977 | 42.147 | 23.362 | 1.00 | 31.16 |
| 2217 | CD2 | TYR | A | 434 | 4.215 | 40.799 | 23.398 | 1.00 | 28.00 |
| 2218 | C | TYR | A | 434 | 5.152 | 36.734 | 24.843 | 1.00 | 35.43 |
| 2219 | O | TYR | A | 434 | 4.047 | 36.297 | 24.585 | 1.00 | 35.51 |
| 2220 | N | PHE | A | 435 | 6.177 | 35.953 | 25.135 | 1.00 | 36.65 |
| 2221 | CA | PHE | A | 435 | 5.974 | 34.531 | 25.333 | 1.00 | 38.18 |
| 2222 | CB | PHE | A | 435 | 7.316 | 33.811 | 25.490 | 1.00 | 37.99 |
| 2223 | CG | PHE | A | 435 | 8.123 | 33.825 | 24.255 | 1.00 | 36.69 |
| 2224 | CD1 | PHE | A | 435 | 9.045 | 34.822 | 24.032 | 1.00 | 36.40 |
| 2225 | CE1 | PHE | A | 435 | 9.821 | 34.827 | 22.857 | 1.00 | 37.93 |
| 2226 | CZ | PHE | A | 435 | 9.637 | 33.861 | 21.920 | 1.00 | 36.67 |
| 2227 | CE2 | PHE | A | 435 | 8.709 | 32.865 | 22.123 | 1.00 | 38.89 |
| 2228 | CD2 | PHE | A | 435 | 7.939 | 32.855 | 23.287 | 1.00 | 39.24 |
| 2229 | C | PHE | A | 435 | 5.084 | 34.262 | 26.538 | 1.00 | 39.85 |
| 2230 | O | PHE | A | 435 | 4.315 | 33.317 | 26.535 | 1.00 | 38.74 |
| 2231 | N | ASP | A | 436 | 5.199 | 35.114 | 27.543 | 1.00 | 42.56 |
| 2232 | CA | ASP | A | 436 | 4.439 | 34.951 | 28.785 | 1.00 | 45.99 |
| 2233 | CB | ASP | A | 436 | 5.129 | 35.712 | 29.937 | 1.00 | 45.36 |
| 2234 | CG | ASP | A | 436 | 6.556 | 35.223 | 30.178 | 1.00 | 45.85 |

FIGURE 3 (Cont.)

| A | B | C | D | E | F | G | H | I | J |
|---|---|---|---|---|---|---|---|---|---|
| 2235 | OD1 | ASP | A | 436 | 7.398 | 35.994 | 30.728 | 1.00 | 43.89 |
| 2236 | OD2 | ASP | A | 436 | 6.916 | 34.062 | 29.840 | 1.00 | 45.65 |
| 2237 | C | ASP | A | 436 | 2.996 | 35.412 | 28.601 | 1.00 | 48.83 |
| 2238 | O | ASP | A | 436 | 2.131 | 35.062 | 29.394 | 1.00 | 49.81 |
| 2239 | N | GLU | A | 437 | 2.772 | 36.179 | 27.525 | 1.00 | 52.27 |
| 2240 | CA | GLU | A | 437 | 1.481 | 36.750 | 27.087 | 1.00 | 54.07 |
| 2241 | CB | GLU | A | 437 | 0.280 | 35.870 | 27.490 | 1.00 | 54.43 |
| 2242 | CG | GLU | A | 437 | -0.422 | 35.162 | 26.323 | 1.00 | 56.65 |
| 2243 | CD | GLU | A | 437 | 0.468 | 34.221 | 25.497 | 1.00 | 59.11 |
| 2244 | OE1 | GLU | A | 437 | 0.850 | 34.580 | 24.353 | 1.00 | 59.50 |
| 2245 | OE2 | GLU | A | 437 | 0.757 | 33.094 | 25.965 | 1.00 | 61.35 |
| 2246 | C | GLU | A | 437 | 1.411 | 38.214 | 27.593 | 1.00 | 55.25 |
| 2247 | O | GLU | A | 437 | 1.593 | 38.464 | 28.772 | 1.00 | 55.79 |
| 2248 | N | ALA | A | 438 | 1.260 | 39.193 | 26.702 | 1.00 | 56.63 |
| 2249 | CA | ALA | A | 438 | 1.128 | 40.613 | 27.128 | 1.00 | 57.41 |
| 2250 | CB | ALA | A | 438 | 2.503 | 41.281 | 27.342 | 1.00 | 57.27 |
| 2251 | C | ALA | A | 438 | 0.288 | 41.444 | 26.158 | 1.00 | 57.72 |
| 2252 | O | ALA | A | 438 | -0.900 | 41.687 | 26.399 | 1.00 | 58.26 |
| 2253 | O | HOH | W | 1 | 6.551 | 50.484 | -5.966 | 1.00 | 24.29 |
| 2254 | O | HOH | W | 2 | 4.448 | 52.833 | -0.469 | 1.00 | 28.54 |
| 2255 | O | HOH | W | 3 | 3.205 | 28.230 | -7.758 | 1.00 | 35.16 |
| 2256 | O | HOH | W | 4 | -1.907 | 49.776 | 13.097 | 1.00 | 32.89 |
| 2257 | O | HOH | W | 5 | 9.099 | 51.050 | -4.379 | 1.00 | 25.18 |
| 2258 | O | HOH | W | 6 | 14.197 | 50.762 | -4.171 | 1.00 | 34.36 |
| 2259 | O | HOH | W | 7 | 8.126 | 39.464 | -13.943 | 1.00 | 31.11 |
| 2260 | O | HOH | W | 8 | 13.238 | 47.786 | 6.939 | 1.00 | 31.46 |
| 2261 | O | HOH | W | 9 | -2.021 | 53.460 | 6.588 | 1.00 | 31.08 |
| 2262 | O | HOH | W | 10 | 19.678 | 54.775 | 3.288 | 1.00 | 27.34 |
| 2263 | O | HOH | W | 11 | 13.371 | 44.195 | -14.581 | 1.00 | 30.55 |
| 2264 | O | HOH | W | 12 | -0.205 | 53.071 | -2.186 | 1.00 | 28.63 |
| 2265 | O | HOH | W | 13 | 6.596 | 46.693 | 14.111 | 1.00 | 30.03 |
| 2266 | O | HOH | W | 14 | 11.351 | 54.006 | 2.018 | 1.00 | 28.17 |
| 2267 | O | HOH | W | 15 | -6.301 | 48.148 | 7.352 | 1.00 | 35.78 |
| 2268 | O | HOH | W | 16 | 4.982 | 30.429 | 1.594 | 1.00 | 34.73 |
| 2269 | O | HOH | W | 17 | 14.586 | 39.349 | -10.389 | 1.00 | 47.32 |
| 2270 | O | HOH | W | 18 | 18.648 | 34.561 | 8.461 | 1.00 | 43.67 |
| 2271 | O | HOH | W | 19 | 2.122 | 44.883 | 23.466 | 1.00 | 41.14 |
| 2272 | O | HOH | W | 20 | -5.295 | 29.850 | 0.397 | 1.00 | 43.39 |
| 2273 | O | HOH | W | 21 | -1.996 | 52.674 | 1.750 | 1.00 | 33.46 |
| 2274 | O | HOH | W | 22 | -1.997 | 43.782 | -8.901 | 1.00 | 44.09 |
| 2275 | O | HOH | W | 23 | -8.054 | 34.995 | -10.297 | 1.00 | 42.88 |
| 2276 | O | HOH | W | 24 | 6.960 | 53.658 | 10.791 | 1.00 | 42.33 |
| 2277 | O | HOH | W | 25 | 16.679 | 40.525 | -0.105 | 1.00 | 29.73 |
| 2278 | O | HOH | W | 27 | 16.714 | 50.945 | -3.257 | 1.00 | 38.02 |
| 2279 | O | HOH | W | 28 | -10.466 | 34.542 | 9.427 | 1.00 | 50.83 |
| 2280 | O | HOH | W | 29 | -2.619 | 53.319 | -0.761 | 1.00 | 36.00 |
| 2281 | O | HOH | W | 30 | 5.444 | 54.271 | 1.680 | 1.00 | 40.97 |
| 2282 | O | HOH | W | 32 | -7.551 | 38.182 | -7.762 | 1.00 | 40.09 |
| 2283 | O | HOH | W | 35 | 21.523 | 33.869 | 33.963 | 1.00 | 34.39 |
| 2284 | O | HOH | W | 36 | 9.212 | 38.879 | 25.074 | 1.00 | 31.36 |
| 2285 | O | HOH | W | 37 | 3.975 | 45.526 | -10.808 | 1.00 | 33.19 |

FIGURE 3 (Cont.)

| A | B | C | D | E | F | G | H | I | J |
|---|---|---|---|---|---|---|---|---|---|
| 2286 | O | HOH | W | 38 | -6.631 | 32.932 | -12.046 | 1.00 | 39.01 |
| 2287 | O | HOH | W | 39 | 5.918 | 30.156 | -9.853 | 1.00 | 36.58 |
| 2288 | O | HOH | W | 40 | -7.741 | 31.987 | 3.411 | 1.00 | 41.41 |
| 2289 | O | HOH | W | 42 | 8.602 | 36.707 | 20.472 | 1.00 | 44.85 |
| 2290 | O | HOH | W | 44 | -8.458 | 34.723 | -5.144 | 1.00 | 34.78 |
| 2291 | O | HOH | W | 45 | 16.223 | 44.708 | 14.570 | 1.00 | 48.35 |
| 2292 | O | HOH | W | 46 | 0.731 | 52.928 | 11.091 | 1.00 | 42.12 |
| 2293 | O | HOH | W | 47 | 0.778 | 48.807 | -9.656 | 1.00 | 36.73 |
| 2294 | O | HOH | W | 48 | 19.877 | 51.504 | 2.489 | 1.00 | 42.13 |
| 2295 | O | HOH | W | 49 | 21.842 | 31.164 | 9.454 | 1.00 | 48.47 |
| 2296 | O | HOH | W | 50 | -4.509 | 43.246 | -9.313 | 1.00 | 56.24 |
| 2297 | O | HOH | W | 51 | 13.428 | 37.128 | -6.688 | 1.00 | 36.34 |
| 2298 | O | HOH | W | 53 | 15.830 | 42.334 | -1.834 | 1.00 | 46.10 |
| 2299 | O | HOH | W | 54 | 14.847 | 44.300 | -0.168 | 1.00 | 34.25 |
| 2300 | O | HOH | W | 55 | 19.238 | 38.535 | 31.006 | 1.00 | 56.19 |
| 2301 | O | HOH | W | 56 | 24.985 | 31.333 | 35.363 | 1.00 | 65.52 |
| 2302 | O | HOH | W | 57 | 18.133 | 37.286 | 11.031 | 1.00 | 43.94 |
| 2303 | O | HOH | W | 58 | -1.209 | 53.947 | 3.983 | 1.00 | 36.04 |
| 2304 | O | HOH | W | 60 | -13.107 | 37.556 | 1.095 | 1.00 | 45.75 |
| 2305 | O | HOH | W | 62 | 16.418 | 40.953 | 14.848 | 1.00 | 36.25 |
| 2306 | O | HOH | W | 63 | 18.750 | 53.175 | -2.582 | 1.00 | 53.02 |
| 2307 | O | HOH | W | 66 | 16.301 | 39.578 | 21.207 | 1.00 | 31.85 |
| 2308 | O | HOH | W | 67 | -4.492 | 27.476 | -10.434 | 1.00 | 48.89 |
| 2309 | O | HOH | W | 70 | 20.378 | 44.535 | 7.203 | 1.00 | 41.38 |
| 2310 | O | HOH | W | 71 | 13.517 | 54.293 | 3.547 | 1.00 | 47.02 |
| 2311 | O | HOH | W | 74 | 14.550 | 40.091 | 19.291 | 1.00 | 32.84 |
| 2312 | O | HOH | W | 75 | -5.846 | 37.151 | -18.471 | 1.00 | 57.88 |
| 2313 | O | HOH | W | 76 | 18.035 | 32.045 | 7.695 | 1.00 | 44.75 |
| 2314 | O | HOH | W | 77 | 4.654 | 31.629 | -11.669 | 1.00 | 39.27 |
| 2315 | O | HOH | W | 79 | 7.818 | 54.682 | -6.375 | 1.00 | 45.64 |
| 2316 | O | HOH | W | 81 | 2.439 | 34.830 | 14.781 | 1.00 | 40.81 |
| 2317 | O | HOH | W | 83 | -7.940 | 48.656 | -6.889 | 1.00 | 35.62 |
| 2318 | O | HOH | W | 84 | 15.568 | 39.134 | 31.277 | 1.00 | 50.02 |
| 2319 | O | HOH | W | 86 | 0.718 | 55.140 | -5.917 | 1.00 | 51.68 |
| 2320 | O | HOH | W | 89 | 19.833 | 35.202 | 19.186 | 1.00 | 43.90 |
| 2321 | O | HOH | W | 90 | -10.677 | 49.793 | -6.526 | 1.00 | 46.05 |
| 2322 | O | HOH | W | 92 | -12.447 | 52.142 | -0.876 | 1.00 | 45.63 |
| 2323 | O | HOH | W | 93 | -9.986 | 47.633 | 7.485 | 1.00 | 54.03 |
| 2324 | O | HOH | W | 95 | 4.851 | 51.601 | 19.098 | 1.00 | 44.53 |
| 2325 | O | HOH | W | 97 | 25.604 | 38.495 | 26.723 | 1.00 | 74.60 |
| 2326 | O | HOH | W | 98 | -4.728 | 51.390 | -7.536 | 1.00 | 45.87 |
| 2327 | O | HOH | W | 100 | -5.131 | 52.296 | 7.046 | 1.00 | 41.30 |
| 2328 | O | HOH | W | 102 | 20.713 | 28.703 | -2.971 | 1.00 | 55.92 |
| 2329 | O | HOH | W | 104 | 23.887 | 22.566 | 30.519 | 1.00 | 54.68 |
| 2330 | O | HOH | W | 105 | 4.621 | 57.347 | -3.174 | 1.00 | 53.92 |
| 2331 | O | HOH | W | 106 | 20.618 | 38.369 | 2.785 | 1.00 | 38.20 |
| 2332 | O | HOH | W | 107 | 27.712 | 36.430 | 11.313 | 1.00 | 52.80 |
| 2333 | O | HOH | W | 108 | 2.119 | 30.113 | 0.985 | 1.00 | 55.12 |
| 2334 | O | HOH | W | 110 | 12.783 | 33.020 | 19.122 | 1.00 | 48.79 |
| 2335 | O | HOH | W | 111 | -14.571 | 32.830 | 3.349 | 1.00 | 48.95 |
| 2336 | O | HOH | W | 112 | -15.685 | 43.602 | -1.833 | 1.00 | 51.49 |

FIGURE 3 (Cont.)

| A | B | C | D | E | F | G | H | I | J |
|---|---|---|---|---|---|---|---|---|---|
| 2337 | O | HOH | W | 113 | 20.773 | 52.636 | -0.133 | 1.00 | 49.69 |
| 2338 | O | HOH | W | 117 | 2.215 | 53.860 | -1.619 | 1.00 | 40.44 |
| 2339 | O | HOH | W | 122 | 17.554 | 12.040 | 24.786 | 1.00 | 59.36 |
| 2340 | O | HOH | W | 124 | 6.452 | 51.506 | 5.728 | 1.00 | 46.78 |

US 7,303,892 B1

SEQUENCE LISTING

<160> NUMBER OF SEQ ID NOS: 4

<210> SEQ ID NO 1
<211> LENGTH: 479
<212> TYPE: PRT
<213> ORGANISM: Homo sapiens
<220> FEATURE:
<221> NAME/KEY: MISC_FEATURE
<222> LOCATION: (1)..(479)
<223> OTHER INFORMATION: Amino acid sequence for full length human wild
      type AKT3
<300> PUBLICATION INFORMATION:
<308> DATABASE ACCESSION NUMBER: Genbank/NP_005456
<309> DATABASE ENTRY DATE: 2002-04-04
<313> RELEVANT RESIDUES: (1)..(461)

<400> SEQUENCE: 1

```
Met Ser Asp Val Thr Ile Val Lys Glu Gly Trp Val Gln Lys Arg Gly
1               5                   10                  15

Glu Tyr Ile Lys Asn Trp Arg Pro Arg Tyr Phe Leu Leu Lys Thr Asp
            20                  25                  30

Gly Ser Phe Ile Gly Tyr Lys Glu Lys Pro Gln Asp Val Asp Leu Pro
        35                  40                  45

Tyr Pro Leu Asn Asn Phe Ser Val Ala Lys Cys Gln Leu Met Lys Thr
    50                  55                  60

Glu Arg Pro Lys Pro Asn Thr Phe Ile Ile Arg Cys Leu Gln Trp Thr
65                  70                  75                  80

Thr Val Ile Glu Arg Thr Phe His Val Asp Thr Pro Glu Glu Arg Glu
                85                  90                  95

Glu Trp Thr Glu Ala Ile Gln Ala Val Ala Asp Arg Leu Gln Arg Gln
            100                 105                 110

Glu Glu Glu Arg Met Asn Cys Ser Pro Thr Ser Gln Ile Asp Asn Ile
        115                 120                 125

Gly Glu Glu Met Asp Ala Ser Thr Thr His His Lys Arg Lys Thr
    130                 135                 140

Met Asn Asp Phe Asp Tyr Leu Lys Leu Leu Gly Lys Gly Thr Phe Gly
145                 150                 155                 160

Lys Val Ile Leu Val Arg Glu Lys Ala Ser Gly Lys Tyr Tyr Ala Met
                165                 170                 175

Lys Ile Leu Lys Lys Glu Val Ile Ile Ala Lys Asp Glu Val Ala His
            180                 185                 190

Thr Leu Thr Glu Ser Arg Val Leu Lys Asn Thr Arg His Pro Phe Leu
        195                 200                 205

Thr Ser Leu Lys Tyr Ser Phe Gln Thr Lys Asp Arg Leu Cys Phe Val
    210                 215                 220

Met Glu Tyr Val Asn Gly Gly Glu Leu Phe Phe His Leu Ser Arg Glu
225                 230                 235                 240
```

```
Arg Val Phe Ser Glu Asp Arg Thr Arg Phe Tyr Gly Ala Glu Ile Val
            245                 250                 255

Ser Ala Leu Asp Tyr Leu His Ser Gly Lys Ile Val Tyr Arg Asp Leu
            260                 265                 270

Lys Leu Glu Asn Leu Met Leu Asp Lys Asp Gly His Ile Lys Ile Thr
            275                 280                 285

Asp Phe Gly Leu Cys Lys Glu Gly Ile Thr Asp Ala Ala Thr Met Lys
290                 295                 300

Thr Phe Cys Gly Thr Pro Glu Tyr Leu Ala Pro Glu Val Leu Glu Asp
305                 310                 315                 320

Asn Asp Tyr Gly Arg Ala Val Asp Trp Trp Gly Leu Gly Val Val Met
            325                 330                 335

Tyr Glu Met Met Cys Gly Arg Leu Pro Phe Tyr Asn Gln Asp His Glu
            340                 345                 350

Lys Leu Phe Glu Leu Ile Leu Met Glu Asp Ile Lys Phe Pro Arg Thr
            355                 360                 365

Leu Ser Ser Asp Ala Lys Ser Leu Leu Ser Gly Leu Leu Ile Lys Asp
            370                 375                 380

Pro Asn Lys Arg Leu Gly Gly Gly Pro Asp Asp Ala Lys Glu Ile Met
385                 390                 395                 400

Arg His Ser Phe Phe Ser Gly Val Asn Trp Gln Asp Val Tyr Asp Lys
            405                 410                 415

Lys Leu Val Pro Pro Phe Lys Pro Gln Val Thr Ser Glu Thr Asp Thr
            420                 425                 430

Arg Tyr Phe Asp Glu Glu Phe Thr Ala Gln Thr Ile Thr Ile Thr Pro
            435                 440                 445

Pro Glu Lys Tyr Asp Glu Asp Gly Met Asp Cys Met Asp Asn Glu Arg
        450                 455                 460

Arg Pro His Phe Pro Gln Phe Ser Tyr Ser Ala Ser Gly Arg Glu
465                 470                 475

<210> SEQ ID NO 2
<211> LENGTH: 978
<212> TYPE: DNA
<213> ORGANISM: Homo sapiens
<220> FEATURE:
<221> NAME/KEY: misc_feature
<222> LOCATION: (1)..(978)
<223> OTHER INFORMATION: Human cDNA sequence encoding residues 136-461
      of AKT3

<400> SEQUENCE: 2
tctacaaccc atcataaaag aaagacaatg aatgattttg actatttgaa actactaggt        60
aaaggcactt ttgggaaagt tattttggtt cgagagaagg caagtggaaa atactatgct       120
atgaagattc tgaagaaaga agtcattatt gcaaaggatg aagtggcaca cactctaact       180
gaaagcagag tattaaagaa cactagacat ccctttttaa catccttgaa atattccttc       240
cagacaaaag accgtttgtg ttttgtgatg gaatatgtta atggggcga gctgttttc         300 catttgtcga gagagcgggt gttctctgag accgcacac gtttctatgg tgcagaaatt        360
gtctctgcct tggactatct acattccgga aagattgtgt accgtgatct caagttggag       420
aatctaatgc tggacaaaga tggccacata aaaattacag attttggact ttgcaaagaa       480
gggatcacag atgcagccac catgaagaca ttctgtggca ctccagaata tctggcacca       540
gaggtgttag aagataatga ctatggccga gcagtagact ggtggggcct aggggttgtc       600
```

```
atgtatgaaa tgatgtgtgg gaggttacct ttctacaacc aggaccatga gaaactttt      660 gaattaatat taatggaaga cattaaattt cctcgaacac tctcttcaga tgcaaaatca      720
ttgctttcag ggctcttgat aaaggatcca aataaacgcc ttggtggagg accagatgat      780
gcaaaagaaa ttatgagaca cagtttcttc tctggagtaa actggcaaga tgtatatgat      840
aaaaagcttg tacctccttt taaacctcaa gtaacatctg agacagatac tagatatttt      900
gatgaagaat ttcagctca gactattaca ataacaccac ctgaaaaata tgatgaggat       960
ggtatggact gcatggac                                                     978
```

```
<210> SEQ ID NO 3
<211> LENGTH: 556
<212> TYPE: PRT
<213> ORGANISM: Artificial
<220> FEATURE:
<223> OTHER INFORMATION: Amino acid sequence for residues 136-461 of
      AKT3 with a cleavable intein tag and cleavage site
<220> FEATURE:
<221> NAME/KEY: MISC_FEATURE
<222> LOCATION: (1)..(226)
<223> OTHER INFORMATION: Cleavable N-terminal intein tag
<220> FEATURE:
<221> NAME/KEY: MISC_FEATURE
<222> LOCATION: (227)..(230)
<223> OTHER INFORMATION: CRSL cleavage site
<220> FEATURE:
<221> NAME/KEY: MISC_FEATURE
<222> LOCATION: (231)..(556)
<223> OTHER INFORMATION: Amino acid sequence for resisues 136-461 of
      AKT3

<400> SEQUENCE: 3

Met Lys Ile Glu Glu Gly Lys Leu Thr Asn Pro Gly Val Ser Ala Trp
 1               5                  10                  15

Gln Val Asn Thr Ala Tyr Thr Ala Gly Gln Leu Val Thr Tyr Asn Gly
                20                  25                  30

Lys Thr Tyr Lys Cys Leu Gln Pro His Thr Ser Leu Ala Gly Trp Glu
            35                  40                  45

Pro Ser Asn Val Pro Ala Leu Trp Gln Leu Gln Asn Asn Gly Asn Asn
        50                  55                  60

Gly Leu Glu Leu Arg Glu Ser Gly Ala Ile Ser Gly Asp Ser Leu Ile
 65                  70                  75                  80

Ser Leu Ala Ser Thr Gly Lys Arg Val Ser Ile Lys Asp Leu Leu Asp
                85                  90                  95

Glu Lys Asp Phe Glu Ile Trp Ala Ile Asn Glu Gln Thr Met Lys Leu
            100                 105                 110

Glu Ser Ala Lys Val Ser Arg Val Phe Cys Thr Gly Lys Lys Leu Val
        115                 120                 125

Tyr Ile Leu Lys Thr Arg Leu Gly Arg Thr Ile Lys Ala Thr Ala Asn
130                 135                 140

His Arg Phe Leu Thr Ile Asp Gly Trp Lys Arg Leu Asp Glu Leu Ser
145                 150                 155                 160

Leu Lys Glu His Ile Ala Leu Pro Arg Lys Leu Glu Ser Ser Ser Leu
                165                 170                 175

Gln Leu Ser Pro Glu Ile Glu Lys Leu Ser Gln Ser Asp Ile Tyr Trp
            180                 185                 190

Asp Ser Ile Val Ser Ile Thr Glu Thr Gly Val Glu Glu Val Phe Asp
        195                 200                 205

Leu Thr Val Pro Gly Pro His Asn Phe Val Ala Asn Asp Ile Ile Val
    210                 215                 220
```

```
His Asn Cys Arg Ser Leu Ser Thr Thr His His Lys Arg Lys Thr Met
225                 230                 235                 240

Asn Asp Phe Asp Tyr Leu Lys Leu Leu Gly Lys Gly Thr Phe Gly Lys
                245                 250                 255

Val Ile Leu Val Arg Glu Lys Ala Ser Gly Lys Tyr Tyr Ala Met Lys
                260                 265                 270

Ile Leu Lys Lys Glu Val Ile Ile Ala Lys Asp Glu Val Ala His Thr
            275                 280                 285

Leu Thr Glu Ser Arg Val Leu Lys Asn Thr Arg His Pro Phe Leu Thr
290                 295                 300

Ser Leu Lys Tyr Ser Phe Gln Thr Lys Asp Arg Leu Cys Phe Val Met
305                 310                 315                 320

Glu Tyr Val Asn Gly Gly Glu Leu Phe Phe His Leu Ser Arg Glu Arg
                325                 330                 335

Val Phe Ser Glu Asp Arg Thr Arg Phe Tyr Gly Ala Glu Ile Val Ser
                340                 345                 350

Ala Leu Asp Tyr Leu His Ser Gly Lys Ile Val Tyr Arg Asp Leu Lys
                355                 360                 365

Leu Glu Asn Leu Met Leu Asp Lys Asp Gly His Ile Lys Ile Thr Asp
370                 375                 380

Phe Gly Leu Cys Lys Glu Gly Ile Thr Asp Ala Ala Thr Met Lys Thr
385                 390                 395                 400

Phe Cys Gly Thr Pro Glu Tyr Leu Ala Pro Glu Val Leu Glu Asp Asn
                405                 410                 415

Asp Tyr Gly Arg Ala Val Asp Trp Trp Gly Leu Gly Val Val Met Tyr
                420                 425                 430

Glu Met Met Cys Gly Arg Leu Pro Phe Tyr Asn Gln Asp His Glu Lys
            435                 440                 445

Leu Phe Glu Leu Ile Leu Met Glu Asp Ile Lys Phe Pro Arg Thr Leu
450                 455                 460

Ser Ser Asp Ala Lys Ser Leu Leu Ser Gly Leu Leu Ile Lys Asp Pro
465                 470                 475                 480

Asn Lys Arg Leu Gly Gly Gly Pro Asp Asp Ala Lys Glu Ile Met Arg
                485                 490                 495

His Ser Phe Phe Ser Gly Val Asn Trp Gln Asp Val Tyr Asp Lys Lys
                500                 505                 510

Leu Val Pro Pro Phe Lys Pro Gln Val Thr Ser Glu Thr Asp Thr Arg
                515                 520                 525

Tyr Phe Asp Glu Glu Phe Thr Ala Gln Thr Ile Thr Ile Thr Pro Pro
530                 535                 540

Glu Lys Tyr Asp Glu Asp Gly Met Asp Cys Met Asp
545                 550                 555

<210> SEQ ID NO 4
<211> LENGTH: 330
<212> TYPE: PRT
<213> ORGANISM: Artificial
<220> FEATURE:
<223> OTHER INFORMATION: CRSL fused to the N-terminal of amino acid
      residues 136-461 of AKT3
<220> FEATURE:
<221> NAME/KEY: MISC_FEATURE
<222> LOCATION: (1)..(4)
<223> OTHER INFORMATION: CRSL cleavage site
<220> FEATURE:
<221> NAME/KEY: MISC_FEATURE
<222> LOCATION: (5)..(330)
```

-continued

<223> OTHER INFORMATION: Amino acid sequence for residues 136-461 of AKT3

<400> SEQUENCE: 4

```
Cys Arg Ser Leu Ser Thr Thr His His Lys Arg Lys Thr Met Asn Asp
 1               5                  10                  15

Phe Asp Tyr Leu Lys Leu Leu Gly Lys Gly Thr Phe Gly Lys Val Ile
             20                  25                  30

Leu Val Arg Glu Lys Ala Ser Gly Lys Tyr Tyr Ala Met Lys Ile Leu
         35                  40                  45

Lys Lys Glu Val Ile Ile Ala Lys Asp Glu Val Ala His Thr Leu Thr
     50                  55                  60

Glu Ser Arg Val Leu Lys Asn Thr Arg His Pro Phe Leu Thr Ser Leu
 65                  70                  75                  80

Lys Tyr Ser Phe Gln Thr Lys Asp Arg Leu Cys Phe Val Met Glu Tyr
                 85                  90                  95

Val Asn Gly Gly Glu Leu Phe Phe His Leu Ser Arg Glu Arg Val Phe
            100                 105                 110

Ser Glu Asp Arg Thr Arg Phe Tyr Gly Ala Glu Ile Val Ser Ala Leu
        115                 120                 125

Asp Tyr Leu His Ser Gly Lys Ile Val Tyr Arg Asp Leu Lys Leu Glu
    130                 135                 140

Asn Leu Met Leu Asp Lys Asp Gly His Ile Lys Ile Thr Asp Phe Gly
145                 150                 155                 160

Leu Cys Lys Glu Gly Ile Thr Asp Ala Ala Thr Met Lys Thr Phe Cys
                165                 170                 175

Gly Thr Pro Glu Tyr Leu Ala Pro Glu Val Leu Glu Asp Asn Asp Tyr
            180                 185                 190

Gly Arg Ala Val Asp Trp Trp Gly Leu Gly Val Val Met Tyr Glu Met
        195                 200                 205

Met Cys Gly Arg Leu Pro Phe Tyr Asn Gln Asp His Glu Lys Leu Phe
    210                 215                 220

Glu Leu Ile Leu Met Glu Asp Ile Lys Phe Pro Arg Thr Leu Ser Ser
225                 230                 235                 240

Asp Ala Lys Ser Leu Leu Ser Gly Leu Leu Ile Lys Asp Pro Asn Lys
                245                 250                 255

Arg Leu Gly Gly Gly Pro Asp Asp Ala Lys Glu Ile Met Arg His Ser
            260                 265                 270

Phe Phe Ser Gly Val Asn Trp Gln Asp Val Tyr Asp Lys Lys Leu Val
        275                 280                 285

Pro Pro Phe Lys Pro Gln Val Thr Ser Glu Thr Asp Thr Arg Tyr Phe
    290                 295                 300

Asp Glu Glu Phe Thr Ala Gln Thr Ile Thr Ile Thr Pro Pro Glu Lys
305                 310                 315                 320

Tyr Asp Glu Asp Gly Met Asp Cys Met Asp
                325                 330
```

CRYSTALLIZATION OF AKT3

RELATED APPLICATION

This application claims the benefit of U.S. Provisional Application No. 60/400,207, filed Jul. 31, 2002, which is incorporated herein by reference.

FIELD OF THE INVENTION

The present invention relates to the family of human serine/threonine protein kinases known as "AKT" and more specifically to a particular AKT known as AKT3. Provided is AKT3 in crystalline form, methods of forming crystals comprising AKT3, methods of using crystals comprising AKT3, a crystal structure of AKT3, and methods of using the crystal structure.

BACKGROUND OF THE INVENTION

A general approach to designing inhibitors that are selective for a given protein is to determine how a putative inhibitor interacts with a three dimensional structure of that protein. For this reason it is useful to obtain the protein in crystalline form and perform X-ray diffraction techniques to determine the protein's three dimensional structure coordinates. Various methods for preparing crystalline proteins are known in the art.

Once protein crystals are produced, crystallographic data can be generated using the crystals to provide useful structural information that assists in the design of small molecules that bind to the active site of the protein and inhibit the protein's activity in vivo. If the protein is crystallized as a complex with a ligand, one can determine both the shape of the protein's binding pocket when bound to the ligand, as well as the amino acid residues that are capable of close contact with the ligand. By knowing the shape and amino acid residues comprised in the binding pocket, one may design new ligands that will interact favorably with the protein. With such structural information, available computational methods may be used to predict how strong the ligand binding interaction will be. Such methods aid in the design of inhibitors that bind strongly, as well as selectively to the protein.

SUMMARY OF THE INVENTION

The present invention is directed to crystals comprising AKT3 and particularly crystals comprising AKT3 that have sufficient size and quality to obtain useful information about the structural properties of AKT3 and molecules or complexes that may associate with AKT3.

In one embodiment, a composition is provided that comprises a protein in crystalline form wherein at least a portion of the protein has 55%, 65%, 75%, 85%, 90%, 95%, 97%, 99% or greater identity with residues 62-479, 132-474, 136-461 or 143-438 of SEQ. ID No. 1.

In one variation, the protein has activity characteristic of AKT3. For example, the protein may optionally be inhibited by inhibitors of wild type AKT3. The protein crystal may also diffract X-rays for a determination of structure coordinates to a resolution of 4 Å, 3.5 Å, 3.0 Å or less.

In one variation, the protein crystal has a crystal lattice in a $P2_12_12_1$ space group. The protein crystal may also have a crystal lattice having unit cell dimensions, +/−5%, of a=48.36 Å b=72.29 Å and c=94.52 Å, $\alpha=\beta=\gamma=90$.

The present invention is also directed to crystallizing AKT3. The present invention is also directed to the conditions useful for crystallizing AKT3. It should be recognized that a wide variety of crystallization methods can be used in combination with the crystallization conditions to form crystals comprising AKT3 including, but not limited to, vapor diffusion, batch, dialysis, and other methods of contacting the protein solution for the purpose of crystallization.

The present invention is also directed to crystallizing AKT3. The present invention is also directed to the conditions useful for crystallizing AKT3. It should be recognized that a wide variety of crystallization methods can be used in combination with the crystallization conditions to form crystals comprising AKT3 including, but not limited to, vapor diffusion, batch, dialysis, and other methods of contacting the protein solution for the purpose of crystallization.

In one embodiment, a method is provided for forming crystals of a protein comprising: forming a crystallization volume comprising: a protein wherein at least a portion of the protein has 55%, 65%, 75%, 85%, 90%, 95%, 97%, 99% or greater identity with residues 479, 132-474, 136-461 or 143-438 of SEQ. ID No. 1; and storing the crystallization volume under conditions suitable for crystal formation.

In one variation, the crystallization volume comprises the protein in a concentration between 1 mg/ml and 50 mg/ml; 5-50% w/v of precipitant wherein the precipitant comprises one or more members of the group consisting of PEG MME (polyethylene glycol monomethyl ether) having a molecular weight range between 300-10000, and PEG having a molecular weight range between 100-10000; optionally 0.05 to 0.5M additives wherein the additives comprises one or more members of the group consisting of sodium chloride, sodium tartrate, ammonium sulphate, sodium formate and lithium chloride; and wherein the crystallization volume has a pH between pH 4 and pH 8.

The method may optionally further comprise forming a protein crystal that has a crystal lattice in a $P2_12_12_1$ space group. The method also optionally further comprises forming a protein crystal that has a crystal lattice having unit cell dimensions, +/−5%, of a=48.36 Å b=72.29 Å and c=94.52 Å, $\alpha=\beta=\gamma=90$. The invention also relates to protein crystals formed by these methods.

The present invention is also directed to a composition comprising an isolated protein that comprises or consists of one or more of the protein sequence(s) of AKT3 taught herein for crystallizing AKT3. The present invention is also directed to a composition comprising an isolated nucleic acid molecule that comprises or consists of the nucleotides for expressing the protein sequence of AKT3 taught herein for crystallizing AKT3.

The present invention is also directed to an expression vector that may be used to express the isolated proteins taught herein for crystallizing AKT3.

The present invention is also directed to an expression vector that may be used to express the isolated proteins taught herein for crystallizing AKT3. In one variation, the expression vector comprises a promoter that promotes expression of the isolated protein.

The present invention is also directed to a cell line transformed or transfected by an isolated nucleic acid molecule or expression vector of the present invention.

The present invention is also directed to structure coordinates for AKT3 as well as structure coordinates that are comparatively similar to these structure coordinates. It is noted that these comparatively similar structure coordinates may encompass proteins with similar sequences and/or structures, such as other serine/threonine protein kinases.

For example, machine-readable data storage media is provided having data storage material encoded with machine-readable data that comprises structure coordinates that are comparatively similar to the structure coordinates of AKT3. The present invention is also directed to a machine readable data storage medium having data storage material encoded with machine readable data, which, when read by an appropriate machine, can display a three dimensional representation of all or a portion of a structure of AKT3 or a model that is comparatively similar to the structure of all or a portion of AKT3.

Various embodiments of machine readable data storage medium are provided that comprise data storage material encoded with machine readable data. The machine readable data comprises: structure coordinates that have a root mean square deviation equal to or less than the RMSD value specified in Columns 3, 4 or 5 of Table 1 when compared to the structure coordinates of FIG. 3, the root mean square deviation being calculated such that the portion of amino acid residues specified in Column 2 of Table 1 of each set of structure coordinates are superimposed and the root mean square deviation is based only on those amino acid residues in the structure coordinates that are also present in the portion of the protein specified in specified in Column 1 of Table 1. The amino acids being overlayed and compared need not to be identical when the RMSD calculation is performed on alpha carbons and main chain atoms but the amino acids being overlayed and compared must have identical side chains when the RMSD calculation is performed on all non-hydrogen atoms.

For example, in one embodiment where the comparison is based on the 4 Angstrom set of amino acid residues (Column 1) and is based on superimposing alpha-carbon atoms (Column 2), the structure coordinates may have a root mean square deviation equal to or less than 0.58 Å when compared to the structure coordinates of FIG. 3.

TABLE 1

| AA RESIDUES TO USE TO PERFORM RMSD COMPARISON | PORTION OF EACH AA RESIDUE USED TO PERFORM RMSD COMPARISON | RMSD VALUE LESS THAN OR EQUAL TO | | |
|---|---|---|---|---|
| Table 2 | alpha-carbon atoms[1] | 0.58 | 0.38 | 0.29 |
| (4 Angstrom set) | main-chain atoms[1] | 0.84 | 0.56 | 0.42 |
| | all non-hydrogen[2] | 1.02 | 0.68 | 0.51 |
| Table 3 | alpha-carbon atoms[1] | 0.64 | 0.43 | 0.32 |
| (7 Angstrom set) | main-chain atoms[1] | 0.71 | 0.47 | 0.35 |
| | all non-hydrogen[2] | 0.88 | 0.59 | 0.44 |
| Table 4 | alpha-carbon atoms[1] | 0.69 | 0.46 | 0.35 |
| (10 Angstrom set) | main-chain atoms[1] | 0.73 | 0.48 | 0.36 |
| | all non-hydrogen[2] | 0.91 | 0.60 | 0.45 |
| 62-479, 132-474, 136- | alpha-carbon atoms[1] | 0.82 | 0.55 | 0.41 |
| 461 or 143-438 of | main-chain atoms[1] | 0.85 | 0.56 | 0.42 |
| SEQ. ID No. 1 | all non-hydrogen[2] | 0.95 | 0.63 | 0.47 |

[1] the RMSD computed between the atoms of all amino acids that are common to both the target and the reference in the aligned and superposed structure. The amino acids need not to be identical.
[2] the RMSD computed only between identical amino acids, which are common to both the target and the reference in the aligned and superposed structure.

The present invention is also directed to a three-dimensional structure of all or a portion of AKT3. This three-dimensional structure may be used to identify binding sites, to provide mutants having desirable binding properties, and ultimately, to design, characterize, or identify ligands capable of interacting with AKT3. Ligands that interact with AKT3 may be any type of atom, compound, protein or chemical group that binds to or otherwise associates with the protein. Examples of types of ligands include natural substrates for AKT3, inhibitors of AKT3, and heavy atoms. The inhibitors of AKT3 may optionally be used as drugs to treat therapeutic indications by modifying the in vivo activity of AKT3.

In various embodiments, methods are provided for displaying a three dimensional representation of a structure of a protein comprising:

taking machine readable data comprising structure coordinates that have a root mean square deviation equal to or less than the RMSD value specified in Columns 3, 4 or 5 of Table 1 when compared to the structure coordinates of FIG. 3, the root mean square deviation being calculated such that the portion of amino acid residues specified in Column 2 of Table 1 of each set of structure coordinates are superimposed and the root mean square deviation is based only on those amino acid residues in the structure coordinates that are also present in the portion of the protein specified in specified in Column 1 of Table 1;

computing a three dimensional representation of a structure based on the structure coordinates; and displaying the three dimensional representation.

The present invention is also directed to a method for solving a three-dimensional crystal structure of a target protein using the structure of AKT3.

In various embodiments, computational methods are provided comprising: taking machine readable data comprising structure coordinates that have a root mean square deviation equal to or less than the RMSD value specified in Columns 3, 4 or 5 of Table 1 when compared to the structure coordinates of FIG. 3, the root mean square deviation being calculated such that the portion of amino acid residues specified in Column 2 of Table 1 of each set of structure coordinates are superimposed and the root mean square deviation is based only on those amino acid residues in the structure coordinates that are also present in the portion of the protein specified in specified in Column 1 of Table 1;

computing phases based on the structural coordinates;

computing an electron density map-based on the computed phases; and determining a three-dimensional crystal structure based on the computed electron density map.

In various embodiments, computational methods are provided comprising: taking an X-ray diffraction pattern of a crystal of the target protein; and computing a three-dimensional electron density map from the X-ray diffraction pattern by molecular replacement, wherein structure coordinates used as a molecular replacement model comprise structure coordinates that have a root mean square deviation equal to or less than the RMSD value specified in Columns 3, 4 or 5 of Table 1 when compared to the structure coordinates of FIG. 3, the root mean square deviation being calculated such that the portion of amino acid residues specified in Column 2 of Table 1 of each set of structure coordinates are superimposed and the root mean square deviation is based only on those amino acid residues in the structure coordinates that are also present in the portion of the protein specified in specified in Column 1 of Table 1.

These methods may optionally further comprise determining a three-dimensional crystal structure based upon the computed three-dimensional electron density map.

The present invention is also directed to using a crystal structure of AKT3, in particular the structure coordinates of AKT3 and the surface contour defined by them, in methods for screening, designing, or optimizing molecules or other chemical entities that interact with and preferably inhibit AKT3.

One skilled in the art will appreciate the numerous uses of the inventions described herein, particularly in the areas of drug design, screening and optimization of drug candidates, as well as in determining additional unknown crystal structures. For example, a further aspect of the present invention relates to using a three-dimensional crystal structure of all or a portion of AKT3 and/or its structure coordinates to evaluate the ability of entities to associate with AKT3. The entities may be any entity that may function as a ligand and thus may be any type of atom, compound, protein (such as antibodies) or chemical group that can bind to or otherwise associate with a protein.

In various embodiments, methods are provided for evaluating a potential of an entity to associate with a protein comprising:

creating a computer model of a protein structure using structure coordinates that comprise structure coordinates that have a root mean square deviation equal to or less than the RMSD value specified in Columns 3, 4 or 5 of Table 1 when compared to the structure coordinates of FIG. 3, the root mean square deviation being calculated such that the portion of amino acid residues specified in Column 2 of Table 1 of each set of structure coordinates are superimposed and the root mean square deviation is based only on those amino acid residues in the structure coordinates that are also present in the portion of the protein specified in specified in Column 1 of Table 1;

performing a fitting operation between the entity and the computer model; and analyzing results of the fitting operation to quantify an association between the entity and the model.

In other embodiments, methods are provided for identifying entities that can associate with a protein comprising:

generating a three-dimensional structure of a protein using structure coordinates that comprise structure coordinates that have a root mean square deviation equal to or less than the RMSD value specified in Columns 3, 4 or 5 of Table 1 when compared to the structure coordinates of FIG. 3, the root mean square deviation being calculated such that the portion of amino acid residues specified in Column 2 of Table 1 of each set of structure coordinates are superimposed and the root mean square deviation is based only on those amino acid residues in the structure coordinates that are also present in the portion of the protein specified in specified in Column 1 of Table 1; and employing the three-dimensional structure to design or select an entity that can associate with the protein; and contacting the entity with a protein wherein at least a portion of the protein has 55%, 65%, 75%, 85%, 90%, 95%, 97%, 99% or greater identity with residues 62-479, 132-474, 136-461 or 143-438 of SEQ. ID No. 1.

In other embodiments, methods are provided for identifying entities that can associate with a protein comprising:

generating a three-dimensional structure of a protein using structure coordinates that comprise structure coordinates that have a root mean square deviation equal to or less than the RMSD value specified in Columns 3, 4 or 5 of Table 1 when compared to the structure coordinates of FIG. 3, the root mean square deviation being calculated such that the portion of amino acid residues specified in Column 2 of Table 1 of each set of structure coordinates are superimposed and the root mean square deviation is based only on those amino acid residues in the structure coordinates that are also present in the portion of the protein specified in specified in Column 1 of Table 1; and employing the three-dimensional structure to design or select an entity that can associate with the protein.

In other embodiments, methods are provided for identifying entities that can associate with a protein comprising:

computing a computer model for a protein binding pocket, at least a portion of the computer model having a surface contour that has a root mean square deviation equal to or less than a given RMSD value specified in Columns 3, 4 or 5 of Table 1 when the coordinates used to compute the surface contour are compared to the structure coordinates of FIG. 3, wherein (a) the root mean square deviation is calculated by the calculation method set forth herein, (b) the portion of amino acid residues associated with the given RMSD value in Table 1 (specified in Column 2 of Table 1) are superimposed according to the RMSD calculation, and (c) the root mean square deviation is calculated based only on those amino acid residues present in both the protein being modeled and the portion of the protein associated with the given RMSD in Table 1 (specified in Column 1 of Table 1); and employing the computer model to design or select an entity that can associate with the protein; and contacting the entity with a protein wherein at least a portion of the protein has 55%, 65%, 75%, 85%, 90%, 95%, 97%, 99% or greater identity with residues 62-479, 132-474, 136-461 or 143-438 of SEQ. ID No. 1.

In other embodiments, methods are provided for identifying entities that can associate with a protein comprising:

computing a computer model for a protein binding pocket, at least a portion of the computer model having a surface contour that has a root mean square deviation equal to or less than a given RMSD value specified in Columns 3, 4 or 5 of Table 1 when the coordinates used to compute the surface contour are compared to the structure coordinates of FIG. 3, wherein (a) the root mean square deviation is calculated by the calculation method set forth herein, (b) the portion of amino acid residues associated with the given RMSD value in Table 1 (specified in Column 2 of Table 1) are superimposed according to the RMSD calculation, and (c) the root mean square deviation is calculated based only on those amino acid residues present in both the protein being modeled and the portion of the protein associated with the given RMSD in Table 1 (specified in Column 1 of Table 1); and employing the computer model to design or select an entity that can associate with the protein.

In other embodiments, methods are provided for evaluating the ability of an entity to associate with a protein, the method comprising:

constructing a computer model defined by structure coordinates that have a root mean square deviation equal to or less than the RMSD value specified in Columns 3, 4 or 5 of Table 1 when compared to the structure coordinates of FIG. 3, the root mean square deviation being calculated such that the portion of amino acid residues specified in Column 2 of Table 1 of each set of structure coordinates are superimposed and the root mean square deviation is based only on those amino acid residues in the structure coordinates that are also present in the portion of the protein specified in specified in Column 1 of Table 1; and selecting an entity to be evaluated by a method selected from the group consisting of (i) assembling molecular fragments into the entity, (ii) selecting an entity from a small molecule database, (iii) de novo ligand design of the entity, and (iv) modifying a known ligand for AKT3, or a portion thereof; performing a fitting program operation between computer models of the entity to be evaluated and the binding pocket in order to provide an energy-minimized configuration of the entity in the binding pocket; and evaluating the results of the fitting operation to quantify the association between the entity and the binding pocket model in order to evaluate the ability of the entity to associate with the binding pocket.

In other embodiments, methods are provided for evaluating the ability of an entity to associate with a protein, the method comprising:

computing a computer model for a protein binding pocket, at least a portion of the computer model having a surface contour that has a root mean square deviation equal to or less than a given RMSD value specified in Columns 3, 4 or 5 of Table 1 when the coordinates used to compute the surface contour are compared to the structure coordinates of FIG. 3, wherein (a) the root mean square deviation is calculated by the calculation method set forth herein, (b) the portion of amino acid residues associated with the given RMSD value in Table 1 (specified in Column 2 of Table 1) are superimposed according to the RMSD calculation, and (c) the root mean square deviation is calculated based only on those amino acid residues present in both the protein being modeled and the portion of the protein associated with the given RMSD in Table 1 (specified in Column 1 of Table 1); and selecting an entity to be evaluated by a method selected from the group consisting of (i) assembling molecular fragments into the entity, (ii) selecting an entity from a small molecule database, (iii) de novo ligand design of the entity, and (iv) modifying a known ligand for AKT3, or a portion thereof; performing a fitting program operation between computer models of the entity to be evaluated and the binding pocket in order to provide an energy-minimized configuration of the entity in the binding pocket; and evaluating the results of the fitting operation to quantify the association between the entity and the binding pocket model in order to evaluate the ability of the entity to associate with the binding pocket.

In regard to each of these embodiments, the protein may optionally have activity characteristic of AKT3. For example, the protein may optionally be inhibited by inhibitors of wild type AKT3.

In another embodiment, a method is provided for identifying an entity that associates with a protein comprising: taking structure coordinates from diffraction data obtained from a crystal of a protein wherein at least a portion of the protein has 55%, 65%, 75%, 85%, 90%, 95%, 97%, 99% or greater identity with residues 62-479, 132-474, 136-461 or 143-438 of SEQ. ID No. 1; and performing rational drug design using a three dimensional structure that is based on the obtained structure coordinates.

The protein crystals may optionally have a crystal lattice with a $P2_12_12_1$ space group and unit cell dimensions, +/−5%, of a=48.36 Å b=72.29 Å and c=94.52 Å, $\alpha=\beta=\gamma=90$.

The method may optionally further comprise selecting one or more entities based on the rational drug design and contacting the selected entities with the protein. The method may also optionally further comprise measuring an activity of the protein when contacted with the one or more entities. The method also may optionally further comprise comparing activity of the protein in a presence of and in the absence of the one or more entities; and selecting entities where activity of the protein changes depending whether a particular entity is present. The method also may optionally further comprise contacting cells expressing the protein with the one or more entities and detecting a change in a phenotype of the cells when a particular entity is present.

BRIEF DESCRIPTION OF THE FIGURES

FIG. 1 illustrates SEQ. ID Nos. 1, 2 and 3 referred to in this application.

FIG. 3 lists a set of atomic structure coordinates for SEQ ID NO: 4 as derived by X-ray crystallography from a crystal that comprises the protein. Reference numbers in column E of FIG. 3 correspond to residue numbers of SEQ ID NO: 1. The following abbreviations are used in FIG. 3: "X, Y, Z" crystallographically define the atomic position of the element measured; "B" is a thermal factor that measures movement of the atom around its atomic center; "Occ" is an occupancy factor that refers to the fraction of the molecules in which each atom occupies the position specified by the coordinates (a value of "1" indicates that each atom has the same conformation, i.e., the same position, in all molecules of the crystal).

DETAILED DESCRIPTION OF THE INVENTION

Figure 2:
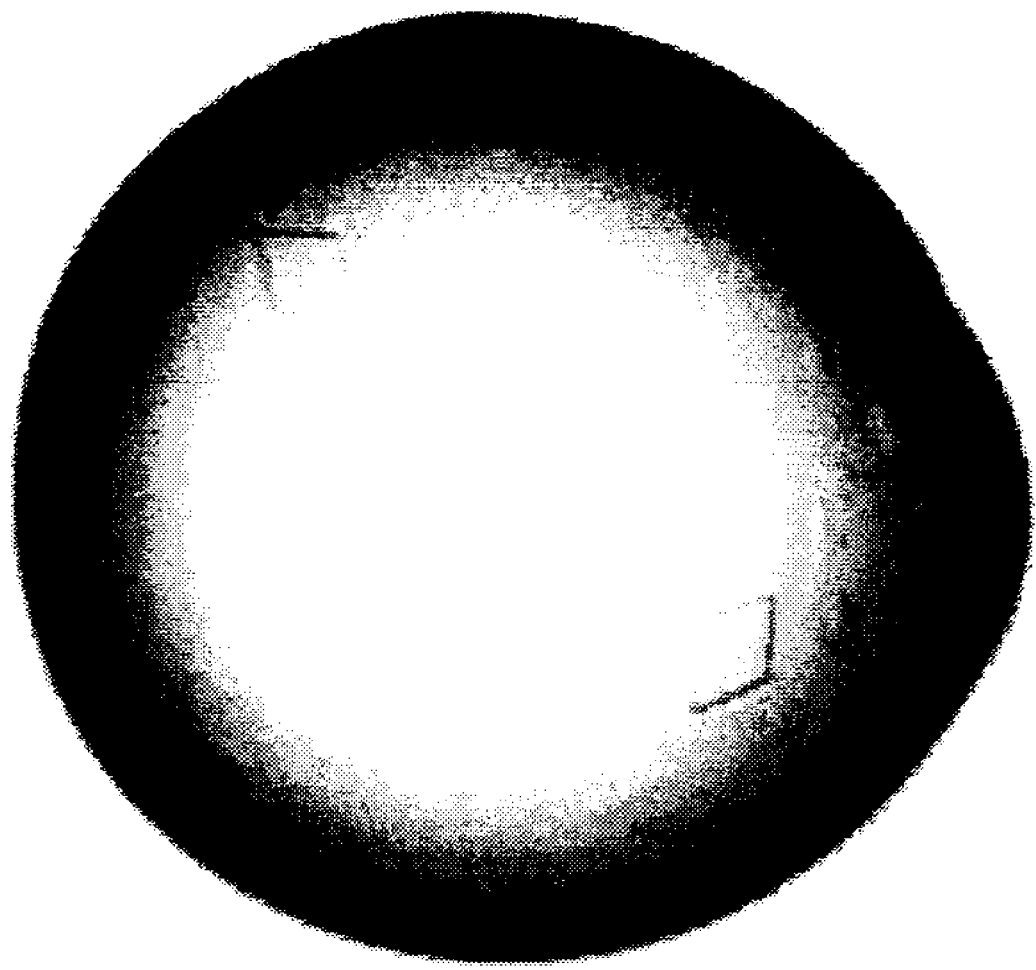
FIG. 2 illustrates a crystal of the complex of ATP with SEQ ID NO: 4.

The present invention relates to a member of the AKT serine/threonine protein kinases family known as AKT3. More specifically, the present invention relates to AKT3 in crystalline form, methods of forming crystals comprising AKT3, methods of using crystals comprising AKT3, a crystal structure of AKT3, and methods of using the crystal structure.

In describing protein structure and function herein, reference is made to amino acids comprising the protein. The amino acids may also be referred to by their conventional abbreviations; A=Ala Alanine; T=Thr=Threonine; V=Val=Valine; C=Cys=Cysteine; L=Leu=Leucine; Y=Tyr=Tyrosine; I=Ile=Isoleucine; N=Asn=Asparagine; P=Pro=Proline; Q=Gln=Glutamine; F=Phe=Phenylalanine; D=Asp=Aspartic Acid; W=Trp=Tryptophan; E=Glu=Glutamic Acid; M=Met=Methionine; K=Lys=Lysine; G=Gly=Glycine; R=Arg=Arginine; S=Ser=Serine; and H=His=Histidine.

1. AKT3

The AKT or protein Kinase B (PKB) family of serine/threonine protein kinases is comprised of 3 highly homologous members, AKT1/PKBα, AKT2/PKBβ and AKT3/PKBγ. The family of AKT proteins are involved in signal transduction pathways that regulate cellular processes including apoptosis, proliferation, differentiation and metabolism. Expression of AKT family members have been found to be altered in many human malignant carcinomas including gastric, breast, prostate, ovarian and pancreatic. AKT3 activity is 20-60-fold higher in hormone-independent breast and prostrate cancer cell lines than in hormone-responsive cell lines and an increase in AKT3 activity was found to correlate with both mRNA and protein levels. Analyses of primary breast carcinoma specimens indicates that AKT3 expression is significantly higher in the more aggressive phenotype associated with hormone-independent tumors.

It should be understood that the methods and compositions provided relating to AKT3 are not intended to be limited to the wild type, full length form of AKT3. Instead, the present invention also relates to fragments and variants of AKT3 as described herein.

In one embodiment, AKT3 comprises the wild-type form of full length AKT3, set forth herein as SEQ. ID No. 1 (GenBank Accession Number NP_005456; Nakatani, K., Sakaue, H., Thompson, D. A., Weigel, R. J. and Roth, R. A., Identification of a human AKT3 (protein kinase B gamma) which contains the regulatory serine phosphorylation site. Biochem. Biophys. Res. Commun. 257 (3), 906-910, 1999).

In another embodiment, AKT3 comprises residues 62-479 of SEQ. ID No. 1 which comprises the kinase domain of wild-type AKT3.

In another embodiment, AKT3 comprises residues 132-474 of SEQ. ID No. 1 which also comprises the kinase domain of wild-type Akt3.

In another embodiment, AKT3 comprises residues 136-461 of SEQ. ID No. 1 which also comprises the kinase domain of wild-type AKT3.

In another embodiment, AKT3 comprises residues 143-438 of SEQ. ID No. 1 which comprises the portion of the kinase domain of wild-type AKT3 that is represented in the set of structural coordinates shown in FIG. 3.

It should be recognized that the invention may be readily extended to various variants of wild-type AKT3 and variants of fragments thereof. In another embodiment, AKT3 comprises a sequence that has at least 65% identity, preferably at least 70%, 80%, 90%, 95% or higher identity with SEQ. ID No. 1.

It is also noted that the above sequences of AKT3 are also intended to encompass isoforms, mutants and fusion proteins of these sequences. An example of a fusion protein is provided by SEQ. ID No. 3, which includes a 230 residue N-terminal tag that may be used to facilitate purification of the protein. The extended construct is cleaved before crystallization leaving four N-terminal residues (CRSL). This region, however, is disordered in the crystal structure and is not represented in the set of structure coordinates shown in FIG. 3.

With the crystal structure provided herein, where amino acid residues are positioned in the structure are now known. As a result, the impact of different substitutions can be more easily predicted and understood.

For example, based on the crystal structure, applicants have determined that the AKT3 amino acids shown in Table 2 are within 4 Angstroms of and therefore close enough to interact with a modeled ATP. Applicants have also determined that the amino acids of Table 3 are within 7 Angstroms of the modeled ATP and therefore are also close enough to interact with that substrate or analogs thereof. Further it has been determined that the amino acids of Table 4 are within 10 Angstroms of the modeled ATP.

One or more of these sets of amino acids is preferably conserved in a variant of AKT3. Hence, AKT3 may optionally comprise a sequence that has at least 65% identity, preferably at least 70%, 80%, 90%, 95% or higher identity with any one of the above sequences (e.g., all of SEQ. ID No. 1 or residues 62-479, 132-474, 136-461 or 143-438 of SEQ. ID No. 1) where at least the residues shown in Tables 2, 3, and/or 4 are conserved with the exception of 0, 1, 2, 3, or 4 residues. It should be recognized that one might optionally vary some of the binding site residues in order to determine the effect such changes have on structure or activity.

TABLE 2

ATP binding site residues within 4 Angstroms of ATP.

| | | |
|---|---|---|
| PHE 159 | LYS 177 | THR 209 |
| GLU 226 | GLU 275 | ASP 289 |
| VAL 228 | MET 278 | GLU 232 |
| THR 288 | PHE 435 | |

TABLE 3

ATP binding site residues within 7 Angstroms of ATP.

| | | |
|---|---|---|
| LEU 154 | ILE 184 | ASN 229 |
| GLY 155 | GLU 189 | GLY 230 |
| GLY 157 | HIS 192 | GLY 231 |
| THR 158 | THR 193 | GLU 232 |
| PHE 159 | GLU 196 | PHE 235 |
| GLY 160 | THR 209 | ASP 271 |
| VAL 162 | SER 210 | LYS 273 |
| TYR 174 | MET 225 | LEU 274 |
| ALA 175 | GLU 226 | GLU 275 |
| LYS 177 | TYR 227 | ASN 276 |
| LEU 179 | VAL 228 | LEU 277 |
| MET 278 | LEU 279 | LYS 286 |
| ILE 287 | THR 288 | ASP 289 |
| PHE 435 | | |

TABLE 4

ATP binding site residues within 10 Angstroms of ATP.

| | | |
|---|---|---|
| LEU 153 | ILE 184 | VAL 228 |
| LEU 154 | LYS 187 | ASN 229 |
| GLY 155 | ASP 188 | GLY 230 |
| LYS 156 | GLU 189 | GLY 231 |
| GLY 157 | HIS 192 | GLU 232 |
| THR 158 | THR 193 | LEU 233 |
| PHE 159 | LEU 194 | PHE 234 |
| GLY 160 | GLU 196 | PHE 235 |
| LYS 161 | SER 197 | HIS 236 |
| VAL 162 | LEU 200 | TYR 269 |
| ILE 163 | PHE 207 | ARG 270 |
| LEU 164 | LEU 208 | ASP 271 |
| TYR 173 | THR 209 | LEU 272 |
| TYR 174 | SER 210 | LYS 273 |
| ALA 175 | LEU 211 | LEU 274 |
| MET 176 | LYS 212 | GLU 275 |
| LYS 177 | PHE 223 | ASN 276 |
| ILE 178 | VAL 224 | LEU 277 |
| LEU 179 | MET 225 | MET 278 |
| LYS 180 | GLU 226 | LEU 279 |
| VAL 183 | TYR 227 | ASP 280 |
| LYS 281 | ILE 285 | LYS 286 |
| ILE 287 | THR 288 | ASP 289 |
| GLU 437 | ALA 310 | TYR 312 |
| GLU 429 | THR 430 | ASP 431 |
| THR 432 | TYR 434 | PHE 435 |
| ASP 436 | | |

With the benefit of the crystal structure and guidance provided by Tables 2, 3 and 4, a wide variety of AKT3 variants (e.g., insertions, deletions, substitutions, etc.) that fall within the above specified identity ranges may be designed and manufactured utilizing recombinant DNA techniques well known to those skilled in the art, particularly in view of the knowledge of the crystal structure provided herein. These modifications can be used in a number of combinations to produce the variants. The present invention is useful for crystallizing and then solving the structure of the range of variants of AKT3.

Variants of AKT3 may be insertional variants in which one or more amino acid residues are introduced into a predetermined site in the AKT3 sequence. For instance, insertional variants can be fusions of heterologous proteins or polypeptides to the amino or carboxyl terminus of the subunits.

Variants of AKT3 also may be substitutional variants in which at least one residue has been removed and a different residue inserted in its place. Non-natural amino acids (i.e. amino acids not normally found in native proteins), as well as isosteric analogs (amino acid or otherwise) may optionally be employed in substitutional variants. Examples of suitable substitutions are well known in the art, such as the Glu→Asp, Ser→Cys, Cys→Ser, and His→Ala for example.

Another class of variants is deletional variants, which are characterized by the removal of one or more amino acid residues from the AKT3 sequence.

Other variants may be produced by chemically modifying amino acids of the native protein (e.g., diethylpyrocarbonate treatment that modifies histidine residues). Preferred are chemical modifications that are specific for certain amino acid side chains. Specificity may also be achieved by blocking other side chains with antibodies directed to the side chains to be protected. Chemical modification includes such reactions as oxidation, reduction, amidation, deamidation, or substitution of bulky groups such as polysaccharides or polyethylene glycol.

Exemplary modifications include the modification of lysinyl and amino terminal residues by reaction with succinic or other carboxylic acid anhydrides. Modification with these agents has the effect of reversing the charge of the lysinyl residues. Other suitable reagents for modifying amino-containing residues include imidoesters such as methyl picolinimidate; pyridoxal phosphate; pyridoxal chloroborohydride; trinitrobenzenesulfonic acid; O-methylisourea, 2,4-pentanedione; and transaminaseN: talyzed reaction with glyoxylate, and N-hydroxysuccinamide esters of polyethylene glycol or other bulky substitutions.

Arginyl residues may be modified by reaction with a number of reagents, including phenylglyoxal, 2,3-butanedione, 1,2-cyclohexanedione, and ninhydrin. Modification of arginine residues requires that the reaction be performed in alkaline conditions because of the high $pK_a$, of the guanidine functional group. Furthermore, these reagents may react with the groups of lysine as well as the arginine epsilon-amino group.

Tyrosyl residues may also be modified to introduce spectral labels into tyrosyl residues by reaction with aromatic diazonium compounds or tetranitromethane, forming 0-acetyl tyrosyl species and 3-nitro derivatives, respectively. Tyrosyl residues may also be iodinated using $^{125}I$ or $^{131}I$ to prepare labeled proteins for use in radioimmunoassays.

Carboxyl side groups (aspartyl or glutamyl) may be selectively modified by reaction with carbodiimides or they may be converted to asparaginyl and glutaminyl residues by reaction with ammonium ions. Conversely, asparaginyl and glutaminyl residues may be deamidated to the corresponding aspartyl or glutamyl residues, respectively, under mildly acidic conditions. Either form of these residues falls within the scope of this invention.

Other modifications that may be formed include the hydroxylation of proline and lysine, phosphorylation of hydroxyl groups of seryl or threonyl groups of lysine, arginine and histidine side chains (T. E. Creighton, *Proteins: Structure and Molecular Properties*, W.H. Freeman & Co., San Francisco, pp. 79-86, 1983), acetylation of the N-terminal amine and amidation of any C-terminal carboxyl group.

As can be seen, modifications of the nucleic sequence encoding AKT3 may be accomplished by a variety of well-known techniques, such as site-directed mutagenesis (see, Gillman and Smith, *Gene* 8:81-97 (1979) and Roberts, S. et al., *Nature* 328:731-734 (1987)). When modifications are made, these modifications may optionally be evaluated for there affect on a variety of different properties including, for example, solubility, crystallizability and a modification to the protein's structure and activity.

In one variation, the variant and/or fragment of wild-type AKT3 is functional in the sense that the resulting protein is capable of associating with at least one same chemical entity that is also capable of selectively associating with a protein comprising the kinase domain of wild-type AKT3 (e.g., residues 143-438 of SEQ. ID No. 1) since this common associative ability evidences that at least a portion of the native structure has been conserved. That chemical entity may optionally be ATP.

It is noted the activity of the native protein need not necessarily be conserved. Rather, amino acid substitutions, additions or deletions that interfere with native activity but which do not significantly alter the three-dimensional structure of the domain are specifically contemplated by the invention. Crystals comprising such variants of AKT3, and the atomic structure coordinates obtained there from, can be used to identify compounds that bind to the native domain. These compounds may affect the activity of the native domain.

Amino acid substitutions, deletions and additions that do not significantly interfere with the three-dimensional structure of AKT3 will depend, in part, on the region where the substitution, addition or deletion occurs in the crystal structure. These modifications to the protein can now be made far more intelligently with the crystal structure information provided herein. In highly variable regions of the molecule, non-conservative substitutions as well as conservative substitutions may be tolerated without significantly disrupting the three-dimensional structure of the molecule. In highly conserved regions, or regions containing significant secondary structure, conservative amino acid substitutions are preferred.

Conservative amino acid substitutions are well known in the art, and include substitutions made on the basis of similarity in polarity, charge, solubility, hydrophobicity, hydrophilicity and/or the amphipathic nature of the amino acid residues involved. For example, negatively charged amino acids include aspartic acid and glutamic acid; positively charged amino acids include lysine and arginine; amino acids with uncharged polar head groups having similar hydrophilicity values include the following: leucine, isoleucine, valine; glycine, alanine; asparagine, glutamine; serine, threonine; phenylalanine, tyrosine. Other conservative amino acid substitutions are well known in the art.

It should be understood that the protein may be produced in whole or in part by chemical synthesis. As a result, the selection of amino acids available for substitution or addition is not limited to the genetically encoded amino acids. Indeed, mutants may optionally contain non-genetically encoded amino acids. Conservative amino acid substitutions for many of the commonly known non-genetically encoded amino acids are well known in the art. Conservative substitutions for other amino acids can be determined based on their physical properties as compared to the properties of the genetically encoded amino acids.

In some instances, it may be particularly advantageous or convenient to substitute, delete and/or add amino acid residues in order to provide convenient cloning sites in cDNA encoding the polypeptide, to aid in purification of the polypeptide, etc. Such substitutions, deletions and/or additions which do not substantially alter the three dimensional structure of AKT3 will be apparent to those having skills in the art, particularly in view of the three dimensional structure of AKT3 provided herein.

2. Cloning, Expression and Purification of AKT3

The gene encoding AKT3 can be isolated from RNA, cDNA or cDNA libraries. In this case, the portion of the gene encoding amino acid residues 136-461, corresponding to the catalytic domain of human AKT3, was isolated and is shown as SEQ. I.D. No. 2.

Construction of expression vectors and recombinant proteins from the DNA sequence encoding AKT3 may be performed by various methods well known in the art. For example, these techniques may be performed according to Sambrook et al., Molecular Cloning-A Laboratory Manual, Cold Spring Harbor, N.Y. (1989), and Kriegler, M., Gene Transfer and Expression, A Laboratory Manual, Stockton Press, New York (1990).

A variety of expression systems and hosts may be used for the expression of AKT3. Example 1 provides one such expression system.

Once expressed, purification steps are employed to produce AKT3 in a relatively homogeneous state. In general, a higher purity solution of a protein increases the likelihood that the protein will crystallize. Typical purification methods include the use of centrifugation, partial fractionation, using salt or organic compounds, dialysis, conventional column chromatography, (such as ion exchange, molecular sizing chromatography, etc.), high performance liquid chromatography (HPLC), and gel electrophoresis methods (see, e.g., Deutcher, "Guide to Protein Purification" in Methods in Enzymology (1990), Academic Press, Berkeley, Calif.).

AKT3 may optionally be affinity labeled during cloning, preferably with an N-terminal SSP (Synechocystis species) intein-CBD (chitin binding domain) tag, in order to facilitate purification. With the use of an affinity label, it is possible to perform a one-step purification process on a purification column that has a unique affinity for the label. The affinity label may be optionally removed after purification. These and other purification methods are known and will be apparent to one of skill in the art.

3. Crystallization & Crystals Comprising AKT3

One aspect of the present invention relates to methods for forming crystals comprising AKT3 as well as crystals comprising AKT3.

In one embodiment, a method for forming crystals comprising AKT3 is provided comprising forming a crystallization volume comprising AKT3, one or more precipitants, optionally a buffer, optionally a monovalent and/or divalent salt and optionally an organic solvent; and storing the crystallization volume under conditions suitable for crystal formation.

In yet another embodiment, a method for forming crystals comprising AKT3 is provided comprising forming a crystallization volume comprising AKT3 in solution comprising the components shown in Table 5; and storing the crystallization volume under conditions suitable for crystal formation.

TABLE 5

| Precipitant |
|---|
| 5-50% w/v of precipitant wherein the precipitant comprises one or more members of the group consisting of PEG MME having a molecular weight range between 300-10000, and PEG having a molecular weight range between 100-10000 |
| pH |
| pH 4-8. Buffers that may be used include, but are not limited to cacodylate, acetate, citrate, MES and combinations thereof. |
| Additives |
| 0.05 to 0.5M additives wherein the additives comprises one or more members of the group consisting of sodium chloride, sodium tartrate, ammonium sulfate, sodium formate, lithium chloride, $Ca^{2+}$, $Zn^{2+}$, $Mg^{2+}$ and $Mn^{2+}$. |
| Protein Concentration |
| 1 mg/ml-50 mg/ml |
| Temperature |
| 1° C.-25° C. |

In yet another embodiment, a method for forming crystals comprising AKT3 is provided comprising forming a crystallization volume comprising AKT3; introducing crystals comprising AKT3 as nucleation sites, and storing the crystallization volume under conditions suitable for crystal formation.

Crystallization experiments may optionally be performed in volumes commonly used in the art, for example typically 15, 10, 5, 2 microliters or less. It is noted that the crystallization volume optionally has a volume of less than 1 microliter, optionally 500, 250, 150, 100, 50 or less nanoliters.

It is also noted that crystallization may be performed by any crystallization method including, but not limited to batch, dialysis and vapor diffusion (e.g., sitting drop and hanging drop) methods. Micro and/or macro seeding of crystals may also be performed to facilitate crystallization.

It should be understood that forming crystals comprising AKT3 and crystals comprising AKT3 according to the invention are not intended to be limited to the wild type, full length AKT3 shown in SEQ. ID No. 1 and to fragments comprising residues 62-479, 132-474, 136-461 or 143-438 of SEQ. ID No. 1. Rather, it should be recognized that the invention may be extended to various other fragments and variants of wild-type AKT3 as described above.

It should also be understood that forming crystals comprising AKT3 and crystals comprising AKT3 according to the invention may be such that AKT3 is complexed with one or more ligands and one or more copies of the same ligand. The ligand used to form the complex may be any ligand capable of binding to AKT3. In one variation, the ligand is a natural substrate. In another variation, the ligand is an inhibitor.

In one particular variation, the ligand binds to the ATP binding site of the protein. Examples of such ligands include, but are not limited to, small molecule inhibitors of AKT3 as well as ATP, ADP, non-hydrolyzable ATP analogs and suicide substrates. Non-hydrolyzable ATP analogs useful in the crystallizable compositions of this invention include AMP-PCH$_2$P, AMP-PNP, AMP-PSP and AMP where the oxygen linking the second and third phosphates of the ATP analogs is replaced by $CH_2$, S (ATPγS) and NH, respectively. An example of a suicidal substrate is 5'-(p- fluorosulfonyl benzoyl) adenosine (FSBA). Preferably, the crystallizable compositions of this invention comprise ATP as the substrate.

Optionally, the AKT3 complex may further comprise divalent cations, especially magnesium and/or manganese that may be introduced in any suitable manner. For example, the cations may be introduced by incubating the desired ligand with a suitable metal salt such as $MgCl_2$ or $MnCl_2$ prior to incubation with the AKT3 protein.

In one particular embodiment, AKT3 crystals have a crystal lattice in the $P2_12_12_1$, space group. AKT3 crystals may also optionally have unit cell dimensions, +/−5%, of a=48.36 Å b=72.29 Å and c=94.52 Å, $\alpha=\beta=\gamma 90$.

AKT3 crystals also preferably are capable of diffracting X-rays for determination of atomic coordinates to a resolution of 4 Å, 3 Å, 2.5 Å, 2 Å or greater.

Crystals comprising AKT3 may be formed by a variety of different methods known in the art. For example, crystallizations may be performed by batch, dialysis, and vapor diffusion (sitting drop and hanging drop) methods. A detailed description of basic protein crystallization setups may be found in McRee, D. and David. P., *Practical Protein Crystallography*, $2^{nd}$ Ed. (1999), Academic Press Inc. Further descriptions regarding performing crystallization experiments are provided in Stevens, et al. (2000) *Curr. Opin. Struct. Biol.*: 10(5):558-63, and U.S. Pat. Nos. 6,296,673, 5,419,278, and 5,096,676.

In one variation, crystals comprising AKT3 are formed by mixing substantially pure AKT3 with an aqueous buffer containing a precipitant at a concentration just below a concentration necessary to precipitate the protein. One suitable precipitant for crystallizing AKT3 is polyethylene glycol (PEG), which combines some of the characteristics of the salts and other organic precipitants (see, for example, Ward et al., *J. Mol. Biol.* 98:161, 1975, and McPherson, *J. Biol. Chem.* 251:6300, 1976.

During a crystallization experiment, water is removed by diffusion or evaporation to increase the concentration of the precipitant, thus creating precipitating conditions for the protein. In one particular variation, crystals are grown by vapor diffusion in hanging drops or sitting drops. According to these methods, a protein/precipitant solution is formed and then allowed to equilibrate in a closed container with a larger aqueous reservoir having a precipitant concentration for producing crystals. The protein/precipitant solution continues to equilibrate until crystals grow.

By performing submicroliter volume sized crystallization experiments, as detailed in U.S. Pat. No. 6,296,673, effective crystallization conditions for forming crystals of an AKT3 complex were obtained. In order to accomplish this, systematic broad screen crystallization trials were performed on an AKT3 complex using the sitting drop technique. In each experiment, a 100 nL mixture of AKT3 complex and precipitant was placed on a platform positioned over a well containing 100 μL of the precipitating solution. Precipitate and crystal formation was detected in the sitting drops. Fine screening was then carried out for those crystallization conditions that appeared to produce precipitate and/or crystal in the drops.

Based on the crystallization experiments that were performed, a thorough understanding of how different crystallization conditions affect AKT3 crystallization was obtained. Based on this understanding, a series of crystallization conditions were identified that may be used to form crystals comprising AKT3. These conditions are summarized in Table 5. A particular example of crystallization conditions that may be used to form crystals diffraction quality crystals of the AKT3 complex is detailed in Example 2. FIG. 2 illustrates crystals of the AKT3 complex formed using the crystallization conditions provided in Table 5.

One skilled in the art will recognize that the crystallization conditions provided in Table 5 and Example 2 can be varied and still yield protein crystals comprising AKT3. For example, it is noted that variations on the crystallization conditions described herein can be readily determined by taking the conditions provided in Table 5 and performing fine screens around those conditions by varying the type and concentration of the components in order to determine additional suitable conditions for crystallizing AKT3, variants of AKT3, and ligand complexes thereof.

Crystals comprising AKT3 have a wide range of uses. For example, now that crystals comprising AKT3 have been produced, it is noted that crystallizations may be performed using such crystals as a nucleation site within a concentrated protein solution. According to this variation, a concentrated protein solution is prepared and a crystalline material (microcrystals) is used to 'seed' the protein solution to assist nucleation for crystal growth. If the concentrations of the protein and any precipitants are optimal for crystal growth, the seed crystal will provide a nucleation site around which a larger crystal forms. Given the ability to form crystals comprising AKT3 according to the present invention, the crystals so formed can be used by this crystallization technique to initiate crystal growth of other AKT3 comprising crystals, including AKT3 complexed to other ligands.

As will be described herein in greater detail, crystals may also be used to perform X-ray or neutron diffraction analysis in order to determine the three-dimensional structure of AKT3 and, in particular, to assist in the identification of its active site. Knowledge of the binding site region allows rational design and construction of ligands including inhibitors. Crystallization and structural determination of AKT3 mutants having altered bioactivity allows the evaluation of whether such changes are caused by general structure deformation or by side chain alterations at the substitution site.

4. X-Ray Data Collection and Structure Determination

Crystals comprising AKT3 may be obtained as described above in Section 3. As described herein, these crystals may then be used to perform X-ray data collection and for structure determination.

In one embodiment, described in Example 2, crystals of an AKT3 complex were obtained where AKT3 has the sequence of residues shown in SEQ. ID No. 3 (the N-terminal fusion protein, underlined in SEQ. ID No. 3, was cleaved leaving residues 227C, 228R, 229S and 230L attached to the AKT3). These particular crystals were used to determine the three dimensional structure of AKT3. However, it is noted that other crystals comprising AKT3 including different AKT3 variants, fragments, and complexes thereof may also be used.

Diffraction data was collected from cryocooled crystals (100K) of AKT3 at the Advanced Light Source beam line 5.0.3 using an ADSC CCD detector. The diffraction pattern of AKT3 displayed symmetry consistent with space group $P2_12_12_1$, with unit cell dimensions a=48.36 Å, b=72.29 Å and c=94.52 Å, $\alpha=\beta=\gamma 90°$. Data were collected and integrated to 2.1 Å with MOSFLM and scaled with SCALA (CCP4 Study Weekend, Eds. Sawyer, L., Isaacs, N. & Bailey, S., 56-62, SERC Daresbury Laboratory, England, 1993).

All crystallographic calculations were performed using the CCP4 program package (Collaborative Computational Project, N. The CCP4 Suite: Programs for Protein Crystallography. *Acta Cryst.* D50, 760-763 (1994)). The initial phases for AKT3 were obtained by the molecular replacement method using the program AMORE. The coordinates of yeast cAPK kinase domain (PDB code 1FOT) were used as a search model (43% identity) for the solution of AKT3 structure. The highest solution from the translational function was subjected to a rigid body rotation followed by refinement against the maximum likelihood method as implemented in REFMAC(CCP4). Rigid body refinement and torsional dynamics refinement was followed by multiple rounds of manual building with Xfit (McRee, D. E. Xtal-View/Xfit-A versatile program for manipulating atomic coordinates and electron density *J. Struct. Biol.* 125, 156-65 (1999)) and/or ARP_WARP map improvement (Perrakis, A., Morris, R. J. & Lamzin, V. S. Automated protein model building combined with iterative structure refinement). The data collection and data refinement statistics are given in Table 6.

TABLE 6

| Crystal data | |
|---|---|
| Ligands | ATP, Mg$^{2+}$ |
| Space group | P2$_1$2$_1$2$_1$ |
| Unit cell dimensions | a = 48.36Å |
| | b = 72.29Å and |
| | c = 94.52Å, |
| | α = β = γ = 90 |
| Data collection | AKT3 |
| X-ray source | B1 5.0.3 |
| Wavelength [Å] | 1.0 |
| Resolution [Å] | 48-2.1 |
| Observations (unique) | 18,169 |
| Redundancy | 3.5 |
| Completeness     overall (outer shell) | 95% (65%) |
| I/σ(I)                  overall (outer shell) | 7.5 (1.5) |
| R$_{symm}$$^1$       overall (outer shell) | 8.4% (49.9%) |
| Refinement | |
| Reflections used | 17,300 |
| R-factor | 21.0% |
| R$_{free}$ | 27.15% |
| r.m.s bonds | 0.022 |
| r.m.s angles | 1.86 |

$^1$R$_{symm}$ = Σ$_{hkl}$Σ$_i$|I(hkl)$_i$ − <I(hkl)>|/Σ$_{hkl}$Σ$_i$<I(hkl)$_i$> over I observations of a reflection hkl During structure determination, it was realized that each unit cell comprised one AKT3 complex. Structure coordinates were determined for this complex and the resultant set of structural coordinates from the refinement are presented in FIG. 3.

It is noted that the sequence of the structure coordinates presented in FIG. 3 differ in some regards from the sequence shown in SEQ. ID No. 1.

For some residues, the electron density obtained was insufficient to identify the side chain. As a result, the side chains of these residues were truncated such that a different amino acid is reported. Table 7 summarizes the differences between SEQ. ID No. 1 and the truncated residues appearing in FIG. 3.

TABLE 7

Truncated Residues in The Structure Coordinates of FIG. 3

| K143-A143 | P310-A310 | E438-A438 |
|---|---|---|

It is also noted structure coordinates are not reported for some residues because the electron density obtained was insufficient to identify the position of these residues. For FIG. 3, structure coordinates for residues 136-142, 291-309, 321-323 and 439-461 (using numbering from SEQ. No. 1) are not reported.

Those of skill in the art understand that a set of structure coordinates (such as those in FIG. 3) for a protein or a protein-complex or a portion thereof, is a relative set of points that define a shape in three dimensions. Thus, it is possible that an entirely different set of structure coordinates could define a similar or identical shape. Moreover, slight variations in the individual coordinates may have little effect on overall shape. In terms of binding pockets, these variations would not be expected to significantly alter the nature of ligands that could associate with those pockets. The term "binding pocket" as used herein refers to a region of the protein that, as a result of its shape, favorably associates with a ligand.

These variations in coordinates may be generated because of mathematical manipulations of the AKT3 structure coordinates. For example, the sets of structure coordinates shown in FIG. 3 could be manipulated by crystallographic permutations of the structure coordinates, fractionalization of the structure coordinates, application of a rotation matrix, integer additions or subtractions to sets of the structure coordinates, inversion of the structure coordinates or any combination of the above.

Alternatively, modifications in the crystal structure due to mutations, additions, substitutions, and/or deletions of amino acids or other changes in any of the components that make up the crystal could also account for variations in structure coordinates. If such variations are within an acceptable standard error as compared to the original coordinates, the resulting three-dimensional shape should be considered to be the same. Thus, for example, a ligand that bound to the active site binding pocket of AKT3 would also be expected to bind to another binding pocket whose structure coordinates defined a shape that fell within the acceptable error.

Various computational methods may be used to determine whether a particular protein or a portion thereof (referred to here as the "target protein"), typically the binding pocket, has a high degree of three-dimensional spatial similarity to another protein (referred to here as the "reference protein") against which the target protein is being compared.

The process of comparing a target protein structure to a reference protein structure may generally be divided into three steps: 1) defining the equivalent residues and/or atoms for the target and reference proteins, 2) performing a fitting operation between the proteins; and 3) analyzing the results. These steps are described in more detail below. All structure comparisons reported herein and the structure comparisons claimed are intended to be based on the particular comparison procedure described below.

Equivalent residues or atoms can be determined based upon an alignment of primary sequences of the proteins, an alignment of their structural domains or as a combination of both. Sequence alignments generally implement the dynamic programming algorithm of Needleman and Wunsch [*J. Mol. Biol.* 48: 442-453, 1970]. For the purpose of this invention the sequence alignment was performed using the publicly available software program MOE (Chemical Computing Group Inc.) package version 2002.3, as described in the accompanying User's Manual. When using the MOE program, alignment was performed in the sequence editor window using the ALIGN option utilizing the following program parameters: Initial pairwise Build-up: ON, Substitution Matrix: Blosum62, Round Robin: ON, Gap Start: 7, Gap Extend: 1, Iterative Refinement: ON, Build-up: TREE- BASED, Secondary Structure: NONE, Structural Alignment: ENABLED, Gap Start: 1, Gap Extend: 0.1

Once aligned, a rigid body fitting operation is performed where the structure for the target protein is translated and rotated to obtain an optimum fit relative to the structure of the reference protein. The fitting operation uses an algorithm that computes the optimum translation and rotation to be applied to the moving structure, such that the root mean square deviation of the fit over the specified pairs of equivalent atoms is an absolute minimum. For the purpose of fitting operations made herein, the publicly available software program MOE (Chemical Computing Group Inc.) v. 2002.3 was used.

The results from this process are typically reported as an RMSD value between two sets of atoms. The term "root mean square deviation" means the square root of the arithmetic mean of the squares of deviations. It is a way to express the deviation or variation from a trend or object. As used herein, an RMSD value refers to a calculated value based on variations in the atomic coordinates of a reference protein from the atomic coordinates of a reference protein or portions of thereof. The structure coordinates for AKT3, provided in FIG. 3, are used as the reference protein in these calculations.

The same set of atoms was used for initial fitting of the structures and for computing root mean square deviation values. For example, if a root mean square deviation (RMSD) between Cα atoms of two proteins is needed, the proteins in question should be superposed only on the Cα atoms and not on any other set of atoms. Similarly, if an RMSD calculation for all atoms is required, the superposition of two structures should be performed on all atoms.

Based on a review of protein structures deposited in the Protein Databank (PDB), 1FOT was identified as having the smallest RMSD values relative to the structure coordinates provided herein. Table 8 below provides a series of RMSD values that were calculated by the above described process using the structure coordinates in FIG. 3 as the reference protein and the structure coordinates from PDB code: IFOT (Yeast cyclic-AMP dependent Protein Kinase Type 1) as the target protein.

TABLE 8

| AA RESIDUES USED TO PERFORM RMSD COMPARISON WITH PDB:1FOT | PORTION OF EACH AA RESIDUE USED TO PERFORM RMSD COMPARISON WITH PDB:1FOT | RMSD [Å] |
|---|---|---|
| Table 2 | alpha-carbon atoms[1] | 1.15 |
| (4 Angstrom set) | main-chain atoms[1] | 1.67 |
|  | all non-hydrogen[2] | 2.04 |
| Table 3 | alpha-carbon atoms[1] | 1.28 |
| (7 Angstrom set) | main-chain atoms[1] | 1.41 |
|  | all non-hydrogen[2] | 1.76 |
| Table 4 | alpha-carbon atoms[1] | 1.38 |
| (10 Angstrom set) | main-chain atoms[1] | 1.45 |
|  | all non-hydrogen[2] | 1.81 |
| 143-438 of | alpha-carbon atoms[1] | 1.64 |
| SEQ. ID No. 1 | main-chain atoms[1] | 1.69 |
|  | all non-hydrogen[2] | 1.89 |

[1] the RMSD computed between the atoms of all amino acids that are common to both the target and the reference in the aligned and superposed structure. The amino acids need not to be identical.
[2] the RMSD computed only between identical amino acids, which are common to both the target and the reference in the aligned and superposed structure.

It is noted that mutants and variants of AKT3 as well as other serine/threonine protein kinases are likely to have similar structures despite having different sequences. For example, the binding pockets of these related proteins are likely to have similar contours. Accordingly, it should be recognized that the structure coordinates and binding pocket models provided herein have utility for these other related proteins.

Accordingly, in one embodiment, the invention relates to data, computer readable media comprising data, and uses of the data where the data comprises all or a portion of the structure coordinates shown in FIG. 3 or structure coordinates having a root mean square deviation (RMSD) equal to or less than the RMSD value specified in Columns 3, 4 or 5 of Table 1 when compared to the structure coordinates of FIG. 3, the root mean square deviation being calculated such that the portion of amino acid residues specified in Column 2 of Table 1 of each set of structure coordinates are superimposed and the root mean square deviation is based only on those amino acid residues in the structure coordinates that are also present in the portion of the protein specified in specified in Column 1 of Table 1.

As noted, there are many different ways to express the surface contours of the AKT3 structure other than by using the structure coordinates provided in FIG. 3. Accordingly, it is noted that the present invention is also directed to any data, computer readable media comprising data, and uses of the data where the data defines a computer model for a protein binding pocket, at least a portion of the computer model having a surface contour that has a root mean square deviation equal to or less than a given RMSD value specified in Columns 3, 4 or 5 of Table 1 when the coordinates used to compute the surface contour are compared to the structure coordinates of FIG. 3, wherein (a) the root mean square deviation is calculated by the calculation method set forth herein, (b) the portion of amino acid residues associated with the given RMSD value in Table I (specified in Column 2 of Table 1) are superimposed according to the RMSD calculation, and (c) the root mean square deviation is calculated based only on those amino acid residues present in both the protein being modeled and the portion of the protein associated with the given RMSD in Table 1 (specified in Column 1 of Table 1).

5. AKT3 Structure

The present invention is also directed to a three-dimensional crystal structure of AKT3. This crystal structure may be used to identify binding sites, to provide mutants having desirable binding properties, and ultimately, to design, characterize, or identify ligands that interact with AKT3.

The three-dimensional crystal structure of AKT3 may be generated, as is known in the art, from the structure coordinates shown in FIG. 3 and similar such coordinates.

The refined crystal structure of AKT3 determined according to the present invention contains amino acids residues 143-438 as numbered according to SEQ. ID No. 1 (based on the coordinates of FIG. 3), however, a bound ATP molecule and two $Mg^{2+}$ ions were not observed in the refined crystal structure. A total of 89 water molecules were included.

Figure 4:
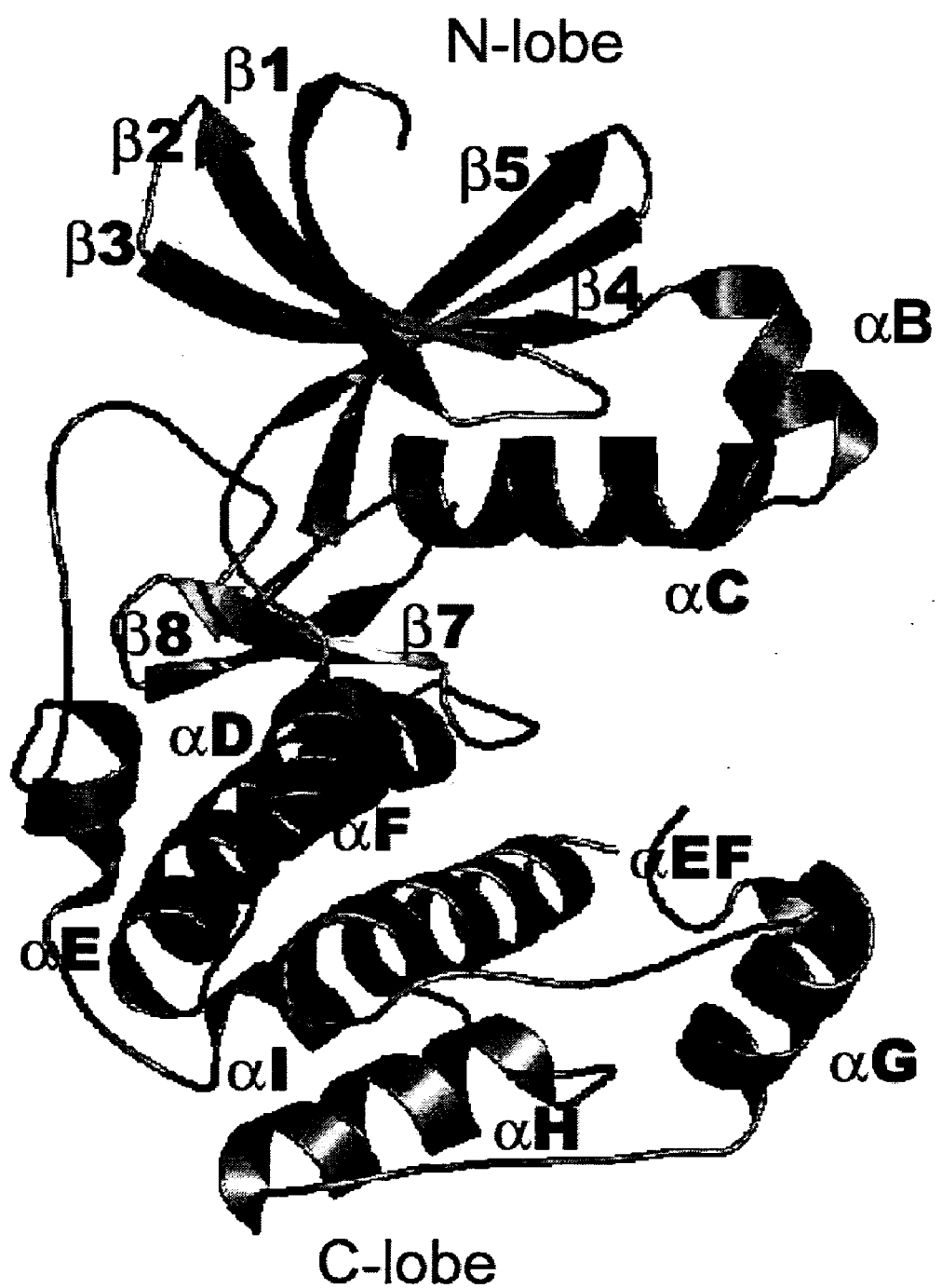
FIG. 4 illustrates a ribbon diagram overview of the structure of SEQ ID NO: 4, highlighting the secondary structural elements of the protein.

FIG. 4 illustrates a ribbon diagram overview of the structure of AKT3, highlighting the secondary structural elements of the protein. As can be seen, the structure exhibits bilobal architecture typical of protein kinase catalytic domains. The smaller N-terminal lobe contains a five-stranded anti-parallel β-sheet (β1-β5) and two α-helices (αB and αC). The C-terminal lobe (residues 230-415) contains two short β-strands (β7 and β8) and seven α-helices (αD-αH).

Kinases show considerable variability in the relative orientation of the N and C lobes, in the position and orientation of the αC, and in the conformation of the activation loop. This relative orientation of the N- and C-terminal lobes is important in kinase function. A catalytically active conformation is generally a closed structure in which the two lobes clamp together bringing conserved residues into catalytically optimal positions. In particular, in the active conformation, the αC helix becomes parallel with the cleft between the lobes and makes tertiary contacts with the C-lobe. In the inactive conformation observed in several unphosphorylated kinase structures the two lobes are spaced apart at a much higher angle and the αC helix is rotated away from the C-lobe.

For AKT3, the activation segment (also known as the activation loop) comprising residues 289-315 is largely disordered and was not included in the coordinates of FIG. 3. An interesting feature of the AKT3 structure is the presence of C-terminal hydrophobic regulatory segment (residues 415-438). This portion of the molecule interacts with the hydrophobic groove of the N-terminal lobe close to the catalytic and substrate binding sites. In particular, the side chain of F435 inserts deeply into the ATP binding pocket making hydrophobic interactions with adjacent residues Y227, L154 and M278. It is likely that this region is involved in the regulation of kinase activity.

Figure 5:
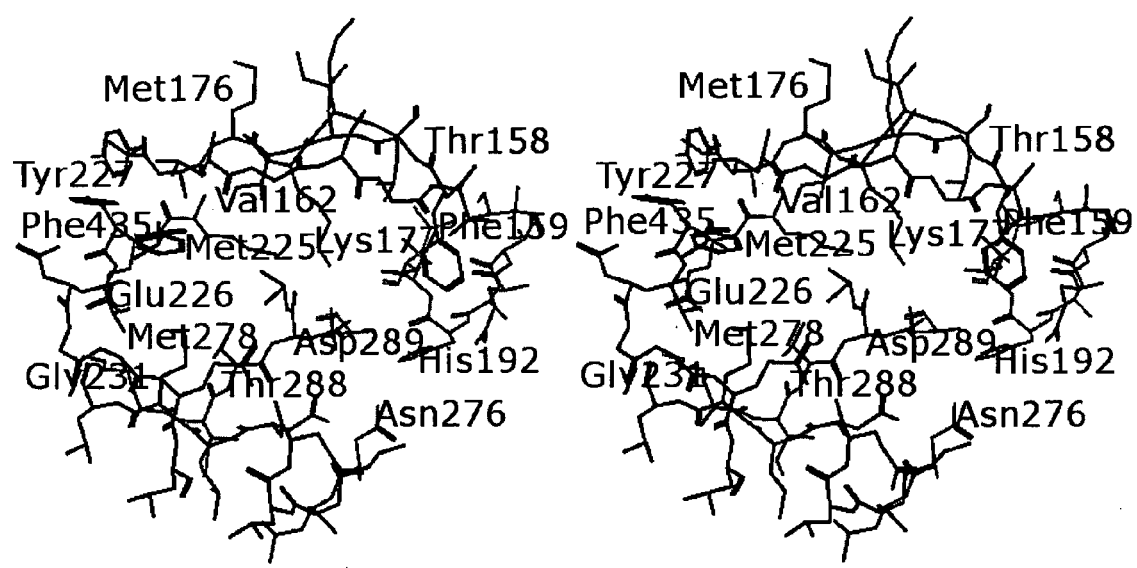
FIG. 5 illustrates the ATP binding site of SEQ ID NO: 4 based on the determined crystal structure for the molecule in the asymmetric unit corresponding to the coordinates shown in FIG. 3.

FIG. 5 illustrates the ATP binding site of AKT3 based on the determined crystal structure for the molecule in the asymmetric unit corresponding to the structure coordinates shown in FIG. 3.

6. AKT3 Binding Pocket and Ligand Interaction

The term "binding site" or "binding pocket", as the terms are used herein, refers to a region of a protein that, as a result of its shape, favorably associates with a ligand or substrate. The term "AKT3-like binding pocket" refers to a portion of a molecule or molecular complex whose shape is sufficiently similar to the AKT3 binding pockets as to bind common ligands. This commonality of shape may be quantitatively defined based on a comparison to a reference point, that reference point being the structure coordinates provided herein. For example the commonality of shape may be quantitatively defined based on a root mean square deviation (RMSD) from the structure coordinates of the backbone atoms of the amino acids that make up the binding pockets in AKT3 (as set forth in FIG. 3).

The "active site binding pockets" or "active site" of AKT3 refers to the area on the surface of AKT3 where the substrate binds.

FIG. 5 illustrates the ATP binding site of SEQ ID NO: 4 based on the determined crystal structure for the molecule in the asymmetric unit corresponding to the structure coordinates shown in FIG. 3. The catalytic site for ATP is located at the interface of the two lobes (FIG. 5), however, the ATP ligand is not present in the crystal structure.

The ATP binding site of protein kinases is a primary target for the design of small molecule inhibitors. The ATP binding site appears well conserved among protein kinases and involves residues protruding from the β1-β2-β3 sheet, helix C, the loop region linking β5 and the C-lobe, and the catalytic loop. The structure of the ATP binding pocket in the AKT3 complex shows considerable sequence variability with other kinases, which is reflective of diversity among kinase sub-families. The ATP binding cleft shows subtle differences in ATP site architecture that may be explored to confer specificity of inhibition.

In resolving the crystal structure of AKT3, applicants determined that AKT3 amino acids in Table 2 (above) are within 4 Angstroms of and therefore close enough to interact with a modeled ATP. Applicants have also determined that the amino acids of Table 3 (above) are within 7 Angstroms of a modeled ATP and therefore are also close enough to interact with that substrate or analogs thereof. Further it has been determined that the amino acids of Table 4 (above) are within 10 Angstroms of the modeled ATP. The 4, 7, and/or 10 Angstroms sets of amino acids are preferably conserved in variants of AKT3. While it is desirable to largely conserve these residues, it should be recognized however that variants may also involve varying 1, 2, 3, 4 or more of the residues set forth in Tables 2, 3, and 4 in order to evaluate the roles these amino acids play in the binding pocket.

With the knowledge of the AKT3 crystal structure provided herein, Applicants define an AKT3 binding pocket as a binding pocket where the relative positioning of the 4, 7, and/or 10 Angstroms sets of amino acids are substantially conserved. Again, it is noted that it may be desirable to form variants where 1, 2, 3, 4 or more of the residues set forth in Tables 2, 3, and 4 are varied in order to evaluate the roles these amino acids play in the binding pocket. Accordingly, any set of structure coordinates for a protein from any source having a root mean square deviation of non-hydrogen atoms of less than 2 Å when superimposed on the non-hydrogen atom positions of the corresponding atomic coordinates of FIG. 3 for the 4, 7, and/or 10 Angstroms sets of amino acids shall be considered identical. As noted previously, the root mean square deviation is intended to be limited to only those non-hydrogen atoms of amino acid residues that are common to both the protein fragment represented in FIG. 3 and the protein whose structure coordinates are being compared to the coordinates shown in FIG. 3 since the sequence of the protein may be varied somewhat.

Accordingly, in one embodiment, the invention relates to data, computer readable media comprising data, and uses of the data where the data comprises the structure coordinates shown in FIG. 3 or structure coordinates having a root mean square deviation of non-hydrogen atoms of less than 3Å when superimposed on the non-hydrogen atom positions of the corresponding atomic coordinates of FIG. 3 for the 4, 7, and/or 10 Angstroms sets of amino acids.

Again, it is noted that the root mean square deviation is intended to be limited to only those non-hydrogen atoms of amino acid residues that are common to both the protein fragment represented in one or more of the tables and the protein whose structure coordinates are being compared to the coordinates shown in FIG. 3.

As noted above, there are many different ways to express the surface contours of the AKT3 structure other than by using the structure coordinates provided in FIG. 3. Accordingly, it is noted that the present invention is also directed to any data, computer readable media comprising data, and uses of the data where the data defines a computer model for a protein binding pocket, at least a portion of the computer model having a surface contour that has a root mean square deviation of less than 3 Å when superimposed on a surface contour defined by atomic coordinates of FIG. 3, the root mean square deviation being calculated based only on non-hydrogen atoms in the structure coordinates of FIG. 3 that are present in residues shown in Tables 2, 3, and/or 4.

Optionally, the root mean square deviation of non-hydrogen atoms is less than 1.5 Å, 1 Å, 0.5 Å, or less.

It will be readily apparent to those of skill in the art that the numbering of amino acids in other isoforms of AKT3 may be different than that set forth for AKT3. Corresponding amino acids in other isoforms of AKT3 are easily identified by visual inspection of the amino acid sequences or by using commercially available homology software programs, as further described below.

7. System For Displaying the Three Dimensional Structure of AKT3

The present invention is also directed to machine-readable data storage media having data storage material encoded with machine-readable data that comprises structure coordinates for AKT3. The present invention is also directed to a machine readable data storage media having data storage material encoded with machine readable data, which, when read by an appropriate machine, can display a three dimensional representation of a structure of AKT3.

All or a portion of the AKT3 coordinate data shown in FIG. 3, when used in conjunction with a computer programmed with software to translate those coordinates into the three-dimensional structure of AKT3 may be used for a variety of purposes, especially for purposes relating to drug discovery. Software for generating three-dimensional graphical representations are known and commercially available. The ready use of the coordinate data requires that it be stored in a computer-readable format. Thus, in accordance with the present invention, data capable of being displayed as the three-dimensional structure of AKT3 and/or portions thereof and/or their structurally similar variants may be stored in a machine-readable storage medium, which is capable of displaying a graphical three-dimensional representation of the structure.

For example, in various embodiments, a computer is provided for producing a three-dimensional representation of at least an AKT3-like binding pocket, the computer comprising:

machine readable data storage medium comprising a data storage material encoded with machine-readable data, the machine readable data comprising structure coordinates that have a root mean square deviation equal to or less than the RMSD value specified in Columns 3, 4 or 5 of Table 1 when compared to the structure coordinates of FIG. 3, the root mean square deviation being calculated such that the portion of amino acid residues specified in Column 2 of Table 1 of each set of structure coordinates are superimposed and the root mean square deviation is based only on those amino acid residues in the structure coordinates that are also present in the portion of the protein specified in specified in Column 1 of Table 1;

a working memory for storing instructions for processing the machine-readable data;

a central-processing unit coupled to the working memory and to the machine-readable data storage medium, for processing the machine-readable data into the three-dimensional representation; and an output hardware coupled to the central processing unit, for receiving the three dimensional representation.

Another embodiment of this invention provides a machine-readable data storage medium, comprising a data storage material encoded with machine readable data which, when used by a machine programmed with instructions for using said data, displays a graphical three-dimensional representation comprising AKT3 or a portion or variant thereof.

In various variations, the machine readable data comprises data for representing a protein based on structure coordinates where the structure coordinates have a root mean square deviation equal to or less than the RMSD value specified in Columns 3, 4 or 5 of Table 1 when compared to the structure coordinates of FIG. 3, the root mean square deviation being calculated such that the portion of amino acid residues specified in Column 2 of Table 1 of each set of structure coordinates are superimposed and the root mean square deviation is based only on those amino acid residues in the structure coordinates that are also present in the portion of the protein specified in specified in Column 1 of Table 1.

According to another embodiment, the machine-readable data storage medium comprises a data storage material encoded with a first set of machine readable data which comprises the Fourier transform of structure coordinates that have a root mean square deviation equal to or less than the RMSD value specified in Columns 3, 4 or 5 of Table 1 when compared to the structure coordinates of FIG. 3, the root mean square deviation being calculated such that the portion of amino acid residues specified in Column 2 of Table 1 of each set of structure coordinates are superimposed and the root mean square deviation is based only on those amino acid residues in the structure coordinates that are also present in the portion of the protein specified in specified in Column 1 of Table 1, and which, when using a machine programmed with instructions for using said data, can be combined with a second set of machine readable data comprising the X-ray diffraction pattern of another molecule or molecular complex to determine at least a portion of the structure coordinates corresponding to the second set of machine readable data. For example, the Fourier transform of the structure coordinates set forth in FIG. 3 may be used to determine at least a portion of the structure coordinates of other AKT3-like enzymes, and isoforms of AKT3.

Optionally, a computer system is provided in combination with the machine-readable data storage medium provided herein. In one embodiment, the computer system comprises a working memory for storing instructions for processing the machine-readable data; a processing unit coupled to the working memory and to the machine-readable data storage medium, for processing the machine-readable data into the three-dimensional representation; and an output hardware coupled to the processing unit, for receiving the three-dimensional representation.

Figure 6:
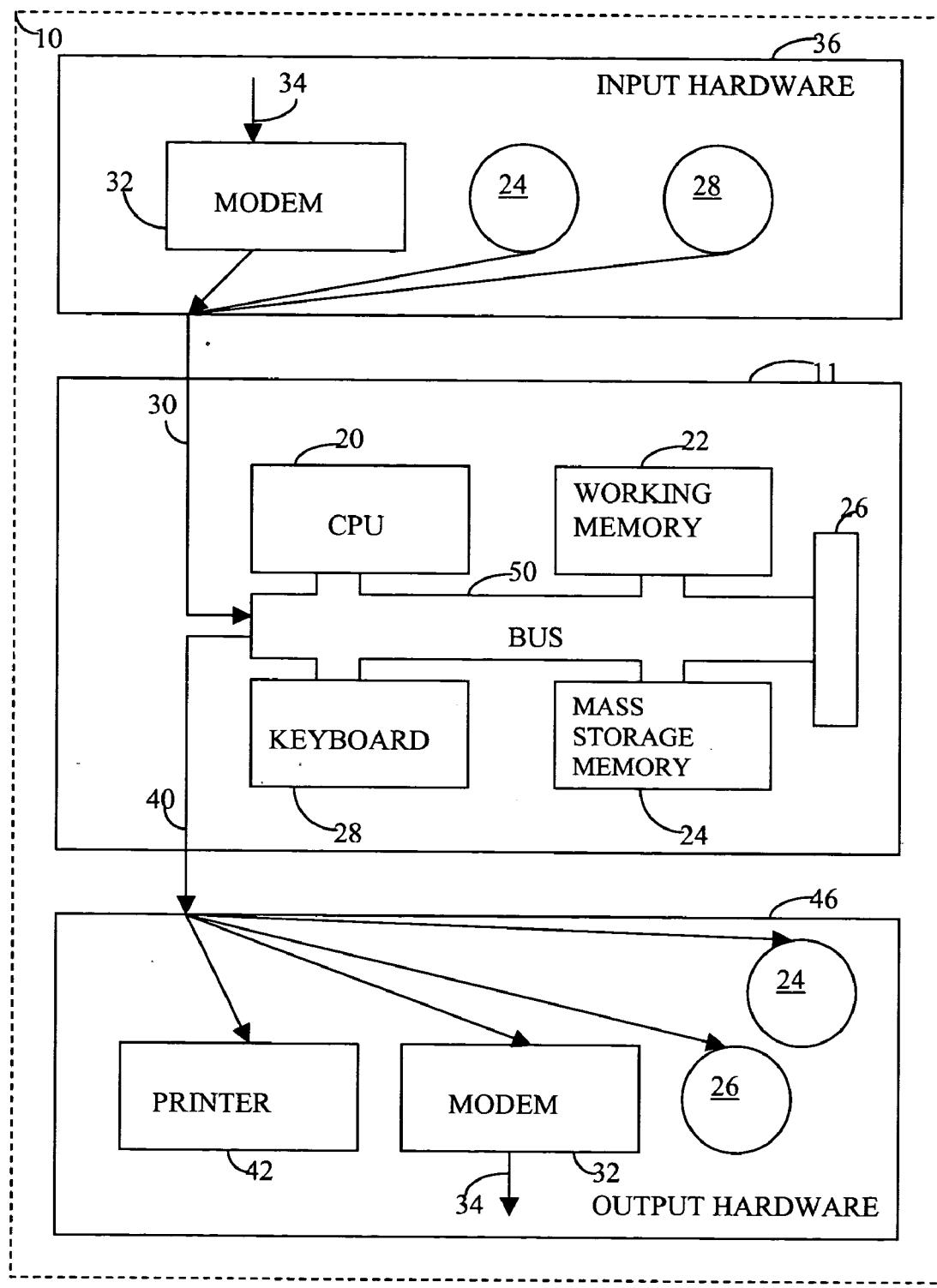
FIG. 6 illustrates a system that may be used to carry out instructions for displaying a crystal structure of AKT3 encoded on a storage medium.

FIG. 6 illustrates an example of a computer system that may be used in combination with storage media according to the present invention. As illustrated, the computer system 10 includes a computer 11 comprising a central processing unit ("CPU") 20, a working memory 22 which may be, e.g., RAM (random-access memory) or "core" memory, mass storage memory 24 (such as one or more disk drives or CD-ROM drives), one or more cathode-ray tube ("CRT") display terminals 26, one or more keyboards 28, one or more input lines 30, and one or more output lines 40, all of which are interconnected by a conventional bi-directional system bus 50.

Input hardware 36, coupled to computer 11 by input lines 30, may be implemented in a variety of ways. For example, machine-readable data of this invention may be inputted via the use of a modem or modems 32 connected by a telephone line or dedicated data line 34. Alternatively or additionally, the input hardware 36 may comprise CD-ROM drives or disk drives 24. In conjunction with display terminal 26, keyboard 28 may also be used as an input device.

Conventional devices may, similarly implement output hardware 46, coupled to computer 11 by output lines 40. By way of example, output hardware 46 may include CRT display terminal 26 for displaying a graphical representation of a binding pocket of this invention using a program such as MOE as described herein. Output hardware might also include a printer 42, so that hard copy output may be produced, or a disk drive 24, to store system output for later use.

In operation, CPU 20 coordinates the use of the various input and output devices 36, 46 coordinates data accesses from mass storage 24 and accesses to and from working memory 22, and determines the sequence of data processing steps. A number of programs may be used to process the machine-readable data of this invention. Such programs are discussed in reference to using the three dimensional structure of AKT3 described herein.

The storage medium encoded with machine-readable data according to the present invention can be any conventional data storage device known in the art. For example, the storage medium can be a conventional floppy diskette or hard disk. The storage medium can also be an optically readable data storage medium, such as a CD-ROM or a DVD-ROM, or a rewritable medium such as a magneto-optical disk that is optically readable and magneto-optically writable.

8. Uses of the Three Dimensional Structure of AKT3

The three-dimensional crystal structure of the present invention may be used to identify AKT3 binding sites, be used as a molecular replacement model to solve the structure of unknown crystallized proteins, to design mutants having desirable binding properties, and ultimately, to design, characterize, identify entities capable of interacting with AKT3 and other structurally similar proteins as well as other uses that would be recognized by one of ordinary skill in the art. Such entities may be chemical entities or proteins. The term "chemical entity", as used herein, refers to chemical compounds, complexes of at least two chemical compounds, and fragments of such compounds.

The AKT3 structure coordinates provided herein are useful for screening and identifying drugs that inhibit AKT3 and other structurally similar proteins. For example, the structure encoded by the data may be computationally evaluated for its ability to associate with putative substrates or ligands. Such compounds that associate with AKT3 may inhibit AKT3, and are potential drug candidates. Additionally or alternatively, the structure encoded by the data may be displayed in a graphical three-dimensional representation on a computer screen. This allows visual inspection of the structure, as well as visual inspection of the structure's association with the compounds.

Thus, according to another embodiment of the present invention, a method is provided for evaluating the potential of an entity to associate with AKT3 or a fragment or variant thereof by using all or a portion of the structure coordinates provided in FIG. 3 or functional equivalents thereof. A method is also provided for evaluating the potential of an entity to associate with AKT3 or a fragment or variant thereof by using structure coordinates similar to all or a portion of the structure coordinates provided in FIG. 3 or functional equivalents thereof.

The method may optionally comprise the steps of: creating a computer model of all or a portion of a protein structure (e.g., a binding pocket) using structure coordinates according to the present invention; performing a fitting operation between the entity and the computer model; and analyzing the results of the fitting operation to quantify the association between the entity and the model. The portion of the protein structure used optionally comprises all of the amino acids listed in Tables 2, 3 and 4 that are present in the structure coordinates being used.

It is noted that the computer model may not necessarily directly use the structure coordinates. Rather, a computer model can be formed that defines a surface contour that is the same or similar to the surface contour defined by the structure coordinates.

The structure coordinates provided herein can also be utilized in a method for identifying a ligand (e.g., entities capable of associating with a protein) of a protein comprising an AKT3-like binding pocket. One embodiment of the method comprises: using all or a portion of the structure coordinates provided herein to generate a three-dimensional structure of an AKT3-like binding pocket; employing the three-dimensional structure to design or select a potential ligand; synthesizing the potential ligand; and contacting the synthesized potential ligand with a protein comprising an AKT3-like binding pocket to determine the ability of the potential ligand to interact with protein. According to this method, the structure coordinates used may have a root mean square deviation equal to or less than the RMSD values specified in Columns 3, 4 or 5 of Table 1 when compared to the structure coordinates of FIG. 3 according to the RMSD calculation method set forth herein, provided that the portion of amino acid residues specified in Column 2 of Table 1 of each set of structure coordinates are superimposed and the root mean square deviation is calculated based only on those amino acid residues in the structure coordinates that are also present in the portion of the protein specified in Column 1 of Table 1. The portion of the protein structure used optionally comprises all of the amino acids listed in Tables 2, 3, and/or 4 that are present.

As noted previously, the three-dimensional structure of an AKT3-like binding pocket need not be generated directly from structure coordinates. Rather, a computer model can be formed that defines a surface contour that is the same or similar to the surface contour defined by the structure coordinates.

A method is also provided for evaluating the ability of an entity, such as a compound or a protein to associate with an AKT3-like binding pocket, the method comprising: constructing a computer model of a binding pocket defined by structure coordinates that have a root mean square deviation equal to or less than the RMSD value specified in Columns 3, 4 or 5 of Table 1 when compared to the structure coordinates of FIG. 3, the root mean square deviation being calculated such that the portion of amino acid residues specified in Column 2 of Table 1 of each set of structure coordinates are superimposed and the root mean square deviation is based only on those amino acid residues in the structure coordinates that are also present in the portion of the protein specified in specified in Column 1 of Table 1; selecting an entity to be evaluated by a method selected from the group consisting of (i) assembling molecular fragments into the entity, (ii) selecting an entity from a small molecule database, (iii) de novo ligand design of the entity, and (iv) modifying a known ligand for AKT3, or a portion thereof; performing a fitting program operation between computer models of the entity to be evaluated and the binding pocket in order to provide an energy-minimized configuration of the entity in the binding pocket; and evaluating the results of the fitting operation to quantify the association between the entity and the binding pocket model in order to evaluate the ability of the entity to associate with the said binding pocket.

The computer model of a binding pocket used in this embodiment need not be generated directly from structure coordinates. Rather, a computer model can be formed that defines a surface contour that is the same or similar to the surface contour defined by the structure coordinates.

Also according to the method, the method may further include synthesizing the entity; and contacting a protein having an AKT3-like binding pocket with the synthesized entity.

With the structure provided herein, the present invention for the first time permits the use of molecular design techniques to identify, select or design potential inhibitors of AKT3, based on the structure of an AKT3-like binding pocket. Such a predictive model is valuable in light of the high costs associated with the preparation and testing of the many diverse compounds that may possibly bind to the AKT3 protein.

According to this invention, a potential AKT3 inhibitor may now be evaluated for its ability to bind an AKT3-like binding pocket prior to its actual synthesis and testing. If a proposed entity is predicted to have insufficient interaction or association with the binding pocket, preparation and testing of the entity can be obviated. However, if the computer modeling indicates a strong interaction, the entity may then be obtained and tested for its ability to bind.

A potential inhibitor of an AKT3-like binding pocket may be computationally evaluated using a series of steps in which chemical entities or fragments are screened and selected for their ability to associate with the AKT3-like binding pockets.

One skilled in the art may use one of several methods to screen entities (whether chemical or protein) for their ability to associate with an AKT3-like binding pocket. This process may begin by visual inspection of, for example, an AKT3-like binding pocket on a computer screen based on the AKT3 structure coordinates in FIG. 3 or other coordinates which define a similar shape generated from the machine-readable storage medium. Selected fragments or chemical entities may then be positioned in a variety of orientations, or docked, within that binding pocket as defined above. Docking may be accomplished using software such as Quanta and Sybyl, followed by energy minimization and molecular dynamics with standard molecular mechanics force fields, such as CHARMM and AMBER.

Specialized computer programs may also assist in the process of selecting entities. These include: GRID (P. J. Goodford, "A Computational Procedure for Determining Energetically Favorable Binding Sites on Biologically Important Macromolecules", J. Med. Chem., 28, pp. 849-857 (1985)). GRID is available from Oxford University, Oxford, UK; MCSS (A. Miranker et al., "Functionality Maps of Binding Sites: A Multiple Copy Simultaneous Search Method." Proteins: Structure, Function and Genetics, 11, pp. 29-34 (1991)). MCSS is available from Molecular Simulations, San Diego, Calif.; AUTODOCK (D. S. Goodsell et al., "Automated Docking of Substrates to Proteins by Simulated Annealing", Proteins: Structure, Function, and Genetics, 8, pp. 195-202 (1990)). AUTODOCK is available from Scripps Research Institute, La Jolla, Calif.; & DOCK (I. D. Kuntz et al., "A Geometric Approach to Macromolecule-Ligand Interactions", J. Mol. Biol., 161, pp. 269-288 (1982)). DOCK is available from University of California, San Francisco, Calif.

Once suitable entities have been selected, they can be designed or assembled. Assembly may be preceded by visual inspection of the relationship of the fragments to each other on the three-dimensional image displayed on a computer screen in relation to the structure coordinates of AKT3. This may then be followed by manual model building using software such as MOE, QUANTA or Sybyl [Tripos Associates, St. Louis, Mo].

Useful programs to aid one of skill in the art in connecting the individual chemical entities or fragments include: CAVEAT (P. A. Bartlett et al, "CAVEAT: A Program to Facilitate the Structure-Derived Design of Biologically Active Molecules", in "Molecular Recognition in Chemical and Biological Problems", Special Pub., Royal Chem. Soc., 78, pp. 182-196 (1989); G. Lauri and P. A. Bartlett, "CAVEAT: a Program to Facilitate the Design of Organic Molecules", J. Comput. Aided Mol. Des., 8, pp. 51-66 (1994)). CAVEAT is available from the University of California, Berkeley, Calif.; 3D Database systems such as ISIS (MDL Information Systems, San Leandro, Calif.). This area is reviewed in Y. C. Martin, "3D Database Searching in Drug Design", J. Med. Chem., 35, pp. 2145-2154 (1992); HOOK (M. B. Eisen et al, "HOOK: A Program for Finding Novel Molecular Architectures that Satisfy the Chemical and Steric Requirements of a Macromolecule Binding Site", Proteins: Struct., Funct., Genet., 19, pp. 199-221 (1994). HOOK is available from Molecular Simulations, San Diego, Calif.

Instead of proceeding to build an inhibitor of an AKT3-like binding pocket in a step-wise fashion one fragment or entity at a time as described above, inhibitory or other AKT3 binding compounds may be designed as a whole or "de novo" using either an empty binding site or optionally including some portion(s) of a known inhibitor(s). There are many de novo ligand design methods including: LUDI (H.-J. Bohm, "The Computer Program LUDI: A New Method for the De Novo Design of Enzyme Inhibitors", J. Comp. Aid. Molec. Design, 6, pp. 61-78 (1992)). LUDI is available from Molecular Simulations Incorporated, San Diego, Calif.; LEGEND (Y. Nishibata et al., Tetrahedron, 47, p. 8985 (1991)). LEGEND is available from Molecular Simulations Incorporated, San Diego, Calif.; LEAPFROG (available from Tripos Associates, St. Louis, Mo.); & SPROUT (V. Gillet et al, "SPROUT: A Program for Structure Generation)", J. Comput. Aided Mol. Design, 7, pp. 127-153 (1993)). SPROUT is available from the University of Leeds, UK.

Other molecular modeling techniques may also be employed in accordance with this invention (see, e.g., Cohen et al., "Molecular Modeling Software and Methods for Medicinal Chemistry, J. Med. Chem., 33, pp. 883-894 (1990); see also, M. A. Navia and M. A. Murcko, "The Use of Structural Information in Drug Design", Current Opinions in Structural Biology, 2, pp. 202-210 (1992); L. M. Balbes et al., "A Perspective of Modem Methods in Computer-Aided Drug Design", in Reviews in Computational Chemistry, Vol. 5, K. B. Lipkowitz and D. B. Boyd, Eds., VCH, New York, pp. 337-380 (1994); see also, W. C. Guida, "Software For Structure-Based Drug Design", Curr. Opin. Struct. Biology, 4, pp. 777-781 (1994)).

Once an entity has been designed or selected, for example, by the above methods, the efficiency with which that entity may bind to an AKT3 binding pocket may be tested and optimized by computational evaluation. For example, an effective AKT3 binding pocket inhibitor preferably demonstrates a relatively small difference in energy between its bound and free states (i.e., a small deformation energy of binding). Thus, the most efficient AKT3 binding pocket inhibitors should preferably be designed with deformation energy of binding of not greater than about 10 kcal/mole, more preferably, not greater than 7 kcal/mole. AKT3 binding pocket inhibitors may interact with the binding pocket in more than one of multiple conformations that are similar in overall binding energy. In those cases, the deformation energy of binding is taken to be the difference between the energy of the free entity and the average energy of the conformations observed when the inhibitor binds to the protein.

An entity designed or selected as binding to an AKT3 binding pocket may be further computationally optimized so that in its bound state it would preferably lack repulsive electrostatic interaction with the target enzyme and with the surrounding water molecules. Such non-complementary electrostatic interactions include repulsive charge-charge, dipole-dipole and charge-dipole interactions.

Specific computer software is available in the art to evaluate compound deformation energy and electrostatic interactions. Examples of programs designed for such uses include: Gaussian 94, revision C (M. J. Frisch, Gaussian, Inc., Pittsburgh, Pa. COPYRGT.1995); AMBER, version 4.1 (P. A. Kollman, University of California at San Francisco, COPYRGT 1995); QUANTA/CHARMM (Molecular Simulations, Inc., San Diego, Calif. COPYRGT.1995); Insight II/Discover (Molecular Simulations, Inc., San Diego, Calif. COPYRGT.1995); DelPhi (Molecular Simulations, Inc., San Diego, Calif. COPYRGT.1995); and AMSOL (Quantum Chemistry Program Exchange, Indiana University). These programs may be implemented, for instance, using a Silicon Graphics workstation such as an Indigo.sup.2 with "IMPACT" graphics. Other hardware systems and software packages will be known to those skilled in the art.

Another approach provided by this invention, is the computational screening of small molecule databases for chemical entities or compounds that can bind in whole, or in part, to an AKT3 binding pocket. In this screening, the quality of fit of such entities to the binding site may be judged either by shape complementarities or by estimated interaction energy [E. C. Meng et al., J. Comp. Chem., 13, 505-524 (1992)].

According to another embodiment, the invention provides compounds that associate with an AKT3-like binding pocket produced or identified by various methods set forth above.

The structure coordinates set forth in FIG. 3 can also be used to aid in obtaining structural information about another crystallized molecule or molecular complex. This may be achieved by any of a number of well-known techniques, including molecular replacement.

For example, a method is also provided for utilizing molecular replacement to obtain structural information about a protein whose structure is unknown comprising the steps of: generating an X-ray diffraction pattern of a crystal of the protein whose structure is unknown; generating a three-dimensional electron density map of the protein whose structure is unknown from the X-ray diffraction pattern by using at least a portion of the structure coordinates set forth in FIG. 3 as a molecular replacement model.

By using molecular replacement, all or part of the structure coordinates of the AKT3 provided by this invention (and set forth in FIG. 3) can be used to determine the structure of another crystallized molecule or molecular complex more quickly and efficiently than attempting an ab initio structure determination. One particular use includes use with other structurally similar proteins. Molecular replacement provides an accurate estimation of the phases for an unknown structure. Phases are a factor in equations used to solve crystal structures that cannot be determined directly. Obtaining accurate values for the phases, by methods other than molecular replacement, is a time-consuming process that involves iterative cycles of approximations and refinements and greatly hinders the solution of crystal structures. However, when the crystal structure of a protein containing at least a homologous portion has been solved, the phases from the known structure provide a satisfactory estimate of the phases for the unknown structure.

Thus, this method involves generating a preliminary model of a molecule or molecular complex whose structure coordinates are unknown, by orienting and positioning the relevant portion of AKT3 according to FIG. 3 within the unit cell of the crystal of the unknown molecule or molecular complex so as best to account for the observed X-ray diffraction pattern of the crystal of the molecule or molecular complex whose structure is unknown. Phases can then be calculated from this model and combined with the observed X-ray diffraction pattern amplitudes to generate an electron density map of the structure whose coordinates are unknown. This, in turn, can be subjected to any well-known model building and structure refinement techniques to provide a final, accurate structure of the unknown crystallized molecule or molecular complex [E. Lattman, "Use of the Rotation and Translation Functions", in Meth. Enzymol., 115, pp. 55-77 (1985); M. G. Rossmann, ed., "The Molecular Replacement Method", Int. Sci. Rev. Ser., No. 13, Gordon & Breach, New York (1972)].

The structure of any portion of any crystallized molecule or molecular complex that is sufficiently homologous to any portion of AKT3 can be resolved by this method.

In one embodiment, the method of molecular replacement is utilized to obtain structural information about the present invention and any other AKT3-like molecule. The structure coordinates of AKT3, as provided by this invention, are particularly useful in solving the structure of other isoforms of AKT3 or AKT3 complexes.

The structure coordinates of AKT3 as provided by this invention are useful in solving the structure of AKT3 variants that have amino acid substitutions, additions and/or deletions (referred to collectively as "AKT3 mutants", as compared to naturally occurring AKT3). These AKT3 mutants may optionally be crystallized in co-complex with a ligand, such as an inhibitor, substrate analogue or a suicide substrate. The crystal structures of a series of such complexes may then be solved by molecular replacement and compared with that of AKT3. Potential sites for modification within the various binding sites of the enzyme may thus be identified. This information provides an additional tool for determining the most efficient binding interactions such as, for example, increased hydrophobic interactions, between AKT3 and a ligand. It is noted that the ligand may be the protein's natural ligand or may be a potential agonist or antagonist of a protein.

All of the complexes referred to above may be studied using well-known X-ray diffraction techniques and may be refined versus 1.5-3 Å resolution X-ray data to an R value of about 0.22 or less using computer software, such as X-PLOR [Yale University, COPYRIGHT.1992, distributed by Molecular Simulations, Inc.; see, e.g., Blundell & Johnson, supra; Meth. Enzymol., Vol. 114 & 115, H. W. Wyckoff et al., eds., Academic Press (1985)]. This information may thus be used to optimize known AKT3 inhibitors, and more importantly, to design new AKT3 inhibitors.

The structure coordinates described above may also be used to derive the dihedral angles, phi and psi, that define the conformation of the amino acids in the protein backbone. As will be understood by those skilled in the art, the $phi_n$ angle refers to the rotation around the bond between the alpha-carbon and the nitrogen, and the $Psi_n$ angle refers to the rotation around the bond between the carbonyl carbon and the alpha-carbon. The subscript "n" identifies the amino acid whose conformation is being described [for a general reference, see Blundell and Johnson, Protein Crystallography, Academic Press, London, 1976].

9. Uses of the Crystal and Diffraction Pattern of AKT3

Crystals, crystallization conditions and the diffraction pattern of AKT3 that can be generated from the crystals also have a range of uses. One particular use relates to screening entities that are not known ligands of AKT3 for their ability to bind to AKT3. For example, with the availability of crystallization conditions, crystals and diffraction patterns of AKT3 provided according to the present invention, it is possible to take a crystal of AKT3; expose the crystal to one or more entities that may be a ligand of AKT3; and determine whether a ligand/AKT3 complex is formed. The crystals of AKT3 may be exposed to potential ligands by various methods, including but not limited to, soaking a crystal in a solution of one or more potential ligands or co-crystallizing AKT3 in the presence of one or more potential ligands. Given the structure coordinates provided herein, once a ligand complex is formed, the structure coordinates can be used as a model in molecular replacement in order to determine the structure of the ligand complex.

Once one or more ligands are identified, structural information from the ligand/AKT3 complex(es) may be used to design new ligands that bind tighter, bind more specifically, have better biological activity or have better safety profile than known ligands.

In one embodiment, a method is provided for identifying a ligand that binds to AKT3 comprising: (a) attempting to crystallize a protein that comprises a sequence wherein at least a portion of the sequence has 55%, 65%, 75%, 85%, 90%, 95%, 97%, 99% or greater identity with SEQ. ID No. 3 in the presence of one or more entities; (b) if crystals of the protein are obtained in step (a), obtaining an X-ray diffraction pattern of the protein crystal; and (c) determining whether a ligand/protein complex was formed by comparing an X-ray diffraction pattern of a crystal of the protein formed in the absence of the one or more entities to the crystal formed in the presence of the one or more entities.

In another embodiment, a method is provided for identifying a ligand that binds to AKT3 comprising: soaking a crystal of a protein wherein at least a portion of the protein has 55%, 65%, 75%, 85%, 90%, 95%, 97%, 99% or greater identity with SEQ. ID No. 3 with one or more entities; determining whether a ligand/protein complex was formed by comparing an X-ray diffraction pattern of a crystal of the protein that has not been soaked with the one or more entities to the crystal that has been soaked with the one or more entities.

Optionally, the method may further comprise converting the diffraction patterns into electron density maps using phases of the protein crystal and comparing the electron density maps.

Libraries of "shape-diverse" compounds may optionally be used to allow direct identification of the ligand-receptor complex even when the ligand is exposed as part of a mixture. According to this variation, the need for time-consuming de-convolution of a hit from the mixture is avoided. More specifically, the calculated electron density function reveals the binding event, identifies the bound compound and provides a detailed 3-D structure of the ligand-receptor complex. Once a hit is found, one may optionally also screen a number of analogs or derivatives of the hit for tighter binding or better biological activity by traditional screening methods. The hit and information about the structure of the target may also be used to develop analogs or derivatives with tighter binding or better biological activity. It is noted that the ligand-AKT3 complex may optionally be exposed to additional iterations of potential ligands so that two or more hits can be linked together to make a more potent ligand. Screening for potential ligands by co-crystallization and/or soaking is further described in U.S. Pat. No. 6,297,021, which is incorporated herein by reference.

EXAMPLES

Example 1

Expression and Purification of AKT3

This example describes the expression of AKT3. It should be noted that a variety of other expression systems and hosts are also suitable for the expression of AKT3, as would be readily appreciated by one of skill in the art.

The portion of the gene encoding residues 136-461(from SEQ. ID No. 1), which corresponds to the catalytic domain of human AKT3, was isolated by PCR from leukocyte cDNA (that had been generated from RNA by reverse transcription) and cloned into the TOPO-activated cloning site of pCR2,1-TOPO. This DNA sequence is presented in SEQ. ID No. 2. The catalytic domain of human AKT3 was then cloned by PCR into the AarI-PstI sites of vector pBADSSP. This vector utilizes the amino-terminal SSP (Synechocystis species) intein-CBD (chitin binding domain) tag commonly used for affinity chromatography purification and on-column target cleavage (New England Biolabs). Expression in this vector generated a fusion of the AKT3 kinase domain with a cleavable (SSP intein-CBD) amino-terminal tag, the amino acid sequence of which is shown, underlined, in FIG. 1 (SEQ. ID No. 3).

Recombinant proteins were isolated from E. coli DH10B-Trl cellular extracts by passage over Chitin (New England Biolabs) resin. The SSP intein-CBD tag was removed by overnight incubation at room temperature of the AKT3-bound resin in a pH7.0 buffer. It is noted that the cleavage reaction leaves 4 amino acids on the amino terminal of the AKT3 kinase domain (Cys-Arg-Ser-Leu, residues 227-230 of SEQ. ID No. 3, FIG. 1). The amino acid sequence of the resulting protein is shown as SEQ. ID NO: 4 in FIG. 1. The AKT3 kinase domain protein purity as determined on denaturing SDS-PAGE gel was 50%. It is noted that the purification process involved the use of egg-white lysozyme that co-eluted in a 50%/50% amount with the AKT3 kinase domain. The egg-white lysozyme was not removed from the AKT3 kinase domain protein preparation for the crystallization trials. AKT3 kinase domain was not phosphorylated during the isolation and purification procedures as confirmed by mass spectrometry. SEQ ID NO: 4 was concentrated to a final concentration of 25.9 mg/ml and stored at 4° C. in a buffer containing 25 mM TRIS-HCl pH 7.6, 250 mM NaCl, 1 mM EDTA and 5 mM DTT.

Example 2

Crystallization of AKT3

This example describes the crystallization of AKT3. It is noted that the precise crystallization conditions used may be further varied, for example by performing a fine screen based on these crystallization conditions.

AKT3 protein samples corresponding to SEQ ID NO: 4 were incubated with 2 mM ATP and 4 mM $MgCl_2$ before setting crystallization trials. Crystals were obtained after an extensive and broad screen of conditions, followed by optimization.

Diffraction quality crystals were grown as in 100 mL sitting droplets using the vapor diffusion method. 50 mL comprising the AKT3 complex (25.9 mg/ml) was mixed with 50 mL from a reservoir solution (100 µL) comprising 0.1M MES pH=6.0 and 15% PEG MME 5000. The resulting solution was incubated over a period of one week at 4° C.

Crystals typically appeared after 24-48 hours and grew to a maximum size within 72 hours. Single crystals were separated from their parent cluster and transferred, briefly, into a cryoprotecting solution containing the reservoir solution supplemented with 30% v/v glycerol. Crystals were then flash frozen by immersion in liquid nitrogen and then stored under liquid nitrogen. A crystal of AKT3 complex produced as described is illustrated in FIG. 2.

While the present invention is disclosed with reference to certain embodiments and examples detailed above, it is to be understood that these embodiments and examples are intended to be illustrative rather than limiting, as it is contemplated that modifications will readily occur to those skilled in the art, which modifications are intended to be within the scope of the invention and the appended claims. All patents, papers, and books cited in this application are incorporated herein in their entirety.

We claim:

1. A composition comprising a protein in crystalline form wherein the protein consists of SEQ ID NO:4, and wherein the protein crystal has a crystal lattice in a $P2_12_12_1$ space group and unit cell dimensions, +/−5%, of a=48.36 Å b72.29 Å and c=94.52 Å, $\alpha=\beta=\gamma=90°$.

2. A composition according to claim 1 wherein the protein crystal diffracts X-rays for a determination of structure coordinates to a resolution having a value that is less than or equal to 3.0 Angstroms.

3. A method for forming a crystal of a protein comprising:
    forming a crystallization volume comprising a precipitant solution and a protein that consists of SEQ ID NO:4, and wherein a protein crystal is formed that has a crystal lattice in a $P2_12_12_1$ space group and unit cell dimensions, +/−5%, of a=48.36 Å b=72.29 Å and c=94.52 Å, $\alpha=\beta=\gamma=90°$; and
    storing the crystallization volume under conditions suitable for formation of a protein crystal.

4. A method according to claim 3 wherein a protein crystal is formed that diffracts X-rays for a determination of structure coordinates to a resolution having a value that is less than or equal to 3.0 Angstroms.

5. A non-crystalline protein consisting of SEQ ID NO:4.

6. A non-crystalline protein consisting of residues 136-461 of SEQ ID NO:1.

7. An isolated non-crystalline protein consisting of residues 136-461 of SEQ ID NO:1.

8. An isolated non-crystalline protein consisting of SEQ ID NO:4.

9. A method for obtaining a three dimensional structure of a protein comprising the steps of:
    (a) obtaining a crystal of a protein whose sequence consists of SEQ ID NO:4, wherein the protein crystal has a crystal lattice in a $P2_12_12_1$ space group and unit cell dimensions, +/−5%, of a=48.36 Å b=72.29 Å and c=94.52 Å, $\alpha=\beta=\gamma=90°$;
    (b) using the crystal obtained in step (a) to obtain an x-ray diffraction pattern; and
    (c) solving the three dimensional structure of the protein from the diffraction pattern obtained in step (b), thereby obtaining the three dimensional structure of the protein.

10. A method for identifying a compound that binds to a protein comprising the steps of:
    (a) obtaining a crystal of a protein whose sequence consists of SEQ ID NO:4, wherein the protein crystal has a crystal lattice in a $P2_12_12_1$ space group and unit cell dimensions, +/−5%, of a=48,36 Å b=72.29 Å and c=94.52 Å, $\alpha=\beta=\gamma=90°$;
    (b) using the crystal obtained in step (a) to obtain an x-ray diffraction pattern;
    (c) solving the three dimensional structure of the protein from the diffraction pattern obtained in step (b), thereby obtaining the three dimensional structure of the protein; and
    (d) identifying one or more compounds that binds to the protein based on the three dimensional structure.

11. The method according to claim 10, further comprising the step of:
    contacting one or more compounds identified in step (d) with the protein whose sequence consists of SEQ ID NO:4.

12. The method according to claim 11 further comprising the step of:
    measuring an activity of the protein whose sequence consists of SEQ ID NO:4, when the protein is contacted with the one or more compounds.

13. The method according to claim 12, further comprising the step of:
    comparing activities of the protein whose sequence consists of SEQ ID NO:4, when the protein is in the presence of and in the absence of the one or more compounds.

14. The method according to claim 10, further comprising the steps of:
    contacting one or more compounds identified in step (d) with a cell that expresses a protein whose sequence consists of SEQ ID NO:4; and
    detecting whether a phenotype of the cell changes when the one or more compounds are present.

* * * * *